US012612612B2

(12) United States Patent  
Perez-Pinera et al.

(10) Patent No.: US 12,612,612 B2  
(45) Date of Patent: Apr. 28, 2026

(54) METHODS FOR EXON SKIPPING AND GENE KNOCKOUT USING BASE EDITORS

(71) Applicant: THE BOARD OF TRUSTEES OF THE UNIVERSITY OF ILLINOIS, Urbana, IL (US)

(72) Inventors: Pablo Perez-Pinera, Urbana, IL (US); Michael P. Gapinske, Urbana, IL (US); Jackson Scott Winter, Palatine, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1491 days.

(21) Appl. No.: 17/260,828

(22) PCT Filed: Jul. 19, 2019

(86) PCT No.: PCT/US2019/042627  
§ 371 (c)(1),  
(2) Date: Jan. 15, 2021

(87) PCT Pub. No.: WO2020/018918  
PCT Pub. Date: Jan. 23, 2020

(65) Prior Publication Data  
US 2021/0309986 A1 Oct. 7, 2021

Related U.S. Application Data

(60) Provisional application No. 62/700,365, filed on Jul. 19, 2018.

(51) Int. Cl.

| | |
|---|---|
| *C12N 9/78* | (2006.01) |
| *A61K 38/00* | (2006.01) |
| *A61P 25/00* | (2006.01) |
| *A61P 43/00* | (2006.01) |
| *C12N 9/22* | (2006.01) |
| *C12N 15/11* | (2006.01) |

(52) U.S. Cl.  
CPC .............. *C12N 9/78* (2013.01); *A61P 25/00* (2018.01); *A61P 43/00* (2018.01); *C12N 9/22* (2013.01); *C12N 15/11* (2013.01); *C12Y 305/04004* (2013.01); *A61K 38/00* (2013.01); *C07K 2319/80* (2013.01); *C12N 2310/20* (2017.05); *C12N 2800/80* (2013.01)

(58) Field of Classification Search  
None  
See application file for complete search history.

(56) References Cited

U.S. PATENT DOCUMENTS

| | | | |
|---|---|---|---|
| 8,697,359 | B1 | 4/2014 | Zhang |
| 9,840,699 | B2 | 12/2017 | Liu et al. |
| 2003/0166160 | A1 | 9/2003 | Hawley et al. |
| 2014/0068797 | A1 | 3/2014 | Doudna et al. |
| 2016/0201089 | A1 | 7/2016 | Gersbach et al. |
| 2017/0204144 | A1 | 7/2017 | Deverman et al. |
| 2018/0127780 | A1 | 5/2018 | Liu et al. |

FOREIGN PATENT DOCUMENTS

| | | |
|---|---|---|
| CN | 106714845 A | 5/2017 |
| WO | 2017193029 A2 | 11/2017 |

OTHER PUBLICATIONS

Bachu et al, "CRISPR-Cas targeted plasmid integration into mammalian cells via non-homologous endjoining", Biotechnology and Bioengineering, vol. 112, No. 10, pp. 2154-2162, Oct. 2015.  
Burghes et al, "Antisense oligonucleotides and spinal muscular atrophy: skipping along", Genes & Development, vol. 24, pp. 1574-1579, (2010).  
Chew et al, "A multifunctional AAV-CRISPR-Cas9 and its host response", Nature Methods, vol. 13, No. 10, pp. 868-879, Oct. 2016.  
Crooke, "Potential roles of antisense technology in cancer chemotherapy", Oncogene, vol. 19, pp. 6651-6659, (2000).  
Gaudelli et al, "Programmable base editing of A•T to G•C in genomic DNA without DNA cleavage", Nature, vol. 551, No. 768, pp. 464-471, Nov. 23, 2017.  
Graveley, "Alternative splicing: increasing diversity in the proteomic world", Trends in Genetics, vol. 17, No. 2, Feb. 2001.  
Hsu et al, "DNA targeting specificity of RNA-guided Cas 9 nucleases", Nature Biotechnology, vol. 21, No. 9, Sep. 2013.  
Hu et al, "Evolved Cas 9 variants with broad PAM compatibility and high DNA specificity", Nature, vol. 556, No. 7699, pp. 57-63, Apr. 5, 2018.  
Kim et al, "CRISPR/Cpf1-mediated DNA-free plant genome editing", Nature Communications, pp. 1-7, Feb. 16, 2016.  
Kim et al, "Increasing the genome-targeting scope and precision of base editing with engineered Cas 9-cytidine deaminase fusions", Nat Biotechnol, vol. 35, No. 4, pp. 371-376, Apr. 2017.  
Komor et al, "Improved base excision repair inhibition and bacteriophage Mu Gam protein yields C:G to T:A base editors with higher efficiency and product purity", Science Advances, vol. 3, pp. 1-9, Aug. 30, 2017.  
Komor et al, "Programmable editing of a target base in genomic DNA without double-stranded DNA cleavage", Nature, vol. 553, No. 7603, pp. 420-424, Oct. 20, 2016.  
Kuscu et al, "CRISPR-STOP: gene silencing through base editing-induced nonsense mutations", Nature Methods, 6 pages, Jun. 5, 2017.  
Long et al, "Correction of diverse muscular dystrophy mutations in human engineered muscle by single-site genome editing", Science Advances, vol. 4, No. 1, Jan. 31, 2018.  
Lundquist et al, "Site-directed Mutagenesis and Characterization Uracil-DNA Glycosylase Inhibitor Protein", The Journal of Biological Chemistry, vol. 272, No. 34, Aug. 22, 1997.  
(Continued)

*Primary Examiner* — Nancy J Leith  
(74) *Attorney, Agent, or Firm* — Lathrop GPM LLP; Lisa Hillman

(57) ABSTRACT

The disclosure provides a versatile method termed CRISPR-SKIP that utilizes cytidine and/or adenine deaminase base editors to program exon skipping by mutating target DNA bases within splice acceptor sites and/or splice enhancer sites. Given its simplicity and precision, CRISPR-SKIP will be broadly applicable in gene therapy and synthetic biology.

14 Claims, 52 Drawing Sheets  
Specification includes a Sequence Listing.

(56)        References Cited

OTHER PUBLICATIONS

Ma et al, "Targeted AID-mediated mutagenesis (TAM) enables efficient genomic diversification in mammalian cells", Nature Methods, vol. 13, pp. 1029-1035, Dec. 2016.

Mou et al, "CRISPR/Casm9-mediated genome editing induces exon skipping by alternative splicing or exon deletion", Genome Biology, vol. 18, No. 108, (2017).

PCT International Application No. PCT/US19/42627, International Search Report of the International Searching Authority, dated Jan. 2, 2020, 5 pages.

PCT International Application No. PCT/US19/42627, Written Opinion of the International Searching Authority, dated Jan. 2, 2020, 9 pages.

Putnam et al, "Protein Mimicry of DNA from Crystal Structures of the Uracil-DNA Glycosylase Inhibitor Protein and its Complex with *Escherichia coli* Uracil-DNA Glycosylase", J. Mol. Biol., vol. 287, pp. 331-346, (1999).

Ravishankar et al, "X-ray analysis of a complex of *Escherichia coli* uracil DNA glycosylase (EcUDG) with a proteinaceous inhibitor. The structure elucidation of a prokaryotic UDG", Nucleic Acids Research, vol. 26, No. 21, pp. 4880-4887, Jan. 1998.

Rees et al, "Improving the DNA specificity and applicability of base editing through protein engineering and protein delivery", Nature Communications, vol. 8, No. 1, pp. 1-10, Jun. 6, 2017.

Serrano-Heras et al, "Phage $29 protein p56 prevents viral DNA replication impairment caused by uracil excision activity of uracil-DNA glycosylase", PNAS, vol. 105, No. 49, pp. 19044-19049, Dec. 9, 2008.

Wang et al, "Uracil-DNA Glycosylase Inhibitor Gene of Bacteriophage PBS2 Encodes a Binding Protein Specific for Uracil-DNA Glycosylase", The Journal of Biological Chemistry, vol. 264, No. 2, pp. 1163-1171, Jan. 15, 1989.

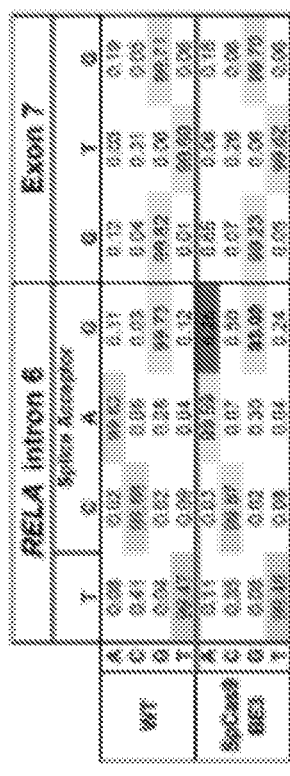
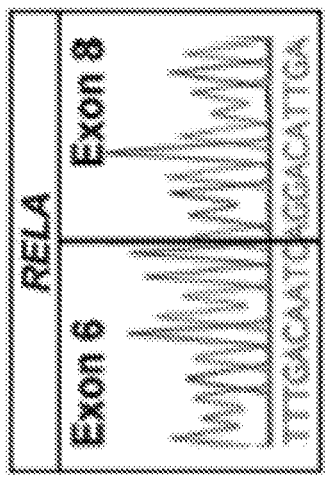
FIG. 2C
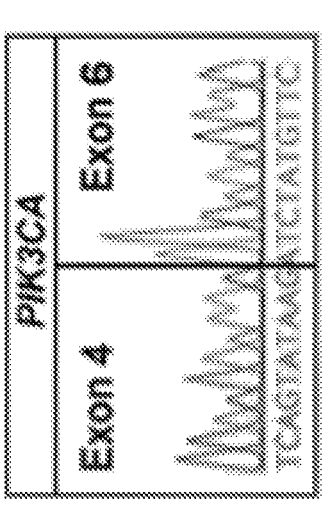
FIG. 2D

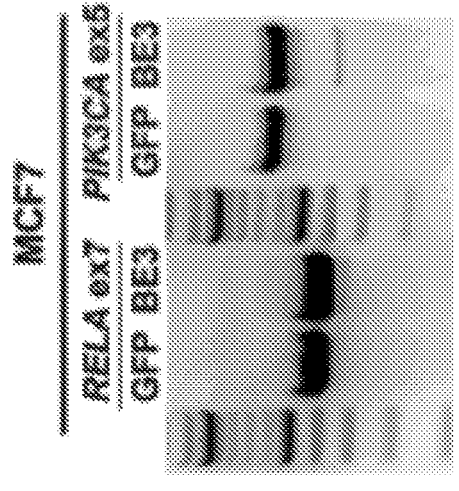
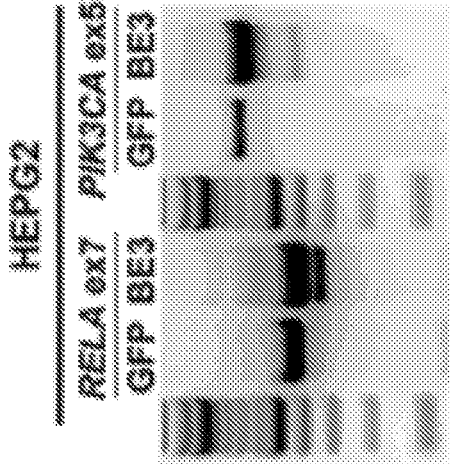
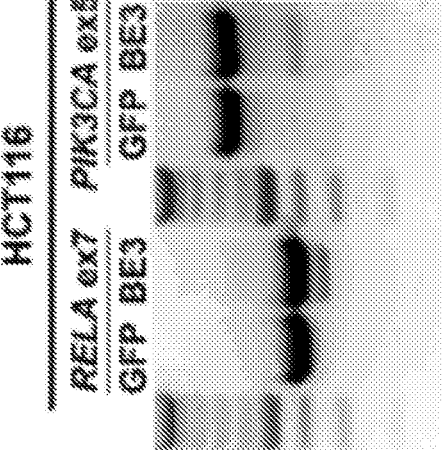
FIG. 3

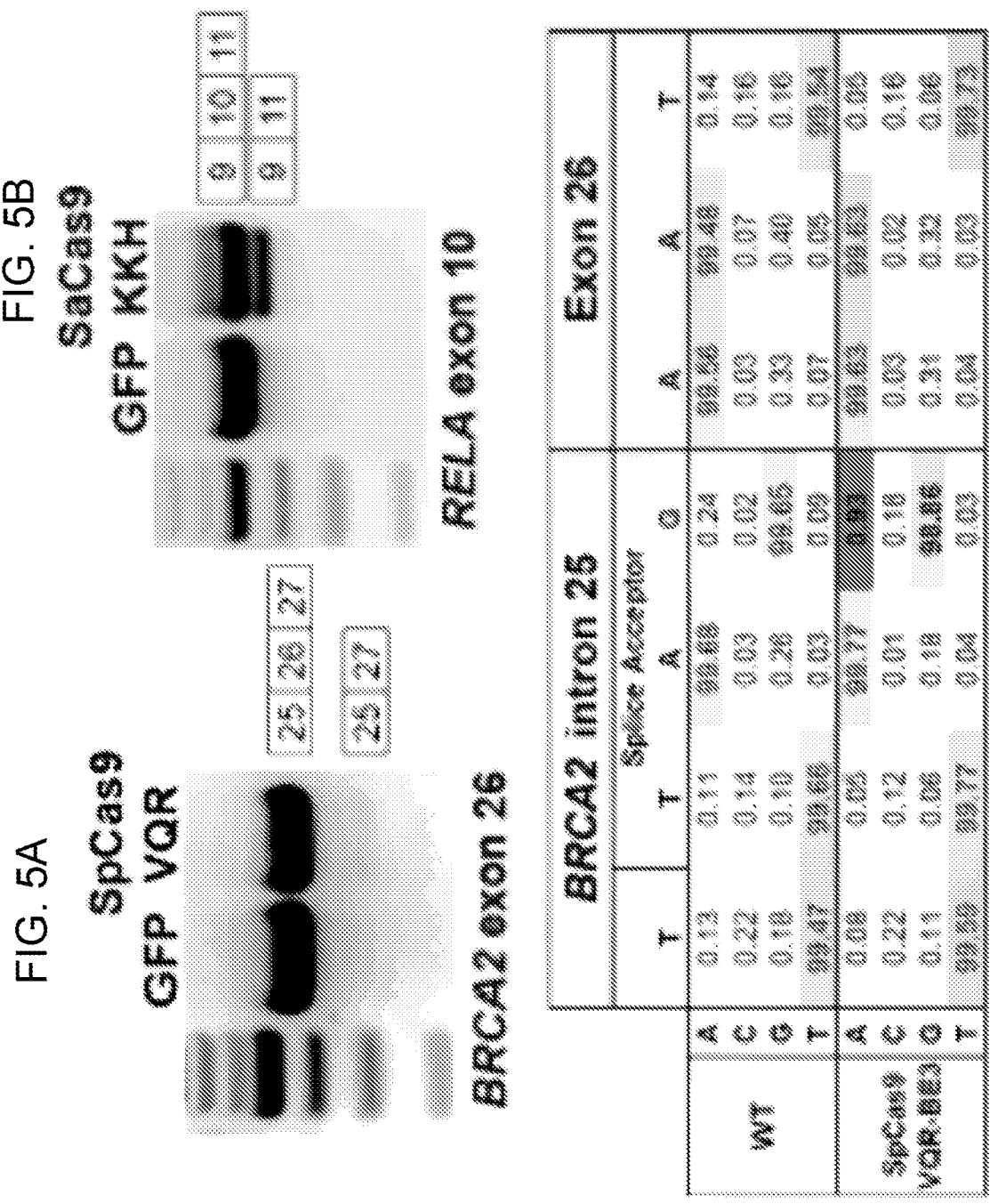

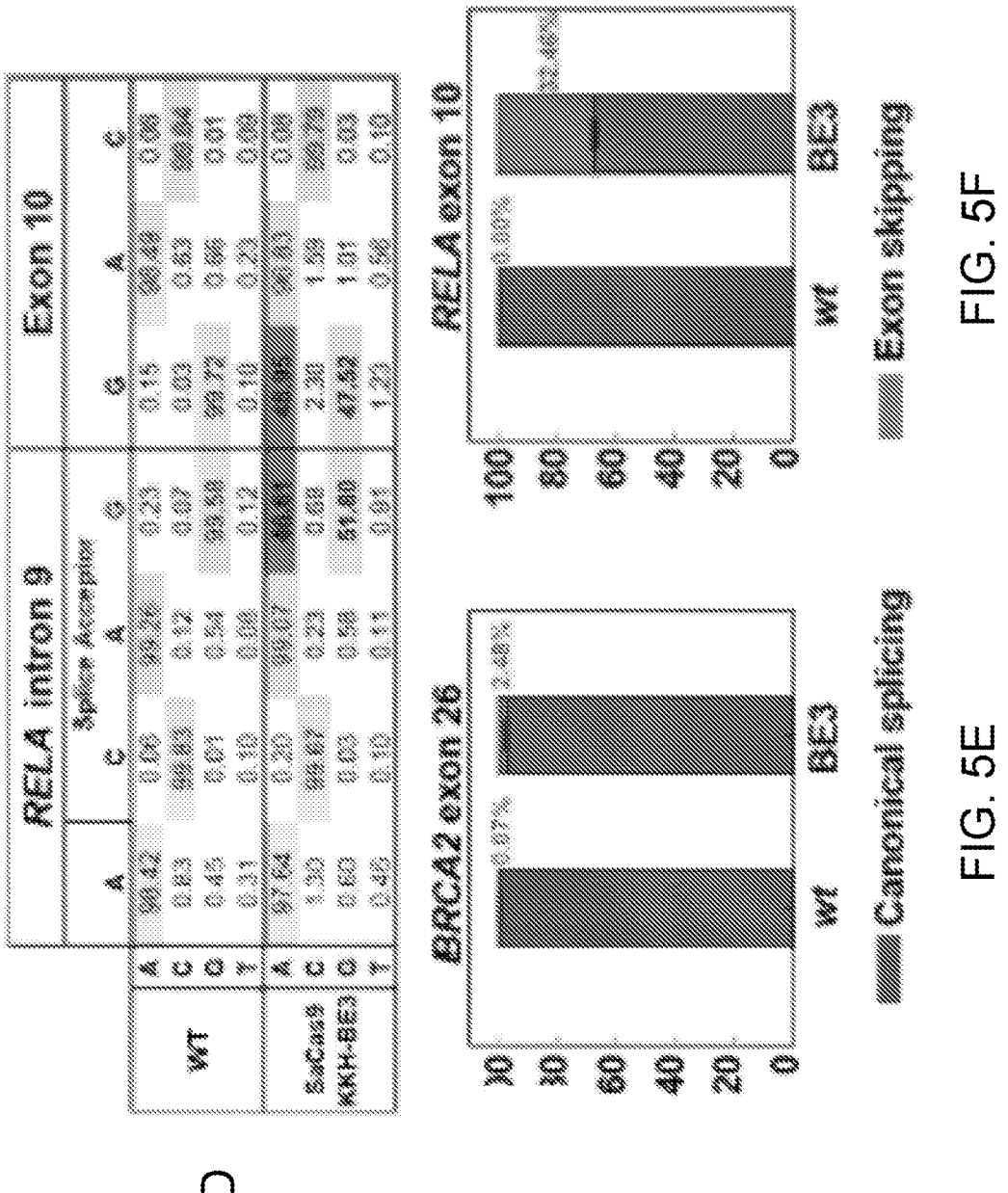

FIG. 8

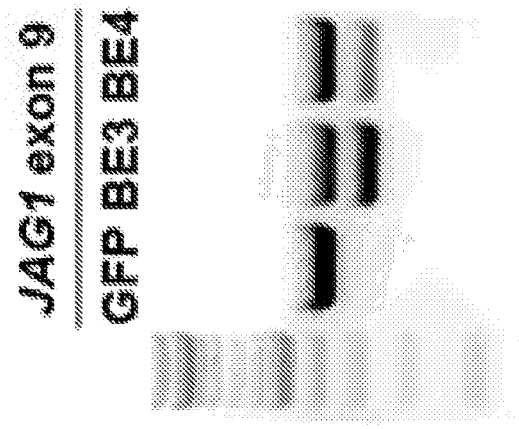
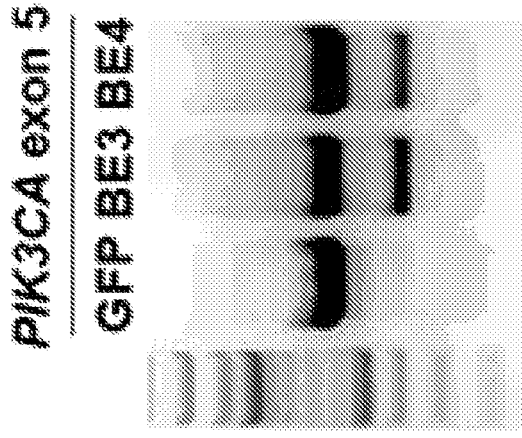
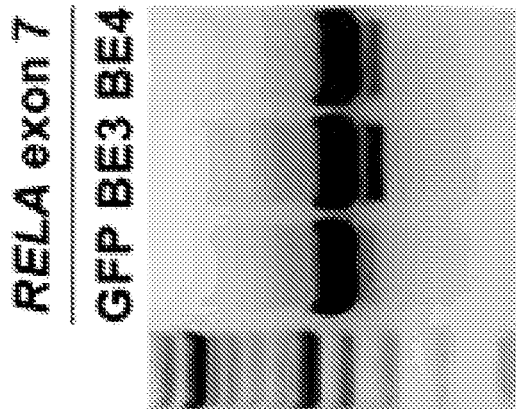
FIG. 14

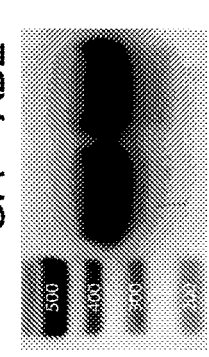
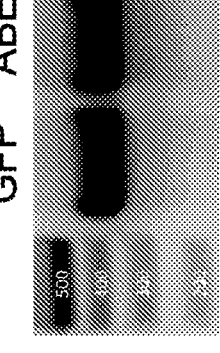
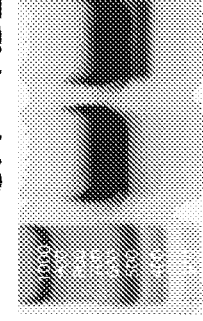
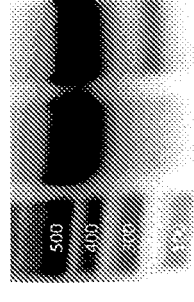
FIG. 17C

FIG. 23A
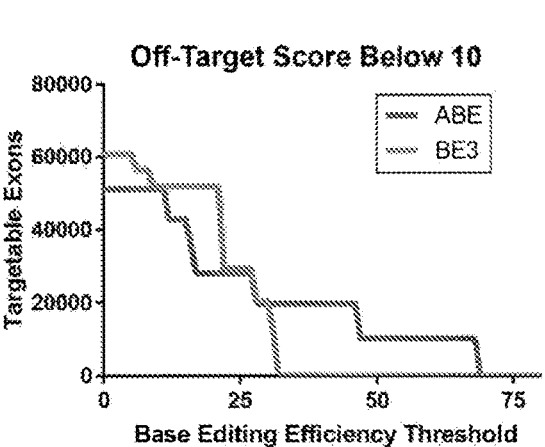
FIG. 23B
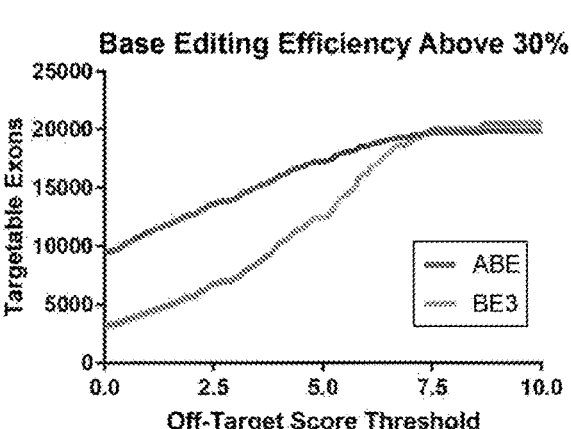
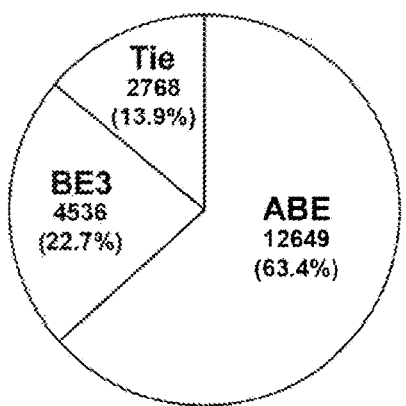
FIG. 23C        FIG. 23D

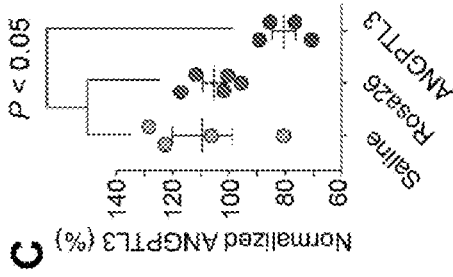
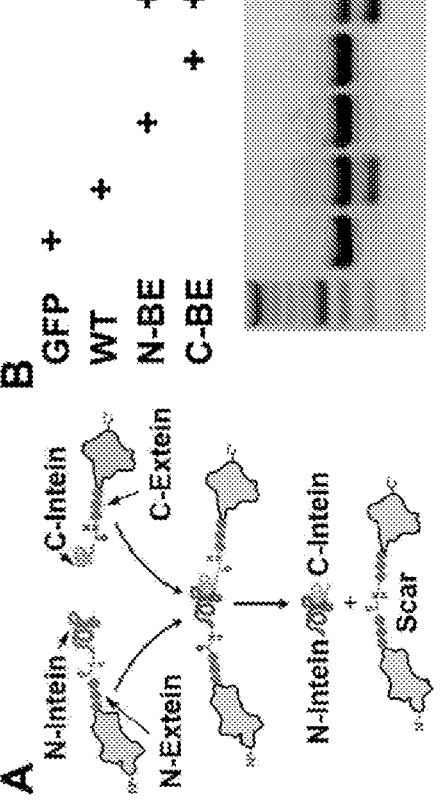
FIG. 38

SEQUENCE LISTING

<160> NUMBER OF SEQ ID NOS: 364

<210> SEQ ID NO 1
<211> LENGTH: 83
<212> TYPE: PRT
<213> ORGANISM: Artificial Sequence
<220> FEATURE:
<223> OTHER INFORMATION: Uniprot: P14739

<400> SEQUENCE: 1

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu

<210> SEQ ID NO 2
<211> LENGTH: 10
<212> TYPE: PRT
<213> ORGANISM: Artificial Sequence
<220> FEATURE:
<223> OTHER INFORMATION: Linker

<400> SEQUENCE: 2

Ala Pro Ala Pro Ala Pro Ala Pro Ala Pro
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Linker

<400> SEQUENCE: 3

Gly Gly Gly Gly Ser
1               5

<210> SEQ ID NO 4
<211> LENGTH: 10
<212> TYPE: PRT
<213> ORGANISM: Artificial Sequence
<220> FEATURE:
<223> OTHER INFORMATION: Linker -continued

```
<400> SEQUENCE: 4

Gly Gly Gly Gly Ser Gly Gly Gly Gly Ser
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Linker

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Linker

<400> SEQUENCE: 6

Gly Gly Gly Gly Ser Gly Gly Gly Gly Ser Gly Gly Gly Gly Ser Gly
1               5                   10                  15

Gly Gly Gly Ser
            20

<210> SEQ ID NO 7
<211> LENGTH: 25
<212> TYPE: PRT
<213> ORGANISM: Artificial Sequence
<220> FEATURE:
<223> OTHER INFORMATION: Linker

<400> SEQUENCE: 7

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 8
<211> LENGTH: 30
<212> TYPE: PRT
<213> ORGANISM: Artificial Sequence
<220> FEATURE:
<223> OTHER INFORMATION: Linker

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 9
<211> LENGTH: 35
<212> TYPE: PRT
<213> ORGANISM: Artificial Sequence
<220> FEATURE:
<223> OTHER INFORMATION: Linker

<400> SEQUENCE: 9

Gly Gly Gly Gly Ser Gly Gly Gly Gly Ser Gly Gly Gly Gly Ser Gly
1               5                   10                  15
```

```
Gly Gly Gly Ser Gly Gly Gly Gly Ser Gly Gly Gly Gly Ser Gly Gly
            20                  25                  30

Gly Gly Ser
        35

<210> SEQ ID NO 10
<211> LENGTH: 37
<212> TYPE: PRT
<213> ORGANISM: Artificial Sequence
<220> FEATURE:
<223> OTHER INFORMATION: Linker

<400> SEQUENCE: 10

Gly Gly Gly Gly Ser Ser Gly Gly Ser Ser Gly Gly Ser Ser Gly Ser
1               5                   10                  15

Glu Thr Pro Gly Thr Ser Glu Ser Ala Thr Pro Glu Ser Ser Gly Gly
            20                  25                  30

Ser Ser Gly Gly Ser
        35

<210> SEQ ID NO 11
<211> LENGTH: 20
<212> TYPE: PRT
<213> ORGANISM: Artificial Sequence
<220> FEATURE:
<223> OTHER INFORMATION: Linker

<400> SEQUENCE: 11

Glu Ala Ala Ala Glu Ala Ala Ala Glu Ala Ala Ala Glu Ala Ala Ala
1               5                   10                  15

Glu Ala Ala Ala
            20

<210> SEQ ID NO 12
<211> LENGTH: 4
<212> TYPE: DNA
<213> ORGANISM: Artificial Sequence
<220> FEATURE:
<223> OTHER INFORMATION: 3' end of splice acceptor site
<220> FEATURE:
<221> NAME/KEY: misc_feature
<222> LOCATION: (1)..(1)
<223> OTHER INFORMATION: n is a, c, g, t or u

<400> SEQUENCE: 12 ncag                                                            4

<210> SEQ ID NO 13
<211> LENGTH: 4
<212> TYPE: DNA
<213> ORGANISM: Artificial Sequence
<220> FEATURE:
<223> OTHER INFORMATION: 3' end of splice acceptor site
<220> FEATURE:
<221> NAME/KEY: misc_feature
<222> LOCATION: (1)..(1)
<223> OTHER INFORMATION: n is a, c, g, t or u

<400> SEQUENCE: 13 ntag                                                            4

<210> SEQ ID NO 14
<211> LENGTH: 4
<212> TYPE: DNA
<213> ORGANISM: Artificial Sequence
<220> FEATURE:
```

```
<223> OTHER INFORMATION: 3' end of splice acceptor site
<220> FEATURE:
<221> NAME/KEY: misc_feature
<222> LOCATION: (1)..(1)
<223> OTHER INFORMATION: n is a, c, g, t or u

<400> SEQUENCE: 14 naag                                                                            4

<210> SEQ ID NO 15
<211> LENGTH: 712
<212> TYPE: PRT
<213> ORGANISM: Artificial Sequence
<220> FEATURE:
<223> OTHER INFORMATION: Synthetic polypeptide

<400> SEQUENCE: 15

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
        50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
        130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320
```

-continued

Ile Lys Arg Tyr Asp Glu His His Gln Asp Leu Thr Leu Leu Lys Ala
            325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
        370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
            405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
        450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
            485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
            565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
        610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
            645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
        690                 695                 700

Glu Asp Ile Gln Lys Ala Gln Val
705                 710

<210> SEQ ID NO 16
<211> LENGTH: 102

<212> TYPE: PRT
<213> ORGANISM: Artificial Sequence
<220> FEATURE:
<223> OTHER INFORMATION: N-terminal intein

<400> SEQUENCE: 16

Cys Leu Ala Gly Asp Thr Leu Ile Thr Leu Ala Asp Gly Arg Arg Val
1               5                   10                  15

Pro Ile Arg Glu Leu Val Ser Gln Gln Asn Phe Ser Val Trp Ala Leu
            20                  25                  30

Asn Pro Gln Thr Tyr Arg Leu Glu Arg Ala Arg Val Ser Arg Ala Phe
        35                  40                  45

Cys Thr Gly Ile Lys Pro Val Tyr Arg Leu Thr Thr Arg Leu Gly Arg
    50                  55                  60

Ser Ile Arg Ala Thr Ala Asn His Arg Phe Leu Thr Pro Gln Gly Trp
65                  70                  75                  80

Lys Arg Val Asp Glu Leu Gln Pro Gly Asp Tyr Leu Ala Leu Pro Arg
                85                  90                  95

Arg Ile Pro Thr Ala Ser
            100

<210> SEQ ID NO 17
<211> LENGTH: 1775
<212> TYPE: PRT
<213> ORGANISM: Artificial Sequence
<220> FEATURE:
<223> OTHER INFORMATION: wtABE
<220> FEATURE:
<221> NAME/KEY: MISC_FEATURE
<222> LOCATION: (1)..(168)
<223> OTHER INFORMATION: Adenine Deaminase Domain
<220> FEATURE:
<221> NAME/KEY: MISC_FEATURE
<222> LOCATION: (169)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(397)
<223> OTHER INFORMATION: Linker region
<220> FEATURE:
<221> NAME/KEY: MISC_FEATURE
<222> LOCATION: (398)..(1768)
<223> OTHER INFORMATION: Cas9-D10A
<220> FEATURE:
<221> NAME/KEY: MISC_FEATURE
<222> LOCATION: (1769)..(1775)
<223> OTHER INFORMATION: NLS

<400> SEQUENCE: 17

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

-continued

```
Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
            130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
                180                 185                 190

Gly Gly Ser Ser Gly Gly Ser Ser Glu Val Glu Phe Ser His Glu Tyr
                195                 200                 205

Trp Met Arg His Ala Leu Thr Leu Ala Lys Arg Ala Arg Asp Glu Arg
            210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
                260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
            290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ser Gly Gly
            355                 360                 365

Ser Ser Gly Gly Ser Ser Gly Ser Glu Thr Pro Gly Thr Ser Glu Ser
            370                 375                 380

Ala Thr Pro Glu Ser Ser Gly Gly Ser Ser Gly Gly Ser Asp Lys Lys
385                 390                 395                 400

Tyr Ser Ile Gly Leu Ala Ile Gly Thr Asn Ser Val Gly Trp Ala Val
                405                 410                 415

Ile Thr Asp Glu Tyr Lys Val Pro Ser Lys Lys Phe Lys Val Leu Gly
            420                 425                 430

Asn Thr Asp Arg His Ser Ile Lys Lys Asn Leu Ile Gly Ala Leu Leu
            435                 440                 445

Phe Asp Ser Gly Glu Thr Ala Glu Ala Thr Arg Leu Lys Arg Thr Ala
            450                 455                 460

Arg Arg Arg Tyr Thr Arg Arg Lys Asn Arg Ile Cys Tyr Leu Gln Glu
465                 470                 475                 480

Ile Phe Ser Asn Glu Met Ala Lys Val Asp Asp Ser Phe Phe His Arg
                485                 490                 495

Leu Glu Glu Ser Phe Leu Val Glu Glu Asp Lys Lys His Glu Arg His
                500                 505                 510
```

```
Pro Ile Phe Gly Asn Ile Val Asp Glu Val Ala Tyr His Glu Lys Tyr
        515                 520             525

Pro Thr Ile Tyr His Leu Arg Lys Lys Leu Val Asp Ser Thr Asp Lys
        530                 535             540

Ala Asp Leu Arg Leu Ile Tyr Leu Ala Leu Ala His Met Ile Lys Phe
545                 550             555                 560

Arg Gly His Phe Leu Ile Glu Gly Asp Leu Asn Pro Asp Asn Ser Asp
                565             570             575

Val Asp Lys Leu Phe Ile Gln Leu Val Gln Thr Tyr Asn Gln Leu Phe
                580             585             590

Glu Glu Asn Pro Ile Asn Ala Ser Gly Val Asp Ala Lys Ala Ile Leu
            595             600             605

Ser Ala Arg Leu Ser Lys Ser Arg Arg Leu Glu Asn Leu Ile Ala Gln
        610             615             620

Leu Pro Gly Glu Lys Lys Asn Gly Leu Phe Gly Asn Leu Ile Ala Leu
625             630             635             640

Ser Leu Gly Leu Thr Pro Asn Phe Lys Ser Asn Phe Asp Leu Ala Glu
                645             650             655

Asp Ala Lys Leu Gln Leu Ser Lys Asp Thr Tyr Asp Asp Asp Leu Asp
                660             665             670

Asn Leu Leu Ala Gln Ile Gly Asp Gln Tyr Ala Asp Leu Phe Leu Ala
            675             680             685

Ala Lys Asn Leu Ser Asp Ala Ile Leu Leu Ser Asp Ile Leu Arg Val
        690             695             700

Asn Thr Glu Ile Thr Lys Ala Pro Leu Ser Ala Ser Met Ile Lys Arg
705             710             715             720

Tyr Asp Glu His His Gln Asp Leu Thr Leu Leu Lys Ala Leu Val Arg
            725             730             735

Gln Gln Leu Pro Glu Lys Tyr Lys Glu Ile Phe Phe Asp Gln Ser Lys
            740             745             750

Asn Gly Tyr Ala Gly Tyr Ile Asp Gly Gly Ala Ser Gln Glu Glu Phe
            755             760             765

Tyr Lys Phe Ile Lys Pro Ile Leu Glu Lys Met Asp Gly Thr Glu Glu
            770             775             780

Leu Leu Val Lys Leu Asn Arg Glu Asp Leu Leu Arg Lys Gln Arg Thr
785             790             795             800

Phe Asp Asn Gly Ser Ile Pro His Gln Ile His Leu Gly Glu Leu His
                805             810             815

Ala Ile Leu Arg Arg Gln Glu Asp Phe Tyr Pro Phe Leu Lys Asp Asn
            820             825             830

Arg Glu Lys Ile Glu Lys Ile Leu Thr Phe Arg Ile Pro Tyr Tyr Val
            835             840             845

Gly Pro Leu Ala Arg Gly Asn Ser Arg Phe Ala Trp Met Thr Arg Lys
        850             855             860

Ser Glu Glu Thr Ile Thr Pro Trp Asn Phe Glu Glu Val Val Asp Lys
865             870             875             880

Gly Ala Ser Ala Gln Ser Phe Ile Glu Arg Met Thr Asn Phe Asp Lys
                885             890             895

Asn Leu Pro Asn Glu Lys Val Leu Pro Lys His Ser Leu Leu Tyr Glu
            900             905             910

Tyr Phe Thr Val Tyr Asn Glu Leu Thr Lys Val Lys Tyr Val Thr Glu
        915             920             925

Gly Met Arg Lys Pro Ala Phe Leu Ser Gly Glu Gln Lys Lys Ala Ile
```

-continued

```
        930              935               940

Val Asp Leu Leu Phe Lys Thr Asn Arg Lys Val Thr Val Lys Gln Leu
945              950               955               960

Lys Glu Asp Tyr Phe Lys Lys Ile Glu Cys Phe Asp Ser Val Glu Ile
                965              970               975

Ser Gly Val Glu Asp Arg Phe Asn Ala Ser Leu Gly Thr Tyr His Asp
            980              985               990

Leu Leu Lys Ile Ile Lys Asp Lys  Asp Phe Leu Asp Asn  Glu Glu Asn
        995              1000              1005

Glu Asp  Ile Leu Glu Asp Ile  Val Leu Thr Leu Thr  Leu Phe Glu
    1010              1015              1020

Asp Arg  Glu Met Ile Glu Glu  Arg Leu Lys Thr Tyr  Ala His Leu
    1025              1030              1035

Phe Asp  Asp Lys Val Met Lys  Gln Leu Lys Arg Arg  Arg Tyr Thr
    1040              1045              1050

Gly Trp  Gly Arg Leu Ser Arg  Lys Leu Ile Asn Gly  Ile Arg Asp
    1055              1060              1065

Lys Gln  Ser Gly Lys Thr Ile  Leu Asp Phe Leu Lys  Ser Asp Gly
    1070              1075              1080

Phe Ala  Asn Arg Asn Phe Met  Gln Leu Ile His Asp  Asp Ser Leu
    1085              1090              1095

Thr Phe  Lys Glu Asp Ile Gln  Lys Ala Gln Val Ser  Gly Gln Gly
    1100              1105              1110

Asp Ser  Leu His Glu His Ile  Ala Asn Leu Ala Gly  Ser Pro Ala
    1115              1120              1125

Ile Lys  Lys Gly Ile Leu Gln  Thr Val Lys Val Val  Asp Glu Leu
    1130              1135              1140

Val Lys  Val Met Gly Arg His  Lys Pro Glu Asn Ile  Val Ile Glu
    1145              1150              1155

Met Ala  Arg Glu Asn Gln Thr  Thr Gln Lys Gly Gln  Lys Asn Ser
    1160              1165              1170

Arg Glu  Arg Met Lys Arg Ile  Glu Glu Gly Ile Lys  Glu Leu Gly
    1175              1180              1185

Ser Gln  Ile Leu Lys Glu His  Pro Val Glu Asn Thr  Gln Leu Gln
    1190              1195              1200

Asn Glu  Lys Leu Tyr Leu Tyr  Tyr Leu Gln Asn Gly  Arg Asp Met
    1205              1210              1215

Tyr Val  Asp Gln Glu Leu Asp  Ile Asn Arg Leu Ser  Asp Tyr Asp
    1220              1225              1230

Val Asp  His Ile Val Pro Gln  Ser Phe Leu Lys Asp  Asp Ser Ile
    1235              1240              1245

Asp Asn  Lys Val Leu Thr Arg  Ser Asp Lys Asn Arg  Gly Lys Ser
    1250              1255              1260

Asp Asn  Val Pro Ser Glu Glu  Val Val Lys Lys Met  Lys Asn Tyr
    1265              1270              1275

Trp Arg  Gln Leu Leu Asn Ala  Lys Leu Ile Thr Gln  Arg Lys Phe
    1280              1285              1290

Asp Asn  Leu Thr Lys Ala Glu  Arg Gly Gly Leu Ser  Glu Leu Asp
    1295              1300              1305

Lys Ala  Gly Phe Ile Lys Arg  Gln Leu Val Glu Thr  Arg Gln Ile
    1310              1315              1320

Thr Lys  His Val Ala Gln Ile  Leu Asp Ser Arg Met  Asn Thr Lys
    1325              1330              1335
```

-continued

```
Tyr Asp  Glu Asn Asp Lys Leu  Ile Arg Glu Val Lys  Val Ile Thr
    1340                 1345              1350

Leu Lys  Ser Lys Leu Val Ser  Asp Phe Arg Lys Asp  Phe Gln Phe
    1355                 1360              1365

Tyr Lys  Val Arg Glu Ile Asn  Asn Tyr His His Ala  His Asp Ala
    1370                 1375              1380

Tyr Leu  Asn Ala Val Val Gly  Thr Ala Leu Ile Lys  Lys Tyr Pro
    1385                 1390              1395

Lys Leu  Glu Ser Glu Phe Val  Tyr Gly Asp Tyr Lys  Val Tyr Asp
    1400                 1405              1410

Val Arg  Lys Met Ile Ala Lys  Ser Glu Gln Glu Ile  Gly Lys Ala
    1415                 1420              1425

Thr Ala  Lys Tyr Phe Phe Tyr  Ser Asn Ile Met Asn  Phe Phe Lys
    1430                 1435              1440

Thr Glu  Ile Thr Leu Ala Asn  Gly Glu Ile Arg Lys  Arg Pro Leu
    1445                 1450              1455

Ile Glu  Thr Asn Gly Glu Thr  Gly Glu Ile Val Trp  Asp Lys Gly
    1460                 1465              1470

Arg Asp  Phe Ala Thr Val Arg  Lys Val Leu Ser Met  Pro Gln Val
    1475                 1480              1485

Asn Ile  Val Lys Lys Thr Glu  Val Gln Thr Gly Gly  Phe Ser Lys
    1490                 1495              1500

Glu Ser  Ile Leu Pro Lys Arg  Asn Ser Asp Lys Leu  Ile Ala Arg
    1505                 1510              1515

Lys Lys  Asp Trp Asp Pro Lys  Lys Tyr Gly Gly Phe  Asp Ser Pro
    1520                 1525              1530

Thr Val  Ala Tyr Ser Val Leu  Val Val Ala Lys Val  Glu Lys Gly
    1535                 1540              1545

Lys Ser  Lys Lys Leu Lys Ser  Val Lys Glu Leu Leu  Gly Ile Thr
    1550                 1555              1560

Ile Met  Glu Arg Ser Ser Phe  Glu Lys Asn Pro Ile  Asp Phe Leu
    1565                 1570              1575

Glu Ala  Lys Gly Tyr Lys Glu  Val Lys Lys Asp Leu  Ile Ile Lys
    1580                 1585              1590

Leu Pro  Lys Tyr Ser Leu Phe  Glu Leu Glu Asn Gly  Arg Lys Arg
    1595                 1600              1605

Met Leu  Ala Ser Ala Gly Glu  Leu Gln Lys Gly Asn  Glu Leu Ala
    1610                 1615              1620

Leu Pro  Ser Lys Tyr Val Asn  Phe Leu Tyr Leu Ala  Ser His Tyr
    1625                 1630              1635

Glu Lys  Leu Lys Gly Ser Pro  Glu Asp Asn Glu Gln  Lys Gln Leu
    1640                 1645              1650

Phe Val  Glu Gln His Lys His  Tyr Leu Asp Glu Ile  Ile Glu Gln
    1655                 1660              1665

Ile Ser  Glu Phe Ser Lys Arg  Val Ile Leu Ala Asp  Ala Asn Leu
    1670                 1675              1680

Asp Lys  Val Leu Ser Ala Tyr  Asn Lys His Arg Asp  Lys Pro Ile
    1685                 1690              1695

Arg Glu  Gln Ala Glu Asn Ile  Ile His Leu Phe Thr  Leu Thr Asn
    1700                 1705              1710

Leu Gly  Ala Pro Ala Ala Phe  Lys Tyr Phe Asp Thr  Thr Ile Asp
    1715                 1720              1725
```

```
Arg Lys  Arg Tyr Thr Ser Thr  Lys Glu Val Leu Asp  Ala Thr Leu
    1730                 1735                 1740

Ile His  Gln Ser Ile Thr Gly  Leu Tyr Glu Thr Arg  Ile Asp Leu
    1745                 1750                 1755

Ser Gln  Leu Gly Gly Asp Ser  Arg Ala Asp Pro Lys  Lys Lys Arg
    1760                 1765                 1770

Lys Val
    1775

<210> SEQ ID NO 18
<211> LENGTH: 1757
<212> TYPE: PRT
<213> ORGANISM: Artificial Sequence
<220> FEATURE:
<223> OTHER INFORMATION: ABE-AP5
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (367)..(379)
<223> OTHER INFORMATION: Linker region
<220> FEATURE:
<221> NAME/KEY: MISC_FEATURE
<222> LOCATION: (380)..(1750)
<223> OTHER INFORMATION: Cas9-D10A
<220> FEATURE:
<221> NAME/KEY: MISC_FEATURE
<222> LOCATION: (1750)..(1757)
<223> OTHER INFORMATION: NLS

<400> SEQUENCE: 18

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175
```

-continued

```
Gly Ser Glu Thr Pro Gly Thr Ser Glu Ser Ala Thr Pro Glu Ser Ser
            180             185             190

Gly Gly Ser Ser Gly Gly Ser Ser Glu Val Glu Phe Ser His Glu Tyr
        195             200             205

Trp Met Arg His Ala Leu Thr Leu Ala Lys Arg Ala Arg Asp Glu Arg
    210             215             220

Glu Val Pro Val Gly Ala Val Leu Val Leu Asn Asn Arg Val Ile Gly
225             230             235             240

Glu Gly Trp Asn Arg Ala Ile Gly Leu His Asp Pro Thr Ala His Ala
                245             250             255

Glu Ile Met Ala Leu Arg Gln Gly Gly Leu Val Met Gln Asn Tyr Arg
            260             265             270

Leu Ile Asp Ala Thr Leu Tyr Val Thr Phe Glu Pro Cys Val Met Cys
        275             280             285

Ala Gly Ala Met Ile His Ser Arg Ile Gly Arg Val Val Phe Gly Val
    290             295             300

Arg Asn Ala Lys Thr Gly Ala Ala Gly Ser Leu Met Asp Val Leu His
305             310             315             320

Tyr Pro Gly Met Asn His Arg Val Glu Ile Thr Glu Gly Ile Leu Ala
                325             330             335

Asp Glu Cys Ala Ala Leu Leu Cys Tyr Phe Phe Arg Met Pro Arg Gln
            340             345             350

Val Phe Asn Ala Gln Lys Lys Ala Gln Ser Ser Thr Asp Ala Ser Ala
        355             360             365

Pro Ala Pro Ala Pro Ala Pro Ala Pro Gly Thr Asp Lys Lys Tyr Ser
    370             375             380

Ile Gly Leu Ala Ile Gly Thr Asn Ser Val Gly Trp Ala Val Ile Thr
385             390             395             400

Asp Glu Tyr Lys Val Pro Ser Lys Lys Phe Lys Val Leu Gly Asn Thr
                405             410             415

Asp Arg His Ser Ile Lys Lys Asn Leu Ile Gly Ala Leu Leu Phe Asp
            420             425             430

Ser Gly Glu Thr Ala Glu Ala Thr Arg Leu Lys Arg Thr Ala Arg Arg
        435             440             445

Arg Tyr Thr Arg Arg Lys Asn Arg Ile Cys Tyr Leu Gln Glu Ile Phe
    450             455             460

Ser Asn Glu Met Ala Lys Val Asp Asp Ser Phe Phe His Arg Leu Glu
465             470             475             480

Glu Ser Phe Leu Val Glu Glu Asp Lys Lys His Glu Arg His Pro Ile
                485             490             495

Phe Gly Asn Ile Val Asp Glu Val Ala Tyr His Glu Lys Tyr Pro Thr
            500             505             510

Ile Tyr His Leu Arg Lys Lys Leu Val Asp Ser Thr Asp Lys Ala Asp
        515             520             525

Leu Arg Leu Ile Tyr Leu Ala Leu Ala His Met Ile Lys Phe Arg Gly
    530             535             540

His Phe Leu Ile Glu Gly Asp Leu Asn Pro Asp Asn Ser Asp Val Asp
545             550             555             560

Lys Leu Phe Ile Gln Leu Val Gln Thr Tyr Asn Gln Leu Phe Glu Glu
                565             570             575

Asn Pro Ile Asn Ala Ser Gly Val Asp Ala Lys Ala Ile Leu Ser Ala
            580             585             590

Arg Leu Ser Lys Ser Arg Arg Leu Glu Asn Leu Ile Ala Gln Leu Pro
```

-continued

```
              595                 600                 605

Gly Glu Lys Lys Asn Gly Leu Phe Gly Asn Leu Ile Ala Leu Ser Leu
    610                 615                 620

Gly Leu Thr Pro Asn Phe Lys Ser Asn Phe Asp Leu Ala Glu Asp Ala
625                 630                 635                 640

Lys Leu Gln Leu Ser Lys Asp Thr Tyr Asp Asp Leu Asp Asn Leu
                645                 650                 655

Leu Ala Gln Ile Gly Asp Gln Tyr Ala Asp Leu Phe Leu Ala Ala Lys
                660                 665                 670

Asn Leu Ser Asp Ala Ile Leu Leu Ser Asp Ile Leu Arg Val Asn Thr
                675                 680                 685

Glu Ile Thr Lys Ala Pro Leu Ser Ala Ser Met Ile Lys Arg Tyr Asp
    690                 695                 700

Glu His His Gln Asp Leu Thr Leu Leu Lys Ala Leu Val Arg Gln Gln
705                 710                 715                 720

Leu Pro Glu Lys Tyr Lys Glu Ile Phe Phe Asp Gln Ser Lys Asn Gly
                725                 730                 735

Tyr Ala Gly Tyr Ile Asp Gly Gly Ala Ser Gln Glu Glu Phe Tyr Lys
                740                 745                 750

Phe Ile Lys Pro Ile Leu Glu Lys Met Asp Gly Thr Glu Glu Leu Leu
                755                 760                 765

Val Lys Leu Asn Arg Glu Asp Leu Leu Arg Lys Gln Arg Thr Phe Asp
    770                 775                 780

Asn Gly Ser Ile Pro His Gln Ile His Leu Gly Glu Leu His Ala Ile
785                 790                 795                 800

Leu Arg Arg Gln Glu Asp Phe Tyr Pro Phe Leu Lys Asp Asn Arg Glu
                805                 810                 815

Lys Ile Glu Lys Ile Leu Thr Phe Arg Ile Pro Tyr Tyr Val Gly Pro
                820                 825                 830

Leu Ala Arg Gly Asn Ser Arg Phe Ala Trp Met Thr Arg Lys Ser Glu
                835                 840                 845

Glu Thr Ile Thr Pro Trp Asn Phe Glu Glu Val Val Asp Lys Gly Ala
    850                 855                 860

Ser Ala Gln Ser Phe Ile Glu Arg Met Thr Asn Phe Asp Lys Asn Leu
865                 870                 875                 880

Pro Asn Glu Lys Val Leu Pro Lys His Ser Leu Leu Tyr Glu Tyr Phe
                885                 890                 895

Thr Val Tyr Asn Glu Leu Thr Lys Val Lys Tyr Val Thr Glu Gly Met
                900                 905                 910

Arg Lys Pro Ala Phe Leu Ser Gly Glu Gln Lys Lys Ala Ile Val Asp
    915                 920                 925

Leu Leu Phe Lys Thr Asn Arg Lys Val Thr Val Lys Gln Leu Lys Glu
    930                 935                 940

Asp Tyr Phe Lys Lys Ile Glu Cys Phe Asp Ser Val Glu Ile Ser Gly
945                 950                 955                 960

Val Glu Asp Arg Phe Asn Ala Ser Leu Gly Thr Tyr His Asp Leu Leu
                965                 970                 975

Lys Ile Ile Lys Asp Lys Asp Phe Leu Asp Asn Glu Glu Asn Glu Asp
                980                 985                 990

Ile Leu Glu Asp Ile Val Leu Thr  Leu Thr Leu Phe Glu  Asp Arg Glu
    995                 1000                1005

Met Ile  Glu Glu Arg Leu Lys  Thr Tyr Ala His Leu  Phe Asp Asp
    1010                1015                1020
```

-continued

```
Lys Val Met Lys Gln Leu Lys  Arg Arg Arg Tyr  Thr  Gly Trp Gly
    1025             1030               1035

Arg Leu Ser Arg Lys Leu Ile  Asn Gly Ile Arg Asp  Lys Gln Ser
    1040             1045               1050

Gly Lys Thr Ile Leu Asp Phe  Leu Lys Ser Asp Gly  Phe Ala Asn
    1055             1060               1065

Arg Asn Phe Met Gln Leu Ile  His Asp Asp Ser Leu  Thr Phe Lys
    1070             1075               1080

Glu Asp Ile Gln Lys Ala Gln  Val Ser Gly Gln Gly  Asp Ser Leu
    1085             1090               1095

His Glu His Ile Ala Asn Leu  Ala Gly Ser Pro Ala  Ile Lys Lys
    1100             1105               1110

Gly Ile Leu Gln Thr Val Lys  Val Val Asp Glu Leu  Val Lys Val
    1115             1120               1125

Met Gly Arg His Lys Pro Glu  Asn Ile Val Ile Glu  Met Ala Arg
    1130             1135               1140

Glu Asn Gln Thr Thr Gln Lys  Gly Gln Lys Asn Ser  Arg Glu Arg
    1145             1150               1155

Met Lys Arg Ile Glu Glu Gly  Ile Lys Glu Leu Gly  Ser Gln Ile
    1160             1165               1170

Leu Lys Glu His Pro Val Glu  Asn Thr Gln Leu Gln  Asn Glu Lys
    1175             1180               1185

Leu Tyr Leu Tyr Tyr Leu Gln  Asn Gly Arg Asp Met  Tyr Val Asp
    1190             1195               1200

Gln Glu Leu Asp Ile Asn Arg  Leu Ser Asp Tyr Asp  Val Asp His
    1205             1210               1215

Ile Val Pro Gln Ser Phe Leu  Lys Asp Asp Ser Ile  Asp Asn Lys
    1220             1225               1230

Val Leu Thr Arg Ser Asp Lys  Asn Arg Gly Lys Ser  Asp Asn Val
    1235             1240               1245

Pro Ser Glu Glu Val Val Lys  Lys Met Lys Asn Tyr  Trp Arg Gln
    1250             1255               1260

Leu Leu Asn Ala Lys Leu Ile  Thr Gln Arg Lys Phe  Asp Asn Leu
    1265             1270               1275

Thr Lys Ala Glu Arg Gly Gly  Leu Ser Glu Leu Asp  Lys Ala Gly
    1280             1285               1290

Phe Ile Lys Arg Gln Leu Val  Glu Thr Arg Gln Ile  Thr Lys His
    1295             1300               1305

Val Ala Gln Ile Leu Asp Ser  Arg Met Asn Thr Lys  Tyr Asp Glu
    1310             1315               1320

Asn Asp Lys Leu Ile Arg Glu  Val Lys Val Ile Thr  Leu Lys Ser
    1325             1330               1335

Lys Leu Val Ser Asp Phe Arg  Lys Asp Phe Gln Phe  Tyr Lys Val
    1340             1345               1350

Arg Glu Ile Asn Asn Tyr His  His Ala His Asp Ala  Tyr Leu Asn
    1355             1360               1365

Ala Val Val Gly Thr Ala Leu  Ile Lys Lys Tyr Pro  Lys Leu Glu
    1370             1375               1380

Ser Glu Phe Val Tyr Gly Asp  Tyr Lys Val Tyr Asp  Val Arg Lys
    1385             1390               1395

Met Ile Ala Lys Ser Glu Gln  Glu Ile Gly Lys Ala  Thr Ala Lys
    1400             1405               1410
```

-continued

```
Tyr Phe  Phe Tyr Ser Asn Ile  Met Asn Phe Phe Lys  Thr Glu Ile
    1415             1420              1425

Thr Leu  Ala Asn Gly Glu Ile  Arg Lys Arg Pro Leu  Ile Glu Thr
    1430             1435              1440

Asn Gly  Glu Thr Gly Glu Ile  Val Trp Asp Lys Gly  Arg Asp Phe
    1445             1450              1455

Ala Thr  Val Arg Lys Val Leu  Ser Met Pro Gln Val  Asn Ile Val
    1460             1465              1470

Lys Lys  Thr Glu Val Gln Thr  Gly Gly Phe Ser Lys  Glu Ser Ile
    1475             1480              1485

Leu Pro  Lys Arg Asn Ser Asp  Lys Leu Ile Ala Arg  Lys Lys Asp
    1490             1495              1500

Trp Asp  Pro Lys Lys Tyr Gly  Gly Phe Asp Ser Pro  Thr Val Ala
    1505             1510              1515

Tyr Ser  Val Leu Val Val Ala  Lys Val Glu Lys Gly  Lys Ser Lys
    1520             1525              1530

Lys Leu  Lys Ser Val Lys Glu  Leu Leu Gly Ile Thr  Ile Met Glu
    1535             1540              1545

Arg Ser  Ser Phe Glu Lys Asn  Pro Ile Asp Phe Leu  Glu Ala Lys
    1550             1555              1560

Gly Tyr  Lys Glu Val Lys Lys  Asp Leu Ile Ile Lys  Leu Pro Lys
    1565             1570              1575

Tyr Ser  Leu Phe Glu Leu Glu  Asn Gly Arg Lys Arg  Met Leu Ala
    1580             1585              1590

Ser Ala  Gly Glu Leu Gln Lys  Gly Asn Glu Leu Ala  Leu Pro Ser
    1595             1600              1605

Lys Tyr  Val Asn Phe Leu Tyr  Leu Ala Ser His Tyr  Glu Lys Leu
    1610             1615              1620

Lys Gly  Ser Pro Glu Asp Asn  Glu Gln Lys Gln Leu  Phe Val Glu
    1625             1630              1635

Gln His  Lys His Tyr Leu Asp  Glu Ile Ile Glu Gln  Ile Ser Glu
    1640             1645              1650

Phe Ser  Lys Arg Val Ile Leu  Ala Asp Ala Asn Leu  Asp Lys Val
    1655             1660              1665

Leu Ser  Ala Tyr Asn Lys His  Arg Asp Lys Pro Ile  Arg Glu Gln
    1670             1675              1680

Ala Glu  Asn Ile Ile His Leu  Phe Thr Leu Thr Asn  Leu Gly Ala
    1685             1690              1695

Pro Ala  Ala Phe Lys Tyr Phe  Asp Thr Thr Ile Asp  Arg Lys Arg
    1700             1705              1710

Tyr Thr  Ser Thr Lys Glu Val  Leu Asp Ala Thr Leu  Ile His Gln
    1715             1720              1725

Ser Ile  Thr Gly Leu Tyr Glu  Thr Arg Ile Asp Leu  Ser Gln Leu
    1730             1735              1740

Gly Gly  Asp Ser Arg Ala Asp  Pro Lys Lys Lys Arg  Lys Val
    1745             1750              1755
```

```
<210> SEQ ID NO 19
<211> LENGTH: 1772
<212> TYPE: PRT
<213> ORGANISM: Artificial Sequence
<220> FEATURE:
<223> OTHER INFORMATION: ABE-GGGGS5
<220> FEATURE:
<221> NAME/KEY: MISC_FEATURE
<222> LOCATION: (1)..(167)
```

<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(394)
<223> OTHER INFORMATION: Linker region
<220> FEATURE:
<221> NAME/KEY: MISC_FEATURE
<222> LOCATION: (395)..(1765)
<223> OTHER INFORMATION: Cas9-D10A
<220> FEATURE:
<221> NAME/KEY: MISC_FEATURE
<222> LOCATION: (1766)..(1772)
<223> OTHER INFORMATION: NLS

<400> SEQUENCE: 19

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
        130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
        275                 280                 285

Ala Gly Ala Met Ile His Ser Arg Ile Gly Arg Val Val Phe Gly Val
```

-continued

```
        290              295              300

Arg Asn Ala Lys Thr Gly Ala Ala Gly Ser Leu Met Asp Val Leu His
305              310              315              320

Tyr Pro Gly Met Asn His Arg Val Glu Ile Thr Glu Gly Ile Leu Ala
                 325              330              335

Asp Glu Cys Ala Ala Leu Leu Cys Tyr Phe Phe Arg Met Pro Arg Gln
                 340              345              350

Val Phe Asn Ala Gln Lys Lys Ala Gln Ser Ser Thr Asp Ala Ser Gly
                 355              360              365

Gly Gly Gly Ser Gly Gly Gly Ser Gly Gly Gly Gly Ser Gly Gly
                 370              375              380

Gly Gly Ser Gly Gly Gly Ser Gly Thr Asp Lys Lys Tyr Ser Ile
385              390              395              400

Gly Leu Ala Ile Gly Thr Asn Ser Val Gly Trp Ala Val Ile Thr Asp
                 405              410              415

Glu Tyr Lys Val Pro Ser Lys Lys Phe Lys Val Leu Gly Asn Thr Asp
                 420              425              430

Arg His Ser Ile Lys Lys Asn Leu Ile Gly Ala Leu Leu Phe Asp Ser
                 435              440              445

Gly Glu Thr Ala Glu Ala Thr Arg Leu Lys Arg Thr Ala Arg Arg Arg
                 450              455              460

Tyr Thr Arg Arg Lys Asn Arg Ile Cys Tyr Leu Gln Glu Ile Phe Ser
465              470              475              480

Asn Glu Met Ala Lys Val Asp Asp Ser Phe Phe His Arg Leu Glu Glu
                 485              490              495

Ser Phe Leu Val Glu Glu Asp Lys Lys His Glu Arg His Pro Ile Phe
                 500              505              510

Gly Asn Ile Val Asp Glu Val Ala Tyr His Glu Lys Tyr Pro Thr Ile
                 515              520              525

Tyr His Leu Arg Lys Lys Leu Val Asp Ser Thr Asp Lys Ala Asp Leu
                 530              535              540

Arg Leu Ile Tyr Leu Ala Leu Ala His Met Ile Lys Phe Arg Gly His
545              550              555              560

Phe Leu Ile Glu Gly Asp Leu Asn Pro Asp Asn Ser Asp Val Asp Lys
                 565              570              575

Leu Phe Ile Gln Leu Val Gln Thr Tyr Asn Gln Leu Phe Glu Glu Asn
                 580              585              590

Pro Ile Asn Ala Ser Gly Val Asp Ala Lys Ala Ile Leu Ser Ala Arg
                 595              600              605

Leu Ser Lys Ser Arg Arg Leu Glu Asn Leu Ile Ala Gln Leu Pro Gly
                 610              615              620

Glu Lys Lys Asn Gly Leu Phe Gly Asn Leu Ile Ala Leu Ser Leu Gly
625              630              635              640

Leu Thr Pro Asn Phe Lys Ser Asn Phe Asp Leu Ala Glu Asp Ala Lys
                 645              650              655

Leu Gln Leu Ser Lys Asp Thr Tyr Asp Asp Asp Leu Asp Asn Leu Leu
                 660              665              670

Ala Gln Ile Gly Asp Gln Tyr Ala Asp Leu Phe Leu Ala Ala Lys Asn
                 675              680              685

Leu Ser Asp Ala Ile Leu Leu Ser Asp Ile Leu Arg Val Asn Thr Glu
                 690              695              700

Ile Thr Lys Ala Pro Leu Ser Ala Ser Met Ile Lys Arg Tyr Asp Glu
705              710              715              720
```

-continued

```
His His Gln Asp Leu Thr Leu Leu Lys Ala Leu Val Arg Gln Gln Leu
                725                 730                 735

Pro Glu Lys Tyr Lys Glu Ile Phe Phe Asp Gln Ser Lys Asn Gly Tyr
            740                 745                 750

Ala Gly Tyr Ile Asp Gly Gly Ala Ser Gln Glu Glu Phe Tyr Lys Phe
            755                 760                 765

Ile Lys Pro Ile Leu Glu Lys Met Asp Gly Thr Glu Glu Leu Leu Val
        770                 775                 780

Lys Leu Asn Arg Glu Asp Leu Leu Arg Lys Gln Arg Thr Phe Asp Asn
785                 790                 795                 800

Gly Ser Ile Pro His Gln Ile His Leu Gly Glu Leu His Ala Ile Leu
                805                 810                 815

Arg Arg Gln Glu Asp Phe Tyr Pro Phe Leu Lys Asp Asn Arg Glu Lys
            820                 825                 830

Ile Glu Lys Ile Leu Thr Phe Arg Ile Pro Tyr Tyr Val Gly Pro Leu
        835                 840                 845

Ala Arg Gly Asn Ser Arg Phe Ala Trp Met Thr Arg Lys Ser Glu Glu
850                 855                 860

Thr Ile Thr Pro Trp Asn Phe Glu Glu Val Val Asp Lys Gly Ala Ser
865                 870                 875                 880

Ala Gln Ser Phe Ile Glu Arg Met Thr Asn Phe Asp Lys Asn Leu Pro
                885                 890                 895

Asn Glu Lys Val Leu Pro Lys His Ser Leu Leu Tyr Glu Tyr Phe Thr
                900                 905                 910

Val Tyr Asn Glu Leu Thr Lys Val Lys Tyr Val Thr Glu Gly Met Arg
            915                 920                 925

Lys Pro Ala Phe Leu Ser Gly Glu Gln Lys Lys Ala Ile Val Asp Leu
        930                 935                 940

Leu Phe Lys Thr Asn Arg Lys Val Thr Val Lys Gln Leu Lys Glu Asp
945                 950                 955                 960

Tyr Phe Lys Lys Ile Glu Cys Phe Asp Ser Val Glu Ile Ser Gly Val
            965                 970                 975

Glu Asp Arg Phe Asn Ala Ser Leu Gly Thr Tyr His Asp Leu Leu Lys
            980                 985                 990

Ile Ile Lys Asp Lys Asp Phe Leu  Asp Asn Glu Glu Asn  Glu Asp Ile
        995                 1000                1005

Leu Glu  Asp Ile Val Leu Thr  Leu Thr Leu Phe Glu  Asp Arg Glu
    1010                1015                1020

Met Ile  Glu Glu Arg Leu Lys  Thr Tyr Ala His Leu  Phe Asp Asp
    1025                1030                1035

Lys Val  Met Lys Gln Leu Lys  Arg Arg Arg Tyr Thr  Gly Trp Gly
    1040                1045                1050

Arg Leu  Ser Arg Lys Leu Ile  Asn Gly Ile Arg Asp  Lys Gln Ser
    1055                1060                1065

Gly Lys  Thr Ile Leu Asp Phe  Leu Lys Ser Asp Gly  Phe Ala Asn
    1070                1075                1080

Arg Asn  Phe Met Gln Leu Ile  His Asp Asp Ser Leu  Thr Phe Lys
    1085                1090                1095

Glu Asp  Ile Gln Lys Ala Gln  Val Ser Gly Gln Gly  Asp Ser Leu
    1100                1105                1110

His Glu  His Ile Ala Asn Leu  Ala Gly Ser Pro Ala  Ile Lys Lys
    1115                1120                1125
```

-continued

```
Gly Ile Leu Gln Thr Val Lys  Val Val Asp Glu Leu  Val Lys Val
1130              1135                1140

Met Gly Arg His Lys Pro Glu  Asn Ile Val Ile Glu  Met Ala Arg
1145              1150                1155

Glu Asn Gln Thr Thr Gln Lys  Gly Gln Lys Asn Ser  Arg Glu Arg
1160              1165                1170

Met Lys Arg Ile Glu Glu Gly  Ile Lys Glu Leu Gly  Ser Gln Ile
1175              1180                1185

Leu Lys Glu His Pro Val Glu  Asn Thr Gln Leu Gln  Asn Glu Lys
1190              1195                1200

Leu Tyr Leu Tyr Tyr Leu Gln  Asn Gly Arg Asp Met  Tyr Val Asp
1205              1210                1215

Gln Glu Leu Asp Ile Asn Arg  Leu Ser Asp Tyr Asp  Val Asp His
1220              1225                1230

Ile Val Pro Gln Ser Phe Leu  Lys Asp Asp Ser Ile  Asp Asn Lys
1235              1240                1245

Val Leu Thr Arg Ser Asp Lys  Asn Arg Gly Lys Ser  Asp Asn Val
1250              1255                1260

Pro Ser Glu Glu Val Val Lys  Lys Met Lys Asn Tyr  Trp Arg Gln
1265              1270                1275

Leu Leu Asn Ala Lys Leu Ile  Thr Gln Arg Lys Phe  Asp Asn Leu
1280              1285                1290

Thr Lys Ala Glu Arg Gly Gly  Leu Ser Glu Leu Asp  Lys Ala Gly
1295              1300                1305

Phe Ile Lys Arg Gln Leu Val  Glu Thr Arg Gln Ile  Thr Lys His
1310              1315                1320

Val Ala Gln Ile Leu Asp Ser  Arg Met Asn Thr Lys  Tyr Asp Glu
1325              1330                1335

Asn Asp Lys Leu Ile Arg Glu  Val Lys Val Ile Thr  Leu Lys Ser
1340              1345                1350

Lys Leu Val Ser Asp Phe Arg  Lys Asp Phe Gln Phe  Tyr Lys Val
1355              1360                1365

Arg Glu Ile Asn Asn Tyr His  His Ala His Asp Ala  Tyr Leu Asn
1370              1375                1380

Ala Val Val Gly Thr Ala Leu  Ile Lys Lys Tyr Pro  Lys Leu Glu
1385              1390                1395

Ser Glu Phe Val Tyr Gly Asp  Tyr Lys Val Tyr Asp  Val Arg Lys
1400              1405                1410

Met Ile Ala Lys Ser Glu Gln  Glu Ile Gly Lys Ala  Thr Ala Lys
1415              1420                1425

Tyr Phe Phe Tyr Ser Asn Ile  Met Asn Phe Phe Lys  Thr Glu Ile
1430              1435                1440

Thr Leu Ala Asn Gly Glu Ile  Arg Lys Arg Pro Leu  Ile Glu Thr
1445              1450                1455

Asn Gly Glu Thr Gly Glu Ile  Val Trp Asp Lys Gly  Arg Asp Phe
1460              1465                1470

Ala Thr Val Arg Lys Val Leu  Ser Met Pro Gln Val  Asn Ile Val
1475              1480                1485

Lys Lys Thr Glu Val Gln Thr  Gly Gly Phe Ser Lys  Glu Ser Ile
1490              1495                1500

Leu Pro Lys Arg Asn Ser Asp  Lys Leu Ile Ala Arg  Lys Lys Asp
1505              1510                1515

Trp Asp Pro Lys Lys Tyr Gly  Gly Phe Asp Ser Pro  Thr Val Ala
```

-continued

```
        1520                    1525                    1530

Tyr  Ser  Val  Leu  Val  Val  Ala  Lys  Val  Glu  Lys  Gly  Lys  Ser  Lys
     1535                    1540                    1545

Lys  Leu  Lys  Ser  Val  Lys  Glu  Leu  Leu  Gly  Ile  Thr  Ile  Met  Glu
     1550                    1555                    1560

Arg  Ser  Ser  Phe  Glu  Lys  Asn  Pro  Ile  Asp  Phe  Leu  Glu  Ala  Lys
     1565                    1570                    1575

Gly  Tyr  Lys  Glu  Val  Lys  Lys  Asp  Leu  Ile  Ile  Lys  Leu  Pro  Lys
     1580                    1585                    1590

Tyr  Ser  Leu  Phe  Glu  Leu  Glu  Asn  Gly  Arg  Lys  Arg  Met  Leu  Ala
     1595                    1600                    1605

Ser  Ala  Gly  Glu  Leu  Gln  Lys  Gly  Asn  Glu  Leu  Ala  Leu  Pro  Ser
     1610                    1615                    1620

Lys  Tyr  Val  Asn  Phe  Leu  Tyr  Leu  Ala  Ser  His  Tyr  Glu  Lys  Leu
     1625                    1630                    1635

Lys  Gly  Ser  Pro  Glu  Asp  Asn  Glu  Gln  Lys  Gln  Leu  Phe  Val  Glu
     1640                    1645                    1650

Gln  His  Lys  His  Tyr  Leu  Asp  Glu  Ile  Ile  Glu  Gln  Ile  Ser  Glu
     1655                    1660                    1665

Phe  Ser  Lys  Arg  Val  Ile  Leu  Ala  Asp  Ala  Asn  Leu  Asp  Lys  Val
     1670                    1675                    1680

Leu  Ser  Ala  Tyr  Asn  Lys  His  Arg  Asp  Lys  Pro  Ile  Arg  Glu  Gln
     1685                    1690                    1695

Ala  Glu  Asn  Ile  Ile  His  Leu  Phe  Thr  Leu  Thr  Asn  Leu  Gly  Ala
     1700                    1705                    1710

Pro  Ala  Ala  Phe  Lys  Tyr  Phe  Asp  Thr  Thr  Ile  Asp  Arg  Lys  Arg
     1715                    1720                    1725

Tyr  Thr  Ser  Thr  Lys  Glu  Val  Leu  Asp  Ala  Thr  Leu  Ile  His  Gln
     1730                    1735                    1740

Ser  Ile  Thr  Gly  Leu  Tyr  Glu  Thr  Arg  Ile  Asp  Leu  Ser  Gln  Leu
     1745                    1750                    1755

Gly  Gly  Asp  Ser  Arg  Ala  Asp  Pro  Lys  Lys  Lys  Arg  Lys  Val
     1760                    1765                    1770
```

```
<210> SEQ ID NO 20
<211> LENGTH: 1804
<212> TYPE: PRT
<213> ORGANISM: Artificial Sequence
<220> FEATURE:
<223> OTHER INFORMATION: ABE-Dual
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(426)
<223> OTHER INFORMATION: Linker region
<220> FEATURE:
<221> NAME/KEY: MISC_FEATURE
<222> LOCATION: (427)..(1800)
<223> OTHER INFORMATION: Cas9-D10A
<220> FEATURE:
<221> NAME/KEY: MISC_FEATURE
```

-continued

```
<222> LOCATION: (427)..(1797)
<223> OTHER INFORMATION: Cas9-D10A
<220> FEATURE:
<221> NAME/KEY: MISC_FEATURE
<222> LOCATION: (1798)..(1804)
<223> OTHER INFORMATION: NLS

<400> SEQUENCE: 20

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ala Ser Ser
        355                 360                 365

Gly Gly Ser Ser Gly Gly Ser Ser Gly Ser Glu Thr Pro Gly Thr Ser
```

-continued

```
            370             375             380

Glu Ser Ala Thr Pro Glu Ser Ser Gly Gly Ser Ser Gly Gly Ser Gly
385             390             395             400

Gly Gly Gly Ser Gly Gly Gly Gly Ser Gly Gly Gly Ser Gly Gly
            405             410             415

Gly Gly Ser Gly Gly Gly Gly Ser Gly Thr Asp Lys Lys Tyr Ser Ile
            420             425             430

Gly Leu Ala Ile Gly Thr Asn Ser Val Gly Trp Ala Val Ile Thr Asp
            435             440             445

Glu Tyr Lys Val Pro Ser Lys Lys Phe Lys Val Leu Gly Asn Thr Asp
            450             455             460

Arg His Ser Ile Lys Lys Asn Leu Ile Gly Ala Leu Leu Phe Asp Ser
465             470             475             480

Gly Glu Thr Ala Glu Ala Thr Arg Leu Lys Arg Thr Ala Arg Arg Arg
            485             490             495

Tyr Thr Arg Arg Lys Asn Arg Ile Cys Tyr Leu Gln Glu Ile Phe Ser
            500             505             510

Asn Glu Met Ala Lys Val Asp Asp Ser Phe Phe His Arg Leu Glu Glu
            515             520             525

Ser Phe Leu Val Glu Glu Asp Lys Lys His Glu Arg His Pro Ile Phe
            530             535             540

Gly Asn Ile Val Asp Glu Val Ala Tyr His Glu Lys Tyr Pro Thr Ile
545             550             555             560

Tyr His Leu Arg Lys Lys Leu Val Asp Ser Thr Asp Lys Ala Asp Leu
            565             570             575

Arg Leu Ile Tyr Leu Ala Leu Ala His Met Ile Lys Phe Arg Gly His
            580             585             590

Phe Leu Ile Glu Gly Asp Leu Asn Pro Asp Asn Ser Asp Val Asp Lys
            595             600             605

Leu Phe Ile Gln Leu Val Gln Thr Tyr Asn Gln Leu Phe Glu Glu Asn
            610             615             620

Pro Ile Asn Ala Ser Gly Val Asp Ala Lys Ala Ile Leu Ser Ala Arg
625             630             635             640

Leu Ser Lys Ser Arg Arg Leu Glu Asn Leu Ile Ala Gln Leu Pro Gly
            645             650             655

Glu Lys Lys Asn Gly Leu Phe Gly Asn Leu Ile Ala Leu Ser Leu Gly
            660             665             670

Leu Thr Pro Asn Phe Lys Ser Asn Phe Asp Leu Ala Glu Asp Ala Lys
            675             680             685

Leu Gln Leu Ser Lys Asp Thr Tyr Asp Asp Asp Leu Asp Asn Leu Leu
            690             695             700

Ala Gln Ile Gly Asp Gln Tyr Ala Asp Leu Phe Leu Ala Ala Lys Asn
705             710             715             720

Leu Ser Asp Ala Ile Leu Leu Ser Asp Ile Leu Arg Val Asn Thr Glu
            725             730             735

Ile Thr Lys Ala Pro Leu Ser Ala Ser Met Ile Lys Arg Tyr Asp Glu
            740             745             750

His His Gln Asp Leu Thr Leu Leu Lys Ala Leu Val Arg Gln Gln Leu
            755             760             765

Pro Glu Lys Tyr Lys Glu Ile Phe Phe Asp Gln Ser Lys Asn Gly Tyr
            770             775             780

Ala Gly Tyr Ile Asp Gly Gly Ala Ser Gln Glu Glu Phe Tyr Lys Phe
785             790             795             800
```

```
Ile Lys Pro Ile Leu Glu Lys Met Asp Gly Thr Glu Glu Leu Leu Val
            805                 810                 815

Lys Leu Asn Arg Glu Asp Leu Leu Arg Lys Gln Arg Thr Phe Asp Asn
            820                 825                 830

Gly Ser Ile Pro His Gln Ile His Leu Gly Glu Leu His Ala Ile Leu
        835                 840                 845

Arg Arg Gln Glu Asp Phe Tyr Pro Phe Leu Lys Asp Asn Arg Glu Lys
    850                 855                 860

Ile Glu Lys Ile Leu Thr Phe Arg Ile Pro Tyr Tyr Val Gly Pro Leu
865                 870                 875                 880

Ala Arg Gly Asn Ser Arg Phe Ala Trp Met Thr Arg Lys Ser Glu Glu
                885                 890                 895

Thr Ile Thr Pro Trp Asn Phe Glu Glu Val Val Asp Lys Gly Ala Ser
            900                 905                 910

Ala Gln Ser Phe Ile Glu Arg Met Thr Asn Phe Asp Lys Asn Leu Pro
            915                 920                 925

Asn Glu Lys Val Leu Pro Lys His Ser Leu Leu Tyr Glu Tyr Phe Thr
    930                 935                 940

Val Tyr Asn Glu Leu Thr Lys Val Lys Tyr Val Thr Glu Gly Met Arg
945                 950                 955                 960

Lys Pro Ala Phe Leu Ser Gly Glu Gln Lys Lys Ala Ile Val Asp Leu
                965                 970                 975

Leu Phe Lys Thr Asn Arg Lys Val Thr Val Lys Gln Leu Lys Glu Asp
            980                 985                 990

Tyr Phe Lys Lys Ile Glu Cys Phe  Asp Ser Val Glu Ile  Ser Gly Val
            995                 1000                1005

Glu Asp  Arg Phe Asn Ala Ser  Leu Gly Thr Tyr His  Asp Leu Leu
    1010                1015                1020

Lys Ile  Ile Lys Asp Lys Asp  Phe Leu Asp Asn Glu  Glu Asn Glu
    1025                1030                1035

Asp Ile  Leu Glu Asp Ile Val  Leu Thr Leu Thr Leu  Phe Glu Asp
    1040                1045                1050

Arg Glu  Met Ile Glu Glu Arg  Leu Lys Thr Tyr Ala  His Leu Phe
    1055                1060                1065

Asp Asp  Lys Val Met Lys Gln  Leu Lys Arg Arg Arg  Tyr Thr Gly
    1070                1075                1080

Trp Gly  Arg Leu Ser Arg Lys  Leu Ile Asn Gly Ile  Arg Asp Lys
    1085                1090                1095

Gln Ser  Gly Lys Thr Ile Leu  Asp Phe Leu Lys Ser  Asp Gly Phe
    1100                1105                1110

Ala Asn  Arg Asn Phe Met Gln  Leu Ile His Asp Asp  Ser Leu Thr
    1115                1120                1125

Phe Lys  Glu Asp Ile Gln Lys  Ala Gln Val Ser Gly  Gln Gly Asp
    1130                1135                1140

Ser Leu  His Glu His Ile Ala  Asn Leu Ala Gly Ser  Pro Ala Ile
    1145                1150                1155

Lys Lys  Gly Ile Leu Gln Thr  Val Lys Val Val Asp  Glu Leu Val
    1160                1165                1170

Lys Val  Met Gly Arg His Lys  Pro Glu Asn Ile Val  Ile Glu Met
    1175                1180                1185

Ala Arg  Glu Asn Gln Thr Thr  Gln Lys Gly Gln Lys  Asn Ser Arg
    1190                1195                1200
```

-continued

```
Glu Arg  Met Lys Arg Ile Glu  Glu Gly Ile Lys Glu  Leu Gly Ser
    1205              1210              1215

Gln Ile  Leu Lys Glu His Pro  Val Glu Asn Thr Gln  Leu Gln Asn
    1220              1225              1230

Glu Lys  Leu Tyr Leu Tyr Tyr  Leu Gln Asn Gly Arg  Asp Met Tyr
    1235              1240              1245

Val Asp  Gln Glu Leu Asp Ile  Asn Arg Leu Ser Asp  Tyr Asp Val
    1250              1255              1260

Asp His  Ile Val Pro Gln Ser  Phe Leu Lys Asp Asp  Ser Ile Asp
    1265              1270              1275

Asn Lys  Val Leu Thr Arg Ser  Asp Lys Asn Arg Gly  Lys Ser Asp
    1280              1285              1290

Asn Val  Pro Ser Glu Glu Val  Val Lys Lys Met Lys  Asn Tyr Trp
    1295              1300              1305

Arg Gln  Leu Leu Asn Ala Lys  Leu Ile Thr Gln Arg  Lys Phe Asp
    1310              1315              1320

Asn Leu  Thr Lys Ala Glu Arg  Gly Gly Leu Ser Glu  Leu Asp Lys
    1325              1330              1335

Ala Gly  Phe Ile Lys Arg Gln  Leu Val Glu Thr Arg  Gln Ile Thr
    1340              1345              1350

Lys His  Val Ala Gln Ile Leu  Asp Ser Arg Met Asn  Thr Lys Tyr
    1355              1360              1365

Asp Glu  Asn Asp Lys Leu Ile  Arg Glu Val Lys Val  Ile Thr Leu
    1370              1375              1380

Lys Ser  Lys Leu Val Ser Asp  Phe Arg Lys Asp Phe  Gln Phe Tyr
    1385              1390              1395

Lys Val  Arg Glu Ile Asn Asn  Tyr His His Ala His  Asp Ala Tyr
    1400              1405              1410

Leu Asn  Ala Val Val Gly Thr  Ala Leu Ile Lys Lys  Tyr Pro Lys
    1415              1420              1425

Leu Glu  Ser Glu Phe Val Tyr  Gly Asp Tyr Lys Val  Tyr Asp Val
    1430              1435              1440

Arg Lys  Met Ile Ala Lys Ser  Glu Gln Glu Ile Gly  Lys Ala Thr
    1445              1450              1455

Ala Lys  Tyr Phe Phe Tyr Ser  Asn Ile Met Asn Phe  Phe Lys Thr
    1460              1465              1470

Glu Ile  Thr Leu Ala Asn Gly  Glu Ile Arg Lys Arg  Pro Leu Ile
    1475              1480              1485

Glu Thr  Asn Gly Glu Thr Gly  Glu Ile Val Trp Asp  Lys Gly Arg
    1490              1495              1500

Asp Phe  Ala Thr Val Arg Lys  Val Leu Ser Met Pro  Gln Val Asn
    1505              1510              1515

Ile Val  Lys Lys Thr Glu Val  Gln Thr Gly Gly Phe  Ser Lys Glu
    1520              1525              1530

Ser Ile  Leu Pro Lys Arg Asn  Ser Asp Lys Leu Ile  Ala Arg Lys
    1535              1540              1545

Lys Asp  Trp Asp Pro Lys Lys  Tyr Gly Gly Phe Asp  Ser Pro Thr
    1550              1555              1560

Val Ala  Tyr Ser Val Leu Val  Val Ala Lys Val Glu  Lys Gly Lys
    1565              1570              1575

Ser Lys  Lys Leu Lys Ser Val  Lys Glu Leu Leu Gly  Ile Thr Ile
    1580              1585              1590

Met Glu  Arg Ser Ser Phe Glu  Lys Asn Pro Ile Asp  Phe Leu Glu
```

```
          1595                1600                1605

Ala Lys  Gly Tyr Lys Glu Val  Lys Lys Asp Leu Ile  Ile Lys Leu
    1610             1615              1620

Pro Lys  Tyr Ser Leu Phe Glu  Leu Glu Asn Gly Arg  Lys Arg Met
    1625             1630              1635

Leu Ala  Ser Ala Gly Glu Leu  Gln Lys Gly Asn Glu  Leu Ala Leu
    1640             1645              1650

Pro Ser  Lys Tyr Val Asn Phe  Leu Tyr Leu Ala Ser  His Tyr Glu
    1655             1660              1665

Lys Leu  Lys Gly Ser Pro Glu  Asp Asn Glu Gln Lys  Gln Leu Phe
    1670             1675              1680

Val Glu  Gln His Lys His Tyr  Leu Asp Glu Ile Ile  Glu Gln Ile
    1685             1690              1695

Ser Glu  Phe Ser Lys Arg Val  Ile Leu Ala Asp Ala  Asn Leu Asp
    1700             1705              1710

Lys Val  Leu Ser Ala Tyr Asn  Lys His Arg Asp Lys  Pro Ile Arg
    1715             1720              1725

Glu Gln  Ala Glu Asn Ile Ile  His Leu Phe Thr Leu  Thr Asn Leu
    1730             1735              1740

Gly Ala  Pro Ala Ala Phe Lys  Tyr Phe Asp Thr Thr  Ile Asp Arg
    1745             1750              1755

Lys Arg  Tyr Thr Ser Thr Lys  Glu Val Leu Asp Ala  Thr Leu Ile
    1760             1765              1770

His Gln  Ser Ile Thr Gly Leu  Tyr Glu Thr Arg Ile  Asp Leu Ser
    1775             1780              1785

Gln Leu  Gly Gly Asp Ser Arg  Ala Asp Pro Lys Lys  Lys Arg Lys
    1790             1795              1800

Val

<210> SEQ ID NO 21
<211> LENGTH: 1767
<212> TYPE: PRT
<213> ORGANISM: Artificial Sequence
<220> FEATURE:
<223> OTHER INFORMATION: ABE-EAAA5
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(364)
<223> OTHER INFORMATION: Linker region
<220> FEATURE:
<221> NAME/KEY: MISC_FEATURE
<222> LOCATION: (365)..(389)
<223> OTHER INFORMATION: Linker region
<220> FEATURE:
<221> NAME/KEY: MISC_FEATURE
<222> LOCATION: (390)..(1760)
<223> OTHER INFORMATION: Cas9-D10A
<220> FEATURE:
<221> NAME/KEY: MISC_FEATURE
<222> LOCATION: (1761)..(1767)
<223> OTHER INFORMATION: NLS

<400> SEQUENCE: 21

Met Ser Glu Val Glu Phe Ser His Glu Tyr Trp Met Arg His Ala Leu
1               5                   10                  15
```

```
Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                    85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
        130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                    165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
        210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
        290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ala Ser Glu
            355                 360                 365

Ala Ala Ala Glu Ala Ala Ala Glu Ala Ala Ala Glu Ala Ala Ala Glu
        370                 375                 380

Ala Ala Ala Gly Thr Asp Lys Lys Tyr Ser Ile Gly Leu Ala Ile Gly
385                 390                 395                 400

Thr Asn Ser Val Gly Trp Ala Val Ile Thr Asp Glu Tyr Lys Val Pro
                405                 410                 415

Ser Lys Lys Phe Lys Val Leu Gly Asn Thr Asp Arg His Ser Ile Lys
            420                 425                 430
```

-continued

```
Lys Asn Leu Ile Gly Ala Leu Leu Phe Asp Ser Gly Glu Thr Ala Glu
        435                 440                 445

Ala Thr Arg Leu Lys Arg Thr Ala Arg Arg Arg Tyr Thr Arg Arg Lys
    450                 455                 460

Asn Arg Ile Cys Tyr Leu Gln Glu Ile Phe Ser Asn Glu Met Ala Lys
465                 470                 475                 480

Val Asp Asp Ser Phe Phe His Arg Leu Glu Glu Ser Phe Leu Val Glu
                485                 490                 495

Glu Asp Lys Lys His Glu Arg His Pro Ile Phe Gly Asn Ile Val Asp
            500                 505                 510

Glu Val Ala Tyr His Glu Lys Tyr Pro Thr Ile Tyr His Leu Arg Lys
            515                 520                 525

Lys Leu Val Asp Ser Thr Asp Lys Ala Asp Leu Arg Leu Ile Tyr Leu
    530                 535                 540

Ala Leu Ala His Met Ile Lys Phe Arg Gly His Phe Leu Ile Glu Gly
545                 550                 555                 560

Asp Leu Asn Pro Asp Asn Ser Asp Val Asp Lys Leu Phe Ile Gln Leu
                565                 570                 575

Val Gln Thr Tyr Asn Gln Leu Phe Glu Glu Asn Pro Ile Asn Ala Ser
                580                 585                 590

Gly Val Asp Ala Lys Ala Ile Leu Ser Ala Arg Leu Ser Lys Ser Arg
            595                 600                 605

Arg Leu Glu Asn Leu Ile Ala Gln Leu Pro Gly Glu Lys Lys Asn Gly
    610                 615                 620

Leu Phe Gly Asn Leu Ile Ala Leu Ser Leu Gly Leu Thr Pro Asn Phe
625                 630                 635                 640

Lys Ser Asn Phe Asp Leu Ala Glu Asp Ala Lys Leu Gln Leu Ser Lys
                645                 650                 655

Asp Thr Tyr Asp Asp Asp Leu Asp Asn Leu Leu Ala Gln Ile Gly Asp
            660                 665                 670

Gln Tyr Ala Asp Leu Phe Leu Ala Ala Lys Asn Leu Ser Asp Ala Ile
            675                 680                 685

Leu Leu Ser Asp Ile Leu Arg Val Asn Thr Glu Ile Thr Lys Ala Pro
    690                 695                 700

Leu Ser Ala Ser Met Ile Lys Arg Tyr Asp Glu His His Gln Asp Leu
705                 710                 715                 720

Thr Leu Leu Lys Ala Leu Val Arg Gln Gln Leu Pro Glu Lys Tyr Lys
                725                 730                 735

Glu Ile Phe Phe Asp Gln Ser Lys Asn Gly Tyr Ala Gly Tyr Ile Asp
            740                 745                 750

Gly Gly Ala Ser Gln Glu Glu Phe Tyr Lys Phe Ile Lys Pro Ile Leu
            755                 760                 765

Glu Lys Met Asp Gly Thr Glu Glu Leu Leu Val Lys Leu Asn Arg Glu
    770                 775                 780

Asp Leu Leu Arg Lys Gln Arg Thr Phe Asp Asn Gly Ser Ile Pro His
785                 790                 795                 800

Gln Ile His Leu Gly Glu Leu His Ala Ile Leu Arg Arg Gln Glu Asp
                805                 810                 815

Phe Tyr Pro Phe Leu Lys Asp Asn Arg Glu Lys Ile Glu Lys Ile Leu
            820                 825                 830

Thr Phe Arg Ile Pro Tyr Tyr Val Gly Pro Leu Ala Arg Gly Asn Ser
    835                 840                 845

Arg Phe Ala Trp Met Thr Arg Lys Ser Glu Glu Thr Ile Thr Pro Trp
```

-continued

```
            850              855              860

Asn Phe Glu Glu Val Val Asp Lys Gly Ala Ser Ala Gln Ser Phe Ile
865             870              875                  880

Glu Arg Met Thr Asn Phe Asp Lys Asn Leu Pro Asn Glu Lys Val Leu
            885              890                  895

Pro Lys His Ser Leu Leu Tyr Glu Tyr Phe Thr Val Tyr Asn Glu Leu
            900              905                  910

Thr Lys Val Lys Tyr Val Thr Glu Gly Met Arg Lys Pro Ala Phe Leu
        915              920                  925

Ser Gly Glu Gln Lys Lys Ala Ile Val Asp Leu Leu Phe Lys Thr Asn
    930              935              940

Arg Lys Val Thr Val Lys Gln Leu Lys Glu Asp Tyr Phe Lys Lys Ile
945             950              955                  960

Glu Cys Phe Asp Ser Val Glu Ile Ser Gly Val Glu Asp Arg Phe Asn
            965              970                  975

Ala Ser Leu Gly Thr Tyr His Asp Leu Leu Lys Ile Ile Lys Asp Lys
            980              985                  990

Asp Phe Leu Asp Asn Glu Glu Asn  Glu Asp Ile Leu Glu  Asp Ile Val
        995              1000                 1005

Leu Thr  Leu Thr Leu Phe Glu  Asp Arg Glu Met Ile  Glu Glu Arg
    1010             1015                 1020

Leu Lys  Thr Tyr Ala His Leu  Phe Asp Asp Lys Val  Met Lys Gln
    1025             1030                 1035

Leu Lys  Arg Arg Arg Tyr Thr  Gly Trp Gly Arg Leu  Ser Arg Lys
    1040             1045                 1050

Leu Ile  Asn Gly Ile Arg Asp  Lys Gln Ser Gly Lys  Thr Ile Leu
    1055             1060                 1065

Asp Phe  Leu Lys Ser Asp Gly  Phe Ala Asn Arg Asn  Phe Met Gln
    1070             1075                 1080

Leu Ile  His Asp Asp Ser Leu  Thr Phe Lys Glu Asp  Ile Gln Lys
    1085             1090                 1095

Ala Gln  Val Ser Gly Gln Gly  Asp Ser Leu His Glu  His Ile Ala
    1100             1105                 1110

Asn Leu  Ala Gly Ser Pro Ala  Ile Lys Lys Gly Ile  Leu Gln Thr
    1115             1120                 1125

Val Lys  Val Val Asp Glu Leu  Val Lys Val Met Gly  Arg His Lys
    1130             1135                 1140

Pro Glu  Asn Ile Val Ile Glu  Met Ala Arg Glu Asn  Gln Thr Thr
    1145             1150                 1155

Gln Lys  Gly Gln Lys Asn Ser  Arg Glu Arg Met Lys  Arg Ile Glu
    1160             1165                 1170

Glu Gly  Ile Lys Glu Leu Gly  Ser Gln Ile Leu Lys  Glu His Pro
    1175             1180                 1185

Val Glu  Asn Thr Gln Leu Gln  Asn Glu Lys Leu Tyr  Leu Tyr Tyr
    1190             1195                 1200

Leu Gln  Asn Gly Arg Asp Met  Tyr Val Asp Gln Glu  Leu Asp Ile
    1205             1210                 1215

Asn Arg  Leu Ser Asp Tyr Asp  Val Asp His Ile Val  Pro Gln Ser
    1220             1225                 1230

Phe Leu  Lys Asp Asp Ser Ile  Asp Asn Lys Val Leu  Thr Arg Ser
    1235             1240                 1245

Asp Lys  Asn Arg Gly Lys Ser  Asp Asn Val Pro Ser  Glu Glu Val
    1250             1255                 1260
```

```
Val Lys  Lys Met Lys Asn Tyr  Trp Arg Gln Leu Leu  Asn Ala Lys
    1265                 1270                 1275

Leu Ile  Thr Gln Arg Lys Phe  Asp Asn Leu Thr Lys  Ala Glu Arg
    1280                 1285                 1290

Gly Gly  Leu Ser Glu Leu Asp  Lys Ala Gly Phe Ile  Lys Arg Gln
    1295                 1300                 1305

Leu Val  Glu Thr Arg Gln Ile  Thr Lys His Val Ala  Gln Ile Leu
    1310                 1315                 1320

Asp Ser  Arg Met Asn Thr Lys  Tyr Asp Glu Asn Asp  Lys Leu Ile
    1325                 1330                 1335

Arg Glu  Val Lys Val Ile Thr  Leu Lys Ser Lys Leu  Val Ser Asp
    1340                 1345                 1350

Phe Arg  Lys Asp Phe Gln Phe  Tyr Lys Val Arg Glu  Ile Asn Asn
    1355                 1360                 1365

Tyr His  His Ala His Asp Ala  Tyr Leu Asn Ala Val  Val Gly Thr
    1370                 1375                 1380

Ala Leu  Ile Lys Lys Tyr Pro  Lys Leu Glu Ser Glu  Phe Val Tyr
    1385                 1390                 1395

Gly Asp  Tyr Lys Val Tyr Asp  Val Arg Lys Met Ile  Ala Lys Ser
    1400                 1405                 1410

Glu Gln  Glu Ile Gly Lys Ala  Thr Ala Lys Tyr Phe  Phe Tyr Ser
    1415                 1420                 1425

Asn Ile  Met Asn Phe Phe Lys  Thr Glu Ile Thr Leu  Ala Asn Gly
    1430                 1435                 1440

Glu Ile  Arg Lys Arg Pro Leu  Ile Glu Thr Asn Gly  Glu Thr Gly
    1445                 1450                 1455

Glu Ile  Val Trp Asp Lys Gly  Arg Asp Phe Ala Thr  Val Arg Lys
    1460                 1465                 1470

Val Leu  Ser Met Pro Gln Val  Asn Ile Val Lys Lys  Thr Glu Val
    1475                 1480                 1485

Gln Thr  Gly Gly Phe Ser Lys  Glu Ser Ile Leu Pro  Lys Arg Asn
    1490                 1495                 1500

Ser Asp  Lys Leu Ile Ala Arg  Lys Lys Asp Trp Asp  Pro Lys Lys
    1505                 1510                 1515

Tyr Gly  Gly Phe Asp Ser Pro  Thr Val Ala Tyr Ser  Val Leu Val
    1520                 1525                 1530

Val Ala  Lys Val Glu Lys Gly  Lys Ser Lys Lys Leu  Lys Ser Val
    1535                 1540                 1545

Lys Glu  Leu Leu Gly Ile Thr  Ile Met Glu Arg Ser  Ser Phe Glu
    1550                 1555                 1560

Lys Asn  Pro Ile Asp Phe Leu  Glu Ala Lys Gly Tyr  Lys Glu Val
    1565                 1570                 1575

Lys Lys  Asp Leu Ile Ile Lys  Leu Pro Lys Tyr Ser  Leu Phe Glu
    1580                 1585                 1590

Leu Glu  Asn Gly Arg Lys Arg  Met Leu Ala Ser Ala  Gly Glu Leu
    1595                 1600                 1605

Gln Lys  Gly Asn Glu Leu Ala  Leu Pro Ser Lys Tyr  Val Asn Phe
    1610                 1615                 1620

Leu Tyr  Leu Ala Ser His Tyr  Glu Lys Leu Lys Gly  Ser Pro Glu
    1625                 1630                 1635

Asp Asn  Glu Gln Lys Gln Leu  Phe Val Glu Gln His  Lys His Tyr
    1640                 1645                 1650
```

```
Leu Asp  Glu Ile Ile Glu Gln  Ile Ser Glu Phe Ser  Lys Arg Val
    1655             1660              1665

Ile Leu  Ala Asp Ala Asn Leu  Asp Lys Val Leu Ser  Ala Tyr Asn
    1670             1675              1680

Lys His  Arg Asp Lys Pro Ile  Arg Glu Gln Ala Glu  Asn Ile Ile
    1685             1690              1695

His Leu  Phe Thr Leu Thr Asn  Leu Gly Ala Pro Ala  Ala Phe Lys
    1700             1705              1710

Tyr Phe  Asp Thr Thr Ile Asp  Arg Lys Arg Tyr Thr  Ser Thr Lys
    1715             1720              1725

Glu Val  Leu Asp Ala Thr Leu  Ile His Gln Ser Ile  Thr Gly Leu
    1730             1735              1740

Tyr Glu  Thr Arg Ile Asp Leu  Ser Gln Leu Gly Gly  Asp Ser Arg
    1745             1750              1755

Ala Asp  Pro Lys Lys Lys Arg  Lys Val
    1760             1765

<210> SEQ ID NO 22
<211> LENGTH: 1866
<212> TYPE: PRT
<213> ORGANISM: Artificial Sequence
<220> FEATURE:
<223> OTHER INFORMATION: ABE-UGI
<220> FEATURE:
<221> NAME/KEY: MISC_FEATURE
<222> LOCATION: (1)..(168)
<223> OTHER INFORMATION: Adenine Deaminase Domain
<220> FEATURE:
<221> NAME/KEY: MISC_FEATURE
<222> LOCATION: (169)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(397)
<223> OTHER INFORMATION: Linker region
<220> FEATURE:
<221> NAME/KEY: MISC_FEATURE
<222> LOCATION: (398)..(1768)
<223> OTHER INFORMATION: Cas9-D10A
<220> FEATURE:
<221> NAME/KEY: MISC_FEATURE
<222> LOCATION: (1769)..(1772)
<223> OTHER INFORMATION: Linker region
<220> FEATURE:
<221> NAME/KEY: MISC_FEATURE
<222> LOCATION: (1773)..(1855)
<223> OTHER INFORMATION: UGI Domain
<220> FEATURE:
<221> NAME/KEY: MISC_FEATURE
<222> LOCATION: (1856)..(1859)
<223> OTHER INFORMATION: Linker region
<220> FEATURE:
<221> NAME/KEY: MISC_FEATURE
<222> LOCATION: (1860)..(1866)
<223> OTHER INFORMATION: NLS

<400> SEQUENCE: 22

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45
```

-continued

```
Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
                100                 105                 110

Ala Ala Gly Ser Leu Met Asp Val Leu His His Pro Gly Met Asn His
                115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
                180                 185                 190

Gly Gly Ser Ser Gly Gly Ser Ser Glu Val Glu Phe Ser His Glu Tyr
                195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
                260                 265                 270

Leu Ile Asp Ala Thr Leu Tyr Val Thr Phe Glu Pro Cys Val Met Cys
    275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
                340                 345                 350

Val Phe Asn Ala Gln Lys Lys Ala Gln Ser Ser Thr Asp Ser Gly Gly
                355                 360                 365

Ser Ser Gly Gly Ser Ser Gly Ser Glu Thr Pro Gly Thr Ser Glu Ser
    370                 375                 380

Ala Thr Pro Glu Ser Ser Gly Gly Ser Ser Gly Gly Ser Asp Lys Lys
385                 390                 395                 400

Tyr Ser Ile Gly Leu Ala Ile Gly Thr Asn Ser Val Gly Trp Ala Val
                405                 410                 415

Ile Thr Asp Glu Tyr Lys Val Pro Ser Lys Lys Phe Lys Val Leu Gly
                420                 425                 430

Asn Thr Asp Arg His Ser Ile Lys Lys Asn Leu Ile Gly Ala Leu Leu
                435                 440                 445

Phe Asp Ser Gly Glu Thr Ala Glu Ala Thr Arg Leu Lys Arg Thr Ala
    450                 455                 460

Arg Arg Arg Tyr Thr Arg Arg Lys Asn Arg Ile Cys Tyr Leu Gln Glu
```

```
465             470             475             480

Ile Phe Ser Asn Glu Met Ala Lys Val Asp Asp Ser Phe Phe His Arg
            485             490             495

Leu Glu Glu Ser Phe Leu Val Glu Glu Asp Lys Lys His Glu Arg His
            500             505             510

Pro Ile Phe Gly Asn Ile Val Asp Glu Val Ala Tyr His Glu Lys Tyr
            515             520             525

Pro Thr Ile Tyr His Leu Arg Lys Lys Leu Val Asp Ser Thr Asp Lys
            530             535             540

Ala Asp Leu Arg Leu Ile Tyr Leu Ala Leu Ala His Met Ile Lys Phe
545             550             555             560

Arg Gly His Phe Leu Ile Glu Gly Asp Leu Asn Pro Asp Asn Ser Asp
            565             570             575

Val Asp Lys Leu Phe Ile Gln Leu Val Gln Thr Tyr Asn Gln Leu Phe
            580             585             590

Glu Glu Asn Pro Ile Asn Ala Ser Gly Val Asp Ala Lys Ala Ile Leu
            595             600             605

Ser Ala Arg Leu Ser Lys Ser Arg Arg Leu Glu Asn Leu Ile Ala Gln
            610             615             620

Leu Pro Gly Glu Lys Lys Asn Gly Leu Phe Gly Asn Leu Ile Ala Leu
625             630             635             640

Ser Leu Gly Leu Thr Pro Asn Phe Lys Ser Asn Phe Asp Leu Ala Glu
            645             650             655

Asp Ala Lys Leu Gln Leu Ser Lys Asp Thr Tyr Asp Asp Asp Leu Asp
            660             665             670

Asn Leu Leu Ala Gln Ile Gly Asp Gln Tyr Ala Asp Leu Phe Leu Ala
            675             680             685

Ala Lys Asn Leu Ser Asp Ala Ile Leu Leu Ser Asp Ile Leu Arg Val
            690             695             700

Asn Thr Glu Ile Thr Lys Ala Pro Leu Ser Ala Ser Met Ile Lys Arg
705             710             715             720

Tyr Asp Glu His His Gln Asp Leu Thr Leu Leu Lys Ala Leu Val Arg
            725             730             735

Gln Gln Leu Pro Glu Lys Tyr Lys Glu Ile Phe Phe Asp Gln Ser Lys
            740             745             750

Asn Gly Tyr Ala Gly Tyr Ile Asp Gly Gly Ala Ser Gln Glu Glu Phe
            755             760             765

Tyr Lys Phe Ile Lys Pro Ile Leu Glu Lys Met Asp Gly Thr Glu Glu
            770             775             780

Leu Leu Val Lys Leu Asn Arg Glu Asp Leu Leu Arg Lys Gln Arg Thr
785             790             795             800

Phe Asp Asn Gly Ser Ile Pro His Gln Ile His Leu Gly Glu Leu His
            805             810             815

Ala Ile Leu Arg Arg Gln Glu Asp Phe Tyr Pro Phe Leu Lys Asp Asn
            820             825             830

Arg Glu Lys Ile Glu Lys Ile Leu Thr Phe Arg Ile Pro Tyr Tyr Val
            835             840             845

Gly Pro Leu Ala Arg Gly Asn Ser Arg Phe Ala Trp Met Thr Arg Lys
            850             855             860

Ser Glu Glu Thr Ile Thr Pro Trp Asn Phe Glu Glu Val Val Asp Lys
865             870             875             880

Gly Ala Ser Ala Gln Ser Phe Ile Glu Arg Met Thr Asn Phe Asp Lys
            885             890             895
```

```
Asn Leu Pro Asn Glu Lys Val Leu Pro Lys His Ser Leu Leu Tyr Glu
        900                   905                   910

Tyr Phe Thr Val Tyr Asn Glu Leu Thr Lys Val Lys Tyr Val Thr Glu
        915                   920                   925

Gly Met Arg Lys Pro Ala Phe Leu Ser Gly Glu Gln Lys Lys Ala Ile
        930                   935                   940

Val Asp Leu Leu Phe Lys Thr Asn Arg Lys Val Thr Val Lys Gln Leu
945                   950                   955                   960

Lys Glu Asp Tyr Phe Lys Lys Ile Glu Cys Phe Asp Ser Val Glu Ile
                965                   970                   975

Ser Gly Val Glu Asp Arg Phe Asn Ala Ser Leu Gly Thr Tyr His Asp
                980                   985                   990

Leu Leu Lys Ile Ile Lys Asp Lys  Asp Phe Leu Asp Asn  Glu Glu Asn
        995                   1000                   1005

Glu Asp  Ile Leu Glu Asp Ile  Val Leu Thr Leu Thr  Leu Phe Glu
    1010                   1015                   1020

Asp Arg  Glu Met Ile Glu Glu  Arg Leu Lys Thr Tyr  Ala His Leu
    1025                   1030                   1035

Phe Asp  Asp Lys Val Met Lys  Gln Leu Lys Arg Arg  Arg Tyr Thr
    1040                   1045                   1050

Gly Trp  Gly Arg Leu Ser Arg  Lys Leu Ile Asn Gly  Ile Arg Asp
    1055                   1060                   1065

Lys Gln  Ser Gly Lys Thr Ile  Leu Asp Phe Leu Lys  Ser Asp Gly
    1070                   1075                   1080

Phe Ala  Asn Arg Asn Phe Met  Gln Leu Ile His Asp  Asp Ser Leu
    1085                   1090                   1095

Thr Phe  Lys Glu Asp Ile Gln  Lys Ala Gln Val Ser  Gly Gln Gly
    1100                   1105                   1110

Asp Ser  Leu His Glu His Ile  Ala Asn Leu Ala Gly  Ser Pro Ala
    1115                   1120                   1125

Ile Lys  Lys Gly Ile Leu Gln  Thr Val Lys Val Val  Asp Glu Leu
    1130                   1135                   1140

Val Lys  Val Met Gly Arg His  Lys Pro Glu Asn Ile  Val Ile Glu
    1145                   1150                   1155

Met Ala  Arg Glu Asn Gln Thr  Thr Gln Lys Gly Gln  Lys Asn Ser
    1160                   1165                   1170

Arg Glu  Arg Met Lys Arg Ile  Glu Glu Gly Ile Lys  Glu Leu Gly
    1175                   1180                   1185

Ser Gln  Ile Leu Lys Glu His  Pro Val Glu Asn Thr  Gln Leu Gln
    1190                   1195                   1200

Asn Glu  Lys Leu Tyr Leu Tyr  Tyr Leu Gln Asn Gly  Arg Asp Met
    1205                   1210                   1215

Tyr Val  Asp Gln Glu Leu Asp  Ile Asn Arg Leu Ser  Asp Tyr Asp
    1220                   1225                   1230

Val Asp  His Ile Val Pro Gln  Ser Phe Leu Lys Asp  Asp Ser Ile
    1235                   1240                   1245

Asp Asn  Lys Val Leu Thr Arg  Ser Asp Lys Asn Arg  Gly Lys Ser
    1250                   1255                   1260

Asp Asn  Val Pro Ser Glu Glu  Val Val Lys Lys Met  Lys Asn Tyr
    1265                   1270                   1275

Trp Arg  Gln Leu Leu Asn Ala  Lys Leu Ile Thr Gln  Arg Lys Phe
    1280                   1285                   1290
```

-continued

```
Asp Asn  Leu Thr Lys Ala Glu  Arg Gly Gly Leu Ser  Glu Leu Asp
    1295             1300              1305

Lys Ala  Gly Phe Ile Lys Arg  Gln Leu Val Glu Thr  Arg Gln Ile
    1310             1315              1320

Thr Lys  His Val Ala Gln Ile  Leu Asp Ser Arg Met  Asn Thr Lys
    1325             1330              1335

Tyr Asp  Glu Asn Asp Lys Leu  Ile Arg Glu Val Lys  Val Ile Thr
    1340             1345              1350

Leu Lys  Ser Lys Leu Val Ser  Asp Phe Arg Lys Asp  Phe Gln Phe
    1355             1360              1365

Tyr Lys  Val Arg Glu Ile Asn  Asn Tyr His His Ala  His Asp Ala
    1370             1375              1380

Tyr Leu  Asn Ala Val Val Gly  Thr Ala Leu Ile Lys  Lys Tyr Pro
    1385             1390              1395

Lys Leu  Glu Ser Glu Phe Val  Tyr Gly Asp Tyr Lys  Val Tyr Asp
    1400             1405              1410

Val Arg  Lys Met Ile Ala Lys  Ser Glu Gln Glu Ile  Gly Lys Ala
    1415             1420              1425

Thr Ala  Lys Tyr Phe Phe Tyr  Ser Asn Ile Met Asn  Phe Phe Lys
    1430             1435              1440

Thr Glu  Ile Thr Leu Ala Asn  Gly Glu Ile Arg Lys  Arg Pro Leu
    1445             1450              1455

Ile Glu  Thr Asn Gly Glu Thr  Gly Glu Ile Val Trp  Asp Lys Gly
    1460             1465              1470

Arg Asp  Phe Ala Thr Val Arg  Lys Val Leu Ser Met  Pro Gln Val
    1475             1480              1485

Asn Ile  Val Lys Lys Thr Glu  Val Gln Thr Gly Gly  Phe Ser Lys
    1490             1495              1500

Glu Ser  Ile Leu Pro Lys Arg  Asn Ser Asp Lys Leu  Ile Ala Arg
    1505             1510              1515

Lys Lys  Asp Trp Asp Pro Lys  Lys Tyr Gly Gly Phe  Asp Ser Pro
    1520             1525              1530

Thr Val  Ala Tyr Ser Val Leu  Val Val Ala Lys Val  Glu Lys Gly
    1535             1540              1545

Lys Ser  Lys Lys Leu Lys Ser  Val Lys Glu Leu Leu  Gly Ile Thr
    1550             1555              1560

Ile Met  Glu Arg Ser Ser Phe  Glu Lys Asn Pro Ile  Asp Phe Leu
    1565             1570              1575

Glu Ala  Lys Gly Tyr Lys Glu  Val Lys Lys Asp Leu  Ile Ile Lys
    1580             1585              1590

Leu Pro  Lys Tyr Ser Leu Phe  Glu Leu Glu Asn Gly  Arg Lys Arg
    1595             1600              1605

Met Leu  Ala Ser Ala Gly Glu  Leu Gln Lys Gly Asn  Glu Leu Ala
    1610             1615              1620

Leu Pro  Ser Lys Tyr Val Asn  Phe Leu Tyr Leu Ala  Ser His Tyr
    1625             1630              1635

Glu Lys  Leu Lys Gly Ser Pro  Glu Asp Asn Glu Gln  Lys Gln Leu
    1640             1645              1650

Phe Val  Glu Gln His Lys His  Tyr Leu Asp Glu Ile  Ile Glu Gln
    1655             1660              1665

Ile Ser  Glu Phe Ser Lys Arg  Val Ile Leu Ala Asp  Ala Asn Leu
    1670             1675              1680

Asp Lys  Val Leu Ser Ala Tyr  Asn Lys His Arg Asp  Lys Pro Ile
```

```
            1685                1690                1695

Arg Glu  Gln Ala Glu Asn Ile  Ile His Leu Phe Thr  Leu Thr Asn
    1700                1705                1710

Leu Gly  Ala Pro Ala Ala Phe  Lys Tyr Phe Asp Thr  Thr Ile Asp
    1715                1720                1725

Arg Lys  Arg Tyr Thr Ser Thr  Lys Glu Val Leu Asp  Ala Thr Leu
    1730                1735                1740

Ile His  Gln Ser Ile Thr Gly  Leu Tyr Glu Thr Arg  Ile Asp Leu
    1745                1750                1755

Ser Gln  Leu Gly Gly Asp Ser  Arg Ala Asp Ser Gly  Gly Ser Thr
    1760                1765                1770

Asn Leu  Ser Asp Ile Ile Glu  Lys Glu Thr Gly Lys  Gln Leu Val
    1775                1780                1785

Ile Gln  Glu Ser Ile Leu Met  Leu Pro Glu Glu Val  Glu Glu Val
    1790                1795                1800

Ile Gly  Asn Lys Pro Glu Ser  Asp Ile Leu Val His  Thr Ala Tyr
    1805                1810                1815

Asp Glu  Ser Thr Asp Glu Asn  Val Met Leu Leu Thr  Ser Asp Ala
    1820                1825                1830

Pro Glu  Tyr Lys Pro Trp Ala  Leu Val Ile Gln Asp  Ser Asn Gly
    1835                1840                1845

Glu Asn  Lys Ile Lys Met Leu  Ser Gly Gly Ser Pro  Lys Lys Lys
    1850                1855                1860

Arg Lys  Val
    1865

<210> SEQ ID NO 23
<211> LENGTH: 1843
<212> TYPE: PRT
<213> ORGANISM: Artificial Sequence
<220> FEATURE:
<223> OTHER INFORMATION: ABE-GGGGS1-UGI
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(374)
<223> OTHER INFORMATION: Linker region
<220> FEATURE:
<221> NAME/KEY: MISC_FEATURE
<222> LOCATION: (375)..(1745)
<223> OTHER INFORMATION: Cas9-D10A
<220> FEATURE:
<221> NAME/KEY: MISC_FEATURE
<222> LOCATION: (1746)..(1832)
<223> OTHER INFORMATION: UGI Domain
<220> FEATURE:
<221> NAME/KEY: MISC_FEATURE
<222> LOCATION: (1833)..(1836)
<223> OTHER INFORMATION: Linker region
<220> FEATURE:
<221> NAME/KEY: MISC_FEATURE
<222> LOCATION: (1837)..(1843)
<223> OTHER INFORMATION: NLS

<400> SEQUENCE: 23
```

-continued

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
        130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
        210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
            290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ala Ser Gly
            355                 360                 365

Gly Gly Gly Ser Gly Thr Asp Lys Lys Tyr Ser Ile Gly Leu Ala Ile
        370                 375                 380

Gly Thr Asn Ser Val Gly Trp Ala Val Ile Thr Asp Glu Tyr Lys Val
385                 390                 395                 400

Pro Ser Lys Lys Phe Lys Val Leu Gly Asn Thr Asp Arg His Ser Ile
                405                 410                 415
```

-continued

```
Lys Lys Asn Leu Ile Gly Ala Leu Leu Phe Asp Ser Gly Glu Thr Ala
            420                 425                 430

Glu Ala Thr Arg Leu Lys Arg Thr Ala Arg Arg Arg Tyr Thr Arg Arg
            435                 440                 445

Lys Asn Arg Ile Cys Tyr Leu Gln Glu Ile Phe Ser Asn Glu Met Ala
        450                 455                 460

Lys Val Asp Asp Ser Phe Phe His Arg Leu Glu Glu Ser Phe Leu Val
465                 470                 475                 480

Glu Glu Asp Lys Lys His Glu Arg His Pro Ile Phe Gly Asn Ile Val
                485                 490                 495

Asp Glu Val Ala Tyr His Glu Lys Tyr Pro Thr Ile Tyr His Leu Arg
            500                 505                 510

Lys Lys Leu Val Asp Ser Thr Asp Lys Ala Asp Leu Arg Leu Ile Tyr
            515                 520                 525

Leu Ala Leu Ala His Met Ile Lys Phe Arg Gly His Phe Leu Ile Glu
        530                 535                 540

Gly Asp Leu Asn Pro Asp Asn Ser Asp Val Asp Lys Leu Phe Ile Gln
545                 550                 555                 560

Leu Val Gln Thr Tyr Asn Gln Leu Phe Glu Glu Asn Pro Ile Asn Ala
                565                 570                 575

Ser Gly Val Asp Ala Lys Ala Ile Leu Ser Ala Arg Leu Ser Lys Ser
            580                 585                 590

Arg Arg Leu Glu Asn Leu Ile Ala Gln Leu Pro Gly Glu Lys Lys Asn
            595                 600                 605

Gly Leu Phe Gly Asn Leu Ile Ala Leu Ser Leu Gly Leu Thr Pro Asn
        610                 615                 620

Phe Lys Ser Asn Phe Asp Leu Ala Glu Asp Ala Lys Leu Gln Leu Ser
625                 630                 635                 640

Lys Asp Thr Tyr Asp Asp Asp Leu Asp Asn Leu Leu Ala Gln Ile Gly
                645                 650                 655

Asp Gln Tyr Ala Asp Leu Phe Leu Ala Ala Lys Asn Leu Ser Asp Ala
            660                 665                 670

Ile Leu Leu Ser Asp Ile Leu Arg Val Asn Thr Glu Ile Thr Lys Ala
        675                 680                 685

Pro Leu Ser Ala Ser Met Ile Lys Arg Tyr Asp Glu His His Gln Asp
        690                 695                 700

Leu Thr Leu Leu Lys Ala Leu Val Arg Gln Gln Leu Pro Glu Lys Tyr
705                 710                 715                 720

Lys Glu Ile Phe Phe Asp Gln Ser Lys Asn Gly Tyr Ala Gly Tyr Ile
                725                 730                 735

Asp Gly Gly Ala Ser Gln Glu Glu Phe Tyr Lys Phe Ile Lys Pro Ile
            740                 745                 750

Leu Glu Lys Met Asp Gly Thr Glu Glu Leu Leu Val Lys Leu Asn Arg
            755                 760                 765

Glu Asp Leu Leu Arg Lys Gln Arg Thr Phe Asp Asn Gly Ser Ile Pro
        770                 775                 780

His Gln Ile His Leu Gly Glu Leu His Ala Ile Leu Arg Arg Gln Glu
785                 790                 795                 800

Asp Phe Tyr Pro Phe Leu Lys Asp Asn Arg Glu Lys Ile Glu Lys Ile
                805                 810                 815

Leu Thr Phe Arg Ile Pro Tyr Tyr Val Gly Pro Leu Ala Arg Gly Asn
            820                 825                 830

Ser Arg Phe Ala Trp Met Thr Arg Lys Ser Glu Glu Thr Ile Thr Pro
```

```
                835              840              845

Trp Asn Phe Glu Glu Val Val Asp Lys Gly Ala Ser Ala Gln Ser Phe
    850              855              860

Ile Glu Arg Met Thr Asn Phe Asp Lys Asn Leu Pro Asn Glu Lys Val
865              870              875              880

Leu Pro Lys His Ser Leu Leu Tyr Glu Tyr Phe Thr Val Tyr Asn Glu
                885              890              895

Leu Thr Lys Val Lys Tyr Val Thr Glu Gly Met Arg Lys Pro Ala Phe
                900              905              910

Leu Ser Gly Glu Gln Lys Lys Ala Ile Val Asp Leu Leu Phe Lys Thr
                915              920              925

Asn Arg Lys Val Thr Val Lys Gln Leu Lys Glu Asp Tyr Phe Lys Lys
    930              935              940

Ile Glu Cys Phe Asp Ser Val Glu Ile Ser Gly Val Glu Asp Arg Phe
945              950              955              960

Asn Ala Ser Leu Gly Thr Tyr His Asp Leu Leu Lys Ile Ile Lys Asp
                965              970              975

Lys Asp Phe Leu Asp Asn Glu Glu Asn Glu Asp Ile Leu Glu Asp Ile
                980              985              990

Val Leu Thr Leu Thr Leu Phe Glu  Asp Arg Glu Met Ile  Glu Glu Arg
                995              1000             1005

Leu Lys  Thr Tyr Ala His Leu  Phe Asp Asp Lys Val  Met Lys Gln
    1010             1015             1020

Leu Lys  Arg Arg Arg Tyr Thr  Gly Trp Gly Arg Leu  Ser Arg Lys
    1025             1030             1035

Leu Ile  Asn Gly Ile Arg Asp  Lys Gln Ser Gly Lys  Thr Ile Leu
    1040             1045             1050

Asp Phe  Leu Lys Ser Asp Gly  Phe Ala Asn Arg Asn  Phe Met Gln
    1055             1060             1065

Leu Ile  His Asp Asp Ser Leu  Thr Phe Lys Glu Asp  Ile Gln Lys
    1070             1075             1080

Ala Gln  Val Ser Gly Gln Gly  Asp Ser Leu His Glu  His Ile Ala
    1085             1090             1095

Asn Leu  Ala Gly Ser Pro Ala  Ile Lys Lys Gly Ile  Leu Gln Thr
    1100             1105             1110

Val Lys  Val Val Asp Glu Leu  Val Lys Val Met Gly  Arg His Lys
    1115             1120             1125

Pro Glu  Asn Ile Val Ile Glu  Met Ala Arg Glu Asn  Gln Thr Thr
    1130             1135             1140

Gln Lys  Gly Gln Lys Asn Ser  Arg Glu Arg Met Lys  Arg Ile Glu
    1145             1150             1155

Glu Gly  Ile Lys Glu Leu Gly  Ser Gln Ile Leu Lys  Glu His Pro
    1160             1165             1170

Val Glu  Asn Thr Gln Leu Gln  Asn Glu Lys Leu Tyr  Leu Tyr Tyr
    1175             1180             1185

Leu Gln  Asn Gly Arg Asp Met  Tyr Val Asp Gln Glu  Leu Asp Ile
    1190             1195             1200

Asn Arg  Leu Ser Asp Tyr Asp  Val Asp His Ile Val  Pro Gln Ser
    1205             1210             1215

Phe Leu  Lys Asp Asp Ser Ile  Asp Asn Lys Val Leu  Thr Arg Ser
    1220             1225             1230

Asp Lys  Asn Arg Gly Lys Ser  Asp Asn Val Pro Ser  Glu Glu Val
    1235             1240             1245
```

-continued

```
Val Lys Lys Met Lys Asn Tyr  Trp Arg Gln Leu Leu  Asn Ala Lys
    1250             1255              1260

Leu Ile Thr Gln Arg Lys Phe  Asp Asn Leu Thr Lys  Ala Glu Arg
    1265             1270              1275

Gly Gly Leu Ser Glu Leu Asp  Lys Ala Gly Phe Ile  Lys Arg Gln
    1280             1285              1290

Leu Val Glu Thr Arg Gln Ile  Thr Lys His Val Ala  Gln Ile Leu
    1295             1300              1305

Asp Ser Arg Met Asn Thr Lys  Tyr Asp Glu Asn Asp  Lys Leu Ile
    1310             1315              1320

Arg Glu Val Lys Val Ile Thr  Leu Lys Ser Lys Leu  Val Ser Asp
    1325             1330              1335

Phe Arg Lys Asp Phe Gln Phe  Tyr Lys Val Arg Glu  Ile Asn Asn
    1340             1345              1350

Tyr His His Ala His Asp Ala  Tyr Leu Asn Ala Val  Val Gly Thr
    1355             1360              1365

Ala Leu Ile Lys Lys Tyr Pro  Lys Leu Glu Ser Glu  Phe Val Tyr
    1370             1375              1380

Gly Asp Tyr Lys Val Tyr Asp  Val Arg Lys Met Ile  Ala Lys Ser
    1385             1390              1395

Glu Gln Glu Ile Gly Lys Ala  Thr Ala Lys Tyr Phe  Phe Tyr Ser
    1400             1405              1410

Asn Ile Met Asn Phe Phe Lys  Thr Glu Ile Thr Leu  Ala Asn Gly
    1415             1420              1425

Glu Ile Arg Lys Arg Pro Leu  Ile Glu Thr Asn Gly  Glu Thr Gly
    1430             1435              1440

Glu Ile Val Trp Asp Lys Gly  Arg Asp Phe Ala Thr  Val Arg Lys
    1445             1450              1455

Val Leu Ser Met Pro Gln Val  Asn Ile Val Lys Lys  Thr Glu Val
    1460             1465              1470

Gln Thr Gly Gly Phe Ser Lys  Glu Ser Ile Leu Pro  Lys Arg Asn
    1475             1480              1485

Ser Asp Lys Leu Ile Ala Arg  Lys Lys Asp Trp Asp  Pro Lys Lys
    1490             1495              1500

Tyr Gly Gly Phe Asp Ser Pro  Thr Val Ala Tyr Ser  Val Leu Val
    1505             1510              1515

Val Ala Lys Val Glu Lys Gly  Lys Ser Lys Lys Leu  Lys Ser Val
    1520             1525              1530

Lys Glu Leu Leu Gly Ile Thr  Ile Met Glu Arg Ser  Ser Phe Glu
    1535             1540              1545

Lys Asn Pro Ile Asp Phe Leu  Glu Ala Lys Gly Tyr  Lys Glu Val
    1550             1555              1560

Lys Lys Asp Leu Ile Ile Lys  Leu Pro Lys Tyr Ser  Leu Phe Glu
    1565             1570              1575

Leu Glu Asn Gly Arg Lys Arg  Met Leu Ala Ser Ala  Gly Glu Leu
    1580             1585              1590

Gln Lys Gly Asn Glu Leu Ala  Leu Pro Ser Lys Tyr  Val Asn Phe
    1595             1600              1605

Leu Tyr Leu Ala Ser His Tyr  Glu Lys Leu Lys Gly  Ser Pro Glu
    1610             1615              1620

Asp Asn Glu Gln Lys Gln Leu  Phe Val Glu Gln His  Lys His Tyr
    1625             1630              1635
```

```
Leu Asp  Glu Ile Ile Glu Gln  Ile Ser Glu Phe Ser  Lys Arg Val
    1640             1645             1650

Ile Leu  Ala Asp Ala Asn Leu  Asp Lys Val Leu Ser  Ala Tyr Asn
    1655             1660             1665

Lys His  Arg Asp Lys Pro Ile  Arg Glu Gln Ala Glu  Asn Ile Ile
    1670             1675             1680

His Leu  Phe Thr Leu Thr Asn  Leu Gly Ala Pro Ala  Ala Phe Lys
    1685             1690             1695

Tyr Phe  Asp Thr Thr Ile Asp  Arg Lys Arg Tyr Thr  Ser Thr Lys
    1700             1705             1710

Glu Val  Leu Asp Ala Thr Leu  Ile His Gln Ser Ile  Thr Gly Leu
    1715             1720             1725

Tyr Glu  Thr Arg Ile Asp Leu  Ser Gln Leu Gly Gly  Asp Ser Arg
    1730             1735             1740

Ala Asp  Ser Gly Gly Ser Thr  Asn Leu Ser Asp Ile  Ile Glu Lys
    1745             1750             1755

Glu Thr  Gly Lys Gln Leu Val  Ile Gln Glu Ser Ile  Leu Met Leu
    1760             1765             1770

Pro Glu  Glu Val Glu Glu Val  Ile Gly Asn Lys Pro  Glu Ser Asp
    1775             1780             1785

Ile Leu  Val His Thr Ala Tyr  Asp Glu Ser Thr Asp  Glu Asn Val
    1790             1795             1800

Met Leu  Leu Thr Ser Asp Ala  Pro Glu Tyr Lys Pro  Trp Ala Leu
    1805             1810             1815

Val Ile  Gln Asp Ser Asn Gly  Glu Asn Lys Ile Lys  Met Leu Ser
    1820             1825             1830

Gly Gly  Ser Pro Lys Lys Lys  Arg Lys Val
    1835             1840
```

```
<210> SEQ ID NO 24
<211> LENGTH: 1848
<212> TYPE: PRT
<213> ORGANISM: Artificial Sequence
<220> FEATURE:
<223> OTHER INFORMATION: ABE-GGGGS2-UGI
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(379)
<223> OTHER INFORMATION: Linker region
<220> FEATURE:
<221> NAME/KEY: MISC_FEATURE
<222> LOCATION: (380)..(1750)
<223> OTHER INFORMATION: Cas9-D10A
<220> FEATURE:
<221> NAME/KEY: MISC_FEATURE
<222> LOCATION: (1751)..(1837)
<223> OTHER INFORMATION: UGI Domain
<220> FEATURE:
<221> NAME/KEY: MISC_FEATURE
<222> LOCATION: (1838)..(1841)
<223> OTHER INFORMATION: Linker region
<220> FEATURE:
<221> NAME/KEY: MISC_FEATURE
```

-continued

<222> LOCATION: (1842)..(1848)
<223> OTHER INFORMATION: NLS

<400> SEQUENCE: 24

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ala Ser Gly
            355                 360                 365

Gly Gly Gly Ser Gly Gly Gly Gly Ser Gly Thr Asp Lys Lys Tyr Ser
    370                 375                 380

Ile Gly Leu Ala Ile Gly Thr Asn Ser Val Gly Trp Ala Val Ile Thr
385                 390                 395                 400
```

-continued

```
Asp Glu Tyr Lys Val Pro Ser Lys Lys Phe Lys Val Leu Gly Asn Thr
            405             410             415

Asp Arg His Ser Ile Lys Lys Asn Leu Ile Gly Ala Leu Leu Phe Asp
            420             425             430

Ser Gly Glu Thr Ala Glu Ala Thr Arg Leu Lys Arg Thr Ala Arg Arg
            435             440             445

Arg Tyr Thr Arg Arg Lys Asn Arg Ile Cys Tyr Leu Gln Glu Ile Phe
    450             455             460

Ser Asn Glu Met Ala Lys Val Asp Asp Ser Phe Phe His Arg Leu Glu
465             470             475             480

Glu Ser Phe Leu Val Glu Glu Asp Lys Lys His Glu Arg His Pro Ile
            485             490             495

Phe Gly Asn Ile Val Asp Glu Val Ala Tyr His Glu Lys Tyr Pro Thr
            500             505             510

Ile Tyr His Leu Arg Lys Lys Leu Val Asp Ser Thr Asp Lys Ala Asp
            515             520             525

Leu Arg Leu Ile Tyr Leu Ala Leu Ala His Met Ile Lys Phe Arg Gly
    530             535             540

His Phe Leu Ile Glu Gly Asp Leu Asn Pro Asp Asn Ser Asp Val Asp
545             550             555             560

Lys Leu Phe Ile Gln Leu Val Gln Thr Tyr Asn Gln Leu Phe Glu Glu
            565             570             575

Asn Pro Ile Asn Ala Ser Gly Val Asp Ala Lys Ala Ile Leu Ser Ala
            580             585             590

Arg Leu Ser Lys Ser Arg Arg Leu Glu Asn Leu Ile Ala Gln Leu Pro
            595             600             605

Gly Glu Lys Lys Asn Gly Leu Phe Gly Asn Leu Ile Ala Leu Ser Leu
    610             615             620

Gly Leu Thr Pro Asn Phe Lys Ser Asn Phe Asp Leu Ala Glu Asp Ala
625             630             635             640

Lys Leu Gln Leu Ser Lys Asp Thr Tyr Asp Asp Asp Leu Asp Asn Leu
            645             650             655

Leu Ala Gln Ile Gly Asp Gln Tyr Ala Asp Leu Phe Leu Ala Ala Lys
            660             665             670

Asn Leu Ser Asp Ala Ile Leu Leu Ser Asp Ile Leu Arg Val Asn Thr
            675             680             685

Glu Ile Thr Lys Ala Pro Leu Ser Ala Ser Met Ile Lys Arg Tyr Asp
    690             695             700

Glu His His Gln Asp Leu Thr Leu Leu Lys Ala Leu Val Arg Gln Gln
705             710             715             720

Leu Pro Glu Lys Tyr Lys Glu Ile Phe Phe Asp Gln Ser Lys Asn Gly
            725             730             735

Tyr Ala Gly Tyr Ile Asp Gly Gly Ala Ser Gln Glu Glu Phe Tyr Lys
            740             745             750

Phe Ile Lys Pro Ile Leu Glu Lys Met Asp Gly Thr Glu Glu Leu Leu
            755             760             765

Val Lys Leu Asn Arg Glu Asp Leu Leu Arg Lys Gln Arg Thr Phe Asp
    770             775             780

Asn Gly Ser Ile Pro His Gln Ile His Leu Gly Glu Leu His Ala Ile
785             790             795             800

Leu Arg Arg Gln Glu Asp Phe Tyr Pro Phe Leu Lys Asp Asn Arg Glu
            805             810             815
```

-continued

```
Lys Ile Glu Lys Ile Leu Thr Phe Arg Ile Pro Tyr Tyr Val Gly Pro
        820                 825                 830

Leu Ala Arg Gly Asn Ser Arg Phe Ala Trp Met Thr Arg Lys Ser Glu
        835                 840                 845

Glu Thr Ile Thr Pro Trp Asn Phe Glu Glu Val Val Asp Lys Gly Ala
        850                 855                 860

Ser Ala Gln Ser Phe Ile Glu Arg Met Thr Asn Phe Asp Lys Asn Leu
865                 870                 875                 880

Pro Asn Glu Lys Val Leu Pro Lys His Ser Leu Leu Tyr Glu Tyr Phe
                885                 890                 895

Thr Val Tyr Asn Glu Leu Thr Lys Val Lys Tyr Val Thr Glu Gly Met
                900                 905                 910

Arg Lys Pro Ala Phe Leu Ser Gly Glu Gln Lys Lys Ala Ile Val Asp
        915                 920                 925

Leu Leu Phe Lys Thr Asn Arg Lys Val Thr Val Lys Gln Leu Lys Glu
        930                 935                 940

Asp Tyr Phe Lys Lys Ile Glu Cys Phe Asp Ser Val Glu Ile Ser Gly
945                 950                 955                 960

Val Glu Asp Arg Phe Asn Ala Ser Leu Gly Thr Tyr His Asp Leu Leu
                965                 970                 975

Lys Ile Ile Lys Asp Lys Asp Phe Leu Asp Asn Glu Glu Asn Glu Asp
                980                 985                 990

Ile Leu Glu Asp Ile Val Leu Thr  Leu Thr Leu Phe Glu  Asp Arg Glu
        995                 1000                1005

Met Ile  Glu Glu Arg Leu Lys  Thr Tyr Ala His Leu  Phe Asp Asp
    1010                1015                1020

Lys Val  Met Lys Gln Leu Lys  Arg Arg Arg Tyr Thr  Gly Trp Gly
    1025                1030                1035

Arg Leu  Ser Arg Lys Leu Ile  Asn Gly Ile Arg Asp  Lys Gln Ser
    1040                1045                1050

Gly Lys  Thr Ile Leu Asp Phe  Leu Lys Ser Asp Gly  Phe Ala Asn
    1055                1060                1065

Arg Asn  Phe Met Gln Leu Ile  His Asp Asp Ser Leu  Thr Phe Lys
    1070                1075                1080

Glu Asp  Ile Gln Lys Ala Gln  Val Ser Gly Gln Gly  Asp Ser Leu
    1085                1090                1095

His Glu  His Ile Ala Asn Leu  Ala Gly Ser Pro Ala  Ile Lys Lys
    1100                1105                1110

Gly Ile  Leu Gln Thr Val Lys  Val Val Asp Glu Leu  Val Lys Val
    1115                1120                1125

Met Gly  Arg His Lys Pro Glu  Asn Ile Val Ile Glu  Met Ala Arg
    1130                1135                1140

Glu Asn  Gln Thr Thr Gln Lys  Gly Gln Lys Asn Ser  Arg Glu Arg
    1145                1150                1155

Met Lys  Arg Ile Glu Glu Gly  Ile Lys Glu Leu Gly  Ser Gln Ile
    1160                1165                1170

Leu Lys  Glu His Pro Val Glu  Asn Thr Gln Leu Gln  Asn Glu Lys
    1175                1180                1185

Leu Tyr  Leu Tyr Tyr Leu Gln  Asn Gly Arg Asp Met  Tyr Val Asp
    1190                1195                1200

Gln Glu  Leu Asp Ile Asn Arg  Leu Ser Asp Tyr Asp  Val Asp His
    1205                1210                1215

Ile Val  Pro Gln Ser Phe Leu  Lys Asp Asp Ser Ile  Asp Asn Lys
```

-continued

```
          1220                1225                1230

Val Leu Thr Arg Ser Asp Lys  Asn Arg Gly Lys Ser  Asp Asn Val
    1235                1240                1245

Pro Ser Glu Glu Val Val Lys  Lys Met Lys Asn Tyr  Trp Arg Gln
    1250                1255                1260

Leu Leu Asn Ala Lys Leu Ile  Thr Gln Arg Lys Phe  Asp Asn Leu
    1265                1270                1275

Thr Lys Ala Glu Arg Gly Gly  Leu Ser Glu Leu Asp  Lys Ala Gly
    1280                1285                1290

Phe Ile Lys Arg Gln Leu Val  Glu Thr Arg Gln Ile  Thr Lys His
    1295                1300                1305

Val Ala Gln Ile Leu Asp Ser  Arg Met Asn Thr Lys  Tyr Asp Glu
    1310                1315                1320

Asn Asp Lys Leu Ile Arg Glu  Val Lys Val Ile Thr  Leu Lys Ser
    1325                1330                1335

Lys Leu Val Ser Asp Phe Arg  Lys Asp Phe Gln Phe  Tyr Lys Val
    1340                1345                1350

Arg Glu Ile Asn Asn Tyr His  His Ala His Asp Ala  Tyr Leu Asn
    1355                1360                1365

Ala Val Val Gly Thr Ala Leu  Ile Lys Lys Tyr Pro  Lys Leu Glu
    1370                1375                1380

Ser Glu Phe Val Tyr Gly Asp  Tyr Lys Val Tyr Asp  Val Arg Lys
    1385                1390                1395

Met Ile Ala Lys Ser Glu Gln  Glu Ile Gly Lys Ala  Thr Ala Lys
    1400                1405                1410

Tyr Phe Phe Tyr Ser Asn Ile  Met Asn Phe Phe Lys  Thr Glu Ile
    1415                1420                1425

Thr Leu Ala Asn Gly Glu Ile  Arg Lys Arg Pro Leu  Ile Glu Thr
    1430                1435                1440

Asn Gly Glu Thr Gly Glu Ile  Val Trp Asp Lys Gly  Arg Asp Phe
    1445                1450                1455

Ala Thr Val Arg Lys Val Leu  Ser Met Pro Gln Val  Asn Ile Val
    1460                1465                1470

Lys Lys Thr Glu Val Gln Thr  Gly Gly Phe Ser Lys  Glu Ser Ile
    1475                1480                1485

Leu Pro Lys Arg Asn Ser Asp  Lys Leu Ile Ala Arg  Lys Lys Asp
    1490                1495                1500

Trp Asp Pro Lys Lys Tyr Gly  Gly Phe Asp Ser Pro  Thr Val Ala
    1505                1510                1515

Tyr Ser Val Leu Val Val Ala  Lys Val Glu Lys Gly  Lys Ser Lys
    1520                1525                1530

Lys Leu Lys Ser Val Lys Glu  Leu Leu Gly Ile Thr  Ile Met Glu
    1535                1540                1545

Arg Ser Ser Phe Glu Lys Asn  Pro Ile Asp Phe Leu  Glu Ala Lys
    1550                1555                1560

Gly Tyr Lys Glu Val Lys Lys  Asp Leu Ile Ile Lys  Leu Pro Lys
    1565                1570                1575

Tyr Ser Leu Phe Glu Leu Glu  Asn Gly Arg Lys Arg  Met Leu Ala
    1580                1585                1590

Ser Ala Gly Glu Leu Gln Lys  Gly Asn Glu Leu Ala  Leu Pro Ser
    1595                1600                1605

Lys Tyr Val Asn Phe Leu Tyr  Leu Ala Ser His Tyr  Glu Lys Leu
    1610                1615                1620
```

-continued

```
Lys Gly  Ser Pro Glu Asp Asn  Glu Gln Lys Gln Leu  Phe Val Glu
    1625                1630                1635

Gln His  Lys His Tyr Leu Asp  Glu Ile Ile Glu Gln  Ile Ser Glu
    1640                1645                1650

Phe Ser  Lys Arg Val Ile Leu  Ala Asp Ala Asn Leu  Asp Lys Val
    1655                1660                1665

Leu Ser  Ala Tyr Asn Lys His  Arg Asp Lys Pro Ile  Arg Glu Gln
    1670                1675                1680

Ala Glu  Asn Ile Ile His Leu  Phe Thr Leu Thr Asn  Leu Gly Ala
    1685                1690                1695

Pro Ala  Ala Phe Lys Tyr Phe  Asp Thr Thr Ile Asp  Arg Lys Arg
    1700                1705                1710

Tyr Thr  Ser Thr Lys Glu Val  Leu Asp Ala Thr Leu  Ile His Gln
    1715                1720                1725

Ser Ile  Thr Gly Leu Tyr Glu  Thr Arg Ile Asp Leu  Ser Gln Leu
    1730                1735                1740

Gly Gly  Asp Ser Arg Ala Asp  Ser Gly Gly Ser Thr  Asn Leu Ser
    1745                1750                1755

Asp Ile  Ile Glu Lys Glu Thr  Gly Lys Gln Leu Val  Ile Gln Glu
    1760                1765                1770

Ser Ile  Leu Met Leu Pro Glu  Glu Val Glu Glu Val  Ile Gly Asn
    1775                1780                1785

Lys Pro  Glu Ser Asp Ile Leu  Val His Thr Ala Tyr  Asp Glu Ser
    1790                1795                1800

Thr Asp  Glu Asn Val Met Leu  Leu Thr Ser Asp Ala  Pro Glu Tyr
    1805                1810                1815

Lys Pro  Trp Ala Leu Val Ile  Gln Asp Ser Asn Gly  Glu Asn Lys
    1820                1825                1830

Ile Lys  Met Leu Ser Gly Gly  Ser Pro Lys Lys Lys  Arg Lys Val
    1835                1840                1845
```

<210> SEQ ID NO 25
<211> LENGTH: 1853
<212> TYPE: PRT
<213> ORGANISM: Artificial Sequence
<220> FEATURE:
<223> OTHER INFORMATION: ABE-GGGGS3-UGI
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(384)
<223> OTHER INFORMATION: Linker region
<220> FEATURE:
<221> NAME/KEY: MISC_FEATURE
<222> LOCATION: (385)..(1755)
<223> OTHER INFORMATION: Cas9-D10A
<220> FEATURE:
<221> NAME/KEY: MISC_FEATURE
<222> LOCATION: (1756)..(1842)
<223> OTHER INFORMATION: UGI Domain
<220> FEATURE:
<221> NAME/KEY: MISC_FEATURE -continued
<222> LOCATION: (1843)..(1846)
<223> OTHER INFORMATION: Linker region
<220> FEATURE:
<221> NAME/KEY: MISC_FEATURE
<222> LOCATION: (1847)..(1853)
<223> OTHER INFORMATION: NLS
<400> SEQUENCE: 25

```
Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
        130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
        260                 265                 270

Leu Ile Asp Ala Thr Leu Tyr Val Thr Phe Glu Pro Cys Val Met Cys
        275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
        340                 345                 350

Val Phe Asn Ala Gln Lys Lys Ala Gln Ser Ser Thr Asp Ala Ser Gly
        355                 360                 365

Gly Gly Gly Ser Gly Gly Gly Gly Ser Gly Gly Gly Gly Ser Gly Thr
```

-continued

```
        370             375             380

Asp Lys Lys Tyr Ser Ile Gly Leu Ala Ile Gly Thr Asn Ser Val Gly
385             390             395             400

Trp Ala Val Ile Thr Asp Glu Tyr Lys Val Pro Ser Lys Lys Phe Lys
                405             410             415

Val Leu Gly Asn Thr Asp Arg His Ser Ile Lys Lys Asn Leu Ile Gly
                420             425             430

Ala Leu Leu Phe Asp Ser Gly Glu Thr Ala Glu Ala Thr Arg Leu Lys
            435             440             445

Arg Thr Ala Arg Arg Arg Tyr Thr Arg Arg Lys Asn Arg Ile Cys Tyr
    450             455             460

Leu Gln Glu Ile Phe Ser Asn Glu Met Ala Lys Val Asp Asp Ser Phe
465             470             475             480

Phe His Arg Leu Glu Glu Ser Phe Leu Val Glu Glu Asp Lys Lys His
                485             490             495

Glu Arg His Pro Ile Phe Gly Asn Ile Val Asp Glu Val Ala Tyr His
                500             505             510

Glu Lys Tyr Pro Thr Ile Tyr His Leu Arg Lys Lys Leu Val Asp Ser
            515             520             525

Thr Asp Lys Ala Asp Leu Arg Leu Ile Tyr Leu Ala Leu Ala His Met
    530             535             540

Ile Lys Phe Arg Gly His Phe Leu Ile Glu Gly Asp Leu Asn Pro Asp
545             550             555             560

Asn Ser Asp Val Asp Lys Leu Phe Ile Gln Leu Val Gln Thr Tyr Asn
                565             570             575

Gln Leu Phe Glu Glu Asn Pro Ile Asn Ala Ser Gly Val Asp Ala Lys
            580             585             590

Ala Ile Leu Ser Ala Arg Leu Ser Lys Ser Arg Arg Leu Glu Asn Leu
            595             600             605

Ile Ala Gln Leu Pro Gly Glu Lys Lys Asn Gly Leu Phe Gly Asn Leu
    610             615             620

Ile Ala Leu Ser Leu Gly Leu Thr Pro Asn Phe Lys Ser Asn Phe Asp
625             630             635             640

Leu Ala Glu Asp Ala Lys Leu Gln Leu Ser Lys Asp Thr Tyr Asp Asp
            645             650             655

Asp Leu Asp Asn Leu Leu Ala Gln Ile Gly Asp Gln Tyr Ala Asp Leu
            660             665             670

Phe Leu Ala Ala Lys Asn Leu Ser Asp Ala Ile Leu Leu Ser Asp Ile
            675             680             685

Leu Arg Val Asn Thr Glu Ile Thr Lys Ala Pro Leu Ser Ala Ser Met
    690             695             700

Ile Lys Arg Tyr Asp Glu His His Gln Asp Leu Thr Leu Leu Lys Ala
705             710             715             720

Leu Val Arg Gln Gln Leu Pro Glu Lys Tyr Lys Glu Ile Phe Phe Asp
                725             730             735

Gln Ser Lys Asn Gly Tyr Ala Gly Tyr Ile Asp Gly Gly Ala Ser Gln
            740             745             750

Glu Glu Phe Tyr Lys Phe Ile Lys Pro Ile Leu Glu Lys Met Asp Gly
            755             760             765

Thr Glu Glu Leu Leu Val Lys Leu Asn Arg Glu Asp Leu Leu Arg Lys
    770             775             780

Gln Arg Thr Phe Asp Asn Gly Ser Ile Pro His Gln Ile His Leu Gly
785             790             795             800
```

-continued

```
Glu Leu His Ala Ile Leu Arg Arg Gln Glu Asp Phe Tyr Pro Phe Leu
            805                 810                 815

Lys Asp Asn Arg Glu Lys Ile Glu Lys Ile Leu Thr Phe Arg Ile Pro
            820                 825                 830

Tyr Tyr Val Gly Pro Leu Ala Arg Gly Asn Ser Arg Phe Ala Trp Met
            835                 840                 845

Thr Arg Lys Ser Glu Glu Thr Ile Thr Pro Trp Asn Phe Glu Glu Val
    850                 855                 860

Val Asp Lys Gly Ala Ser Ala Gln Ser Phe Ile Glu Arg Met Thr Asn
865                 870                 875                 880

Phe Asp Lys Asn Leu Pro Asn Glu Lys Val Leu Pro Lys His Ser Leu
            885                 890                 895

Leu Tyr Glu Tyr Phe Thr Val Tyr Asn Glu Leu Thr Lys Val Lys Tyr
            900                 905                 910

Val Thr Glu Gly Met Arg Lys Pro Ala Phe Leu Ser Gly Glu Gln Lys
            915                 920                 925

Lys Ala Ile Val Asp Leu Leu Phe Lys Thr Asn Arg Lys Val Thr Val
    930                 935                 940

Lys Gln Leu Lys Glu Asp Tyr Phe Lys Lys Ile Glu Cys Phe Asp Ser
945                 950                 955                 960

Val Glu Ile Ser Gly Val Glu Asp Arg Phe Asn Ala Ser Leu Gly Thr
            965                 970                 975

Tyr His Asp Leu Leu Lys Ile Ile Lys Asp Lys Asp Phe Leu Asp Asn
            980                 985                 990

Glu Glu Asn Glu Asp Ile Leu Glu  Asp Ile Val Leu Thr  Leu Thr Leu
            995                 1000                1005

Phe Glu  Asp Arg Glu Met Ile  Glu Glu Arg Leu Lys  Thr Tyr Ala
    1010                1015                1020

His Leu  Phe Asp Asp Lys Val  Met Lys Gln Leu Lys  Arg Arg Arg
    1025                1030                1035

Tyr Thr  Gly Trp Gly Arg Leu  Ser Arg Lys Leu Ile  Asn Gly Ile
    1040                1045                1050

Arg Asp  Lys Gln Ser Gly Lys  Thr Ile Leu Asp Phe  Leu Lys Ser
    1055                1060                1065

Asp Gly  Phe Ala Asn Arg Asn  Phe Met Gln Leu Ile  His Asp Asp
    1070                1075                1080

Ser Leu  Thr Phe Lys Glu Asp  Ile Gln Lys Ala Gln  Val Ser Gly
    1085                1090                1095

Gln Gly  Asp Ser Leu His Glu  His Ile Ala Asn Leu  Ala Gly Ser
    1100                1105                1110

Pro Ala  Ile Lys Lys Gly Ile  Leu Gln Thr Val Lys  Val Val Asp
    1115                1120                1125

Glu Leu  Val Lys Val Met Gly  Arg His Lys Pro Glu  Asn Ile Val
    1130                1135                1140

Ile Glu  Met Ala Arg Glu Asn  Gln Thr Thr Gln Lys  Gly Gln Lys
    1145                1150                1155

Asn Ser  Arg Glu Arg Met Lys  Arg Ile Glu Glu Gly  Ile Lys Glu
    1160                1165                1170

Leu Gly  Ser Gln Ile Leu Lys  Glu His Pro Val Glu  Asn Thr Gln
    1175                1180                1185

Leu Gln  Asn Glu Lys Leu Tyr  Leu Tyr Tyr Leu Gln  Asn Gly Arg
    1190                1195                1200
```

-continued

```
Asp Met  Tyr Val Asp Gln Glu  Leu Asp Ile Asn Arg  Leu Ser Asp
    1205             1210              1215

Tyr Asp  Val Asp His Ile Val  Pro Gln Ser Phe Leu  Lys Asp Asp
    1220             1225              1230

Ser Ile  Asp Asn Lys Val Leu  Thr Arg Ser Asp Lys  Asn Arg Gly
    1235             1240              1245

Lys Ser  Asp Asn Val Pro Ser  Glu Glu Val Val Lys  Lys Met Lys
    1250             1255              1260

Asn Tyr  Trp Arg Gln Leu Leu  Asn Ala Lys Leu Ile  Thr Gln Arg
    1265             1270              1275

Lys Phe  Asp Asn Leu Thr Lys  Ala Glu Arg Gly Gly  Leu Ser Glu
    1280             1285              1290

Leu Asp  Lys Ala Gly Phe Ile  Lys Arg Gln Leu Val  Glu Thr Arg
    1295             1300              1305

Gln Ile  Thr Lys His Val Ala  Gln Ile Leu Asp Ser  Arg Met Asn
    1310             1315              1320

Thr Lys  Tyr Asp Glu Asn Asp  Lys Leu Ile Arg Glu  Val Lys Val
    1325             1330              1335

Ile Thr  Leu Lys Ser Lys Leu  Val Ser Asp Phe Arg  Lys Asp Phe
    1340             1345              1350

Gln Phe  Tyr Lys Val Arg Glu  Ile Asn Asn Tyr His  His Ala His
    1355             1360              1365

Asp Ala  Tyr Leu Asn Ala Val  Val Gly Thr Ala Leu  Ile Lys Lys
    1370             1375              1380

Tyr Pro  Lys Leu Glu Ser Glu  Phe Val Tyr Gly Asp  Tyr Lys Val
    1385             1390              1395

Tyr Asp  Val Arg Lys Met Ile  Ala Lys Ser Glu Gln  Glu Ile Gly
    1400             1405              1410

Lys Ala  Thr Ala Lys Tyr Phe  Phe Tyr Ser Asn Ile  Met Asn Phe
    1415             1420              1425

Phe Lys  Thr Glu Ile Thr Leu  Ala Asn Gly Glu Ile  Arg Lys Arg
    1430             1435              1440

Pro Leu  Ile Glu Thr Asn Gly  Glu Thr Gly Glu Ile  Val Trp Asp
    1445             1450              1455

Lys Gly  Arg Asp Phe Ala Thr  Val Arg Lys Val Leu  Ser Met Pro
    1460             1465              1470

Gln Val  Asn Ile Val Lys Lys  Thr Glu Val Gln Thr  Gly Gly Phe
    1475             1480              1485

Ser Lys  Glu Ser Ile Leu Pro  Lys Arg Asn Ser Asp  Lys Leu Ile
    1490             1495              1500

Ala Arg  Lys Lys Asp Trp Asp  Pro Lys Lys Tyr Gly  Gly Phe Asp
    1505             1510              1515

Ser Pro  Thr Val Ala Tyr Ser  Val Leu Val Val Ala  Lys Val Glu
    1520             1525              1530

Lys Gly  Lys Ser Lys Lys Leu  Lys Ser Val Lys Glu  Leu Leu Gly
    1535             1540              1545

Ile Thr  Ile Met Glu Arg Ser  Ser Phe Glu Lys Asn  Pro Ile Asp
    1550             1555              1560

Phe Leu  Glu Ala Lys Gly Tyr  Lys Glu Val Lys Lys  Asp Leu Ile
    1565             1570              1575

Ile Lys  Leu Pro Lys Tyr Ser  Leu Phe Glu Leu Glu  Asn Gly Arg
    1580             1585              1590

Lys Arg  Met Leu Ala Ser Ala  Gly Glu Leu Gln Lys  Gly Asn Glu
```

-continued

```
            1595                1600                1605

Leu Ala  Leu Pro Ser Lys Tyr  Val Asn Phe Leu Tyr  Leu Ala Ser
    1610                1615                1620

His Tyr  Glu Lys Leu Lys Gly  Ser Pro Glu Asp Asn  Glu Gln Lys
    1625                1630                1635

Gln Leu  Phe Val Glu Gln His  Lys His Tyr Leu Asp  Glu Ile Ile
    1640                1645                1650

Glu Gln  Ile Ser Glu Phe Ser  Lys Arg Val Ile Leu  Ala Asp Ala
    1655                1660                1665

Asn Leu  Asp Lys Val Leu Ser  Ala Tyr Asn Lys His  Arg Asp Lys
    1670                1675                1680

Pro Ile  Arg Glu Gln Ala Glu  Asn Ile Ile His Leu  Phe Thr Leu
    1685                1690                1695

Thr Asn  Leu Gly Ala Pro Ala  Ala Phe Lys Tyr Phe  Asp Thr Thr
    1700                1705                1710

Ile Asp  Arg Lys Arg Tyr Thr  Ser Thr Lys Glu Val  Leu Asp Ala
    1715                1720                1725

Thr Leu  Ile His Gln Ser Ile  Thr Gly Leu Tyr Glu  Thr Arg Ile
    1730                1735                1740

Asp Leu  Ser Gln Leu Gly Gly  Asp Ser Arg Ala Asp  Ser Gly Gly
    1745                1750                1755

Ser Thr  Asn Leu Ser Asp Ile  Ile Glu Lys Glu Thr  Gly Lys Gln
    1760                1765                1770

Leu Val  Ile Gln Glu Ser Ile  Leu Met Leu Pro Glu  Glu Val Glu
    1775                1780                1785

Glu Val  Ile Gly Asn Lys Pro  Glu Ser Asp Ile Leu  Val His Thr
    1790                1795                1800

Ala Tyr  Asp Glu Ser Thr Asp  Glu Asn Val Met Leu  Leu Thr Ser
    1805                1810                1815

Asp Ala  Pro Glu Tyr Lys Pro  Trp Ala Leu Val Ile  Gln Asp Ser
    1820                1825                1830

Asn Gly  Glu Asn Lys Ile Lys  Met Leu Ser Gly Gly  Ser Pro Lys
    1835                1840                1845

Lys Lys  Arg Lys Val
    1850
```

```
<210> SEQ ID NO 26
<211> LENGTH: 1858
<212> TYPE: PRT
<213> ORGANISM: Artificial Sequence
<220> FEATURE:
<223> OTHER INFORMATION: ABE-GGGGS4-UGI
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(389)
<223> OTHER INFORMATION: Linker region
<220> FEATURE:
<221> NAME/KEY: MISC_FEATURE
<222> LOCATION: (390)..(1760)
```

```
<223> OTHER INFORMATION: Cas9-D10A
<220> FEATURE:
<221> NAME/KEY: MISC_FEATURE
<222> LOCATION: (1761)..(1764)
<223> OTHER INFORMATION: Linker region
<220> FEATURE:
<221> NAME/KEY: MISC_FEATURE
<222> LOCATION: (1765)..(1847)
<223> OTHER INFORMATION: UGI Domain
<220> FEATURE:
<221> NAME/KEY: MISC_FEATURE
<222> LOCATION: (1848)..(1851)
<223> OTHER INFORMATION: Linker region
<220> FEATURE:
<221> NAME/KEY: MISC_FEATURE
<222> LOCATION: (1852)..(1858)
<223> OTHER INFORMATION: NLS

<400> SEQUENCE: 26

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
                20                  25                  30

Val Leu Val His Asn Asn Arg Val Ile Gly Glu Gly Trp Asn Arg Pro
            35                  40                  45

Ile Gly Arg His Asp Pro Thr Ala His Ala Glu Ile Met Ala Leu Arg
        50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
        130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
        210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
        275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320
```

-continued

```
Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ala Ser Gly
            355                 360                 365

Gly Gly Gly Ser Gly Gly Gly Gly Ser Gly Gly Gly Gly Ser Gly Gly
            370                 375                 380

Gly Gly Ser Gly Thr Asp Lys Lys Tyr Ser Ile Gly Leu Ala Ile Gly
385                 390                 395                 400

Thr Asn Ser Val Gly Trp Ala Val Ile Thr Asp Glu Tyr Lys Val Pro
                405                 410                 415

Ser Lys Lys Phe Lys Val Leu Gly Asn Thr Asp Arg His Ser Ile Lys
                420                 425                 430

Lys Asn Leu Ile Gly Ala Leu Leu Phe Asp Ser Gly Glu Thr Ala Glu
            435                 440                 445

Ala Thr Arg Leu Lys Arg Thr Ala Arg Arg Arg Tyr Thr Arg Arg Lys
            450                 455                 460

Asn Arg Ile Cys Tyr Leu Gln Glu Ile Phe Ser Asn Glu Met Ala Lys
465                 470                 475                 480

Val Asp Asp Ser Phe Phe His Arg Leu Glu Glu Ser Phe Leu Val Glu
                485                 490                 495

Glu Asp Lys Lys His Glu Arg His Pro Ile Phe Gly Asn Ile Val Asp
            500                 505                 510

Glu Val Ala Tyr His Glu Lys Tyr Pro Thr Ile Tyr His Leu Arg Lys
            515                 520                 525

Lys Leu Val Asp Ser Thr Asp Lys Ala Asp Leu Arg Leu Ile Tyr Leu
    530                 535                 540

Ala Leu Ala His Met Ile Lys Phe Arg Gly His Phe Leu Ile Glu Gly
545                 550                 555                 560

Asp Leu Asn Pro Asp Asn Ser Asp Val Asp Lys Leu Phe Ile Gln Leu
                565                 570                 575

Val Gln Thr Tyr Asn Gln Leu Phe Glu Glu Asn Pro Ile Asn Ala Ser
            580                 585                 590

Gly Val Asp Ala Lys Ala Ile Leu Ser Ala Arg Leu Ser Lys Ser Arg
            595                 600                 605

Arg Leu Glu Asn Leu Ile Ala Gln Leu Pro Gly Glu Lys Lys Asn Gly
    610                 615                 620

Leu Phe Gly Asn Leu Ile Ala Leu Ser Leu Gly Leu Thr Pro Asn Phe
625                 630                 635                 640

Lys Ser Asn Phe Asp Leu Ala Glu Asp Ala Lys Leu Gln Leu Ser Lys
                645                 650                 655

Asp Thr Tyr Asp Asp Asp Leu Asp Asn Leu Leu Ala Gln Ile Gly Asp
            660                 665                 670

Gln Tyr Ala Asp Leu Phe Leu Ala Ala Lys Asn Leu Ser Asp Ala Ile
            675                 680                 685

Leu Leu Ser Asp Ile Leu Arg Val Asn Thr Glu Ile Thr Lys Ala Pro
    690                 695                 700

Leu Ser Ala Ser Met Ile Lys Arg Tyr Asp Glu His His Gln Asp Leu
705                 710                 715                 720

Thr Leu Leu Lys Ala Leu Val Arg Gln Gln Leu Pro Glu Lys Tyr Lys
                725                 730                 735
```

Glu Ile Phe Phe Asp Gln Ser Lys Asn Gly Tyr Ala Gly Tyr Ile Asp
            740                 745                 750

Gly Gly Ala Ser Gln Glu Glu Phe Tyr Lys Phe Ile Lys Pro Ile Leu
        755                 760                 765

Glu Lys Met Asp Gly Thr Glu Glu Leu Leu Val Lys Leu Asn Arg Glu
    770                 775                 780

Asp Leu Leu Arg Lys Gln Arg Thr Phe Asp Asn Gly Ser Ile Pro His
785                 790                 795                 800

Gln Ile His Leu Gly Glu Leu His Ala Ile Leu Arg Arg Gln Glu Asp
                805                 810                 815

Phe Tyr Pro Phe Leu Lys Asp Asn Arg Glu Lys Ile Glu Lys Ile Leu
            820                 825                 830

Thr Phe Arg Ile Pro Tyr Tyr Val Gly Pro Leu Ala Arg Gly Asn Ser
        835                 840                 845

Arg Phe Ala Trp Met Thr Arg Lys Ser Glu Glu Thr Ile Thr Pro Trp
    850                 855                 860

Asn Phe Glu Glu Val Val Asp Lys Gly Ala Ser Ala Gln Ser Phe Ile
865                 870                 875                 880

Glu Arg Met Thr Asn Phe Asp Lys Asn Leu Pro Asn Glu Lys Val Leu
                885                 890                 895

Pro Lys His Ser Leu Leu Tyr Glu Tyr Phe Thr Val Tyr Asn Glu Leu
            900                 905                 910

Thr Lys Val Lys Tyr Val Thr Glu Gly Met Arg Lys Pro Ala Phe Leu
            915                 920                 925

Ser Gly Glu Gln Lys Lys Ala Ile Val Asp Leu Leu Phe Lys Thr Asn
    930                 935                 940

Arg Lys Val Thr Val Lys Gln Leu Lys Glu Asp Tyr Phe Lys Lys Ile
945                 950                 955                 960

Glu Cys Phe Asp Ser Val Glu Ile Ser Gly Val Glu Asp Arg Phe Asn
                965                 970                 975

Ala Ser Leu Gly Thr Tyr His Asp Leu Leu Lys Ile Ile Lys Asp Lys
            980                 985                 990

Asp Phe Leu Asp Asn Glu Glu Asn  Glu Asp Ile Leu Glu  Asp Ile Val
            995                 1000                1005

Leu Thr  Leu Thr Leu Phe Glu  Asp Arg Glu Met Ile  Glu Glu Arg
    1010                1015                1020

Leu Lys  Thr Tyr Ala His Leu  Phe Asp Asp Lys Val  Met Lys Gln
    1025                1030                1035

Leu Lys  Arg Arg Arg Tyr Thr  Gly Trp Gly Arg Leu  Ser Arg Lys
    1040                1045                1050

Leu Ile  Asn Gly Ile Arg Asp  Lys Gln Ser Gly Lys  Thr Ile Leu
    1055                1060                1065

Asp Phe  Leu Lys Ser Asp Gly  Phe Ala Asn Arg Asn  Phe Met Gln
    1070                1075                1080

Leu Ile  His Asp Asp Ser Leu  Thr Phe Lys Glu Asp  Ile Gln Lys
    1085                1090                1095

Ala Gln  Val Ser Gly Gln Gly  Asp Ser Leu His Glu  His Ile Ala
    1100                1105                1110

Asn Leu  Ala Gly Ser Pro Ala  Ile Lys Lys Gly Ile  Leu Gln Thr
    1115                1120                1125

Val Lys  Val Val Asp Glu Leu  Val Lys Val Met Gly  Arg His Lys
    1130                1135                1140

Pro Glu  Asn Ile Val Ile Glu  Met Ala Arg Glu Asn  Gln Thr Thr

-continued

```
            1145                    1150                    1155

Gln Lys  Gly Gln Lys Asn Ser  Arg Glu Arg Met Lys  Arg Ile Glu
    1160                1165                1170

Glu Gly  Ile Lys Glu Leu Gly  Ser Gln Ile Leu Lys  Glu His Pro
    1175                1180                1185

Val Glu  Asn Thr Gln Leu Gln  Asn Glu Lys Leu Tyr  Leu Tyr Tyr
    1190                1195                1200

Leu Gln  Asn Gly Arg Asp Met  Tyr Val Asp Gln Glu  Leu Asp Ile
    1205                1210                1215

Asn Arg  Leu Ser Asp Tyr Asp  Val Asp His Ile Val  Pro Gln Ser
    1220                1225                1230

Phe Leu  Lys Asp Asp Ser Ile  Asp Asn Lys Val Leu  Thr Arg Ser
    1235                1240                1245

Asp Lys  Asn Arg Gly Lys Ser  Asp Asn Val Pro Ser  Glu Glu Val
    1250                1255                1260

Val Lys  Lys Met Lys Asn Tyr  Trp Arg Gln Leu Leu  Asn Ala Lys
    1265                1270                1275

Leu Ile  Thr Gln Arg Lys Phe  Asp Asn Leu Thr Lys  Ala Glu Arg
    1280                1285                1290

Gly Gly  Leu Ser Glu Leu Asp  Lys Ala Gly Phe Ile  Lys Arg Gln
    1295                1300                1305

Leu Val  Glu Thr Arg Gln Ile  Thr Lys His Val Ala  Gln Ile Leu
    1310                1315                1320

Asp Ser  Arg Met Asn Thr Lys  Tyr Asp Glu Asn Asp  Lys Leu Ile
    1325                1330                1335

Arg Glu  Val Lys Val Ile Thr  Leu Lys Ser Lys Leu  Val Ser Asp
    1340                1345                1350

Phe Arg  Lys Asp Phe Gln Phe  Tyr Lys Val Arg Glu  Ile Asn Asn
    1355                1360                1365

Tyr His  His Ala His Asp Ala  Tyr Leu Asn Ala Val  Val Gly Thr
    1370                1375                1380

Ala Leu  Ile Lys Lys Tyr Pro  Lys Leu Glu Ser Glu  Phe Val Tyr
    1385                1390                1395

Gly Asp  Tyr Lys Val Tyr Asp  Val Arg Lys Met Ile  Ala Lys Ser
    1400                1405                1410

Glu Gln  Glu Ile Gly Lys Ala  Thr Ala Lys Tyr Phe  Phe Tyr Ser
    1415                1420                1425

Asn Ile  Met Asn Phe Phe Lys  Thr Glu Ile Thr Leu  Ala Asn Gly
    1430                1435                1440

Glu Ile  Arg Lys Arg Pro Leu  Ile Glu Thr Asn Gly  Glu Thr Gly
    1445                1450                1455

Glu Ile  Val Trp Asp Lys Gly  Arg Asp Phe Ala Thr  Val Arg Lys
    1460                1465                1470

Val Leu  Ser Met Pro Gln Val  Asn Ile Val Lys Lys  Thr Glu Val
    1475                1480                1485

Gln Thr  Gly Gly Phe Ser Lys  Glu Ser Ile Leu Pro  Lys Arg Asn
    1490                1495                1500

Ser Asp  Lys Leu Ile Ala Arg  Lys Lys Asp Trp Asp  Pro Lys Lys
    1505                1510                1515

Tyr Gly  Gly Phe Asp Ser Pro  Thr Val Ala Tyr Ser  Val Leu Val
    1520                1525                1530

Val Ala  Lys Val Glu Lys Gly  Lys Ser Lys Lys Leu  Lys Ser Val
    1535                1540                1545
```

-continued

```
Lys Glu  Leu Leu Gly Ile Thr  Ile Met Glu Arg Ser  Ser Phe Glu
    1550              1555          1560

Lys Asn  Pro Ile Asp Phe Leu  Glu Ala Lys Gly Tyr  Lys Glu Val
    1565              1570          1575

Lys Lys  Asp Leu Ile Ile Lys  Leu Pro Lys Tyr Ser  Leu Phe Glu
    1580              1585          1590

Leu Glu  Asn Gly Arg Lys Arg  Met Leu Ala Ser Ala  Gly Glu Leu
    1595              1600          1605

Gln Lys  Gly Asn Glu Leu Ala  Leu Pro Ser Lys Tyr  Val Asn Phe
    1610              1615          1620

Leu Tyr  Leu Ala Ser His Tyr  Glu Lys Leu Lys Gly  Ser Pro Glu
    1625              1630          1635

Asp Asn  Glu Gln Lys Gln Leu  Phe Val Glu Gln His  Lys His Tyr
    1640              1645          1650

Leu Asp  Glu Ile Ile Glu Gln  Ile Ser Glu Phe Ser  Lys Arg Val
    1655              1660          1665

Ile Leu  Ala Asp Ala Asn Leu  Asp Lys Val Leu Ser  Ala Tyr Asn
    1670              1675          1680

Lys His  Arg Asp Lys Pro Ile  Arg Glu Gln Ala Glu  Asn Ile Ile
    1685              1690          1695

His Leu  Phe Thr Leu Thr Asn  Leu Gly Ala Pro Ala  Ala Phe Lys
    1700              1705          1710

Tyr Phe  Asp Thr Thr Ile Asp  Arg Lys Arg Tyr Thr  Ser Thr Lys
    1715              1720          1725

Glu Val  Leu Asp Ala Thr Leu  Ile His Gln Ser Ile  Thr Gly Leu
    1730              1735          1740

Tyr Glu  Thr Arg Ile Asp Leu  Ser Gln Leu Gly Gly  Asp Ser Arg
    1745              1750          1755

Ala Asp  Ser Gly Gly Ser Thr  Asn Leu Ser Asp Ile  Ile Glu Lys
    1760              1765          1770

Glu Thr  Gly Lys Gln Leu Val  Ile Gln Glu Ser Ile  Leu Met Leu
    1775              1780          1785

Pro Glu  Glu Val Glu Glu Val  Ile Gly Asn Lys Pro  Glu Ser Asp
    1790              1795          1800

Ile Leu  Val His Thr Ala Tyr  Asp Glu Ser Thr Asp  Glu Asn Val
    1805              1810          1815

Met Leu  Leu Thr Ser Asp Ala  Pro Glu Tyr Lys Pro  Trp Ala Leu
    1820              1825          1830

Val Ile  Gln Asp Ser Asn Gly  Glu Asn Lys Ile Lys  Met Leu Ser
    1835              1840          1845

Gly Gly  Ser Pro Lys Lys Lys  Arg Lys Val
    1850              1855
```

```
<210> SEQ ID NO 27
<211> LENGTH: 1863
<212> TYPE: PRT
<213> ORGANISM: Artificial Sequence
<220> FEATURE:
<223> OTHER INFORMATION: ABE-GGGGS5-UGI
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
```

```
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(394)
<223> OTHER INFORMATION: Linker region
<220> FEATURE:
<221> NAME/KEY: MISC_FEATURE
<222> LOCATION: (395)..(1765)
<223> OTHER INFORMATION: Cas9-D10A
<220> FEATURE:
<221> NAME/KEY: MISC_FEATURE
<222> LOCATION: (1766)..(1769)
<223> OTHER INFORMATION: Linker region
<220> FEATURE:
<221> NAME/KEY: MISC_FEATURE
<222> LOCATION: (1770)..(1852)
<223> OTHER INFORMATION: UGI Domain
<220> FEATURE:
<221> NAME/KEY: MISC_FEATURE
<222> LOCATION: (1853)..(1856)
<223> OTHER INFORMATION: Linker region
<220> FEATURE:
<221> NAME/KEY: MISC_FEATURE
<222> LOCATION: (1857)..(1863)
<223> OTHER INFORMATION: NLS

<400> SEQUENCE: 27

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255
```

-continued

```
Glu Ile Met Ala Leu Arg Gln Gly Gly Leu Val Met Gln Asn Tyr Arg
        260             265             270

Leu Ile Asp Ala Thr Leu Tyr Val Thr Phe Glu Pro Cys Val Met Cys
        275             280             285

Ala Gly Ala Met Ile His Ser Arg Ile Gly Arg Val Val Phe Gly Val
        290             295             300

Arg Asn Ala Lys Thr Gly Ala Ala Gly Ser Leu Met Asp Val Leu His
305             310             315             320

Tyr Pro Gly Met Asn His Arg Val Glu Ile Thr Glu Gly Ile Leu Ala
            325             330             335

Asp Glu Cys Ala Ala Leu Leu Cys Tyr Phe Phe Arg Met Pro Arg Gln
            340             345             350

Val Phe Asn Ala Gln Lys Lys Ala Gln Ser Ser Thr Asp Ala Ser Gly
            355             360             365

Gly Gly Gly Ser Gly Gly Gly Gly Ser Gly Gly Gly Gly Ser Gly Gly
            370             375             380

Gly Gly Ser Gly Gly Gly Gly Ser Gly Thr Asp Lys Lys Tyr Ser Ile
385             390             395             400

Gly Leu Ala Ile Gly Thr Asn Ser Val Gly Trp Ala Val Ile Thr Asp
            405             410             415

Glu Tyr Lys Val Pro Ser Lys Lys Phe Lys Val Leu Gly Asn Thr Asp
            420             425             430

Arg His Ser Ile Lys Lys Asn Leu Ile Gly Ala Leu Leu Phe Asp Ser
            435             440             445

Gly Glu Thr Ala Glu Ala Thr Arg Leu Lys Arg Thr Ala Arg Arg Arg
            450             455             460

Tyr Thr Arg Arg Lys Asn Arg Ile Cys Tyr Leu Gln Glu Ile Phe Ser
465             470             475             480

Asn Glu Met Ala Lys Val Asp Asp Ser Phe Phe His Arg Leu Glu Glu
            485             490             495

Ser Phe Leu Val Glu Glu Asp Lys Lys His Glu Arg His Pro Ile Phe
            500             505             510

Gly Asn Ile Val Asp Glu Val Ala Tyr His Glu Lys Tyr Pro Thr Ile
            515             520             525

Tyr His Leu Arg Lys Lys Leu Val Asp Ser Thr Asp Lys Ala Asp Leu
        530             535             540

Arg Leu Ile Tyr Leu Ala Leu Ala His Met Ile Lys Phe Arg Gly His
545             550             555             560

Phe Leu Ile Glu Gly Asp Leu Asn Pro Asp Asn Ser Asp Val Asp Lys
            565             570             575

Leu Phe Ile Gln Leu Val Gln Thr Tyr Asn Gln Leu Phe Glu Glu Asn
            580             585             590

Pro Ile Asn Ala Ser Gly Val Asp Ala Lys Ala Ile Leu Ser Ala Arg
            595             600             605

Leu Ser Lys Ser Arg Arg Leu Glu Asn Leu Ile Ala Gln Leu Pro Gly
        610             615             620

Glu Lys Lys Asn Gly Leu Phe Gly Asn Leu Ile Ala Leu Ser Leu Gly
625             630             635             640

Leu Thr Pro Asn Phe Lys Ser Asn Phe Asp Leu Ala Glu Asp Ala Lys
            645             650             655

Leu Gln Leu Ser Lys Asp Thr Tyr Asp Asp Asp Leu Asp Asn Leu Leu
            660             665             670

Ala Gln Ile Gly Asp Gln Tyr Ala Asp Leu Phe Leu Ala Ala Lys Asn
```

-continued

```
              675                680                685

Leu Ser Asp Ala Ile Leu Leu Ser Asp Ile Leu Arg Val Asn Thr Glu
    690                695                700

Ile Thr Lys Ala Pro Leu Ser Ala Ser Met Ile Lys Arg Tyr Asp Glu
705                710                715                720

His His Gln Asp Leu Thr Leu Leu Lys Ala Leu Val Arg Gln Gln Leu
                  725                730                735

Pro Glu Lys Tyr Lys Glu Ile Phe Phe Asp Gln Ser Lys Asn Gly Tyr
              740                745                750

Ala Gly Tyr Ile Asp Gly Gly Ala Ser Gln Glu Glu Phe Tyr Lys Phe
              755                760                765

Ile Lys Pro Ile Leu Glu Lys Met Asp Gly Thr Glu Glu Leu Leu Val
    770                775                780

Lys Leu Asn Arg Glu Asp Leu Leu Arg Lys Gln Arg Thr Phe Asp Asn
785                790                795                800

Gly Ser Ile Pro His Gln Ile His Leu Gly Glu Leu His Ala Ile Leu
                  805                810                815

Arg Arg Gln Glu Asp Phe Tyr Pro Phe Leu Lys Asp Asn Arg Glu Lys
              820                825                830

Ile Glu Lys Ile Leu Thr Phe Arg Ile Pro Tyr Tyr Val Gly Pro Leu
              835                840                845

Ala Arg Gly Asn Ser Arg Phe Ala Trp Met Thr Arg Lys Ser Glu Glu
    850                855                860

Thr Ile Thr Pro Trp Asn Phe Glu Glu Val Val Asp Lys Gly Ala Ser
865                870                875                880

Ala Gln Ser Phe Ile Glu Arg Met Thr Asn Phe Asp Lys Asn Leu Pro
                  885                890                895

Asn Glu Lys Val Leu Pro Lys His Ser Leu Leu Tyr Glu Tyr Phe Thr
              900                905                910

Val Tyr Asn Glu Leu Thr Lys Val Lys Tyr Val Thr Glu Gly Met Arg
              915                920                925

Lys Pro Ala Phe Leu Ser Gly Glu Gln Lys Lys Ala Ile Val Asp Leu
    930                935                940

Leu Phe Lys Thr Asn Arg Lys Val Thr Val Lys Gln Leu Lys Glu Asp
945                950                955                960

Tyr Phe Lys Lys Ile Glu Cys Phe Asp Ser Val Glu Ile Ser Gly Val
                  965                970                975

Glu Asp Arg Phe Asn Ala Ser Leu Gly Thr Tyr His Asp Leu Leu Lys
              980                985                990

Ile Ile Lys Asp Lys Asp Phe Leu  Asp Asn Glu Glu Asn  Glu Asp Ile
              995                1000                1005

Leu Glu  Asp Ile Val Leu Thr  Leu Thr Leu Phe Glu  Asp Arg Glu
    1010                1015                1020

Met Ile  Glu Glu Arg Leu Lys  Thr Tyr Ala His Leu  Phe Asp Asp
    1025                1030                1035

Lys Val  Met Lys Gln Leu Lys  Arg Arg Arg Tyr Thr  Gly Trp Gly
    1040                1045                1050

Arg Leu  Ser Arg Lys Leu Ile  Asn Gly Ile Arg Asp  Lys Gln Ser
    1055                1060                1065

Gly Lys  Thr Ile Leu Asp Phe  Leu Lys Ser Asp Gly  Phe Ala Asn
    1070                1075                1080

Arg Asn  Phe Met Gln Leu Ile  His Asp Asp Ser Leu  Thr Phe Lys
    1085                1090                1095
```

-continued

```
Glu Asp  Ile Gln Lys Ala Gln  Val Ser Gly Gln Gly  Asp Ser Leu
    1100                1105                1110

His Glu  His Ile Ala Asn Leu  Ala Gly Ser Pro Ala  Ile Lys Lys
    1115                1120                1125

Gly Ile  Leu Gln Thr Val Lys  Val Val Asp Glu Leu  Val Lys Val
    1130                1135                1140

Met Gly  Arg His Lys Pro Glu  Asn Ile Val Ile Glu  Met Ala Arg
    1145                1150                1155

Glu Asn  Gln Thr Thr Gln Lys  Gly Gln Lys Asn Ser  Arg Glu Arg
    1160                1165                1170

Met Lys  Arg Ile Glu Glu Gly  Ile Lys Glu Leu Gly  Ser Gln Ile
    1175                1180                1185

Leu Lys  Glu His Pro Val Glu  Asn Thr Gln Leu Gln  Asn Glu Lys
    1190                1195                1200

Leu Tyr  Leu Tyr Tyr Leu Gln  Asn Gly Arg Asp Met  Tyr Val Asp
    1205                1210                1215

Gln Glu  Leu Asp Ile Asn Arg  Leu Ser Asp Tyr Asp  Val Asp His
    1220                1225                1230

Ile Val  Pro Gln Ser Phe Leu  Lys Asp Asp Ser Ile  Asp Asn Lys
    1235                1240                1245

Val Leu  Thr Arg Ser Asp Lys  Asn Arg Gly Lys Ser  Asp Asn Val
    1250                1255                1260

Pro Ser  Glu Glu Val Val Lys  Lys Met Lys Asn Tyr  Trp Arg Gln
    1265                1270                1275

Leu Leu  Asn Ala Lys Leu Ile  Thr Gln Arg Lys Phe  Asp Asn Leu
    1280                1285                1290

Thr Lys  Ala Glu Arg Gly Gly  Leu Ser Glu Leu Asp  Lys Ala Gly
    1295                1300                1305

Phe Ile  Lys Arg Gln Leu Val  Glu Thr Arg Gln Ile  Thr Lys His
    1310                1315                1320

Val Ala  Gln Ile Leu Asp Ser  Arg Met Asn Thr Lys  Tyr Asp Glu
    1325                1330                1335

Asn Asp  Lys Leu Ile Arg Glu  Val Lys Val Ile Thr  Leu Lys Ser
    1340                1345                1350

Lys Leu  Val Ser Asp Phe Arg  Lys Asp Phe Gln Phe  Tyr Lys Val
    1355                1360                1365

Arg Glu  Ile Asn Asn Tyr His  His Ala His Asp Ala  Tyr Leu Asn
    1370                1375                1380

Ala Val  Val Gly Thr Ala Leu  Ile Lys Lys Tyr Pro  Lys Leu Glu
    1385                1390                1395

Ser Glu  Phe Val Tyr Gly Asp  Tyr Lys Val Tyr Asp  Val Arg Lys
    1400                1405                1410

Met Ile  Ala Lys Ser Glu Gln  Glu Ile Gly Lys Ala  Thr Ala Lys
    1415                1420                1425

Tyr Phe  Phe Tyr Ser Asn Ile  Met Asn Phe Phe Lys  Thr Glu Ile
    1430                1435                1440

Thr Leu  Ala Asn Gly Glu Ile  Arg Lys Arg Pro Leu  Ile Glu Thr
    1445                1450                1455

Asn Gly  Glu Thr Gly Glu Ile  Val Trp Asp Lys Gly  Arg Asp Phe
    1460                1465                1470

Ala Thr  Val Arg Lys Val Leu  Ser Met Pro Gln Val  Asn Ile Val
    1475                1480                1485
```

-continued

```
Lys Lys Thr Glu Val Gln Thr Gly Gly Phe Ser Lys Glu Ser Ile
    1490                1495                1500

Leu Pro Lys Arg Asn Ser Asp Lys Leu Ile Ala Arg Lys Lys Asp
    1505                1510                1515

Trp Asp Pro Lys Lys Tyr Gly Gly Phe Asp Ser Pro Thr Val Ala
    1520                1525                1530

Tyr Ser Val Leu Val Val Ala Lys Val Glu Lys Gly Lys Ser Lys
    1535                1540                1545

Lys Leu Lys Ser Val Lys Glu Leu Leu Gly Ile Thr Ile Met Glu
    1550                1555                1560

Arg Ser Ser Phe Glu Lys Asn Pro Ile Asp Phe Leu Glu Ala Lys
    1565                1570                1575

Gly Tyr Lys Glu Val Lys Lys Asp Leu Ile Ile Lys Leu Pro Lys
    1580                1585                1590

Tyr Ser Leu Phe Glu Leu Glu Asn Gly Arg Lys Arg Met Leu Ala
    1595                1600                1605

Ser Ala Gly Glu Leu Gln Lys Gly Asn Glu Leu Ala Leu Pro Ser
    1610                1615                1620

Lys Tyr Val Asn Phe Leu Tyr Leu Ala Ser His Tyr Glu Lys Leu
    1625                1630                1635

Lys Gly Ser Pro Glu Asp Asn Glu Gln Lys Gln Leu Phe Val Glu
    1640                1645                1650

Gln His Lys His Tyr Leu Asp Glu Ile Ile Glu Gln Ile Ser Glu
    1655                1660                1665

Phe Ser Lys Arg Val Ile Leu Ala Asp Ala Asn Leu Asp Lys Val
    1670                1675                1680

Leu Ser Ala Tyr Asn Lys His Arg Asp Lys Pro Ile Arg Glu Gln
    1685                1690                1695

Ala Glu Asn Ile Ile His Leu Phe Thr Leu Thr Asn Leu Gly Ala
    1700                1705                1710

Pro Ala Ala Phe Lys Tyr Phe Asp Thr Thr Ile Asp Arg Lys Arg
    1715                1720                1725

Tyr Thr Ser Thr Lys Glu Val Leu Asp Ala Thr Leu Ile His Gln
    1730                1735                1740

Ser Ile Thr Gly Leu Tyr Glu Thr Arg Ile Asp Leu Ser Gln Leu
    1745                1750                1755

Gly Gly Asp Ser Arg Ala Asp Ser Gly Gly Ser Thr Asn Leu Ser
    1760                1765                1770

Asp Ile Ile Glu Lys Glu Thr Gly Lys Gln Leu Val Ile Gln Glu
    1775                1780                1785

Ser Ile Leu Met Leu Pro Glu Glu Val Glu Glu Val Ile Gly Asn
    1790                1795                1800

Lys Pro Glu Ser Asp Ile Leu Val His Thr Ala Tyr Asp Glu Ser
    1805                1810                1815

Thr Asp Glu Asn Val Met Leu Leu Thr Ser Asp Ala Pro Glu Tyr
    1820                1825                1830

Lys Pro Trp Ala Leu Val Ile Gln Asp Ser Asn Gly Glu Asn Lys
    1835                1840                1845

Ile Lys Met Leu Ser Gly Gly Ser Pro Lys Lys Lys Arg Lys Val
    1850                1855                1860
```

<210> SEQ ID NO 28
<211> LENGTH: 1868
<212> TYPE: PRT

```
<213> ORGANISM: Artificial Sequence
<220> FEATURE:
<223> OTHER INFORMATION: ABE-GGGGS6-UGI
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(399)
<223> OTHER INFORMATION: Linker region
<220> FEATURE:
<221> NAME/KEY: MISC_FEATURE
<222> LOCATION: (400)..(1770)
<223> OTHER INFORMATION: Cas9-D10A
<220> FEATURE:
<221> NAME/KEY: MISC_FEATURE
<222> LOCATION: (1771)..(1774)
<223> OTHER INFORMATION: Linker region
<220> FEATURE:
<221> NAME/KEY: MISC_FEATURE
<222> LOCATION: (1775)..(1857)
<223> OTHER INFORMATION: UGI Domain
<220> FEATURE:
<221> NAME/KEY: MISC_FEATURE
<222> LOCATION: (1858)..(1861)
<223> OTHER INFORMATION: Linker region
<220> FEATURE:
<221> NAME/KEY: MISC_FEATURE
<222> LOCATION: (1862)..(1868)
<223> OTHER INFORMATION: NLS

<400> SEQUENCE: 28

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
```

-continued

```
                195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
                260                 265                 270

Leu Ile Asp Ala Thr Leu Tyr Val Thr Phe Glu Pro Cys Val Met Cys
                275                 280                 285

Ala Gly Ala Met Ile His Ser Arg Ile Gly Arg Val Val Phe Gly Val
                290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
                340                 345                 350

Val Phe Asn Ala Gln Lys Lys Ala Gln Ser Ser Thr Asp Ala Ser Gly
                355                 360                 365

Gly Gly Gly Ser Gly Gly Gly Gly Ser Gly Gly Gly Gly Ser Gly Gly
    370                 375                 380

Gly Gly Ser Gly Gly Gly Gly Ser Gly Gly Gly Gly Ser Gly Thr Asp
385                 390                 395                 400

Lys Lys Tyr Ser Ile Gly Leu Ala Ile Gly Thr Asn Ser Val Gly Trp
                405                 410                 415

Ala Val Ile Thr Asp Glu Tyr Lys Val Pro Ser Lys Lys Phe Lys Val
                420                 425                 430

Leu Gly Asn Thr Asp Arg His Ser Ile Lys Lys Asn Leu Ile Gly Ala
    435                 440                 445

Leu Leu Phe Asp Ser Gly Glu Thr Ala Glu Ala Thr Arg Leu Lys Arg
    450                 455                 460

Thr Ala Arg Arg Arg Tyr Thr Arg Arg Lys Asn Arg Ile Cys Tyr Leu
465                 470                 475                 480

Gln Glu Ile Phe Ser Asn Glu Met Ala Lys Val Asp Asp Ser Phe Phe
                485                 490                 495

His Arg Leu Glu Glu Ser Phe Leu Val Glu Glu Asp Lys Lys His Glu
                500                 505                 510

Arg His Pro Ile Phe Gly Asn Ile Val Asp Glu Val Ala Tyr His Glu
                515                 520                 525

Lys Tyr Pro Thr Ile Tyr His Leu Arg Lys Lys Leu Val Asp Ser Thr
    530                 535                 540

Asp Lys Ala Asp Leu Arg Leu Ile Tyr Leu Ala Leu Ala His Met Ile
545                 550                 555                 560

Lys Phe Arg Gly His Phe Leu Ile Glu Gly Asp Leu Asn Pro Asp Asn
                565                 570                 575

Ser Asp Val Asp Lys Leu Phe Ile Gln Leu Val Gln Thr Tyr Asn Gln
                580                 585                 590

Leu Phe Glu Glu Asn Pro Ile Asn Ala Ser Gly Val Asp Ala Lys Ala
                595                 600                 605

Ile Leu Ser Ala Arg Leu Ser Lys Ser Arg Arg Leu Glu Asn Leu Ile
    610                 615                 620
```

Ala Gln Leu Pro Gly Glu Lys Lys Asn Gly Leu Phe Gly Asn Leu Ile
625                 630                 635                 640

Ala Leu Ser Leu Gly Leu Thr Pro Asn Phe Lys Ser Asn Phe Asp Leu
                645                 650                 655

Ala Glu Asp Ala Lys Leu Gln Leu Ser Lys Asp Thr Tyr Asp Asp Asp
                660                 665                 670

Leu Asp Asn Leu Leu Ala Gln Ile Gly Asp Gln Tyr Ala Asp Leu Phe
                675                 680                 685

Leu Ala Ala Lys Asn Leu Ser Asp Ala Ile Leu Leu Ser Asp Ile Leu
                690                 695                 700

Arg Val Asn Thr Glu Ile Thr Lys Ala Pro Leu Ser Ala Ser Met Ile
705                 710                 715                 720

Lys Arg Tyr Asp Glu His His Gln Asp Leu Thr Leu Leu Lys Ala Leu
                725                 730                 735

Val Arg Gln Gln Leu Pro Glu Lys Tyr Lys Glu Ile Phe Phe Asp Gln
                740                 745                 750

Ser Lys Asn Gly Tyr Ala Gly Tyr Ile Asp Gly Gly Ala Ser Gln Glu
                755                 760                 765

Glu Phe Tyr Lys Phe Ile Lys Pro Ile Leu Glu Lys Met Asp Gly Thr
                770                 775                 780

Glu Glu Leu Leu Val Lys Leu Asn Arg Glu Asp Leu Leu Arg Lys Gln
785                 790                 795                 800

Arg Thr Phe Asp Asn Gly Ser Ile Pro His Gln Ile His Leu Gly Glu
                805                 810                 815

Leu His Ala Ile Leu Arg Arg Gln Glu Asp Phe Tyr Pro Phe Leu Lys
                820                 825                 830

Asp Asn Arg Glu Lys Ile Glu Lys Ile Leu Thr Phe Arg Ile Pro Tyr
                835                 840                 845

Tyr Val Gly Pro Leu Ala Arg Gly Asn Ser Arg Phe Ala Trp Met Thr
850                 855                 860

Arg Lys Ser Glu Glu Thr Ile Thr Pro Trp Asn Phe Glu Glu Val Val
865                 870                 875                 880

Asp Lys Gly Ala Ser Ala Gln Ser Phe Ile Glu Arg Met Thr Asn Phe
                885                 890                 895

Asp Lys Asn Leu Pro Asn Glu Lys Val Leu Pro Lys His Ser Leu Leu
                900                 905                 910

Tyr Glu Tyr Phe Thr Val Tyr Asn Glu Leu Thr Lys Val Lys Tyr Val
                915                 920                 925

Thr Glu Gly Met Arg Lys Pro Ala Phe Leu Ser Gly Glu Gln Lys Lys
                930                 935                 940

Ala Ile Val Asp Leu Leu Phe Lys Thr Asn Arg Lys Val Thr Val Lys
945                 950                 955                 960

Gln Leu Lys Glu Asp Tyr Phe Lys Lys Ile Glu Cys Phe Asp Ser Val
                965                 970                 975

Glu Ile Ser Gly Val Glu Asp Arg Phe Asn Ala Ser Leu Gly Thr Tyr
                980                 985                 990

His Asp Leu Leu Lys Ile Ile Lys Asp Lys Asp Phe Leu Asp Asn Glu
                995                 1000                1005

Glu Asn Glu Asp Ile Leu Glu Asp Ile Val Leu Thr Leu Thr Leu
        1010                1015                1020

Phe Glu Asp Arg Glu Met Ile Glu Glu Arg Leu Lys Thr Tyr Ala
        1025                1030                1035

-continued

```
His Leu  Phe Asp Asp Lys Val  Met Lys Gln Leu Lys  Arg Arg Arg
    1040             1045              1050

Tyr Thr  Gly Trp Gly Arg Leu  Ser Arg Lys Leu Ile  Asn Gly Ile
    1055             1060              1065

Arg Asp  Lys Gln Ser Gly Lys  Thr Ile Leu Asp Phe  Leu Lys Ser
    1070             1075              1080

Asp Gly  Phe Ala Asn Arg Asn  Phe Met Gln Leu Ile  His Asp Asp
    1085             1090              1095

Ser Leu  Thr Phe Lys Glu Asp  Ile Gln Lys Ala Gln  Val Ser Gly
    1100             1105              1110

Gln Gly  Asp Ser Leu His Glu  His Ile Ala Asn Leu  Ala Gly Ser
    1115             1120              1125

Pro Ala  Ile Lys Lys Gly Ile  Leu Gln Thr Val Lys  Val Val Asp
    1130             1135              1140

Glu Leu  Val Lys Val Met Gly  Arg His Lys Pro Glu  Asn Ile Val
    1145             1150              1155

Ile Glu  Met Ala Arg Glu Asn  Gln Thr Thr Gln Lys  Gly Gln Lys
    1160             1165              1170

Asn Ser  Arg Glu Arg Met Lys  Arg Ile Glu Glu Gly  Ile Lys Glu
    1175             1180              1185

Leu Gly  Ser Gln Ile Leu Lys  Glu His Pro Val Glu  Asn Thr Gln
    1190             1195              1200

Leu Gln  Asn Glu Lys Leu Tyr  Leu Tyr Tyr Leu Gln  Asn Gly Arg
    1205             1210              1215

Asp Met  Tyr Val Asp Gln Glu  Leu Asp Ile Asn Arg  Leu Ser Asp
    1220             1225              1230

Tyr Asp  Val Asp His Ile Val  Pro Gln Ser Phe Leu  Lys Asp Asp
    1235             1240              1245

Ser Ile  Asp Asn Lys Val Leu  Thr Arg Ser Asp Lys  Asn Arg Gly
    1250             1255              1260

Lys Ser  Asp Asn Val Pro Ser  Glu Glu Val Val Lys  Lys Met Lys
    1265             1270              1275

Asn Tyr  Trp Arg Gln Leu Leu  Asn Ala Lys Leu Ile  Thr Gln Arg
    1280             1285              1290

Lys Phe  Asp Asn Leu Thr Lys  Ala Glu Arg Gly Gly  Leu Ser Glu
    1295             1300              1305

Leu Asp  Lys Ala Gly Phe Ile  Lys Arg Gln Leu Val  Glu Thr Arg
    1310             1315              1320

Gln Ile  Thr Lys His Val Ala  Gln Ile Leu Asp Ser  Arg Met Asn
    1325             1330              1335

Thr Lys  Tyr Asp Glu Asn Asp  Lys Leu Ile Arg Glu  Val Lys Val
    1340             1345              1350

Ile Thr  Leu Lys Ser Lys Leu  Val Ser Asp Phe Arg  Lys Asp Phe
    1355             1360              1365

Gln Phe  Tyr Lys Val Arg Glu  Ile Asn Asn Tyr His  His Ala His
    1370             1375              1380

Asp Ala  Tyr Leu Asn Ala Val  Val Gly Thr Ala Leu  Ile Lys Lys
    1385             1390              1395

Tyr Pro  Lys Leu Glu Ser Glu  Phe Val Tyr Gly Asp  Tyr Lys Val
    1400             1405              1410

Tyr Asp  Val Arg Lys Met Ile  Ala Lys Ser Glu Gln  Glu Ile Gly
    1415             1420              1425

Lys Ala  Thr Ala Lys Tyr Phe  Phe Tyr Ser Asn Ile  Met Asn Phe
```

-continued

```
        1430                1435                1440

Phe Lys Thr Glu Ile Thr Leu  Ala Asn Gly Glu Ile  Arg Lys Arg
    1445                1450                1455

Pro Leu Ile Glu Thr Asn Gly  Glu Thr Gly Glu Ile  Val Trp Asp
    1460                1465                1470

Lys Gly Arg Asp Phe Ala Thr  Val Arg Lys Val Leu  Ser Met Pro
    1475                1480                1485

Gln Val Asn Ile Val Lys Lys  Thr Glu Val Gln Thr  Gly Gly Phe
    1490                1495                1500

Ser Lys Glu Ser Ile Leu Pro  Lys Arg Asn Ser Asp  Lys Leu Ile
    1505                1510                1515

Ala Arg Lys Lys Asp Trp Asp  Pro Lys Lys Tyr Gly  Gly Phe Asp
    1520                1525                1530

Ser Pro Thr Val Ala Tyr Ser  Val Leu Val Val Ala  Lys Val Glu
    1535                1540                1545

Lys Gly Lys Ser Lys Lys Leu  Lys Ser Val Lys Glu  Leu Leu Gly
    1550                1555                1560

Ile Thr Ile Met Glu Arg Ser  Ser Phe Glu Lys Asn  Pro Ile Asp
    1565                1570                1575

Phe Leu Glu Ala Lys Gly Tyr  Lys Glu Val Lys Lys  Asp Leu Ile
    1580                1585                1590

Ile Lys Leu Pro Lys Tyr Ser  Leu Phe Glu Leu Glu  Asn Gly Arg
    1595                1600                1605

Lys Arg Met Leu Ala Ser Ala  Gly Glu Leu Gln Lys  Gly Asn Glu
    1610                1615                1620

Leu Ala Leu Pro Ser Lys Tyr  Val Asn Phe Leu Tyr  Leu Ala Ser
    1625                1630                1635

His Tyr Glu Lys Leu Lys Gly  Ser Pro Glu Asp Asn  Glu Gln Lys
    1640                1645                1650

Gln Leu Phe Val Glu Gln His  Lys His Tyr Leu Asp  Glu Ile Ile
    1655                1660                1665

Glu Gln Ile Ser Glu Phe Ser  Lys Arg Val Ile Leu  Ala Asp Ala
    1670                1675                1680

Asn Leu Asp Lys Val Leu Ser  Ala Tyr Asn Lys His  Arg Asp Lys
    1685                1690                1695

Pro Ile Arg Glu Gln Ala Glu  Asn Ile Ile His Leu  Phe Thr Leu
    1700                1705                1710

Thr Asn Leu Gly Ala Pro Ala  Ala Phe Lys Tyr Phe  Asp Thr Thr
    1715                1720                1725

Ile Asp Arg Lys Arg Tyr Thr  Ser Thr Lys Glu Val  Leu Asp Ala
    1730                1735                1740

Thr Leu Ile His Gln Ser Ile  Thr Gly Leu Tyr Glu  Thr Arg Ile
    1745                1750                1755

Asp Leu Ser Gln Leu Gly Gly  Asp Ser Arg Ala Asp  Ser Gly Gly
    1760                1765                1770

Ser Thr Asn Leu Ser Asp Ile  Ile Glu Lys Glu Thr  Gly Lys Gln
    1775                1780                1785

Leu Val Ile Gln Glu Ser Ile  Leu Met Leu Pro Glu  Glu Val Glu
    1790                1795                1800

Glu Val Ile Gly Asn Lys Pro  Glu Ser Asp Ile Leu  Val His Thr
    1805                1810                1815

Ala Tyr Asp Glu Ser Thr Asp  Glu Asn Val Met Leu  Leu Thr Ser
    1820                1825                1830
```

-continued

```
Asp Ala  Pro Glu Tyr Lys Pro  Trp Ala Leu Val Ile  Gln Asp Ser
    1835             1840                1845

Asn Gly  Glu Asn Lys Ile Lys  Met Leu Ser Gly Gly  Ser Pro Lys
    1850             1855                1860

Lys Lys  Arg Lys Val
    1865
```

```
<210> SEQ ID NO 29
<211> LENGTH: 1873
<212> TYPE: PRT
<213> ORGANISM: Artificial Sequence
<220> FEATURE:
<223> OTHER INFORMATION: ABE-GGGGS7-UGI
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(404)
<223> OTHER INFORMATION: Linker region
<220> FEATURE:
<221> NAME/KEY: MISC_FEATURE
<222> LOCATION: (405)..(1775)
<223> OTHER INFORMATION: Cas9-D10A
<220> FEATURE:
<221> NAME/KEY: MISC_FEATURE
<222> LOCATION: (1776)..(1779)
<223> OTHER INFORMATION: Linker region
<220> FEATURE:
<221> NAME/KEY: MISC_FEATURE
<222> LOCATION: (1780)..(1862)
<223> OTHER INFORMATION: UGI Domain
<220> FEATURE:
<221> NAME/KEY: MISC_FEATURE
<222> LOCATION: (1863)..(1866)
<223> OTHER INFORMATION: Linker region
<220> FEATURE:
<221> NAME/KEY: MISC_FEATURE
<222> LOCATION: (1867)..(1873)
<223> OTHER INFORMATION: NLS

<400> SEQUENCE: 29

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125
```

-continued

```
Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
                180                 185                 190

Gly Gly Ser Ser Gly Gly Ser Ser Glu Val Glu Phe Ser His Glu Tyr
                195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
                260                 265                 270

Leu Ile Asp Ala Thr Leu Tyr Val Thr Phe Glu Pro Cys Val Met Cys
                275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
                340                 345                 350

Val Phe Asn Ala Gln Lys Lys Ala Gln Ser Ser Thr Asp Ala Ser Gly
                355                 360                 365

Gly Gly Gly Ser Gly Gly Gly Gly Ser Gly Gly Gly Gly Ser Gly Gly
    370                 375                 380

Gly Gly Ser Gly Gly Gly Gly Ser Gly Gly Gly Gly Ser Gly Gly Gly
385                 390                 395                 400

Gly Ser Gly Thr Asp Lys Lys Tyr Ser Ile Gly Leu Ala Ile Gly Thr
                405                 410                 415

Asn Ser Val Gly Trp Ala Val Ile Thr Asp Glu Tyr Lys Val Pro Ser
                420                 425                 430

Lys Lys Phe Lys Val Leu Gly Asn Thr Asp Arg His Ser Ile Lys Lys
                435                 440                 445

Asn Leu Ile Gly Ala Leu Leu Phe Asp Ser Gly Glu Thr Ala Glu Ala
    450                 455                 460

Thr Arg Leu Lys Arg Thr Ala Arg Arg Arg Tyr Thr Arg Arg Lys Asn
465                 470                 475                 480

Arg Ile Cys Tyr Leu Gln Glu Ile Phe Ser Asn Glu Met Ala Lys Val
                485                 490                 495

Asp Asp Ser Phe Phe His Arg Leu Glu Glu Ser Phe Leu Val Glu Glu
                500                 505                 510

Asp Lys Lys His Glu Arg His Pro Ile Phe Gly Asn Ile Val Asp Glu
                515                 520                 525

Val Ala Tyr His Glu Lys Tyr Pro Thr Ile Tyr His Leu Arg Lys Lys
    530                 535                 540
```

-continued

```
Leu Val Asp Ser Thr Asp Lys Ala Asp Leu Arg Leu Ile Tyr Leu Ala
545                 550                 555                 560

Leu Ala His Met Ile Lys Phe Arg Gly His Phe Leu Ile Glu Gly Asp
                565                 570                 575

Leu Asn Pro Asp Asn Ser Asp Val Asp Lys Leu Phe Ile Gln Leu Val
                580                 585                 590

Gln Thr Tyr Asn Gln Leu Phe Glu Glu Asn Pro Ile Asn Ala Ser Gly
            595                 600                 605

Val Asp Ala Lys Ala Ile Leu Ser Ala Arg Leu Ser Lys Ser Arg Arg
        610                 615                 620

Leu Glu Asn Leu Ile Ala Gln Leu Pro Gly Glu Lys Lys Asn Gly Leu
625                 630                 635                 640

Phe Gly Asn Leu Ile Ala Leu Ser Leu Gly Leu Thr Pro Asn Phe Lys
                645                 650                 655

Ser Asn Phe Asp Leu Ala Glu Asp Ala Lys Leu Gln Leu Ser Lys Asp
                660                 665                 670

Thr Tyr Asp Asp Asp Leu Asp Asn Leu Leu Ala Gln Ile Gly Asp Gln
            675                 680                 685

Tyr Ala Asp Leu Phe Leu Ala Ala Lys Asn Leu Ser Asp Ala Ile Leu
        690                 695                 700

Leu Ser Asp Ile Leu Arg Val Asn Thr Glu Ile Thr Lys Ala Pro Leu
705                 710                 715                 720

Ser Ala Ser Met Ile Lys Arg Tyr Asp Glu His His Gln Asp Leu Thr
                725                 730                 735

Leu Leu Lys Ala Leu Val Arg Gln Gln Leu Pro Glu Lys Tyr Lys Glu
                740                 745                 750

Ile Phe Phe Asp Gln Ser Lys Asn Gly Tyr Ala Gly Tyr Ile Asp Gly
            755                 760                 765

Gly Ala Ser Gln Glu Glu Phe Tyr Lys Phe Ile Lys Pro Ile Leu Glu
        770                 775                 780

Lys Met Asp Gly Thr Glu Glu Leu Leu Val Lys Leu Asn Arg Glu Asp
785                 790                 795                 800

Leu Leu Arg Lys Gln Arg Thr Phe Asp Asn Gly Ser Ile Pro His Gln
                805                 810                 815

Ile His Leu Gly Glu Leu His Ala Ile Leu Arg Arg Gln Glu Asp Phe
                820                 825                 830

Tyr Pro Phe Leu Lys Asp Asn Arg Glu Lys Ile Glu Lys Ile Leu Thr
            835                 840                 845

Phe Arg Ile Pro Tyr Tyr Val Gly Pro Leu Ala Arg Gly Asn Ser Arg
        850                 855                 860

Phe Ala Trp Met Thr Arg Lys Ser Glu Glu Thr Ile Thr Pro Trp Asn
865                 870                 875                 880

Phe Glu Glu Val Val Asp Lys Gly Ala Ser Ala Gln Ser Phe Ile Glu
                885                 890                 895

Arg Met Thr Asn Phe Asp Lys Asn Leu Pro Asn Glu Lys Val Leu Pro
                900                 905                 910

Lys His Ser Leu Leu Tyr Glu Tyr Phe Thr Val Tyr Asn Glu Leu Thr
            915                 920                 925

Lys Val Lys Tyr Val Thr Glu Gly Met Arg Lys Pro Ala Phe Leu Ser
        930                 935                 940

Gly Glu Gln Lys Lys Ala Ile Val Asp Leu Leu Phe Lys Thr Asn Arg
945                 950                 955                 960

Lys Val Thr Val Lys Gln Leu Lys Glu Asp Tyr Phe Lys Lys Ile Glu
```

-continued

```
                965             970             975

Cys Phe Asp Ser Val Glu Ile Ser Gly Val Glu Asp Arg Phe Asn Ala
            980             985             990

Ser Leu Gly Thr Tyr His Asp Leu  Leu Lys Ile Ile Lys  Asp Lys Asp
        995             1000            1005

Phe Leu Asp Asn Glu Glu Asn  Glu Asp Ile Leu Glu  Asp Ile Val
    1010            1015            1020

Leu Thr  Leu Thr Leu Phe Glu  Asp Arg Glu Met Ile  Glu Glu Arg
    1025            1030            1035

Leu Lys  Thr Tyr Ala His Leu  Phe Asp Asp Lys Val  Met Lys Gln
    1040            1045            1050

Leu Lys  Arg Arg Arg Tyr Thr  Gly Trp Gly Arg Leu  Ser Arg Lys
    1055            1060            1065

Leu Ile  Asn Gly Ile Arg Asp  Lys Gln Ser Gly Lys  Thr Ile Leu
    1070            1075            1080

Asp Phe  Leu Lys Ser Asp Gly  Phe Ala Asn Arg Asn  Phe Met Gln
    1085            1090            1095

Leu Ile  His Asp Asp Ser Leu  Thr Phe Lys Glu Asp  Ile Gln Lys
    1100            1105            1110

Ala Gln  Val Ser Gly Gln Gly  Asp Ser Leu His Glu  His Ile Ala
    1115            1120            1125

Asn Leu  Ala Gly Ser Pro Ala  Ile Lys Lys Gly Ile  Leu Gln Thr
    1130            1135            1140

Val Lys  Val Val Asp Glu Leu  Val Lys Val Met Gly  Arg His Lys
    1145            1150            1155

Pro Glu  Asn Ile Val Ile Glu  Met Ala Arg Glu Asn  Gln Thr Thr
    1160            1165            1170

Gln Lys  Gly Gln Lys Asn Ser  Arg Glu Arg Met Lys  Arg Ile Glu
    1175            1180            1185

Glu Gly  Ile Lys Glu Leu Gly  Ser Gln Ile Leu Lys  Glu His Pro
    1190            1195            1200

Val Glu  Asn Thr Gln Leu Gln  Asn Glu Lys Leu Tyr  Leu Tyr Tyr
    1205            1210            1215

Leu Gln  Asn Gly Arg Asp Met  Tyr Val Asp Gln Glu  Leu Asp Ile
    1220            1225            1230

Asn Arg  Leu Ser Asp Tyr Asp  Val Asp His Ile Val  Pro Gln Ser
    1235            1240            1245

Phe Leu  Lys Asp Asp Ser Ile  Asp Asn Lys Val Leu  Thr Arg Ser
    1250            1255            1260

Asp Lys  Asn Arg Gly Lys Ser  Asp Asn Val Pro Ser  Glu Glu Val
    1265            1270            1275

Val Lys  Lys Met Lys Asn Tyr  Trp Arg Gln Leu Leu  Asn Ala Lys
    1280            1285            1290

Leu Ile  Thr Gln Arg Lys Phe  Asp Asn Leu Thr Lys  Ala Glu Arg
    1295            1300            1305

Gly Gly  Leu Ser Glu Leu Asp  Lys Ala Gly Phe Ile  Lys Arg Gln
    1310            1315            1320

Leu Val  Glu Thr Arg Gln Ile  Thr Lys His Val Ala  Gln Ile Leu
    1325            1330            1335

Asp Ser  Arg Met Asn Thr Lys  Tyr Asp Glu Asn Asp  Lys Leu Ile
    1340            1345            1350

Arg Glu  Val Lys Val Ile Thr  Leu Lys Ser Lys Leu  Val Ser Asp
    1355            1360            1365
```

-continued

```
Phe Arg Lys Asp Phe Gln Phe  Tyr Lys Val Arg Glu  Ile Asn Asn
    1370            1375            1380

Tyr His  His Ala His Asp Ala  Tyr Leu Asn Ala Val  Val Gly Thr
    1385            1390            1395

Ala Leu  Ile Lys Lys Tyr Pro  Lys Leu Glu Ser Glu  Phe Val Tyr
    1400            1405            1410

Gly Asp  Tyr Lys Val Tyr Asp  Val Arg Lys Met Ile  Ala Lys Ser
    1415            1420            1425

Glu Gln  Glu Ile Gly Lys Ala  Thr Ala Lys Tyr Phe  Phe Tyr Ser
    1430            1435            1440

Asn Ile  Met Asn Phe Phe Lys  Thr Glu Ile Thr Leu  Ala Asn Gly
    1445            1450            1455

Glu Ile  Arg Lys Arg Pro Leu  Ile Glu Thr Asn Gly  Glu Thr Gly
    1460            1465            1470

Glu Ile  Val Trp Asp Lys Gly  Arg Asp Phe Ala Thr  Val Arg Lys
    1475            1480            1485

Val Leu  Ser Met Pro Gln Val  Asn Ile Val Lys Lys  Thr Glu Val
    1490            1495            1500

Gln Thr  Gly Gly Phe Ser Lys  Glu Ser Ile Leu Pro  Lys Arg Asn
    1505            1510            1515

Ser Asp  Lys Leu Ile Ala Arg  Lys Lys Asp Trp Asp  Pro Lys Lys
    1520            1525            1530

Tyr Gly  Gly Phe Asp Ser Pro  Thr Val Ala Tyr Ser  Val Leu Val
    1535            1540            1545

Val Ala  Lys Val Glu Lys Gly  Lys Ser Lys Lys Leu  Lys Ser Val
    1550            1555            1560

Lys Glu  Leu Leu Gly Ile Thr  Ile Met Glu Arg Ser  Ser Phe Glu
    1565            1570            1575

Lys Asn  Pro Ile Asp Phe Leu  Glu Ala Lys Gly Tyr  Lys Glu Val
    1580            1585            1590

Lys Lys  Asp Leu Ile Ile Lys  Leu Pro Lys Tyr Ser  Leu Phe Glu
    1595            1600            1605

Leu Glu  Asn Gly Arg Lys Arg  Met Leu Ala Ser Ala  Gly Glu Leu
    1610            1615            1620

Gln Lys  Gly Asn Glu Leu Ala  Leu Pro Ser Lys Tyr  Val Asn Phe
    1625            1630            1635

Leu Tyr  Leu Ala Ser His Tyr  Glu Lys Leu Lys Gly  Ser Pro Glu
    1640            1645            1650

Asp Asn  Glu Gln Lys Gln Leu  Phe Val Glu Gln His  Lys His Tyr
    1655            1660            1665

Leu Asp  Glu Ile Ile Glu Gln  Ile Ser Glu Phe Ser  Lys Arg Val
    1670            1675            1680

Ile Leu  Ala Asp Ala Asn Leu  Asp Lys Val Leu Ser  Ala Tyr Asn
    1685            1690            1695

Lys His  Arg Asp Lys Pro Ile  Arg Glu Gln Ala Glu  Asn Ile Ile
    1700            1705            1710

His Leu  Phe Thr Leu Thr Asn  Leu Gly Ala Pro Ala  Ala Phe Lys
    1715            1720            1725

Tyr Phe  Asp Thr Thr Ile Asp  Arg Lys Arg Tyr Thr  Ser Thr Lys
    1730            1735            1740

Glu Val  Leu Asp Ala Thr Leu  Ile His Gln Ser Ile  Thr Gly Leu
    1745            1750            1755
```

-continued

```
Tyr Glu  Thr Arg Ile Asp Leu  Ser Gln Leu Gly Gly  Asp Ser Arg
    1760             1765             1770

Ala Asp  Ser Gly Gly Ser Thr  Asn Leu Ser Asp Ile  Ile Glu Lys
    1775             1780             1785

Glu Thr  Gly Lys Gln Leu Val  Ile Gln Glu Ser Ile  Leu Met Leu
    1790             1795             1800

Pro Glu  Glu Val Glu Glu Val  Ile Gly Asn Lys Pro  Glu Ser Asp
    1805             1810             1815

Ile Leu  Val His Thr Ala Tyr  Asp Glu Ser Thr Asp  Glu Asn Val
    1820             1825             1830

Met Leu  Leu Thr Ser Asp Ala  Pro Glu Tyr Lys Pro  Trp Ala Leu
    1835             1840             1845

Val Ile  Gln Asp Ser Asn Gly  Glu Asn Lys Ile Lys  Met Leu Ser
    1850             1855             1860

Gly Gly  Ser Pro Lys Lys Lys  Arg Lys Val
    1865             1870
```

```
<210> SEQ ID NO 30
<211> LENGTH: 1211
<212> TYPE: PRT
<213> ORGANISM: Artificial Sequence
<220> FEATURE:
<223> OTHER INFORMATION: N-ABE
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(387)
<223> OTHER INFORMATION: Linker region
<220> FEATURE:
<221> NAME/KEY: MISC_FEATURE
<222> LOCATION: (388)..(1109)
<223> OTHER INFORMATION: Cas9-D10A
<220> FEATURE:
<221> NAME/KEY: MISC_FEATURE
<222> LOCATION: (1110)..(1211)
<223> OTHER INFORMATION: N-terminal Intein

<400> SEQUENCE: 30

Met Ser Glu Val Glu Phe Ser His Glu Tyr Trp Met Arg His Ala Leu
1               5               10              15

Thr Leu Ala Lys Arg Ala Trp Asp Glu Arg Glu Val Pro Val Gly Ala
            20              25              30

Val Leu Val His Asn Asn Arg Val Ile Gly Glu Gly Trp Asn Arg Pro
        35              40              45

Ile Gly Arg His Asp Pro Thr Ala His Ala Glu Ile Met Ala Leu Arg
    50              55              60

Gln Gly Gly Leu Val Met Gln Asn Tyr Arg Leu Ile Asp Ala Thr Leu
65              70              75              80

Tyr Val Thr Leu Glu Pro Cys Val Met Cys Ala Gly Ala Met Ile His
            85              90              95

Ser Arg Ile Gly Arg Val Val Phe Gly Ala Arg Asp Ala Lys Thr Gly
            100             105             110
```

-continued

```
Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
                180                 185                 190

Gly Gly Ser Ser Gly Gly Ser Ser Glu Val Glu Phe Ser His Glu Tyr
                195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
                260                 265                 270

Leu Ile Asp Ala Thr Leu Tyr Val Thr Phe Glu Pro Cys Val Met Cys
                275                 280                 285

Ala Gly Ala Met Ile His Ser Arg Ile Gly Arg Val Val Phe Gly Val
        290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
                340                 345                 350

Val Phe Asn Ala Gln Lys Lys Ala Gln Ser Ser Thr Asp Ser Gly Gly
        355                 360                 365

Ser Ser Gly Gly Ser Ser Gly Ser Glu Thr Pro Gly Thr Ser Glu Ser
    370                 375                 380

Ala Thr Pro Glu Ser Ser Gly Gly Ser Ser Gly Gly Ser Asp Lys Lys
385                 390                 395                 400

Tyr Ser Ile Gly Leu Ala Ile Gly Thr Asn Ser Val Gly Trp Ala Val
                405                 410                 415

Ile Thr Asp Glu Tyr Lys Val Pro Ser Lys Lys Phe Lys Val Leu Gly
                420                 425                 430

Asn Thr Asp Arg His Ser Ile Lys Lys Asn Leu Ile Gly Ala Leu Leu
        435                 440                 445

Phe Asp Ser Gly Glu Thr Ala Glu Ala Thr Arg Leu Lys Arg Thr Ala
    450                 455                 460

Arg Arg Arg Tyr Thr Arg Arg Lys Asn Arg Ile Cys Tyr Leu Gln Glu
465                 470                 475                 480

Ile Phe Ser Asn Glu Met Ala Lys Val Asp Asp Ser Phe Phe His Arg
                485                 490                 495

Leu Glu Glu Ser Phe Leu Val Glu Glu Asp Lys Lys His Glu Arg His
                500                 505                 510

Pro Ile Phe Gly Asn Ile Val Asp Glu Val Ala Tyr His Glu Lys Tyr
        515                 520                 525

Pro Thr Ile Tyr His Leu Arg Lys Lys Leu Val Asp Ser Thr Asp Lys
```

-continued

```
              530                 535                 540

Ala Asp Leu Arg Leu Ile Tyr Leu Ala Leu Ala His Met Ile Lys Phe
545                 550                 555                 560

Arg Gly His Phe Leu Ile Glu Gly Asp Leu Asn Pro Asp Asn Ser Asp
                565                 570                 575

Val Asp Lys Leu Phe Ile Gln Leu Val Gln Thr Tyr Asn Gln Leu Phe
                580                 585                 590

Glu Glu Asn Pro Ile Asn Ala Ser Gly Val Asp Ala Lys Ala Ile Leu
                595                 600                 605

Ser Ala Arg Leu Ser Lys Ser Arg Arg Leu Glu Asn Leu Ile Ala Gln
                610                 615                 620

Leu Pro Gly Glu Lys Lys Asn Gly Leu Phe Gly Asn Leu Ile Ala Leu
625                 630                 635                 640

Ser Leu Gly Leu Thr Pro Asn Phe Lys Ser Asn Phe Asp Leu Ala Glu
                645                 650                 655

Asp Ala Lys Leu Gln Leu Ser Lys Asp Thr Tyr Asp Asp Asp Leu Asp
                660                 665                 670

Asn Leu Leu Ala Gln Ile Gly Asp Gln Tyr Ala Asp Leu Phe Leu Ala
                675                 680                 685

Ala Lys Asn Leu Ser Asp Ala Ile Leu Leu Ser Asp Ile Leu Arg Val
                690                 695                 700

Asn Thr Glu Ile Thr Lys Ala Pro Leu Ser Ala Ser Met Ile Lys Arg
705                 710                 715                 720

Tyr Asp Glu His His Gln Asp Leu Thr Leu Leu Lys Ala Leu Val Arg
                725                 730                 735

Gln Gln Leu Pro Glu Lys Tyr Lys Glu Ile Phe Phe Asp Gln Ser Lys
                740                 745                 750

Asn Gly Tyr Ala Gly Tyr Ile Asp Gly Gly Ala Ser Gln Glu Glu Phe
                755                 760                 765

Tyr Lys Phe Ile Lys Pro Ile Leu Glu Lys Met Asp Gly Thr Glu Glu
                770                 775                 780

Leu Leu Val Lys Leu Asn Arg Glu Asp Leu Leu Arg Lys Gln Arg Thr
785                 790                 795                 800

Phe Asp Asn Gly Ser Ile Pro His Gln Ile His Leu Gly Glu Leu His
                805                 810                 815

Ala Ile Leu Arg Arg Gln Glu Asp Phe Tyr Pro Phe Leu Lys Asp Asn
                820                 825                 830

Arg Glu Lys Ile Glu Lys Ile Leu Thr Phe Arg Ile Pro Tyr Tyr Val
                835                 840                 845

Gly Pro Leu Ala Arg Gly Asn Ser Arg Phe Ala Trp Met Thr Arg Lys
850                 855                 860

Ser Glu Glu Thr Ile Thr Pro Trp Asn Phe Glu Glu Val Val Asp Lys
865                 870                 875                 880

Gly Ala Ser Ala Gln Ser Phe Ile Glu Arg Met Thr Asn Phe Asp Lys
                885                 890                 895

Asn Leu Pro Asn Glu Lys Val Leu Pro Lys His Ser Leu Leu Tyr Glu
                900                 905                 910

Tyr Phe Thr Val Tyr Asn Glu Leu Thr Lys Val Lys Tyr Val Thr Glu
                915                 920                 925

Gly Met Arg Lys Pro Ala Phe Leu Ser Gly Glu Gln Lys Lys Ala Ile
                930                 935                 940

Val Asp Leu Leu Phe Lys Thr Asn Arg Lys Val Thr Val Lys Gln Leu
945                 950                 955                 960
```

-continued

```
Lys Glu Asp Tyr Phe Lys Lys Ile Glu Cys Phe Asp Ser Val Glu Ile
                965             970             975

Ser Gly Val Glu Asp Arg Phe Asn Ala Ser Leu Gly Thr Tyr His Asp
            980             985             990

Leu Leu Lys Ile Ile Lys Asp Lys  Asp Phe Leu Asp Asn  Glu Glu Asn
        995             1000            1005

Glu Asp  Ile Leu Glu Asp Ile  Val Leu Thr Leu Thr  Leu Phe Glu
    1010            1015            1020

Asp Arg  Glu Met Ile Glu Glu  Arg Leu Lys Thr Tyr  Ala His Leu
    1025            1030            1035

Phe Asp  Asp Lys Val Met Lys  Gln Leu Lys Arg Arg  Arg Tyr Thr
    1040            1045            1050

Gly Trp  Gly Arg Leu Ser Arg  Lys Leu Ile Asn Gly  Ile Arg Asp
    1055            1060            1065

Lys Gln  Ser Gly Lys Thr Ile  Leu Asp Phe Leu Lys  Ser Asp Gly
    1070            1075            1080

Phe Ala  Asn Arg Asn Phe Met  Gln Leu Ile His Asp  Asp Ser Leu
    1085            1090            1095

Thr Phe  Lys Glu Asp Ile Gln  Lys Ala Gln Val Cys  Leu Ala Gly
    1100            1105            1110

Asp Thr  Leu Ile Thr Leu Ala  Asp Gly Arg Arg Val  Pro Ile Arg
    1115            1120            1125

Glu Leu  Val Ser Gln Gln Asn  Phe Ser Val Trp Ala  Leu Asn Pro
    1130            1135            1140

Gln Thr  Tyr Arg Leu Glu Arg  Ala Arg Val Ser Arg  Ala Phe Cys
    1145            1150            1155

Thr Gly  Ile Lys Pro Val Tyr  Arg Leu Thr Thr Arg  Leu Gly Arg
    1160            1165            1170

Ser Ile  Arg Ala Thr Ala Asn  His Arg Phe Leu Thr  Pro Gln Gly
    1175            1180            1185

Trp Lys  Arg Val Asp Glu Leu  Gln Pro Gly Asp Tyr  Leu Ala Leu
    1190            1195            1200

Pro Arg  Arg Ile Pro Thr Ala  Ser
    1205            1210
```

```
<210> SEQ ID NO 31
<211> LENGTH: 718
<212> TYPE: PRT
<213> ORGANISM: Artificial Sequence
<220> FEATURE:
<223> OTHER INFORMATION: C-ABE
<220> FEATURE:
<221> NAME/KEY: MISC_FEATURE
<222> LOCATION: (1)..(52)
<223> OTHER INFORMATION: C-terminal Intein
<220> FEATURE:
<221> NAME/KEY: MISC_FEATURE
<222> LOCATION: (53)..(711)
<223> OTHER INFORMATION: Cas9-D10A
<220> FEATURE:
<221> NAME/KEY: MISC_FEATURE
<222> LOCATION: (712)..(718)
<223> OTHER INFORMATION: NLS

<400> SEQUENCE: 31

Met Ala Ala Ala Cys Pro Glu Leu Arg Gln Leu Ala Gln Ser Asp Val
1               5               10              15

Tyr Trp Asp Pro Ile Val Ser Ile Glu Pro Asp Gly Val Glu Glu Val
            20              25              30
```

```
Phe Asp Leu Thr Val Pro Gly Pro His Asn Phe Val Ala Asn Asp Ile
        35              40              45

Ile Ala His Asn Ser Gly Gln Gly Asp Ser Leu His Glu His Ile Ala
        50              55              60

Asn Leu Ala Gly Ser Pro Ala Ile Lys Lys Gly Ile Leu Gln Thr Val
65              70              75              80

Lys Val Val Asp Glu Leu Val Lys Val Met Gly Arg His Lys Pro Glu
            85              90              95

Asn Ile Val Ile Glu Met Ala Arg Glu Asn Gln Thr Thr Gln Lys Gly
            100             105             110

Gln Lys Asn Ser Arg Glu Arg Met Lys Arg Ile Glu Glu Gly Ile Lys
        115             120             125

Glu Leu Gly Ser Gln Ile Leu Lys Glu His Pro Val Glu Asn Thr Gln
    130             135             140

Leu Gln Asn Glu Lys Leu Tyr Leu Tyr Tyr Leu Gln Asn Gly Arg Asp
145             150             155             160

Met Tyr Val Asp Gln Glu Leu Asp Ile Asn Arg Leu Ser Asp Tyr Asp
            165             170             175

Val Asp His Ile Val Pro Gln Ser Phe Leu Lys Asp Asp Ser Ile Asp
        180             185             190

Asn Lys Val Leu Thr Arg Ser Asp Lys Asn Arg Gly Lys Ser Asp Asn
        195             200             205

Val Pro Ser Glu Glu Val Val Lys Lys Met Lys Asn Tyr Trp Arg Gln
    210             215             220

Leu Leu Asn Ala Lys Leu Ile Thr Gln Arg Lys Phe Asp Asn Leu Thr
225             230             235             240

Lys Ala Glu Arg Gly Gly Leu Ser Glu Leu Asp Lys Ala Gly Phe Ile
            245             250             255

Lys Arg Gln Leu Val Glu Thr Arg Gln Ile Thr Lys His Val Ala Gln
        260             265             270

Ile Leu Asp Ser Arg Met Asn Thr Lys Tyr Asp Glu Asn Asp Lys Leu
        275             280             285

Ile Arg Glu Val Lys Val Ile Thr Leu Lys Ser Lys Leu Val Ser Asp
    290             295             300

Phe Arg Lys Asp Phe Gln Phe Tyr Lys Val Arg Glu Ile Asn Asn Tyr
305             310             315             320

His His Ala His Asp Ala Tyr Leu Asn Ala Val Val Gly Thr Ala Leu
            325             330             335

Ile Lys Lys Tyr Pro Lys Leu Glu Ser Glu Phe Val Tyr Gly Asp Tyr
            340             345             350

Lys Val Tyr Asp Val Arg Lys Met Ile Ala Lys Ser Glu Gln Glu Ile
        355             360             365

Gly Lys Ala Thr Ala Lys Tyr Phe Phe Tyr Ser Asn Ile Met Asn Phe
    370             375             380

Phe Lys Thr Glu Ile Thr Leu Ala Asn Gly Glu Ile Arg Lys Arg Pro
385             390             395             400

Leu Ile Glu Thr Asn Gly Glu Thr Gly Glu Ile Val Trp Asp Lys Gly
            405             410             415

Arg Asp Phe Ala Thr Val Arg Lys Val Leu Ser Met Pro Gln Val Asn
            420             425             430

Ile Val Lys Lys Thr Glu Val Gln Thr Gly Gly Phe Ser Lys Glu Ser
        435             440             445
```

-continued

```
Ile Leu Pro Lys Arg Asn Ser Asp Lys Leu Ile Ala Arg Lys Lys Asp
    450                 455                 460

Trp Asp Pro Lys Lys Tyr Gly Gly Phe Asp Ser Pro Thr Val Ala Tyr
465                 470                 475                 480

Ser Val Leu Val Val Ala Lys Val Glu Lys Gly Lys Ser Lys Lys Leu
                485                 490                 495

Lys Ser Val Lys Glu Leu Leu Gly Ile Thr Ile Met Glu Arg Ser Ser
                500                 505                 510

Phe Glu Lys Asn Pro Ile Asp Phe Leu Glu Ala Lys Gly Tyr Lys Glu
            515                 520                 525

Val Lys Lys Asp Leu Ile Ile Lys Leu Pro Lys Tyr Ser Leu Phe Glu
    530                 535                 540

Leu Glu Asn Gly Arg Lys Arg Met Leu Ala Ser Ala Gly Glu Leu Gln
545                 550                 555                 560

Lys Gly Asn Glu Leu Ala Leu Pro Ser Lys Tyr Val Asn Phe Leu Tyr
                565                 570                 575

Leu Ala Ser His Tyr Glu Lys Leu Lys Gly Ser Pro Glu Asp Asn Glu
            580                 585                 590

Gln Lys Gln Leu Phe Val Glu Gln His Lys His Tyr Leu Asp Glu Ile
    595                 600                 605

Ile Glu Gln Ile Ser Glu Phe Ser Lys Arg Val Ile Leu Ala Asp Ala
    610                 615                 620

Asn Leu Asp Lys Val Leu Ser Ala Tyr Asn Lys His Arg Asp Lys Pro
625                 630                 635                 640

Ile Arg Glu Gln Ala Glu Asn Ile Ile His Leu Phe Thr Leu Thr Asn
                645                 650                 655

Leu Gly Ala Pro Ala Ala Phe Lys Tyr Phe Asp Thr Thr Ile Asp Arg
            660                 665                 670

Lys Arg Tyr Thr Ser Thr Lys Glu Val Leu Asp Ala Thr Leu Ile His
    675                 680                 685

Gln Ser Ile Thr Gly Leu Tyr Glu Thr Arg Ile Asp Leu Ser Gln Leu
    690                 695                 700

Gly Gly Asp Ser Arg Ala Asp Pro Lys Lys Lys Arg Lys Val
705                 710                 715
```

<210> SEQ ID NO 32
<211> LENGTH: 1208
<212> TYPE: PRT
<213> ORGANISM: Artificial Sequence
<220> FEATURE:
<223> OTHER INFORMATION: N-ABE-AAV
<220> FEATURE:
<221> NAME/KEY: MISC_FEATURE
<222> LOCATION: (1)..(167)
<223> OTHER INFORMATION: Adenine Deaminase Domain
<220> FEATURE:
<221> NAME/KEY: MISC_FEATURE
<222> LOCATION: (168)..(199)
<223> OTHER INFORMATION: Linker region
<220> FEATURE:
<221> NAME/KEY: MISC_FEATURE
<222> LOCATION: (200)..(365)
<223> OTHER INFORMATION: Adenine Deaminase Domain
<220> FEATURE:
<221> NAME/KEY: MISC_FEATURE
<222> LOCATION: (366)..(394)
<223> OTHER INFORMATION: Linker region
<220> FEATURE:
<221> NAME/KEY: MISC_FEATURE
<222> LOCATION: (395)..(1106)
<223> OTHER INFORMATION: Cas9-D10A
<220> FEATURE:

<221> NAME/KEY: MISC_FEATURE
<222> LOCATION: (1107)..(1208)
<223> OTHER INFORMATION: N-terminal Intein

<400> SEQUENCE: 32

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
        210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
            275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ala Ser Gly
            355                 360                 365

Gly Gly Gly Ser Gly Gly Gly Gly Ser Gly Gly Gly Ser Gly Gly
    370                 375                 380

Gly Gly Ser Gly Gly Gly Gly Ser Gly Thr Asp Lys Lys Tyr Ser Ile

```
385                   390                   395                   400
Gly Leu Ala Ile Gly Thr Asn Ser Val Gly Trp Ala Val Ile Thr Asp
                405                   410                   415

Glu Tyr Lys Val Pro Ser Lys Lys Phe Lys Val Leu Gly Asn Thr Asp
            420                   425                   430

Arg His Ser Ile Lys Lys Asn Leu Ile Gly Ala Leu Leu Phe Asp Ser
            435                   440                   445

Gly Glu Thr Ala Glu Ala Thr Arg Leu Lys Arg Thr Ala Arg Arg Arg
        450                   455                   460

Tyr Thr Arg Arg Lys Asn Arg Ile Cys Tyr Leu Gln Glu Ile Phe Ser
465                   470                   475                   480

Asn Glu Met Ala Lys Val Asp Asp Ser Phe Phe His Arg Leu Glu Glu
                485                   490                   495

Ser Phe Leu Val Glu Glu Asp Lys Lys His Glu Arg His Pro Ile Phe
            500                   505                   510

Gly Asn Ile Val Asp Glu Val Ala Tyr His Glu Lys Tyr Pro Thr Ile
            515                   520                   525

Tyr His Leu Arg Lys Lys Leu Val Asp Ser Thr Asp Lys Ala Asp Leu
        530                   535                   540

Arg Leu Ile Tyr Leu Ala Leu Ala His Met Ile Lys Phe Arg Gly His
545                   550                   555                   560

Phe Leu Ile Glu Gly Asp Leu Asn Pro Asp Asn Ser Asp Val Asp Lys
                565                   570                   575

Leu Phe Ile Gln Leu Val Gln Thr Tyr Asn Gln Leu Phe Glu Glu Asn
            580                   585                   590

Pro Ile Asn Ala Ser Gly Val Asp Ala Lys Ala Ile Leu Ser Ala Arg
            595                   600                   605

Leu Ser Lys Ser Arg Arg Leu Glu Asn Leu Ile Ala Gln Leu Pro Gly
        610                   615                   620

Glu Lys Lys Asn Gly Leu Phe Gly Asn Leu Ile Ala Leu Ser Leu Gly
625                   630                   635                   640

Leu Thr Pro Asn Phe Lys Ser Asn Phe Asp Leu Ala Glu Asp Ala Lys
                645                   650                   655

Leu Gln Leu Ser Lys Asp Thr Tyr Asp Asp Asp Leu Asp Asn Leu Leu
            660                   665                   670

Ala Gln Ile Gly Asp Gln Tyr Ala Asp Leu Phe Leu Ala Ala Lys Asn
            675                   680                   685

Leu Ser Asp Ala Ile Leu Leu Ser Asp Ile Leu Arg Val Asn Thr Glu
        690                   695                   700

Ile Thr Lys Ala Pro Leu Ser Ala Ser Met Ile Lys Arg Tyr Asp Glu
705                   710                   715                   720

His His Gln Asp Leu Thr Leu Leu Lys Ala Leu Val Arg Gln Gln Leu
                725                   730                   735

Pro Glu Lys Tyr Lys Glu Ile Phe Phe Asp Gln Ser Lys Asn Gly Tyr
            740                   745                   750

Ala Gly Tyr Ile Asp Gly Gly Ala Ser Gln Glu Glu Phe Tyr Lys Phe
            755                   760                   765

Ile Lys Pro Ile Leu Glu Lys Met Asp Gly Thr Glu Glu Leu Leu Val
        770                   775                   780

Lys Leu Asn Arg Glu Asp Leu Leu Arg Lys Gln Arg Thr Phe Asp Asn
785                   790                   795                   800

Gly Ser Ile Pro His Gln Ile His Leu Gly Glu Leu His Ala Ile Leu
            805                   810                   815
```

-continued

```
Arg Arg Gln Glu Asp Phe Tyr Pro Phe Leu Lys Asp Asn Arg Glu Lys
        820                 825                 830

Ile Glu Lys Ile Leu Thr Phe Arg Ile Pro Tyr Tyr Val Gly Pro Leu
        835                 840                 845

Ala Arg Gly Asn Ser Arg Phe Ala Trp Met Thr Arg Lys Ser Glu Glu
    850                 855                 860

Thr Ile Thr Pro Trp Asn Phe Glu Glu Val Val Asp Lys Gly Ala Ser
865                 870                 875                 880

Ala Gln Ser Phe Ile Glu Arg Met Thr Asn Phe Asp Lys Asn Leu Pro
            885                 890                 895

Asn Glu Lys Val Leu Pro Lys His Ser Leu Leu Tyr Glu Tyr Phe Thr
        900                 905                 910

Val Tyr Asn Glu Leu Thr Lys Val Lys Tyr Val Thr Glu Gly Met Arg
        915                 920                 925

Lys Pro Ala Phe Leu Ser Gly Glu Gln Lys Lys Ala Ile Val Asp Leu
    930                 935                 940

Leu Phe Lys Thr Asn Arg Lys Val Thr Val Lys Gln Leu Lys Glu Asp
945                 950                 955                 960

Tyr Phe Lys Lys Ile Glu Cys Phe Asp Ser Val Glu Ile Ser Gly Val
            965                 970                 975

Glu Asp Arg Phe Asn Ala Ser Leu Gly Thr Tyr His Asp Leu Leu Lys
            980                 985                 990

Ile Ile Lys Asp Lys Asp Phe Leu  Asp Asn Glu Glu Asn  Glu Asp Ile
        995                 1000                1005

Leu Glu  Asp Ile Val Leu Thr  Leu Thr Leu Phe Glu  Asp Arg Glu
    1010                1015                1020

Met Ile  Glu Glu Arg Leu Lys  Thr Tyr Ala His Leu  Phe Asp Asp
    1025                1030                1035

Lys Val  Met Lys Gln Leu Lys  Arg Arg Arg Tyr Thr  Gly Trp Gly
    1040                1045                1050

Arg Leu  Ser Arg Lys Leu Ile  Asn Gly Ile Arg Asp  Lys Gln Ser
    1055                1060                1065

Gly Lys  Thr Ile Leu Asp Phe  Leu Lys Ser Asp Gly  Phe Ala Asn
    1070                1075                1080

Arg Asn  Phe Met Gln Leu Ile  His Asp Asp Ser Leu  Thr Phe Lys
    1085                1090                1095

Glu Asp  Ile Gln Lys Ala Gln  Val Cys Leu Ala Gly  Asp Thr Leu
    1100                1105                1110

Ile Thr  Leu Ala Asp Gly Arg  Arg Val Pro Ile Arg  Glu Leu Val
    1115                1120                1125

Ser Gln  Gln Asn Phe Ser Val  Trp Ala Leu Asn Pro  Gln Thr Tyr
    1130                1135                1140

Arg Leu  Glu Arg Ala Arg Val  Ser Arg Ala Phe Cys  Thr Gly Ile
    1145                1150                1155

Lys Pro  Val Tyr Arg Leu Thr  Thr Arg Leu Gly Arg  Ser Ile Arg
    1160                1165                1170

Ala Thr  Ala Asn His Arg Phe  Leu Thr Pro Gln Gly  Trp Lys Arg
    1175                1180                1185

Val Asp  Glu Leu Gln Pro Gly  Asp Tyr Leu Ala Leu  Pro Arg Arg
    1190                1195                1200

Ile Pro  Thr Ala Ser
    1205
```

-continued

```
<210> SEQ ID NO 33
<211> LENGTH: 833
<212> TYPE: PRT
<213> ORGANISM: Artificial Sequence
<220> FEATURE:
<223> OTHER INFORMATION: C-ABE-AAV
<220> FEATURE:
<221> NAME/KEY: MISC_FEATURE
<222> LOCATION: (1)..(52)
<223> OTHER INFORMATION: C-terminal Intein
<220> FEATURE:
<221> NAME/KEY: MISC_FEATURE
<222> LOCATION: (53)..(707)
<223> OTHER INFORMATION: Cas9-D10A
<220> FEATURE:
<221> NAME/KEY: MISC_FEATURE
<222> LOCATION: (708)..(711)
<223> OTHER INFORMATION: Linker region
<220> FEATURE:
<221> NAME/KEY: MISC_FEATURE
<222> LOCATION: (712)..(795)
<223> OTHER INFORMATION: UGI Domain
<220> FEATURE:
<221> NAME/KEY: MISC_FEATURE
<222> LOCATION: (796)..(822)
<223> OTHER INFORMATION: 3x HA Tag
<220> FEATURE:
<221> NAME/KEY: MISC_FEATURE
<222> LOCATION: (823)..(826)
<223> OTHER INFORMATION: Linker region
<220> FEATURE:
<221> NAME/KEY: MISC_FEATURE
<222> LOCATION: (826)..(833)
<223> OTHER INFORMATION: NLS

<400> SEQUENCE: 33

Met Ala Ala Ala Cys Pro Glu Leu Arg Gln Leu Ala Gln Ser Asp Val
1               5                   10                  15

Tyr Trp Asp Pro Ile Val Ser Ile Glu Pro Asp Gly Val Glu Glu Val
                20                  25                  30

Phe Asp Leu Thr Val Pro Gly Pro His Asn Phe Val Ala Asn Asp Ile
            35                  40                  45

Ile Ala His Asn Ser Gly Gln Gly Asp Ser Leu His Glu His Ile Ala
        50                  55                  60

Asn Leu Ala Gly Ser Pro Ala Ile Lys Lys Gly Ile Leu Gln Thr Val
65                  70                  75                  80

Lys Val Val Asp Glu Leu Val Lys Val Met Gly Arg His Lys Pro Glu
                85                  90                  95

Asn Ile Val Ile Glu Met Ala Arg Glu Asn Gln Thr Thr Gln Lys Gly
                100                 105                 110

Gln Lys Asn Ser Arg Glu Arg Met Lys Arg Ile Glu Glu Gly Ile Lys
            115                 120                 125

Glu Leu Gly Ser Gln Ile Leu Lys Glu His Pro Val Glu Asn Thr Gln
        130                 135                 140

Leu Gln Asn Glu Lys Leu Tyr Leu Tyr Tyr Leu Gln Asn Gly Arg Asp
145                 150                 155                 160

Met Tyr Val Asp Gln Glu Leu Asp Ile Asn Arg Leu Ser Asp Tyr Asp
                165                 170                 175

Val Asp His Ile Val Pro Gln Ser Phe Leu Lys Asp Asp Ser Ile Asp
                180                 185                 190

Asn Lys Val Leu Thr Arg Ser Asp Lys Asn Arg Gly Lys Ser Asp Asn
            195                 200                 205

Val Pro Ser Glu Glu Val Val Lys Lys Met Lys Asn Tyr Trp Arg Gln
        210                 215                 220
```

```
Leu Leu Asn Ala Lys Leu Ile Thr Gln Arg Lys Phe Asp Asn Leu Thr
225                 230                 235                 240

Lys Ala Glu Arg Gly Gly Leu Ser Glu Leu Asp Lys Ala Gly Phe Ile
                245                 250                 255

Lys Arg Gln Leu Val Glu Thr Arg Gln Ile Thr Lys His Val Ala Gln
                260                 265                 270

Ile Leu Asp Ser Arg Met Asn Thr Lys Tyr Asp Glu Asn Asp Lys Leu
                275                 280                 285

Ile Arg Glu Val Lys Val Ile Thr Leu Lys Ser Lys Leu Val Ser Asp
            290                 295                 300

Phe Arg Lys Asp Phe Gln Phe Tyr Lys Val Arg Glu Ile Asn Asn Tyr
305                 310                 315                 320

His His Ala His Asp Ala Tyr Leu Asn Ala Val Val Gly Thr Ala Leu
                325                 330                 335

Ile Lys Lys Tyr Pro Lys Leu Glu Ser Glu Phe Val Tyr Gly Asp Tyr
                340                 345                 350

Lys Val Tyr Asp Val Arg Lys Met Ile Ala Lys Ser Glu Gln Glu Ile
                355                 360                 365

Gly Lys Ala Thr Ala Lys Tyr Phe Phe Tyr Ser Asn Ile Met Asn Phe
            370                 375                 380

Phe Lys Thr Glu Ile Thr Leu Ala Asn Gly Glu Ile Arg Lys Arg Pro
385                 390                 395                 400

Leu Ile Glu Thr Asn Gly Glu Thr Gly Glu Ile Val Trp Asp Lys Gly
                405                 410                 415

Arg Asp Phe Ala Thr Val Arg Lys Val Leu Ser Met Pro Gln Val Asn
                420                 425                 430

Ile Val Lys Lys Thr Glu Val Gln Thr Gly Gly Phe Ser Lys Glu Ser
            435                 440                 445

Ile Leu Pro Lys Arg Asn Ser Asp Lys Leu Ile Ala Arg Lys Lys Asp
            450                 455                 460

Trp Asp Pro Lys Lys Tyr Gly Gly Phe Asp Ser Pro Thr Val Ala Tyr
465                 470                 475                 480

Ser Val Leu Val Val Ala Lys Val Glu Lys Gly Lys Ser Lys Lys Leu
                485                 490                 495

Lys Ser Val Lys Glu Leu Leu Gly Ile Thr Ile Met Glu Arg Ser Ser
            500                 505                 510

Phe Glu Lys Asn Pro Ile Asp Phe Leu Glu Ala Lys Gly Tyr Lys Glu
            515                 520                 525

Val Lys Lys Asp Leu Ile Ile Lys Leu Pro Lys Tyr Ser Leu Phe Glu
            530                 535                 540

Leu Glu Asn Gly Arg Lys Arg Met Leu Ala Ser Ala Gly Glu Leu Gln
545                 550                 555                 560

Lys Gly Asn Glu Leu Ala Leu Pro Ser Lys Tyr Val Asn Phe Leu Tyr
                565                 570                 575

Leu Ala Ser His Tyr Glu Lys Leu Lys Gly Ser Pro Glu Asp Asn Glu
                580                 585                 590

Gln Lys Gln Leu Phe Val Glu Gln His Lys His Tyr Leu Asp Glu Ile
            595                 600                 605

Ile Glu Gln Ile Ser Glu Phe Ser Lys Arg Val Ile Leu Ala Asp Ala
            610                 615                 620

Asn Leu Asp Lys Val Leu Ser Ala Tyr Asn Lys His Arg Asp Lys Pro
625                 630                 635                 640
```

-continued

```
Ile Arg Glu Gln Ala Glu Asn Ile Ile His Leu Phe Thr Leu Thr Asn
            645                 650                 655

Leu Gly Ala Pro Ala Ala Phe Lys Tyr Phe Asp Thr Thr Ile Asp Arg
            660                 665                 670

Lys Arg Tyr Thr Ser Thr Lys Glu Val Leu Asp Ala Thr Leu Ile His
        675                 680                 685

Gln Ser Ile Thr Gly Leu Tyr Glu Thr Arg Ile Asp Leu Ser Gln Leu
    690                 695                 700

Gly Gly Asp Ser Gly Gly Ser Thr Asn Leu Ser Asp Ile Ile Glu Lys
705                 710                 715                 720

Glu Thr Gly Lys Gln Leu Val Ile Gln Glu Ser Ile Leu Met Leu Pro
                725                 730                 735

Glu Glu Val Glu Glu Val Ile Gly Asn Lys Pro Glu Ser Asp Ile Leu
            740                 745                 750

Val His Thr Ala Tyr Asp Glu Ser Thr Asp Glu Asn Val Met Leu Leu
            755                 760                 765

Thr Ser Asp Ala Pro Glu Tyr Lys Pro Trp Ala Leu Val Ile Gln Asp
    770                 775                 780

Ser Asn Gly Glu Asn Lys Ile Lys Met Leu Ser Tyr Pro Tyr Asp Val
785                 790                 795                 800

Pro Asp Tyr Ala Tyr Pro Tyr Asp Val Pro Asp Tyr Ala Tyr Pro Tyr
                805                 810                 815

Asp Val Pro Asp Tyr Ala Ser Gly Gly Ser Pro Lys Lys Lys Arg Lys
            820                 825                 830

Val
```

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
aatcctgtta aagtataaaa                                                         20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
gagccctgaa caaataaaag                                                         20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gagccctgaa caaataaaag                                                         20

<210> SEQ ID NO 37
<211> LENGTH: 20
<212> TYPE: DNA
<213> ORGANISM: Artificial Sequence -continued

```
<220> FEATURE:
<223> OTHER INFORMATION: Synthetic oligonucleotide

<400> SEQUENCE: 37
aatattctaa gaaaataagt                                        20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ctcttcctgc aaaagaaaat                                        20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
aattattctg caatgggaat                                        20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
acccctgaga ggatgaagca                                        20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
ggcactggaa tgaacaacaa                                        20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tggcactgga atgaacaaca                                        20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
aatgtctggt caacaagaaa                                        20
```

-continued

```
<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
aaatcctaga agaggagaag                                                    20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
gagccctggg aagggagaca                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
tcttcaccta ccaaggaaac                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
tatactgtaa gagattaagg                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
tagtgtctgt gtgggagaaa                                                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
atacatctgt gtatgagaaa                                                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide
```

-continued

<400> SEQUENCE: 50
ggaactgcca agaaaacagg                                                      20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
acctgaggca gtgaaaacaa                                                      20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
tgggtcctgt agggcaaggg                                                      20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
gttgagctac agacacagca                                                      20

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 54
aacaggagaa ggggtgactg ac                                                   22

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 55
ttccaatgtg gtctttgcag ct                                                   22

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 56
gctacaccac ccacccttag tt                                                   22

<210> SEQ ID NO 57

-continued

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 57
ttcctgcagg catgacagag aa                                                      22

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 58
agatgtgggg gtctcactat gttg                                                    24

<210> SEQ ID NO 59
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 59
agctgccagt ttccatatga tcca                                                    24

<210> SEQ ID NO 60
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 60
cacagccagg cagtctgtat ct                                                      22

<210> SEQ ID NO 61
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 61
tggggcttca agaggtgtac ag                                                      22

<210> SEQ ID NO 62
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 62
aggacttgag ccccaatctt cc                                                      22

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63
```
gtgtacggcc ctgaagtaca gt                                          22

<210> SEQ ID NO 64
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 64
tctgctagtc caaaagaggg cc                                          22

<210> SEQ ID NO 65
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 65
ctgtgcagcc ggagaaacaa at                                          22

<210> SEQ ID NO 66
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 66
aagcaatctg ccaacttcag cc                                          22

<210> SEQ ID NO 67
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 67
cagtgacttc ccgacccagt ag                                          22

<210> SEQ ID NO 68
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 68
cccttccagg attctagccg ag                                          22

<210> SEQ ID NO 69
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 69
aaacatggca gtgacaccaa cc                                          22

<210> SEQ ID NO 70
<211> LENGTH: 22
<212> TYPE: DNA

-continued

```
<213> ORGANISM: Artificial Sequence
<220> FEATURE:
<223> OTHER INFORMATION: Synthetic oligonucleotide

<400> SEQUENCE: 70
gagccagaac ctgagcctgt ta                                              22

<210> SEQ ID NO 71
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 71
aggaggaaag tgcaccatgt ca                                              22

<210> SEQ ID NO 72
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 72
gaggtagact gaggcttcca gc                                              22

<210> SEQ ID NO 73
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 73
gatgcaaagg cctcagctgt tt                                              22

<210> SEQ ID NO 74
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 74
gctcaactgg tgtgtgcaga tc                                              22

<210> SEQ ID NO 75
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 75
tcacggaact ttgggcgact at                                              22

<210> SEQ ID NO 76
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 76
accgtggact tcttcaggta gc                                              22
```

-continued

```
<210> SEQ ID NO 77
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 77
gctccaaaac cacaagccag tt                                              22

<210> SEQ ID NO 78
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 78
ctcgcaatga ggtttggtgg ac                                              22

<210> SEQ ID NO 79
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 79
gtatttcccc caggcagact gt                                              22

<210> SEQ ID NO 80
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 80
cttgtagcag gtgtctggct ct                                              22

<210> SEQ ID NO 81
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 81
ggggcacaca cacttaaatc cg                                              22

<210> SEQ ID NO 82
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 82
gaggcagctg taaggagacc tc                                              22

<210> SEQ ID NO 83
<211> LENGTH: 22
<212> TYPE: DNA
<213> ORGANISM: Artificial Sequence
<220> FEATURE:
```

<223> OTHER INFORMATION: Synthetic oligonucleotide

<400> SEQUENCE: 83
ctgcatagcc aggtggacag at                                              22

<210> SEQ ID NO 84
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 84
gaacttgtag caacacaggc cc                                              22

<210> SEQ ID NO 85
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 85
aggagttgac accatcgatg ca                                              22

<210> SEQ ID NO 86
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 86
agctaaaccg caacagtcat gc                                              22

<210> SEQ ID NO 87
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 87
ccatctgagg ttttgccacc ac                                              22

<210> SEQ ID NO 88
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 88
cggatttaag tgtgtgtgcc cc                                              22

<210> SEQ ID NO 89
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 89
ttctggcagg gattaggctc ac                                              22

-continued

```
<210> SEQ ID NO 90
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 90
aagcttgctc ccgttctctc tt                                              22

<210> SEQ ID NO 91
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 91
cagaagagcc agaggagatg gg                                              22

<210> SEQ ID NO 92
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 92
gacgacgagg atgaggatgg ag                                              22

<210> SEQ ID NO 93
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 93
cacccctttc ccttggcttc ta                                              22

<210> SEQ ID NO 94
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 94
ctgaggtctg cacatcctgg aa                                              22

<210> SEQ ID NO 95
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 95
cactgcaaaa ccccttccac tc                                              22

<210> SEQ ID NO 96
<211> LENGTH: 22
<212> TYPE: DNA
<213> ORGANISM: Artificial Sequence
<220> FEATURE:
<223> OTHER INFORMATION: Synthetic oligonucleotide
```

-continued

<400> SEQUENCE: 96
actgccctag agcctgagta ct                                          22

<210> SEQ ID NO 97
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 97
cacgcagcat cttgaacatg gt                                          22

<210> SEQ ID NO 98
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 98
ccatgttcaa gctgaccgca at                                          22

<210> SEQ ID NO 99
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 99
gctggcggtc aggtacttct ta                                          22

<210> SEQ ID NO 100
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 100
ggggtttcac cgttttagcc ag                                          22

<210> SEQ ID NO 101
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 101
acatcaaatt gggcatcctc cc                                          22

<210> SEQ ID NO 102
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 102
tcttcaccag aattgccaaa gc                                          22

<210> SEQ ID NO 103
<211> LENGTH: 22

```
<212> TYPE: DNA
<213> ORGANISM: Artificial Sequence
<220> FEATURE:
<223> OTHER INFORMATION: Synthetic oligonucleotide

<400> SEQUENCE: 103
tccacctggg attggaacaa gg                                              22

<210> SEQ ID NO 104
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 104
accagtaggc aaccgtgaag aa                                              22

<210> SEQ ID NO 105
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 105
tcgggataca gaccaattgg ca                                              22

<210> SEQ ID NO 106
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 106
tagctattcc cacgcaggac tg                                              22

<210> SEQ ID NO 107
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 107
ttccattgcc tcgacttgcc ta                                              22

<210> SEQ ID NO 108
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 108
tttcctgcat ctccctcact gg                                              22

<210> SEQ ID NO 109
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 109
```

-continued

```
acagcattca ggtcgtagtc cc                                       22

<210> SEQ ID NO 110
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 110
cagattggca cccactggac ta                                       22

<210> SEQ ID NO 111
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 111
agatcttgag ctcggcagtg tt                                       22

<210> SEQ ID NO 112
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 112
cctggtcccg tgaaatacac ct                                       22

<210> SEQ ID NO 113
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 113
cccacgagct tgtaggaaag ga                                       22

<210> SEQ ID NO 114
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 114
tgctcaggga tgacgtaaag gg                                       22

<210> SEQ ID NO 115
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 115
caacagaggc ctccaaaagc tg                                       22

<210> SEQ ID NO 116
<211> LENGTH: 22
<212> TYPE: DNA
<213> ORGANISM: Artificial Sequence
```

-continued

```
<220> FEATURE:
<223> OTHER INFORMATION: Synthetic oligonucleotide

<400> SEQUENCE: 116
aatccttacc tggcttgggg ac                                    22

<210> SEQ ID NO 117
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 117
aacactgccg agctcaagat ct                                    22

<210> SEQ ID NO 118
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 118
tgctcaggga tgacgtaaag gg                                    22

<210> SEQ ID NO 119
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 119
ggaggaaagc cagactctcc tg                                    22

<210> SEQ ID NO 120
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 120
agagtgttca tcctcccagc ac                                    22

<210> SEQ ID NO 121
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 121
actgtgggtg agatcatgtg gg                                    22

<210> SEQ ID NO 122
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 122
ttcgttgggt gggtagatgg ac                                    22
```

-continued

```
<210> SEQ ID NO 123
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 123
gctgcctact ctgcctactc ag                                        22

<210> SEQ ID NO 124
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 124
gtccataggc ctcaccagac tg                                        22

<210> SEQ ID NO 125
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 125
ttctgaagga agacgcctgg ag                                        22

<210> SEQ ID NO 126
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 126
gctgcaataa acatgggtgt gc                                        22

<210> SEQ ID NO 127
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 127
aattccctgg catttaggtt gagc                                      24

<210> SEQ ID NO 128
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 128
gcagaatgca gactttccct ttca                                      24

<210> SEQ ID NO 129
<211> LENGTH: 22
<212> TYPE: DNA
<213> ORGANISM: Artificial Sequence
<220> FEATURE:
<223> OTHER INFORMATION: Synthetic oligonucleotide
```

269 270

-continued

<400> SEQUENCE: 129
ggtgcctatc cctgccttgt at                                          22

<210> SEQ ID NO 130
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 130
ttttacttcg ccttggcaca cc                                          22

<210> SEQ ID NO 131
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 131
cacgcccctg taatcccaac ta                                          22

<210> SEQ ID NO 132
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 132
gtggtcttct tcccacctcc tc                                          22

<210> SEQ ID NO 133
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 133
gaaatcacgc cactgcattc ca                                          22

<210> SEQ ID NO 134
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 134
gattcaccca cttttcccag cg                                          22

<210> SEQ ID NO 135
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 135
tgcaaattca cagcaaagca gga                                         23

<210> SEQ ID NO 136

-continued

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 136
acattgaccc cagttgctct ct                                               22

<210> SEQ ID NO 137
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 137
tgctgctact cttttctgga cact                                             24

<210> SEQ ID NO 138
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 138
ggagcaattc cactgatgca tctc                                             24

<210> SEQ ID NO 139
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 139
gcactcccac tgcctgtatt ga                                               22

<210> SEQ ID NO 140
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 140
gagtagggga aaagagggga gc                                               22

<210> SEQ ID NO 141
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 141
tcagagactc catgatgcca tgtt                                             24

<210> SEQ ID NO 142
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 142
```

-continued

```
gctatgttgt cctggctaga gtgt                                        24

<210> SEQ ID NO 143
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 143
gggtggtaga caagaagcct ca                                          22

<210> SEQ ID NO 144
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 144
ggcacagaca gaccacaaaa gg                                          22

<210> SEQ ID NO 145
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 145
aagccacgtt agcattttcc cttc                                        24

<210> SEQ ID NO 146
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 146
aggcacttaa tcttagagat gggct                                       25

<210> SEQ ID NO 147
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 147
tcagagatat gtcccctgcc ct                                          22

<210> SEQ ID NO 148
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 148
tgctttgagg atgcctttgc tg                                          22

<210> SEQ ID NO 149
<211> LENGTH: 24
<212> TYPE: DNA
```

-continued

```
<213> ORGANISM: Artificial Sequence
<220> FEATURE:
<223> OTHER INFORMATION: Synthetic oligonucleotide

<400> SEQUENCE: 149
ttctgcatca gagctgtaag aggt                                              24

<210> SEQ ID NO 150
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 150
caccagtagc tacaaaaagc agga                                              24

<210> SEQ ID NO 151
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 151
cagtgggtgg tatgggtcct tt                                                22

<210> SEQ ID NO 152
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 152
ggtgaatggg gttgcaagga tg                                                22

<210> SEQ ID NO 153
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 153
tggggacggg gttagaaatc ac                                                22

<210> SEQ ID NO 154
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 154
taagcaaaca gggagctgag ct                                                22

<210> SEQ ID NO 155
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 155
cagaacagac gctggtaaca caatt                                             25
```

-continued

```
<210> SEQ ID NO 156
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 156
gcagataatt ttaatgctca gccgc                                        25

<210> SEQ ID NO 157
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 157
gagtcaaagc caatcgtcgc aa                                           22

<210> SEQ ID NO 158
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 158
tgtggttact gtaggcaagg ca                                           22

<210> SEQ ID NO 159
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 159
tgccattccc taaacaacag ttg                                          23

<210> SEQ ID NO 160
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 160
ggaggtgctg ttaggaaccc at                                           22

<210> SEQ ID NO 161
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 161
acccgcctgt aatcccagtt ac                                           22

<210> SEQ ID NO 162
<211> LENGTH: 22
<212> TYPE: DNA
<213> ORGANISM: Artificial Sequence
<220> FEATURE:
```

-continued

<223> OTHER INFORMATION: Synthetic oligonucleotide

<400> SEQUENCE: 162
catttgagtt ttgcatgcgc gt                                                     22

<210> SEQ ID NO 163
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 163
actggcctag atgtacgtgt ct                                                     22

<210> SEQ ID NO 164
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 164
atgctctact gccttgctgt ca                                                     22

<210> SEQ ID NO 165
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 165
acaagaaagc tgtactggcc ct                                                     22

<210> SEQ ID NO 166
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 166
tttgtgcaag gatgagaggg ga                                                     22

<210> SEQ ID NO 167
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 167
cttcactgct ggagggaatg ga                                                     22

<210> SEQ ID NO 168
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 168
tggcctccgg gtttattcat gt                                                     22

-continued

```
<210> SEQ ID NO 169
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 169
tttgatcacg ccactgcatt cc                                          22

<210> SEQ ID NO 170
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 170
ttagctggat atggtggtgg gc                                          22

<210> SEQ ID NO 171
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 171
aggaggatgc tggagtgaga ga                                          22

<210> SEQ ID NO 172
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 172
aaggcccctg aatctgcatt ct                                          22

<210> SEQ ID NO 173
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 173
actttagtct gcgccagagg ag                                          22

<210> SEQ ID NO 174
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 174
cggcgtcagg taaaacaggt tc                                          22

<210> SEQ ID NO 175
<211> LENGTH: 22
<212> TYPE: DNA
<213> ORGANISM: Artificial Sequence
<220> FEATURE:
<223> OTHER INFORMATION: Synthetic oligonucleotide
```

-continued

```
<400> SEQUENCE: 175
ccttgggccc ttctgtaatc ca                                              22

<210> SEQ ID NO 176
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 176
caacccagat ggctccacta ca                                              22

<210> SEQ ID NO 177
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 177
ccagtggagc ctctgaagag ag                                              22

<210> SEQ ID NO 178
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 178
tcagtagttc aagaccagcc cg                                              22

<210> SEQ ID NO 179
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 179
atctgggttg ccacagaagt ct                                              22

<210> SEQ ID NO 180
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 180
tgggctggtt aggtagagga gt                                              22

<210> SEQ ID NO 181
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 181
tcaactcgag tccaattccc cc                                              22

<210> SEQ ID NO 182
<211> LENGTH: 22
```

-continued

```
<212> TYPE: DNA
<213> ORGANISM: Artificial Sequence
<220> FEATURE:
<223> OTHER INFORMATION: Synthetic oligonucleotide

<400> SEQUENCE: 182
agaagggctt ttcaggagag gg                                                 22

<210> SEQ ID NO 183
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 183
tttagtagag acggggtttc accg                                               24

<210> SEQ ID NO 184
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 184
tgatgggggc actgaagtca at                                                 22

<210> SEQ ID NO 185
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 185
tgactagaag ggtggcaatg ca                                                 22

<210> SEQ ID NO 186
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 186 cggccttta cgtttaagcc gt                                                  22

<210> SEQ ID NO 187
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 187
ctcttcctcc ccagcttgtc tc                                                 22

<210> SEQ ID NO 188
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 188
```

-continued

```
agtacagaaa gcgggcctta gg                                            22

<210> SEQ ID NO 189
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 189
aggagggtgg atcatctgag gt                                            22

<210> SEQ ID NO 190
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 190
ttaagccctg tgagccacct tt                                            22

<210> SEQ ID NO 191
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 191
tgtatgtgaa tgagcgggtg gt                                            22

<210> SEQ ID NO 192
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 192
agcatggctt gattccctga ct                                            22

<210> SEQ ID NO 193
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 193
agtactgcag tctggcccaa at                                            22

<210> SEQ ID NO 194
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 194
aagtcaagct gtgctcaggg at                                            22

<210> SEQ ID NO 195
<211> LENGTH: 22
<212> TYPE: DNA
<213> ORGANISM: Artificial Sequence
```

```
<220> FEATURE:
<223> OTHER INFORMATION: Synthetic oligonucleotide

<400> SEQUENCE: 195
aggagaaaat tcttgggcag ca                                              22

<210> SEQ ID NO 196
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 196
cctgactctc ctgaagacct gc                                              22

<210> SEQ ID NO 197
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 197
tgtgtagctt gcaaaagaca gca                                             23

<210> SEQ ID NO 198
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 198
cccaatttcc caatggctgc tt                                              22

<210> SEQ ID NO 199
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 199
ttcgagcaat tctcctgcct ca                                              22

<210> SEQ ID NO 200
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 200
gttcctgctt tcccgtcact tg                                              22

<210> SEQ ID NO 201
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 201
tggatccagc agctcaatga ca                                              22
```

-continued

<210> SEQ ID NO 202
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 202
ataccggctg tgtgcttagt gt                                                          22

<210> SEQ ID NO 203
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 203
gaccctgttg tattgccect ct                                                          22

<210> SEQ ID NO 204
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 204
cgtgacagtc tcagggacca at                                                          22

<210> SEQ ID NO 205
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 205
taaggcactg tgctgagagc tc                                                          22

<210> SEQ ID NO 206
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 206
cagaacaaag cagctgatgg ca                                                          22

<210> SEQ ID NO 207
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 207
gtcccttgcc taacacctca gt                                                          22

<210> SEQ ID NO 208
<211> LENGTH: 22
<212> TYPE: DNA
<213> ORGANISM: Artificial Sequence
<220> FEATURE:
<223> OTHER INFORMATION: Synthetic oligonucleotide -continued

```
<400> SEQUENCE: 208
gccttggaac agaggatggg at                                          22

<210> SEQ ID NO 209
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 209
gaagttcaag accagcatgg cc                                          22

<210> SEQ ID NO 210
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 210
agggcgaggt ttgctactga at                                          22

<210> SEQ ID NO 211
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 211
gaaacaccat ggaacgtgca ct                                          22

<210> SEQ ID NO 212
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 212
tatacgacca caggttctgg cc                                          22

<210> SEQ ID NO 213
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 213
caggccttct tgactggagg aa                                          22

<210> SEQ ID NO 214
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 214
gtgaggggaa tggagcagta gt                                          22

<210> SEQ ID NO 215
```

<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 215
cagaggttgc ggtaagtgga ga                                                           22

<210> SEQ ID NO 216
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 216
atcctctgtg tgctccaagg tc                                                           22

<210> SEQ ID NO 217
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 217
agggctagtt gtctgaggac tt                                                           22

<210> SEQ ID NO 218
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 218
tatgagtggt cactgggcag ag                                                           22

<210> SEQ ID NO 219
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 219
ttgcgccagg taagatttcc ag                                                           22

<210> SEQ ID NO 220
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 220
tgcgggtagg ggaaaatgtt ct                                                           22

<210> SEQ ID NO 221
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 221

-continued

```
catgccctgt ctccagctct ta                                                    22

<210> SEQ ID NO 222
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 222
cctcaaacca tcctcccacc tt                                                     22

<210> SEQ ID NO 223
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 223
acgtgtatcc atgtctgtta gcct                                                   24

<210> SEQ ID NO 224
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 224
ggttgatctc atgttgcctt gctt                                                   24

<210> SEQ ID NO 225
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 225
catagcccag gaacacaggt ca                                                     22

<210> SEQ ID NO 226
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 226
tgcagctgaa ggtaagagag gt                                                     22

<210> SEQ ID NO 227
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 227
aactcaggct ctcagcttca gg                                                     22

<210> SEQ ID NO 228
<211> LENGTH: 22
<212> TYPE: DNA
```

-continued

```
<213> ORGANISM: Artificial Sequence
<220> FEATURE:
<223> OTHER INFORMATION: Synthetic oligonucleotide

<400> SEQUENCE: 228
gtgctatggt ttcctggtgc ac                                         22

<210> SEQ ID NO 229
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 229
ggcctgaccc tttgctttca tc                                         22

<210> SEQ ID NO 230
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 230
gtctgctctg gttttggctt cc                                         22

<210> SEQ ID NO 231
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 231
aagtatattg agcggcccct cc                                         22

<210> SEQ ID NO 232
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 232
ctgttggatg caaggacagc tg                                         22

<210> SEQ ID NO 233
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 233
tgagtgaaca aagtgcggat tctg                                       24

<210> SEQ ID NO 234
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 234
tgacagctgc cactcattat ctgt                                       24
```

```
<210> SEQ ID NO 235
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 235
ggcaccacag tacaaatcag gtg                                            23

<210> SEQ ID NO 236
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 236
cttgctcatg aaaggctctg agc                                            23

<210> SEQ ID NO 237
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 237
tgtaatctcc accccttctg cag                                            23

<210> SEQ ID NO 238
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 238
ttcaccacct cattgcacac atg                                            23

<210> SEQ ID NO 239
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 239
ccatctgtga cagagccttg ga                                             22

<210> SEQ ID NO 240
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 240
ctgggagggg tggagcttta aa                                             22

<210> SEQ ID NO 241
<211> LENGTH: 22
<212> TYPE: DNA
<213> ORGANISM: Artificial Sequence
<220> FEATURE:
```

-continued

<223> OTHER INFORMATION: Synthetic oligonucleotide

<400> SEQUENCE: 241
ccacttctct acccactcag cc                                        22

<210> SEQ ID NO 242
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 242
atggtggctt ggatcttggt ga                                        22

<210> SEQ ID NO 243
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 243
tgttctcaca gagtggagag cg                                        22

<210> SEQ ID NO 244
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 244
ccgagaaatg cagacccagg ta                                        22

<210> SEQ ID NO 245
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 245
ctgcggtctc tctgtcttca ca                                        22

<210> SEQ ID NO 246
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 246
cctgcgtgaa ttcatagacg cc                                        22

<210> SEQ ID NO 247
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 247
agacaggttc tcgctctgtc ac                                         22

```
<210> SEQ ID NO 248
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 248
aattgcaagc cgtcagtgaa gg                                          22

<210> SEQ ID NO 249
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 249
atctggtgtg aatggggaag gg                                          22

<210> SEQ ID NO 250
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 250
atacccacac ctgacccaca tg                                          22

<210> SEQ ID NO 251
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 251
gacaccatcc tcaacgccat tg                                          22

<210> SEQ ID NO 252
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 252
cagccaccaa agtatcggga ga                                          22

<210> SEQ ID NO 253
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 253
acctgcagct accgagaaac tt                                          22

<210> SEQ ID NO 254
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 254
tctcaaacag acagcgggca ta                                                    22

<210> SEQ ID NO 255
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 255
aatcatcccc cattccccat cc                                                    22

<210> SEQ ID NO 256
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 256
aactcccatt ccctccttct gc                                                    22

<210> SEQ ID NO 257
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 257
caccctgatg tcgcagccta ta                                                    22

<210> SEQ ID NO 258
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 258
ctgaaacgtg gtccatgaca gc                                                    22

<210> SEQ ID NO 259
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 259
tgcctggaca agaatgagct ca                                                    22

<210> SEQ ID NO 260
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 260
ctctaggaga cagtggggtc ct                                                    22

<210> SEQ ID NO 261
<211> LENGTH: 22

-continued

```
<212> TYPE: DNA
<213> ORGANISM: Artificial Sequence
<220> FEATURE:
<223> OTHER INFORMATION: Synthetic oligonucleotide

<400> SEQUENCE: 261
tctgtgcgtc tcaactatgg ca                                            22

<210> SEQ ID NO 262
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 262
gcttccggta gtctgggttc tt                                            22

<210> SEQ ID NO 263
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 263
gtcaagtggc tcaacgagaa cg                                            22

<210> SEQ ID NO 264
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 264
tccaagacca ctgagctcat gg                                            22

<210> SEQ ID NO 265
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 265
tgtggttaaa ctcctgcacc ca                                            22

<210> SEQ ID NO 266
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 266
cccctgcagc tactctttgg at                                            22

<210> SEQ ID NO 267
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 267
```

-continued

```
acactgtctc tctccctagg ca                                                   22

<210> SEQ ID NO 268
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 268
gcaggacact agggagtcaa gg                                                   22

<210> SEQ ID NO 269
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 269
gctttctttc ctttcgcgct ct                                                   22

<210> SEQ ID NO 270
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 270
gtgggagatc tggtttccgg aa                                                   22

<210> SEQ ID NO 271
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 271
tcccgagcct ccttcctctc                                                      20

<210> SEQ ID NO 272
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 272
atccctgtcc ggatgctg                                                        18

<210> SEQ ID NO 273
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 273
gtaggccatc ttctgtggga ca                                                   22

<210> SEQ ID NO 274
<211> LENGTH: 22
<212> TYPE: DNA
<213> ORGANISM: Artificial Sequence
```

-continued

<220> FEATURE:
<223> OTHER INFORMATION: Synthetic oligonucleotide

<400> SEQUENCE: 274
tgtactccga aagcaggtcc tg                                          22

<210> SEQ ID NO 275
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 275
atgtgcccga tctgcgatct ta                                          22

<210> SEQ ID NO 276
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 276
gccagtctaa cagcatgcag tg                                          22

<210> SEQ ID NO 277
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 277
gcgaaaggtg tgaacagatg ct                                          22

<210> SEQ ID NO 278
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 278
acatatcccg tgtttgctgc ac                                          22

<210> SEQ ID NO 279
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 279
aggagactgc acgttctttg ga                                          22

<210> SEQ ID NO 280
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 280
ttcctcacct ccaggcttca tg                                          22

-continued

```
<210> SEQ ID NO 281
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 281
tttcaatgca aagctccccc ac                                           22

<210> SEQ ID NO 282
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 282
taaagcctgg cctcgacatg aa                                           22

<210> SEQ ID NO 283
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 283
caccctgatg tcgcagccta ta                                           22

<210> SEQ ID NO 284
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 284
gcaagtccct ggtcttcttg gt                                           22

<210> SEQ ID NO 285
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 285
ctgttctgac ttccctccct cc                                           22

<210> SEQ ID NO 286
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 286
tgggacttgg ctcacctgaa tc                                           22

<210> SEQ ID NO 287
<211> LENGTH: 22
<212> TYPE: DNA
<213> ORGANISM: Artificial Sequence
<220> FEATURE:
<223> OTHER INFORMATION: Synthetic oligonucleotide
```

-continued

```
<400> SEQUENCE: 287
ctgtcaatag ggcctagcac ca                                          22

<210> SEQ ID NO 288
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 288
ctgccaagtg acctcctctc aa                                          22

<210> SEQ ID NO 289
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 289
catccaccac caagagctga ga                                          22

<210> SEQ ID NO 290
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 290
cccaccctct cactctgtct tg                                          22

<210> SEQ ID NO 291
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 291
accactcatt ctggcatcgt ga                                          22

<210> SEQ ID NO 292
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 292
cctgccactc tccacttctc tc                                          22

<210> SEQ ID NO 293
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 293
tgtgccggat cttagcctca aa                                          22

<210> SEQ ID NO 294
```

-continued

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 294
aaaggaggag agctgcgttc at                                           22

<210> SEQ ID NO 295
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 295
tgcctggaca agaatgagct ca                                           22

<210> SEQ ID NO 296
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 296
tcggagaagt aggagccctc tc                                           22

<210> SEQ ID NO 297
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 297
ctgtgggtgt gtgtgtgaat gg                                           22

<210> SEQ ID NO 298
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 298
gcagggggtt gctaagtagt ca                                           22

<210> SEQ ID NO 299
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 299
tgcctcctgc ttgtactctt cc                                           22

<210> SEQ ID NO 300
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 300
```

-continued

```
gcttactggg ccatctcagt ga                                        22

<210> SEQ ID NO 301
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 301
gtagggtttg gccttttgct cc                                        22

<210> SEQ ID NO 302
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 302
ccccaggtaa aagcaccagg ta                                        22

<210> SEQ ID NO 303
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 303
tgtctgtcct ggtcacggat tc                                        22

<210> SEQ ID NO 304
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 304
cctgtggttc tgggagtctc tg                                        22

<210> SEQ ID NO 305
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 305
aaagggactg tggcatctcc tc                                        22

<210> SEQ ID NO 306
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 306
tcacaggcat caaggtggta gg                                        22

<210> SEQ ID NO 307
<211> LENGTH: 22
<212> TYPE: DNA
```

-continued

```
<213> ORGANISM: Artificial Sequence
<220> FEATURE:
<223> OTHER INFORMATION: Synthetic oligonucleotide

<400> SEQUENCE: 307
tctgtgcgtc tcaactatgg ca                                      22

<210> SEQ ID NO 308
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 308
tgttctccac cgacgagtac ag                                      22

<210> SEQ ID NO 309
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 309
gagacgggct ttcactgtgt tg                                      22

<210> SEQ ID NO 310
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 310
aacggggtac ttgtctggat gg                                      22

<210> SEQ ID NO 311
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 311
tgcttttgaa catgccagcc at                                      22

<210> SEQ ID NO 312
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 312
ccaggaaggc tttgcttcca ag                                      22

<210> SEQ ID NO 313
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 313
aacccctgaa cgagtgggaa tt                                      22
```

-continued

```
<210> SEQ ID NO 314
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 314
tcccacaaat cctccactgg tg                                                 22

<210> SEQ ID NO 315
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 315
atccggttca gtggactctg tg                                                 22

<210> SEQ ID NO 316
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 316
aatgtctgcg ggtctctgtc tc                                                 22

<210> SEQ ID NO 317
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 317
ggaacacagg gttgatgcca tg                                                 22

<210> SEQ ID NO 318
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 318
tcctgaagtg cgagtactgt gg                                                 22

<210> SEQ ID NO 319
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 319
catctttgtc accaccacag gc                                                 22

<210> SEQ ID NO 320
<211> LENGTH: 22
<212> TYPE: DNA
<213> ORGANISM: Artificial Sequence
<220> FEATURE:
```

-continued

```
<223> OTHER INFORMATION: Synthetic oligonucleotide

<400> SEQUENCE: 320
aggtactggg cttgcttctc ag                                            22

<210> SEQ ID NO 321
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 321
ctgcagaaac aaatcattg                                                19

<210> SEQ ID NO 322
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 322
tccgcagctg ttcagcccct                                               20

<210> SEQ ID NO 323
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 323
acacaggatg gtgtgagga                                                19

<210> SEQ ID NO 324
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 324
gcgtgtaggt ggaccggtat                                               20

<210> SEQ ID NO 325
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 325
caccgctgca gaaacaaatc attg                                          24

<210> SEQ ID NO 326
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 326
aaaccaatga tttgtttctg cagc                                          24
```

-continued

```
<210> SEQ ID NO 327
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 327
caccgtccgc agctgttcag cccct                                     25

<210> SEQ ID NO 328
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 328
aaacaggggc tgaacagctg cggac                                     25

<210> SEQ ID NO 329
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 329
caccgacaca ggatggtgtg agga                                      24

<210> SEQ ID NO 330
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 330
aaactcctca caccatcctg tgtc                                      24

<210> SEQ ID NO 331
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 331
caccggcgtg taggtggacc ggtat                                     25

<210> SEQ ID NO 332
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 332
aaacataccg gtccacctac acgcc                                     25

<210> SEQ ID NO 333
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 333
caccgctcct aggagggcgt gcgca                                              25

<210> SEQ ID NO 334
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 334
aaactgcgca cgccctccta ggagc                                             25

<210> SEQ ID NO 335
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 335
caccgtgaaa gaaagaaagg ggagg                                             25

<210> SEQ ID NO 336
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 336
aaaccctccc ctttctttct ttcac                                             25

<210> SEQ ID NO 337
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 337
caccgaatct aggaaaagca tcacc                                             25

<210> SEQ ID NO 338
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 338
aaacggtgat gcttttccta gattc                                             25

<210> SEQ ID NO 339
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 339
cccttgtttt cactgcctca ggt                                               23

<210> SEQ ID NO 340
<211> LENGTH: 23

-continued

```
<212> TYPE: DNA
<213> ORGANISM: Artificial Sequence
<220> FEATURE:
<223> OTHER INFORMATION: Synthetic oligonucleotide

<400> SEQUENCE: 340
acctgaggca gtgaaaacaa ggg                                          23

<210> SEQ ID NO 341
<211> LENGTH: 20
<212> TYPE: DNA
<213> ORGANISM: Artificial Sequence
<220> FEATURE:
<223> OTHER INFORMATION: Synthetic nucleotide

<400> SEQUENCE: 341
tttgacaatc aggacattga                                              20

<210> SEQ ID NO 342
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 342
tcagtataag atctatgttc                                              20

<210> SEQ ID NO 343
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 343
attttgtttc tcccacacag acacta                                       26

<210> SEQ ID NO 344
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 344
tagtgtctgt gtgggagaaa caaaat                                       26

<210> SEQ ID NO 345
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 345
attgtctttc tcatacacag atgtat                                       26

<210> SEQ ID NO 346
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 346
```

-continued

```
atacatctgt gtatgagaaa gacaat                                    26

<210> SEQ ID NO 347
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 347
ctgcagaaac aaatcattgt gg                                        22

<210> SEQ ID NO 348
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 348
actcaataac tttgacgctg gacgtaaaga aa                             32

<210> SEQ ID NO 349
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 349
gcgtgtaggt ggaccggtat cgg                                       23

<210> SEQ ID NO 350
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 350
caccgtgtag gctccaaaac caagg                                     25

<210> SEQ ID NO 351
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 351
caccgttgta ggctccaaaa ccaag                                     25

<210> SEQ ID NO 352
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 352
caccgttttg taggctccaa aacca                                     25

<210> SEQ ID NO 353
<211> LENGTH: 61
<212> TYPE: DNA
<213> ORGANISM: Artificial Sequence
```

-continued

<220> FEATURE:
<223> OTHER INFORMATION: Synthetic oligonucleotide

<400> SEQUENCE: 353
tgaatttgtt tttgtaggct ccaaaaccaa ggagggagtg gtgcatggtg tggcaacagg      60
t                                                                     61

<210> SEQ ID NO 354
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 354
acctgttgcc acaccatgca ccactccctc cttggttttg gagcctacaa aaacaattca      60

<210> SEQ ID NO 355
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 355
caccggagcc tacaaaaaca aattc                                           25

<210> SEQ ID NO 356
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 356
caccgagcct acaaaaacaa attca                                           25

<210> SEQ ID NO 357
<211> LENGTH: 18
<212> TYPE: PRT
<213> ORGANISM: Artificial Sequence
<220> FEATURE:
<223> OTHER INFORMATION: Synthetic peptide

<400> SEQUENCE: 357

Met Ala Thr Leu Glu Lys Leu Met Lys Ala Phe Glu Ser Leu Lys Ser
1               5                   10                  15

Phe Gln

<210> SEQ ID NO 358
<211> LENGTH: 60
<212> TYPE: PRT
<213> ORGANISM: Artificial Sequence
<220> FEATURE:
<223> OTHER INFORMATION: Synthetic peptide

<400> SEQUENCE: 358

Asp Ile Leu Ser His Ser Ser Ser Gln Val Ser Ala Val Pro Ser Ala
1               5                   10                  15

Asp Pro Ala Met Asp Leu Asn Asp Gly Gln Ala Ser Ser Pro Ile Ser
            20                  25                  30

Asp Ser Gln Thr Thr Glu Gly Pro Asp Ser Ala Val Thr Ala Val Pro
        35                  40                  45

-continued

```
Ser Asp Ser Ser Glu Ile Val Leu Asp Gly Thr Asp
   50                  55                 60
```

```
<210> SEQ ID NO 359
<211> LENGTH: 9
<212> TYPE: PRT
<213> ORGANISM: Artificial Sequence
<220> FEATURE:
<223> OTHER INFORMATION: Synthetic peptide

<400> SEQUENCE: 359

Asp Ile Leu Ser His Ser Ser Ser Gln
1               5
```

```
<210> SEQ ID NO 360
<211> LENGTH: 6
<212> TYPE: PRT
<213> ORGANISM: Artificial Sequence
<220> FEATURE:
<223> OTHER INFORMATION: Synthetic peptide

<400> SEQUENCE: 360

Val Leu Asp Gly Thr Asp
1               5
```

```
<210> SEQ ID NO 361
<211> LENGTH: 124
<212> TYPE: DNA
<213> ORGANISM: Artificial Sequence
<220> FEATURE:
<223> OTHER INFORMATION: Synthetic oligonucleotide

<400> SEQUENCE: 361
tgaccctgac cctgccatgg acctgaatga tgggacccag gcctcgtcgc ccatcagcga    60
cagctcccag accaccaccg aagggcctga ttcagctgtt accccttcag acagttctga   120
aatt                                                               124
```

```
<210> SEQ ID NO 362
<211> LENGTH: 124
<212> TYPE: DNA
<213> ORGANISM: Artificial Sequence
<220> FEATURE:
<223> OTHER INFORMATION: Synthetic oligonucleotide

<400> SEQUENCE: 362
aatttcagaa ctgtctgaag gggtaacatc tgaatcaggc ccttcggtgg tggtctggga    60
gctgtcgctg atgggcgacg aggcctgggt cccatcattc aggtccatgg cagggtcagg   120
gtca                                                               124
```

```
<210> SEQ ID NO 363
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 363
ctttttggta tcttacagga actccaggat ggcattggg                          39
```

```
<210> SEQ ID NO 364
<211> LENGTH: 39
<212> TYPE: DNA
<213> ORGANISM: Artificial Sequence
<220> FEATURE:
```

-continued

```
<223> OTHER INFORMATION: Synthetic oligonucleotide
<220> FEATURE:
<221> NAME/KEY: misc_feature
<222> LOCATION: (15)..(15)
<223> OTHER INFORMATION: n is a, c, g, or t

<400> SEQUENCE: 364 cttttggta tcttncagga actccaggat ggcattggg                           39
```

METHODS FOR EXON SKIPPING AND GENE KNOCKOUT USING BASE EDITORS

PRIORITY

This application is a 371 International of PCT Application Number PCT/US19/42627, filed Jul. 19, 2019, which claims the benefit of U.S. provisional application Ser. No. 62/700,365, filed Jul. 19, 2018, which are incorporated by reference herein in their entirety.

STATEMENT REGARDING FEDERALLY SPONSORED RESEARCH OR DEVELOPMENT

This invention was made with government support under R01CA163336, R03EB026064, R01GM127497 awarded by the National Institutes of Health. This invention was made with government support under 17SDG33650087 awarded by the American Heart Association. This invention was made with government support under DGE-1746047 awarded by the National Science Foundation. The government has certain rights in the invention.

BACKGROUND

Programmable nucleases have been used to introduce targeted modifications within a native genomic DNA context (Gaj T, et al, *Trends Biotechnol* 2013, 31:397-405). While multiple nuclease architectures have been successfully utilized for genome editing, the clustered regularly interspaced short palindromic repeats (CRISPR)-CRISPR-associated (Cas) system (Cong L, et al, *Science* 2013, 339:819-823; Jinek M, et al, *Elife* 2013, 2:e00471; Mali P, et al., *Science* 2013, 339:823-826) has rapidly become the most popular approach because of its flexibility, versatility and efficacy. CRISPR-Cas9 gene editing is typically accomplished by introducing double-strand breaks (DSBs) at target sites in genomic DNA, which are most commonly repaired by non-homologous end-joining (NHEJ), a mutagenic pathway that creates random insertions and deletions that can be used to knockout genes (Gaj T, et al, *Trends Biotechnol* 2013, 31:397-405). However, concerns over off-target mutations and stochastic outcomes of NHEJ-based editing methods (Nelson C E, et al, *Nat Biotechnol* 2016, 34:298-299) have elicited the development of Cas9 isoforms that introduce DSBs with improved specificity (Kleinstiver B P, et al, *Nature* 2016, 529:490-495; Liang X, et al, *J Biotechnol* 2015, 208:44-53; Slaymaker I M, et al, *Science* 2016, 351:84-88) or other technologies that do not rely on the stochastic repair of DSBs.

Previously, targeted exon skipping has been accomplished by directing antisense oligonucleotides (AONs) to splice acceptor sites in order to block the native splice machinery and prevent incorporation of the exon into the mature transcript. However, the transient nature of these therapies necessitates repeated injections to achieve any lasting effects. More recently, permanent genome editing strategies such as CRISPR-Cas9 has been shown to induce exon skipping (Mou, H. et al, *Genome Biol* 18, 108, doi:10.1186/s13059-017-1237-8 (2017)) which can be harnessed for therapeutic potential. While methods involving double stranded breaks are able to skip the targeted exon, the DNA repair mechanisms associated with them can result in unpredictable phenotypic outcomes. Additionally, there is a concern for unintended nuclease activity at off-target sites which emphasizes the importance of using gene editing methods that are less damaging to genomic DNA.

SUMMARY

Provided herein is a fusion protein comprising (i) at least two tRNA-specific adenosine deaminases (TadA) domains (ii) a linker; and (iii) a RNA-guided DNA endonuclease having nickase activity protein.

Further provided herein is a method for inducing selective exon skipping comprising: contacting one or more DNA target sequences with (i) a single guide RNA (sgRNA) molecule having complementarity to the one or more DNA target sequences; and (ii) a fusion protein comprising at least two tRNA-specific adenosine deaminases (TadA) domains a linker; and a RNA-guided DNA endonuclease having nickase activity protein.

Further provided herein is a recombinant system comprising: a first construct comprising (i) a polynucleotide encoding tRNA-specific adenosine deaminase (TadA) (ii) a polynucleotide encoding a linker (iii) a first part of a polynucleotide encoding a RNA-guided DNA endonuclease having nickase activity domain and (iv) a polynucleotide encoding an N-terminal intein; and a second construct comprising (i) a polynucleotide encoding a C-terminal intein and (ii) a second part of a polynucleotide encoding the RNA-guided DNA endonuclease having nickase activity domain.

Further provided herein is a recombinant system comprising: a first construct comprising (i) a polynucleotide encoding a cytidine deaminase domain (ii) a polynucleotide encoding a linker (iii) a first part of a polynucleotide encoding nickase SpCas9 and (iv) a polynucleotide encoding an N-terminal intein; and a second construct comprising (i) a polynucleotide encoding a C-terminal intein (ii) a second part of a polynucleotide encoding nickase SpCas9 and (iii) a polynucleotide encoding a uracil glycosylase inhibitor.

Further provided herein is a method for inducing selective exon skipping comprising: contacting a DNA target sequence with (i) a single guide RNA (sgRNA) molecule having complementarity to the DNA target sequence and (ii) a cytidine deaminase base editor.

Further provided herein is a method of treating Huntington disease in a subject comprising contacting a cell in the subject with (i) a single guide RNA (sgRNA) molecule having complementarity to a target sequence in the Huntington gene and (ii) a cytidine deaminase base editor.

Further provided herein is a method of treating Duchenne Muscular Dystrophy in a subject comprising contacting a cell in the subject with (i) a single guide RNA (sgRNA) molecule having complementarity to a target sequence in the dystrophin gene and (ii) a cytidine deaminase base editor.

BRIEF DESCRIPTION OF TIE DRAWINGS

The features, objects and advantages other than those set forth above will become more readily apparent when consideration is given to the detailed description below. Such detailed description makes reference to the following drawings, wherein:

FIGS. 1A-1B illustrate CRISPR-SKIP targeting strategy. FIG. 1A is a schematic representation of the consensus sequence of splice acceptors. FIG. 1B is a schematic illustrating that in the presence of an appropriate PAM sequence, base editors can be utilized to deaminate the cytidine in the antisense strand, which is complementary of the conserved guanosine in the splice acceptor, thus resulting in the disruption of the splice acceptor and exon skipping.

FIGS. 2A-2E illustrate that single base editing of splice acceptor consensus sequences enabled programmable exon skipping. FIG. 2A illustrates that 293T cells were transfected with C>T base editors and sgRNAs targeting the splice acceptor of exon 7 in RELA. RT-PCR was used to detect exon skipping over 10 days. The top sequence is SEQ ID NO:339; the bottom sequence is SEQ ID NO:340. FIG. 2B illustrates that skipping of RELA exon 7 and PIK3CA exon 5 was induced by C>T base editors, but not by the sgRNA alone or in combination with dead Cas9 or D10A nickase Cas9. FIG. 2C illustrates that Sanger sequencing of the exon-skipped amplicon was used to demonstrate successful exon skipping of RELA exon 7 and PIK3CA exon 5. The top sequence is SEQ ID NO:340, the bottom sequence is SEQ ID NO:341. FIG. 2D illustrates that deep sequencing of genomic DNA in wt cells and cells treated with C>T base editors targeting RELA exon 7 and PIK3CA exon 5 was used to calculate the modification rate. FIG. 2E illustrates quantification of the rate of exon skipping of RELA exon 7 and PIK3CA exon 5 by deep sequencing of mature mRNA, which was amplified by RT-PCR.

FIG. 3 illustrates that CRISPR-SKIP was effective across a panel of cell lines. CRISPR-SKIP induced skipping of RELA exon 7 and PIK3CA exon 5 in the cell lines HCT116, HEPG2, and MCF7.

FIG. 4 illustrates the comparison of CRISPR-SKIP with active SpCas9 for inducing exon skipping. CRISPR-SKIP was utilized to target the splice acceptors of RELA exon 7, PIK3CA exon 5, and JAG1 exon 9. In parallel, sgRNAs targeting the same exons were co-transfected with active Cas9 to induce exon skipping. Analysis by PCR demonstrated that CRISPR-SKIP induced exon skipping at equal or greater rate than active SpCas9 in each of three exons tested.

FIGS. 5A-5F illustrate that different Cas9 scaffolds increased the number of CRISPR-SKIP target exons. FIG. 5A illustrates that RT-PCR analysis demonstrated that SpCas9-VQR-BE3 and SaCas9-KKH-BE3 (FIG. 5B) can induce exon skipping of BRCA2 exon 26 and RELA exon 10, respectively. FIG. 5C illustrates that deep sequencing of genomic DNA revealed that targeted mutations introduced by SpCas9-VQR-BE3 were found in 0.93% of reads at the BRCA2 exon 26 splice acceptor, while SaCas9-KKH-BE3 induced targeted mutations in 46.61% of reads at RELA exon 10 splice acceptor. FIG. 5D illustrates that deep sequencing was performed in biological duplicates, and the results were combined. FIG. 5E illustrates quantification of the rate of exon skipping of BRCA2 exon 26 and (FIG. 5F) RELA exon 10 by deep sequencing of mature mRNA, which was amplified by RT-PCR. RNAseq was performed on biological duplicates and a single estimate of the proportion and confidence intervals were obtained.

FIG. 6 illustrates that CRISPR-SKIP can be used to simultaneously skip multiple exons within the same transcript. SaCas9-KKH-BE3 was used to target PIK3CA exons 11 and 12. RT-PCR demonstrated that both sgRNAs induced skipping of the targeted exon and, when used together, induced skipping of both exons simultaneously. The top left sequence is SEQ ID NO:343; the top right sequence is SEQ ID NO:345; the bottom left sequence is SEQ ID NO:344, the bottom right sequence is SEQ ID NO: 346.

FIGS. 7A-7B illustrate genome-wide computational estimation of targetability by CRISPR-SKIP. FIG. 7A illustrates the estimation of the number of exons that can be targeted by each base editor with estimated efficiency of editing flanking intronic G at or above the corresponding value on the x-axis. Only exons with maximum off-target score below 10 were considered. FIG. 7B illustrates the estimation of the number of exons that can be targeted by each base editor with maximum off-target score at or below the corresponding value on the x axis. Only exons for which the estimated efficiency of editing the flanking G nucleotide was above 20% were considered.

FIG. 8 illustrates the expanded view of NGS analysis shown in FIG. 2D. Deep sequencing performed on biological duplicates and averaged.

Figures 10, 11:
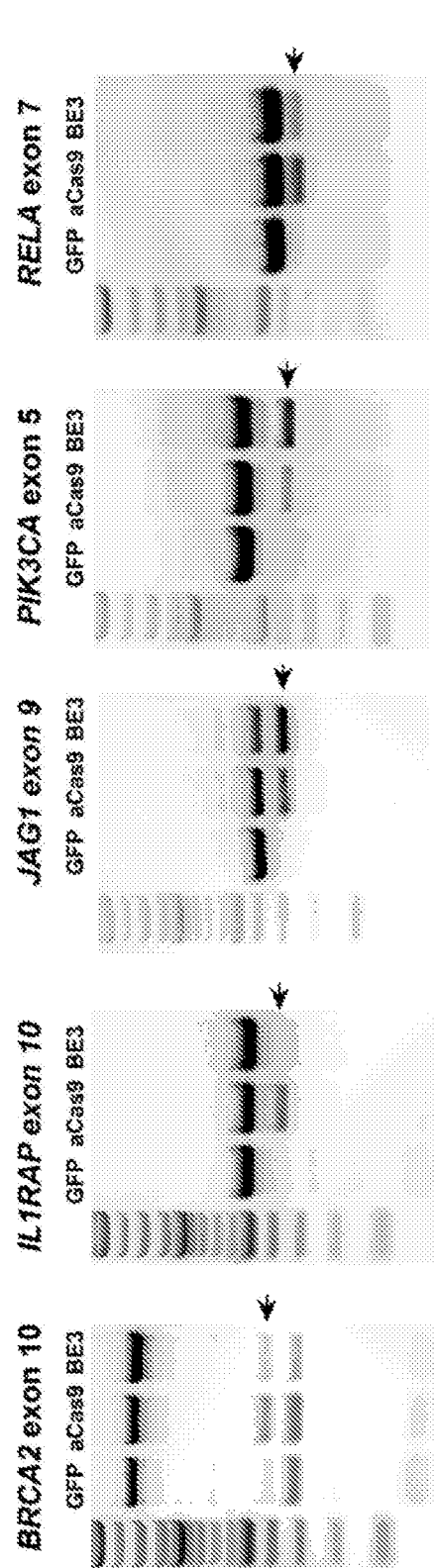

FIG. 10 illustrates the comparison of CRISPR-SKIP and active SpCas9 using the same sgRNAs targeting the splice acceptor of BRCA2 exon 10, IL1RAP exon 10, JAG1 exon 9, PIK3CA exon 5 and RELA exon 7.

FIG. 11 illustrates the expanded view of NGS analysis shown in FIGS. 5C and 5D. Deep sequencing performed on biological duplicates and averaged.

Figure 12:
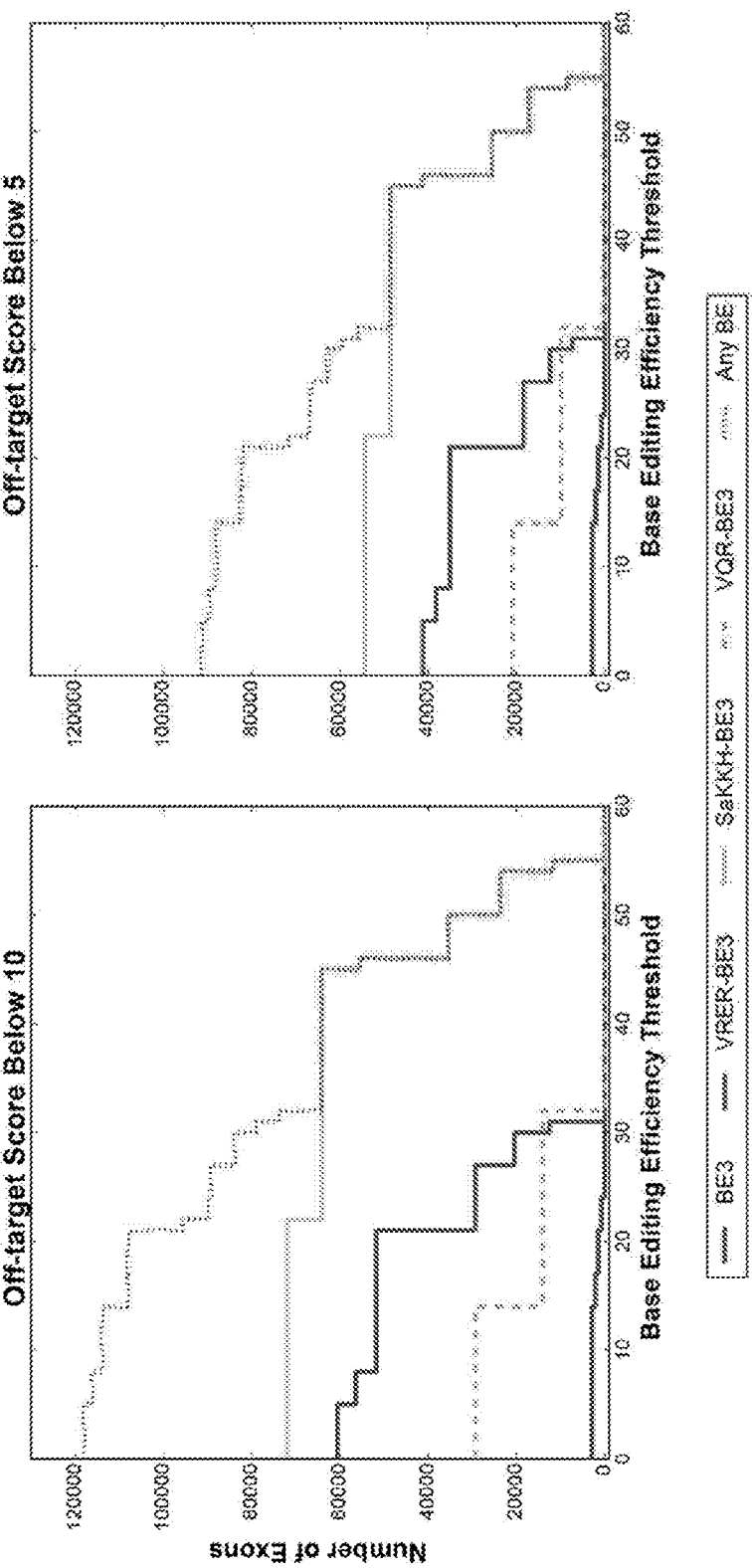

FIG. 12 illustrates the estimation of the number of exons that can be targeted by each base editor with subplots filtered by the maximum allowed off-target score. The y-axis denotes the number of exons that can be targeted with estimated efficiency of modifying intronic flanking G at or above the corresponding value on the x-axis.

Figure 13:
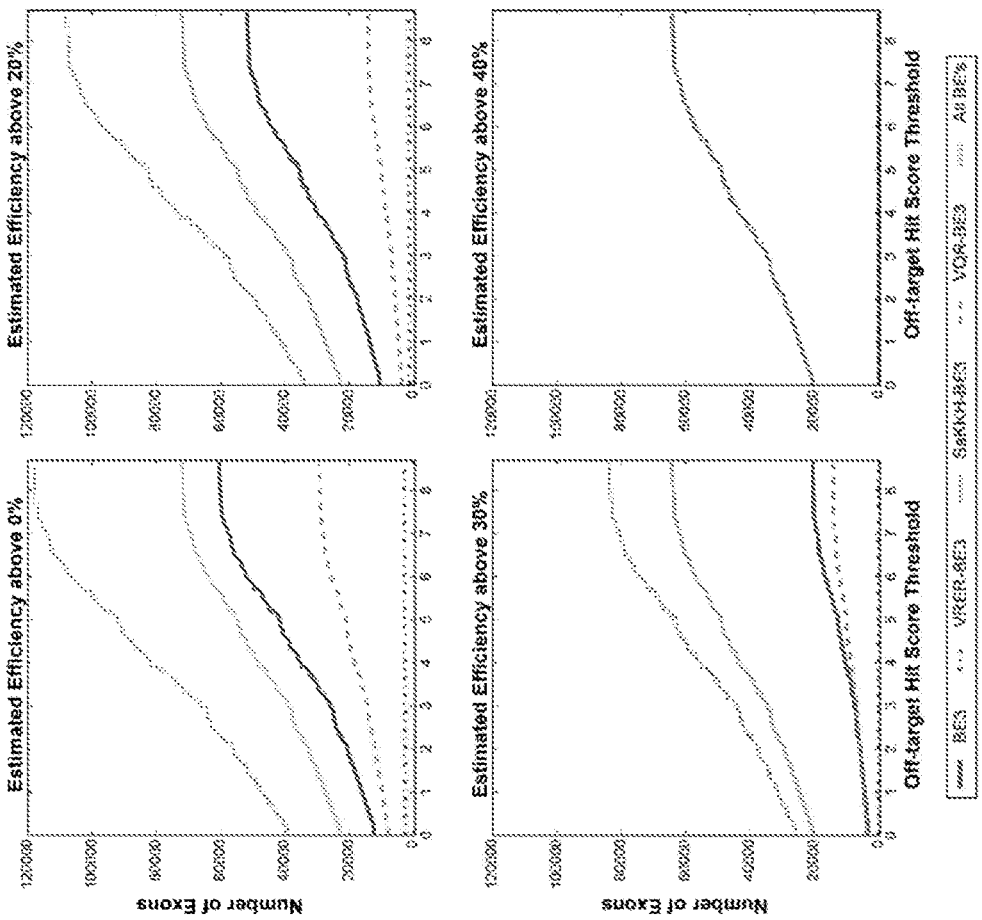

FIG. 13 illustrates the estimation of the number of exons that can be targeted by each base editor with subplots filtered by estimated efficiency of editing the flanking G nucleotide. The y-axis denotes the number of exons that can be targeted with maximum off-target score at or below the corresponding value on the x-axis.

FIG. 14 illustrates the comparison of CRISPR-SKIP using the C>T base editors BE3 or BE4 for inducing skipping of PIK3CA exon 5, RELA exon 7, and JAG1 exon 9 by RT-PCR analysis.

Figures 15A, 15B:
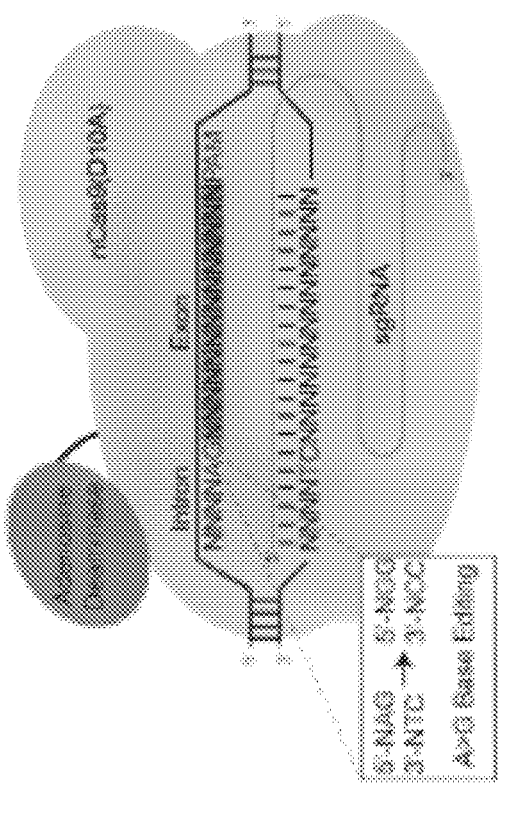

FIGS. 15A-15B illustrate the CRISPR-SKIP targeting strategy targeting the conserved adenosine and the schematic representation of the consensus sequence of splice acceptors.

Figures 16A, 16B, 16C:
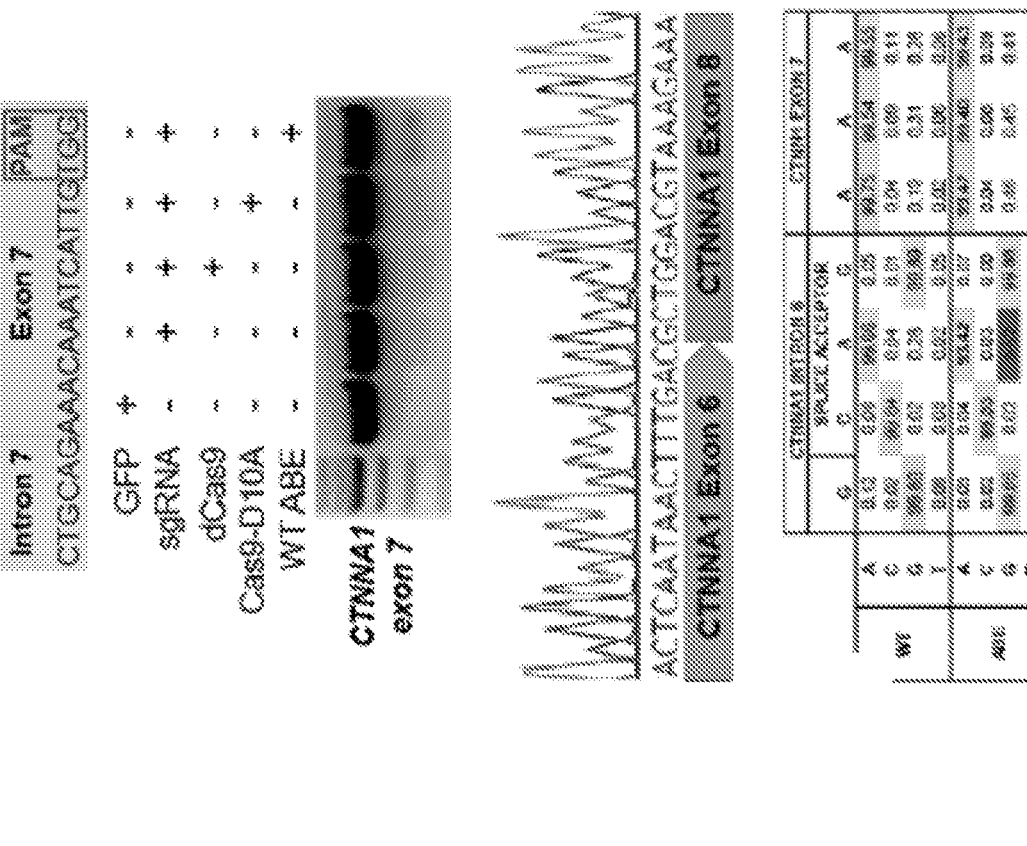

FIGS. 16A-16C illustrate skipping rates of CTNNA1 exon 7. FIG. 16A shows HEK293T cells were transfected with wt ABE and a sgRNA targeting the splice acceptor site of CTNNA1 exon 7. The sequence is SEQ ID NO:347. Targeted exon skipping was observed after performing RT-PCR that could not be induced by the sgRNA alone, or in combination with dead Cas9 or D10A nickase Cas9. FIG. 16B shows sanger sequencing of the shorter transcript confirmed exclusion of exon 7. The sequence is SEQ ID NO:348. FIG. 16C shows high throughput sequencing confirmed targeted A>G mutations within the CTNNA1 exon 7 splice acceptor site.

Figures 17A, 17B:
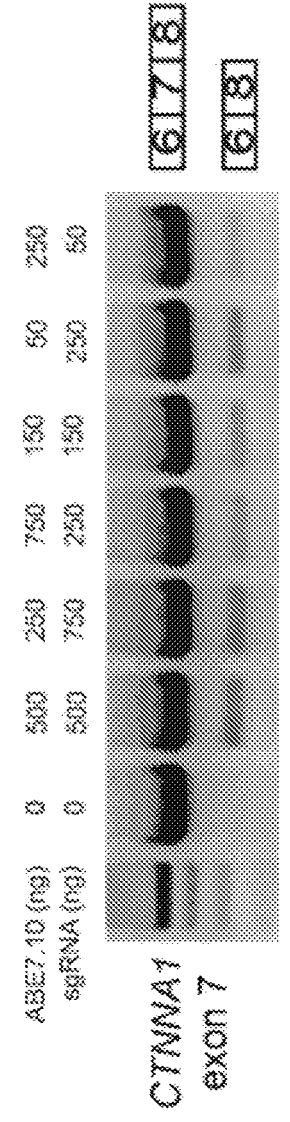

FIG. 17A shows exon skipping in 293T cells transfected with ABE7.10 and CTNNA1 exon 7 sgRNA over a 10-day period. FIG. 17B shows the comparison of exon skipping of CTNNA1 exon 7 with varying doses of ABE7.10 and sgRNA. FIG. 17C shows RT-PCR products demonstrating targeted exon skipping of CTNNA1 exon 7 in HEPG2 cells, AHCY exon 9 in HCT116 cells, and CTNNB1 in mouse Neruro2A and mouse Hepa1-6 cells.

Figures 18A, 18B:
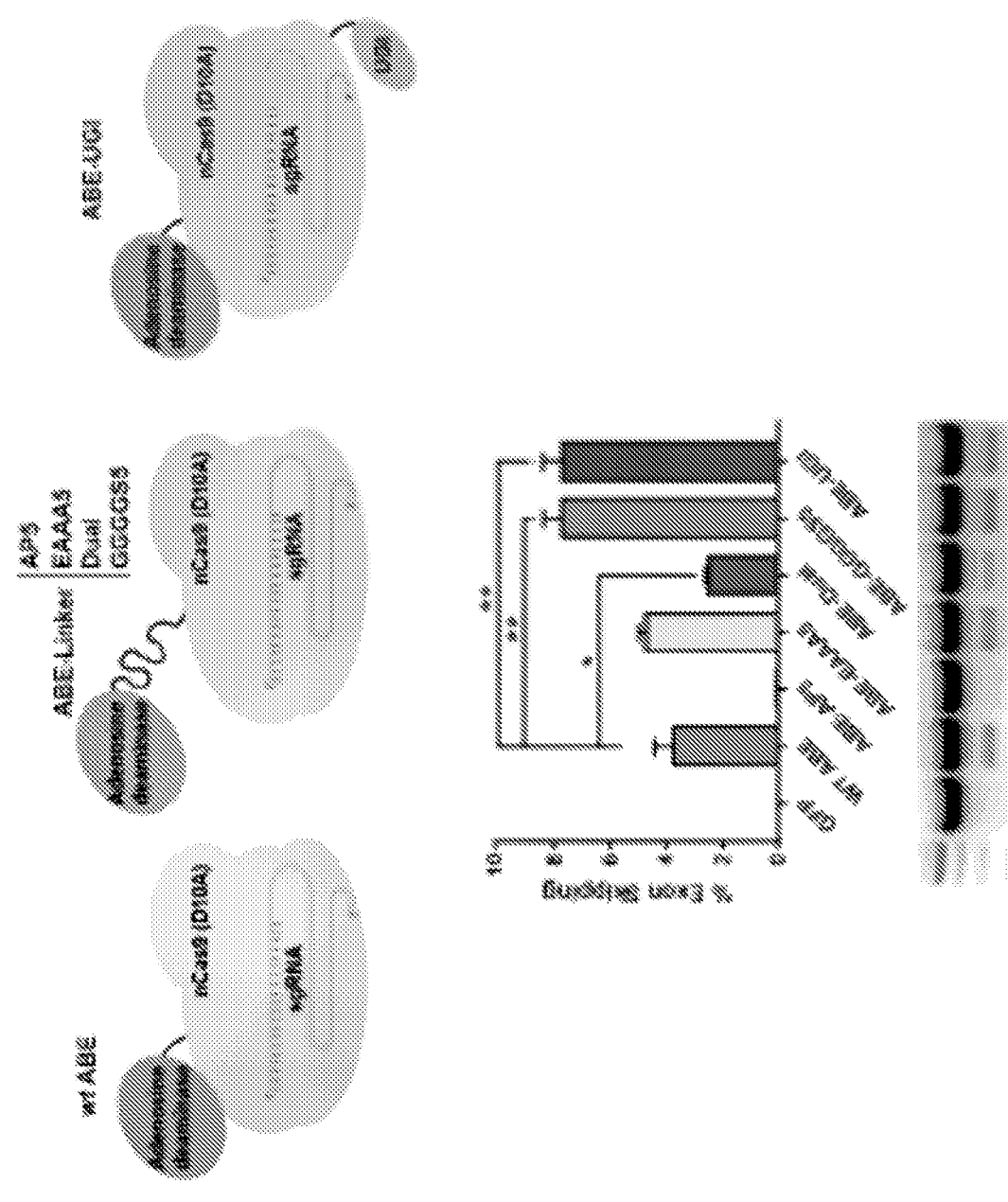

FIG. 18A illustrates a schematic representation of several of the ABE variants that were constructed by either modifying the linker tethering nCas9 and the deaminase domain or by fusing a UGI. FIG. 18B shows that high throughput sequencing of cDNA demonstrated significantly increased levels of exon skipping by several of the ABE variants as compared to wt ABE. * and ** correspond to P<0.05 and P<0.01 respectively by two-tailed unpaired Student's t-test (n=3).

Figures 19A, 19B:
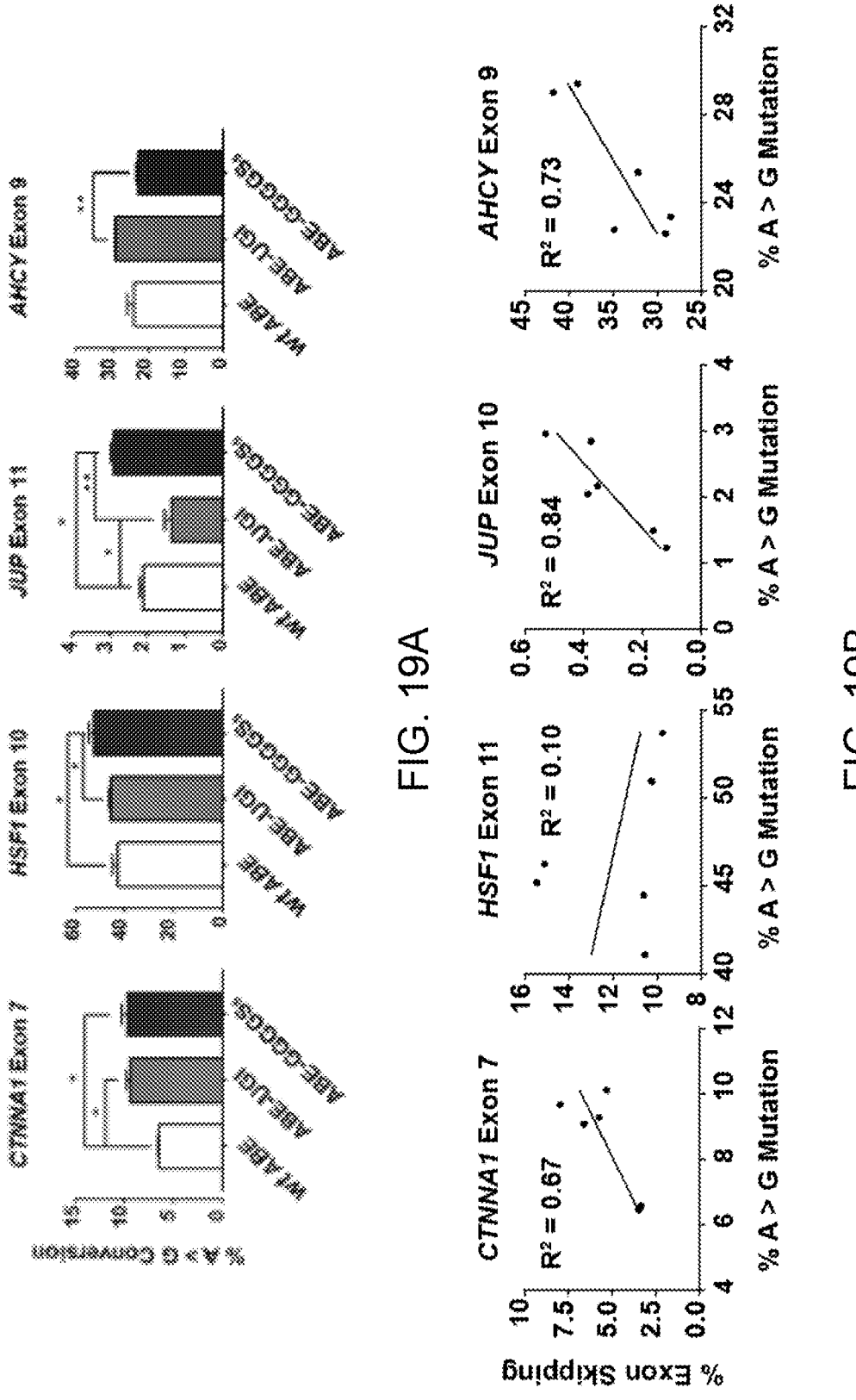

FIG. 19A shows that high throughput sequencing of genomic DNA and cDNA was used to quantify rates of A>G genomic DNA mutation and rates of exon skipping across multiple targets using several ABE variants. *, and  correspond to P<0.05 and P<0.01 respectively by two-tailed unpaired Students t-test (n=2). FIG. 19**B illustrates rates of exon skipping showed a linear co-relation with rates of A>G mutations within splice acceptor sites for most targets tested.

Figure 20:
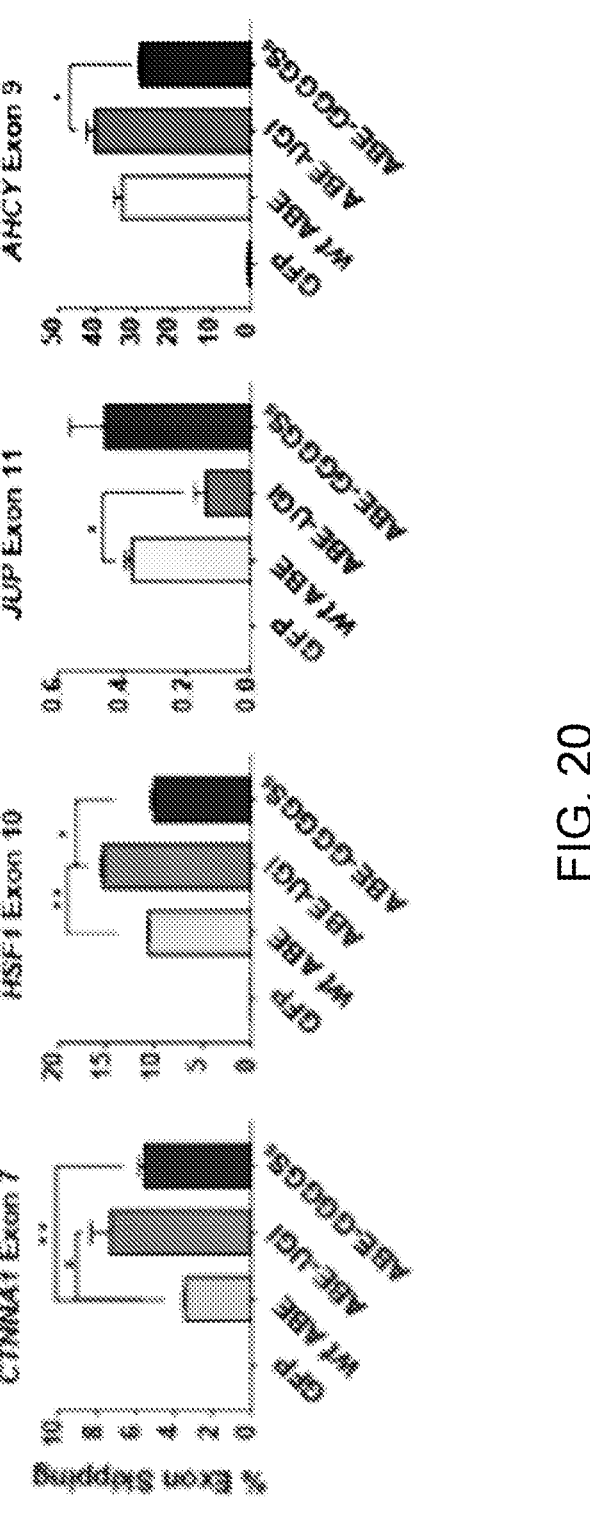

FIG. 20 shows that high throughput sequencing of cDNA was used to quantify rates of exon skipping across multiple targets using several ABE variants. *, and ** correspond to P<0.05 and P<0.01 respectively by two-tailed unpaired Students t-test across 2 biological replicates.

Figure 21A:
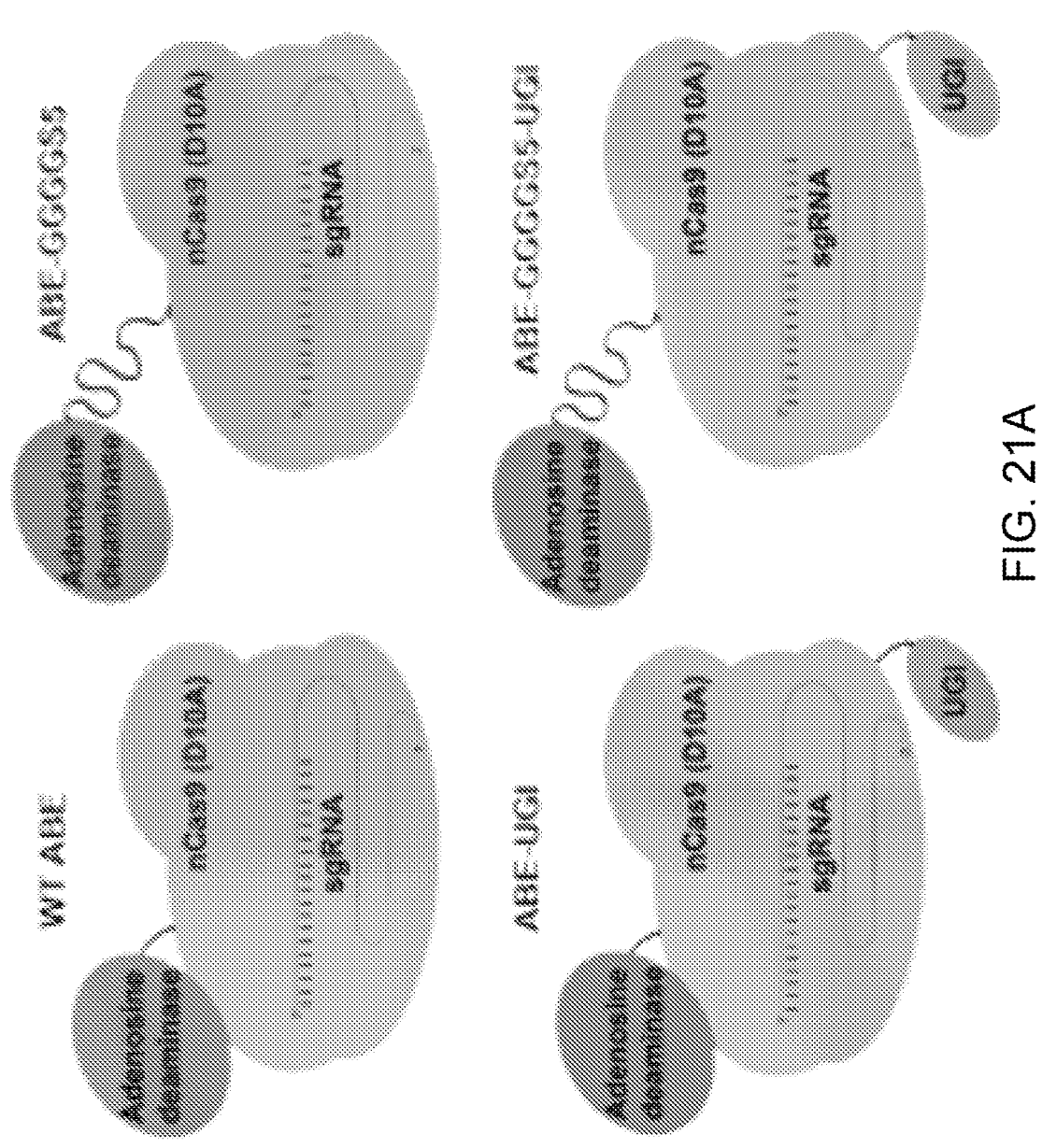
Figures 21B, 21C:
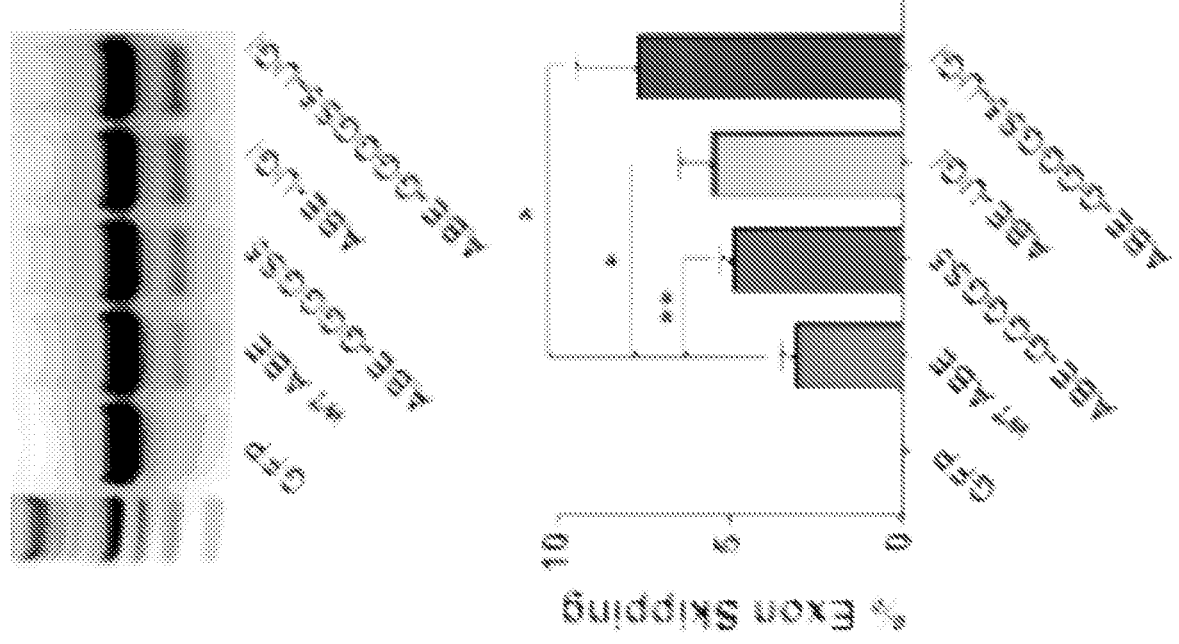

FIG. 21A shows a schematic representation of the ABE variants constructed by either modifying the linker tethering nCas9 and the deaminase domain, by fusing ABE with a UGI or both. GGGGS$_5$ is SEQ ID NO:7. FIG. 21B shows that combining the GGGGS$_5$ (SEQ ID NO:7) linker and UGI domain within the same ABE construct led to higher rates of exon skipping than the ABEs containing each component individually, suggesting an increased A>G mutation rates in genomic DNA when both domains are used. FIG. 21C shows that high throughput sequencing analysis of RT-PCR products demonstrated significantly increased levels of exon skipping by several of the ABE variants compared with wt ABE. (* and  correspond to P<0.05 and P<0.01 respectively by two-tailed unpaired Student's t-test, n=3). GGGGS$_5$ is SEQ ID NO:7. FIG. 21**D shows estimates of positional A>G modification efficiencies at each of the target A's within the protospacer of A-Rich Target 1 and A-Rich Target 2 using EditR software (n=3). Position 1 represents the base farthest from the start of the PAM using a 20 bp sgRNA. ABE-GGGGS constructs enabled editing of position 4, which was not observed with wt ABE. Additionally, shorter linker lengths corresponded to higher editing rates for positions 4 and 5, with ABE-GGGGS1 achieving the highest rates of base editing.

Figure 22A:
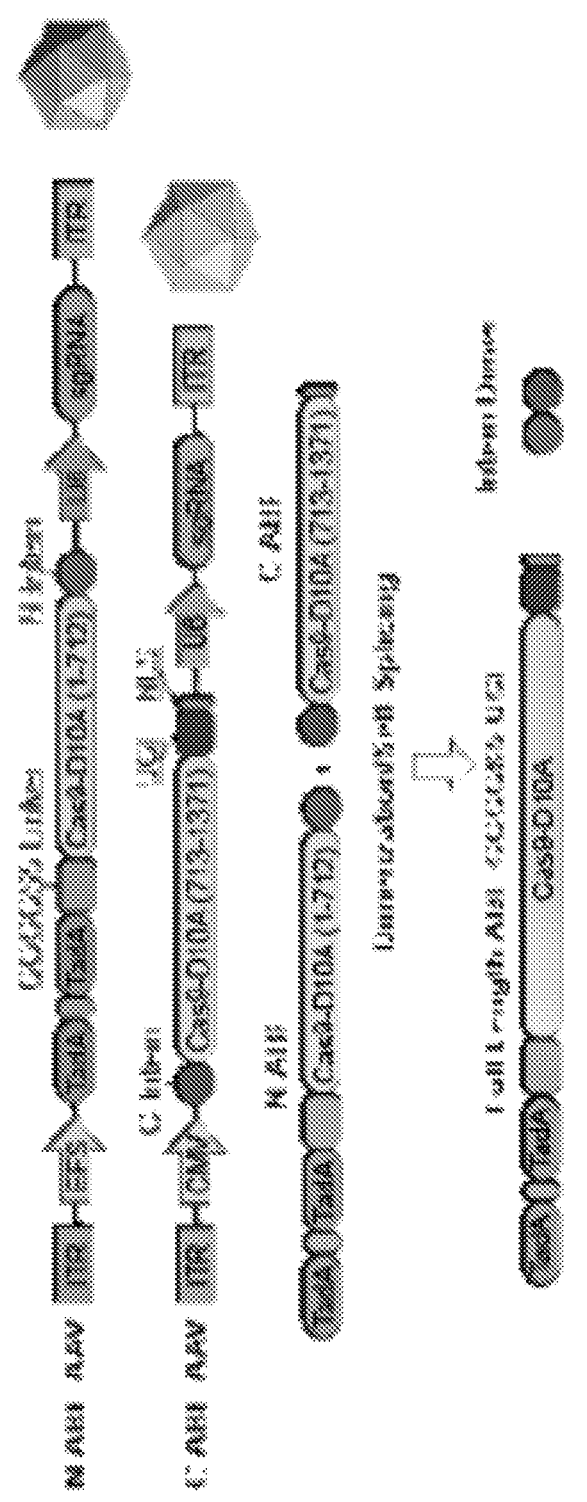
Figures 22B, 22C, 22D, 22E:
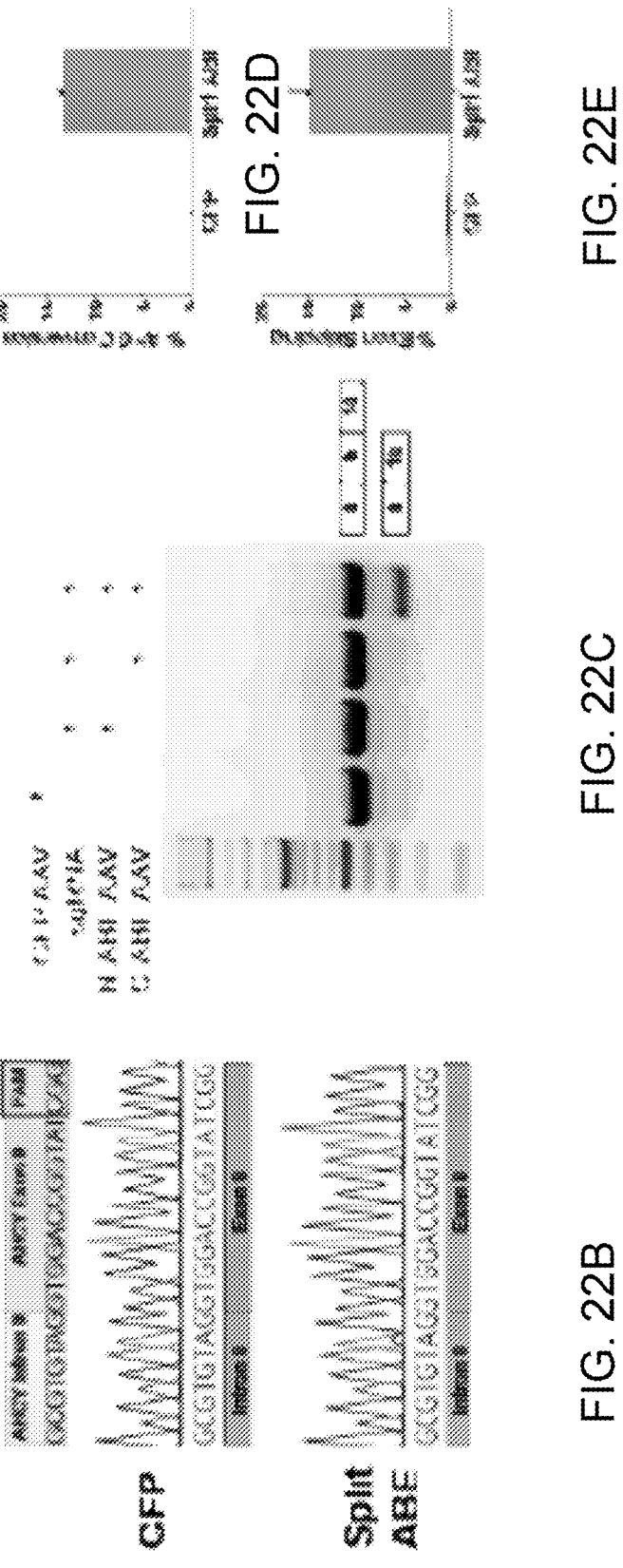
Figure 22F:
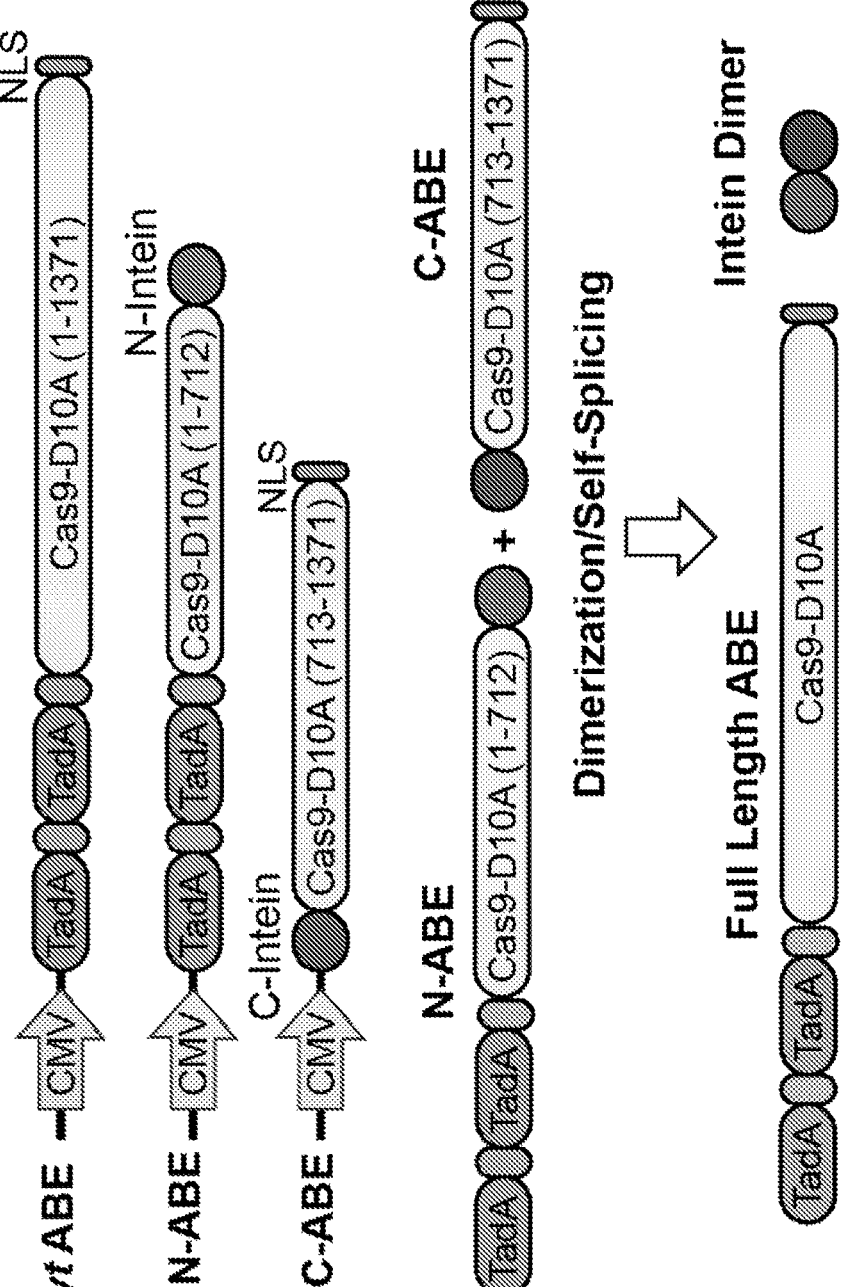
Figure 22H:
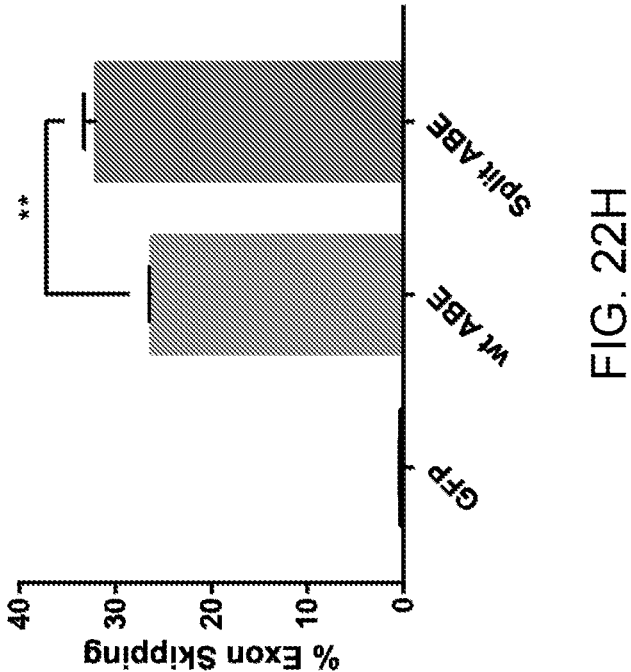
Figure 22G:
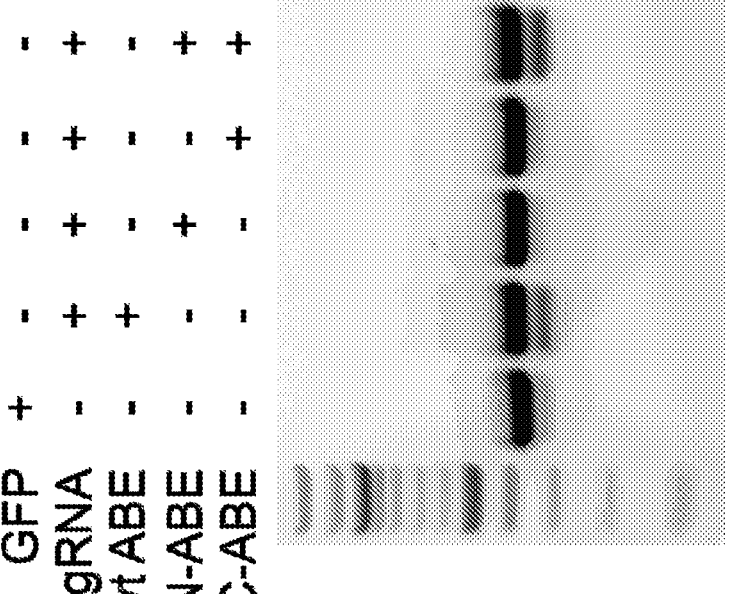

FIG. 22A illustrates the schematics of the split-ABE AAV system. N-terminal and C-terminal intein sequences reconstitute the full-length protein when co-expressed within the cell. FIG. 22B shows sanger sequencing traces from genomic DNA prepared from HEK293T cells transduced with either GFP-AAV or both N-ABE AAV and C-ABE AAV. A>G mutations were only observed when both N-ABE AAV and C-ABE AAV particles were delivered. GCGTGTAGGTGGACCGGTATCGG is SEQ ID NO:349. FIG. 22C shows that RT-PCR products confirmed that exon skipping only occurred when both N-ABE AAV and C-ABE AAV were co-delivered. FIG. 22D shows the quantification of A>G mutation rates in the samples described in 7b using EditR (n=3) and FIG. 22E shows exon skipping rates by densitometry analysis of RT-PCR products (n=3). FIG. 22F shows a schematic representation of the split-ABE plasmid system. N-terminal and C-terminal intein sequences reconstitute the full-length protein when co-expressed within the cell. FIG. 22G shows HEK293T cells were transfected with either GFP or a combination of sgRNA targeting AHCY exon 9 and N-ABE, C-ABE or both and their RNA was used in RT-PCR to detect targeted exon skipping of HSF1 exon 11. Only when both split ABE plasmids were present was exon skipping detected. FIG. 22H shows high throughput sequencing analysis of RT-PCR products demonstrated significantly increased levels of exon skipping by the split ABE system at 32.0% compared to 26.2% with the full length wt ABE (P=0.002 by two-tailed unpaired Students t-test (n=3).

FIG. 23A shows the genome-wide computational estimate of the number of inner exons that can be targeted by ABE and BE3 with predicted editing efficiency of the target base at or above the value on the x-axis. Only sgRNAs with an off-target score below 10 were considered. FIG. 23B shows the estimation of the number of inner exons that can be targeted by ABE and BE3 using sgRNAs with off-target scores at or below the value on the x-axis. Only sgRNAs with an on-target base editing efficiency above 30% were considered. Exons that could be targeted with either ABE or BE3 were compared to determine which base editor would have an sgRNA with (FIG. 23C) the highest predicted base editing efficiency or (FIG. 23D) the lowest off-target score. All sgRNAs with off-target scores at or below 10 were considered for FIG. 23C and FIG. 23D.

Figure 24:
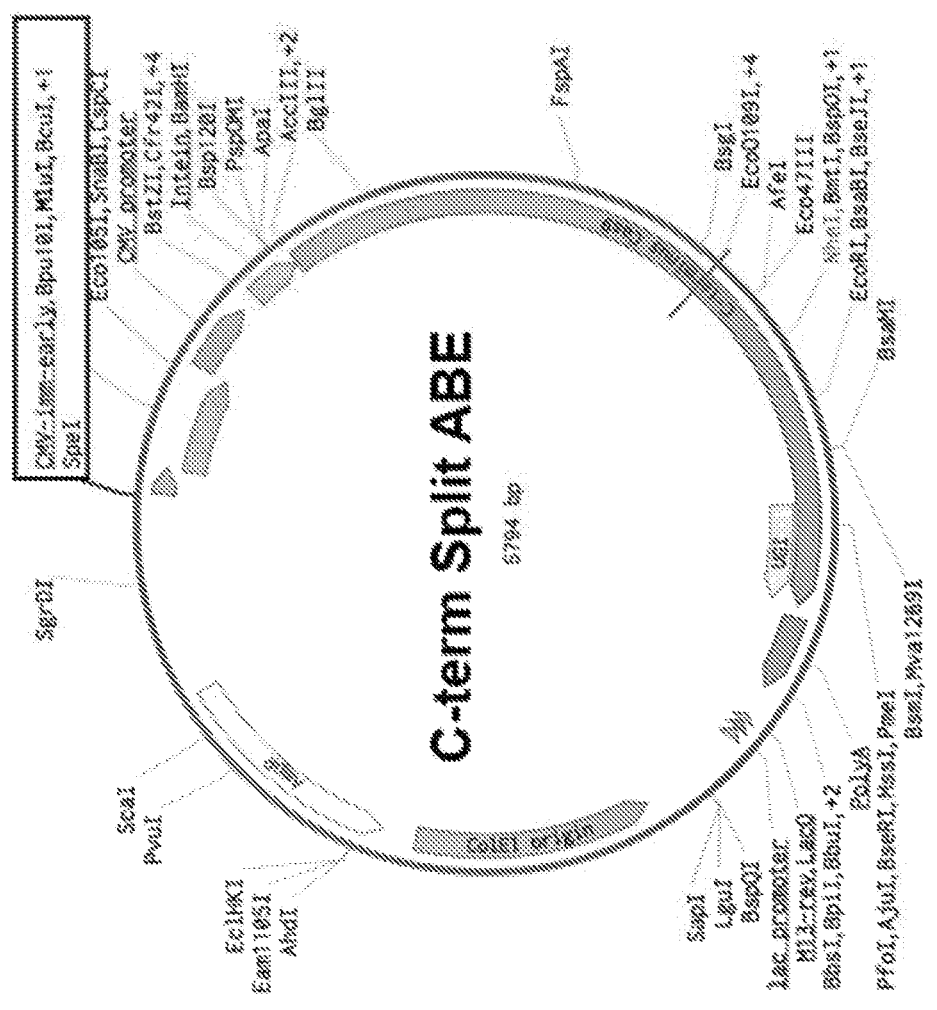
Figure 25:
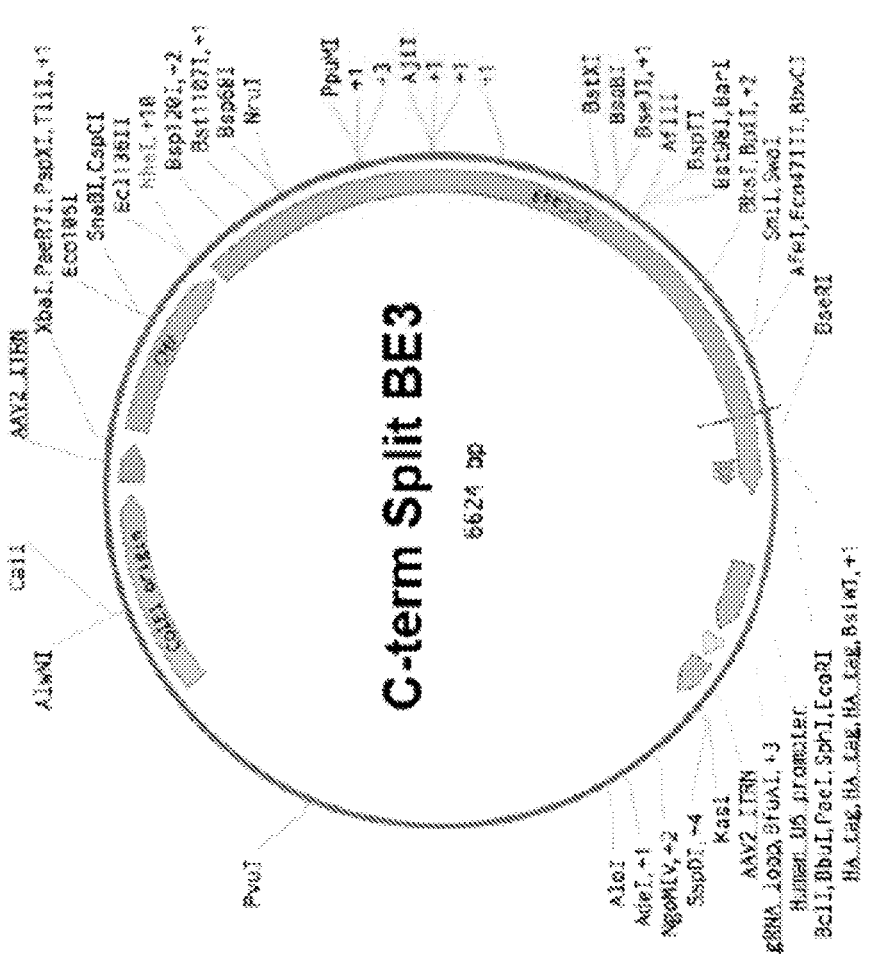
Figure 26:
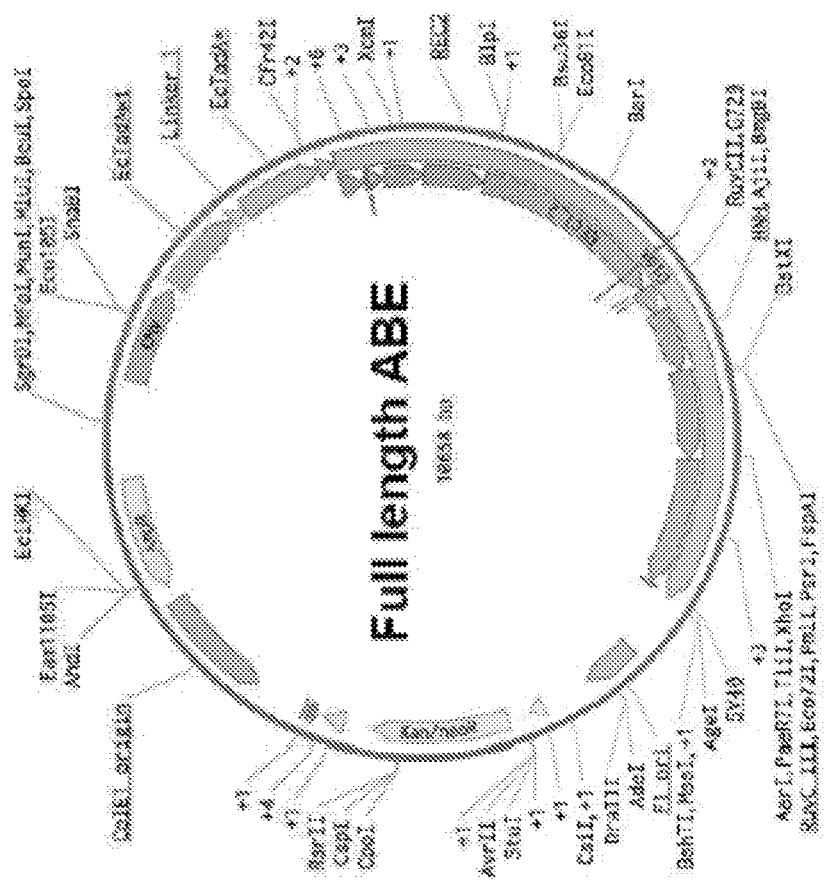
Figure 27:
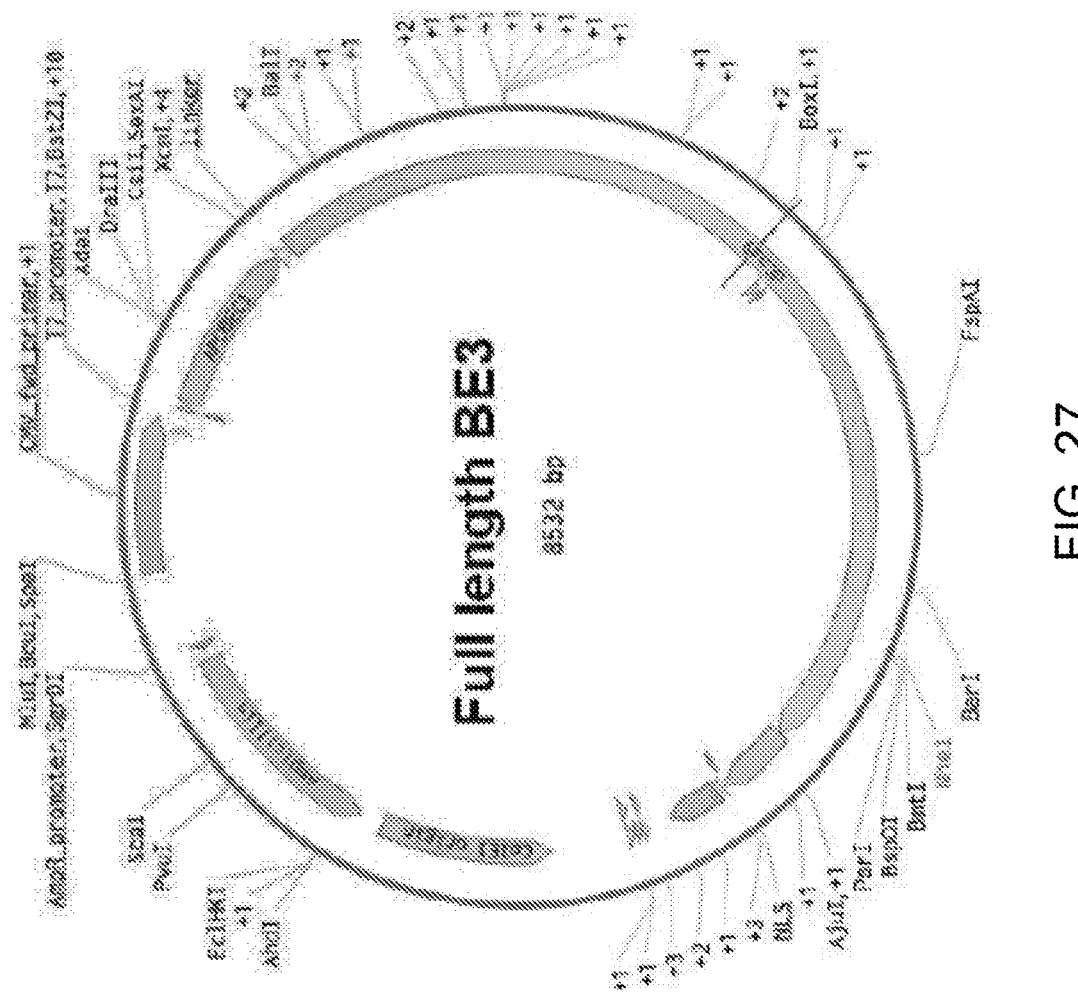
Figure 28:
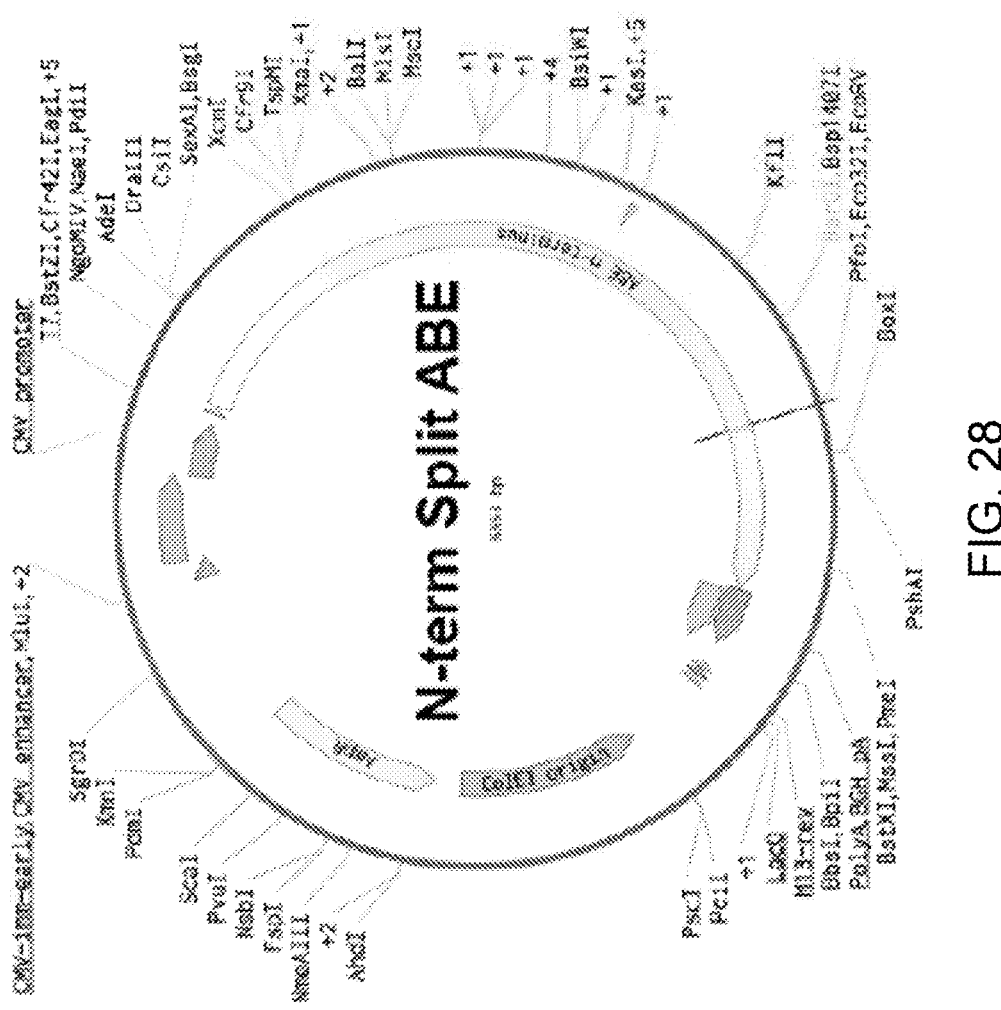
Figure 29:
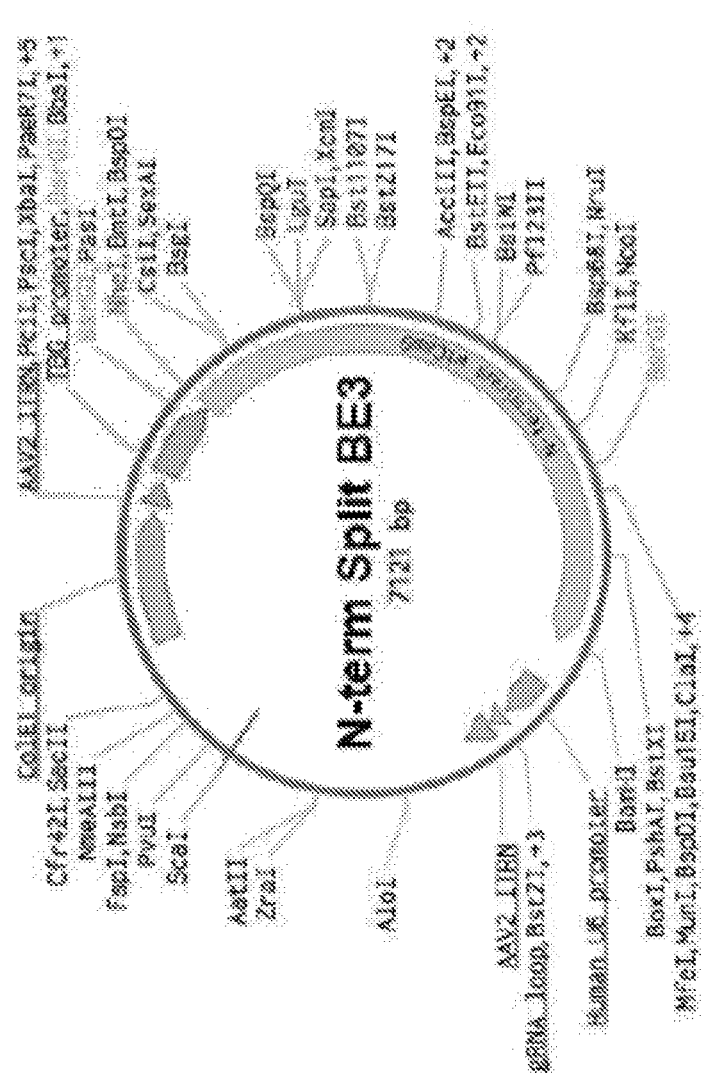
Figure 30:
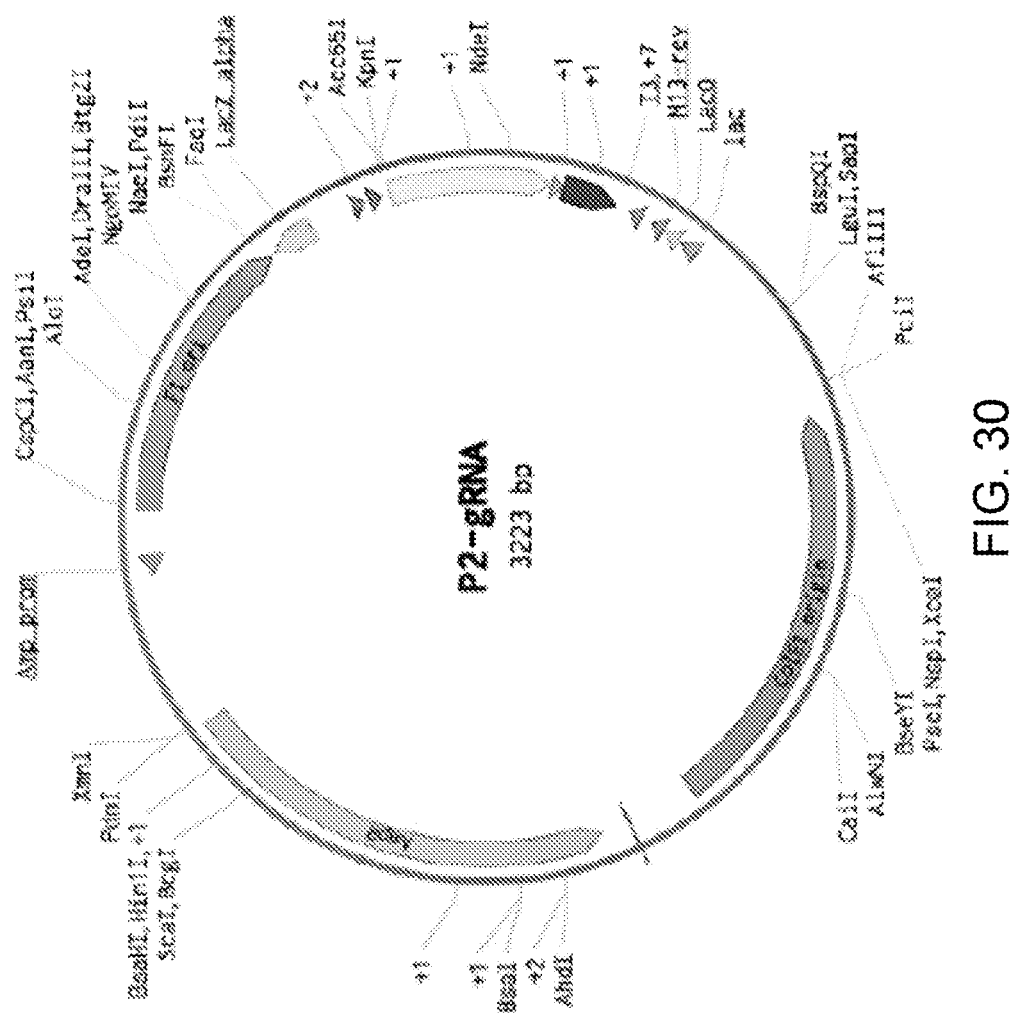
Figure 31:
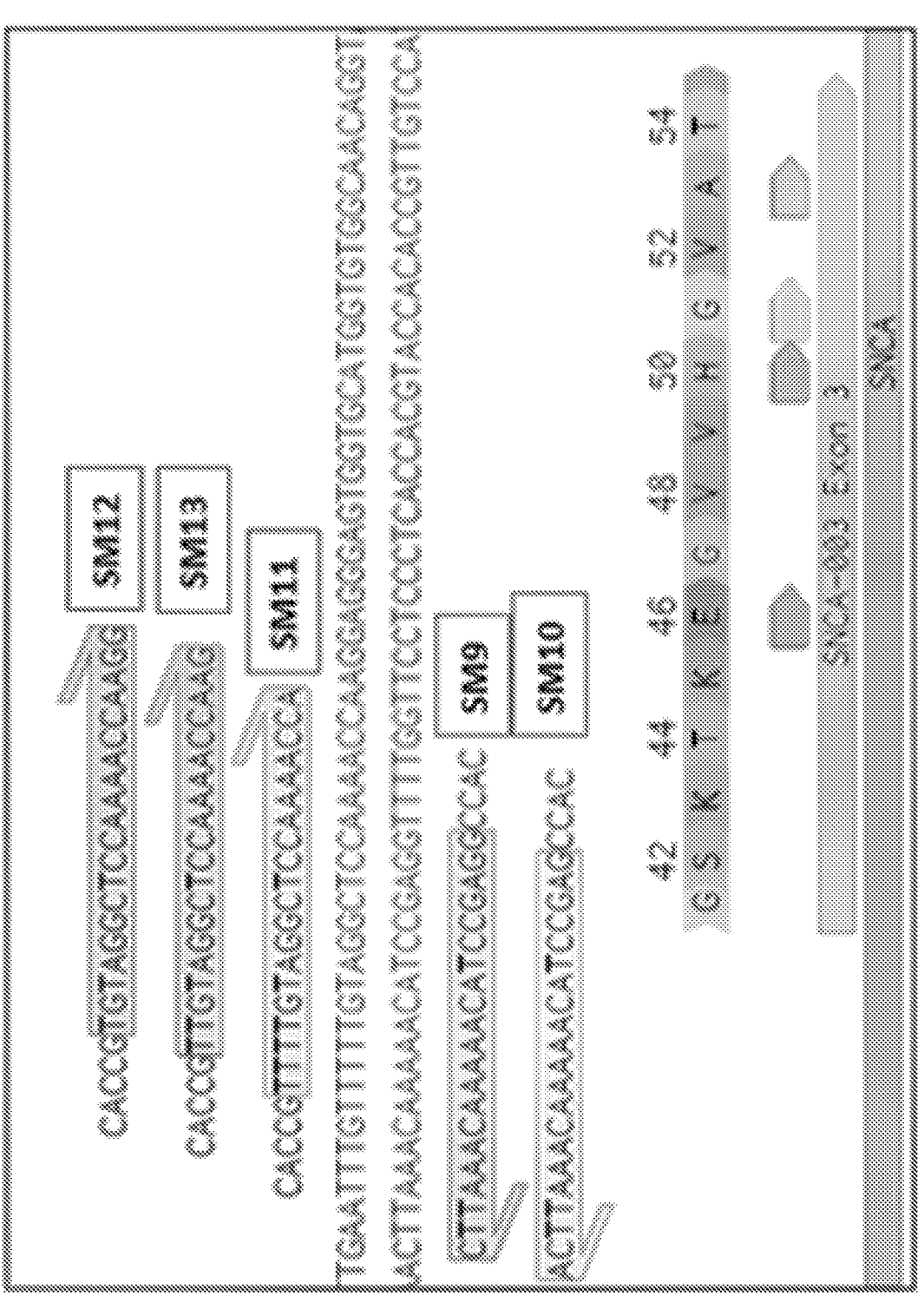

FIG. 24 illustrates the plasmid map C-term Split ABE.
FIG. 25 illustrates the plasmid map C-term Split BE3.
FIG. 26 illustrates the plasmid map full length ABE.
FIG. 27 illustrates the plasmid map full length BE3.
FIG. 28 illustrates the plasmid map N-term Split ABE.
FIG. 29 illustrates the plasmid map N-term Split BE3.
FIG. 30 illustrates the plasmid map P2-gRNA.
FIG. 31 illustrates shows sgRNA targeting in the synuclein (SNCA) gene. SM12 is SEQ ID NO:350; SM13 is SEQ ID NO:351; SM11 is SEQ ID NO:352; TGAATTTGTTTTTGTAGGCTCCAAAACCAAGGAGG-GAGTGGTGCATGGTGTGGCA ACAGGT is SEQ ID NO:353; ACCTGTTGCCACACCATGCACCACTCCCTC CTTGGTTTTGGAGCCTACAAAAACAATTCA is SEQ ID NO:354; SM9 is SEQ ID NO:355; SM10 is SEQ ID NO:356; GSKTKEGVVHGVAT is SEQ ID NO:357.

Figures 32, 33:
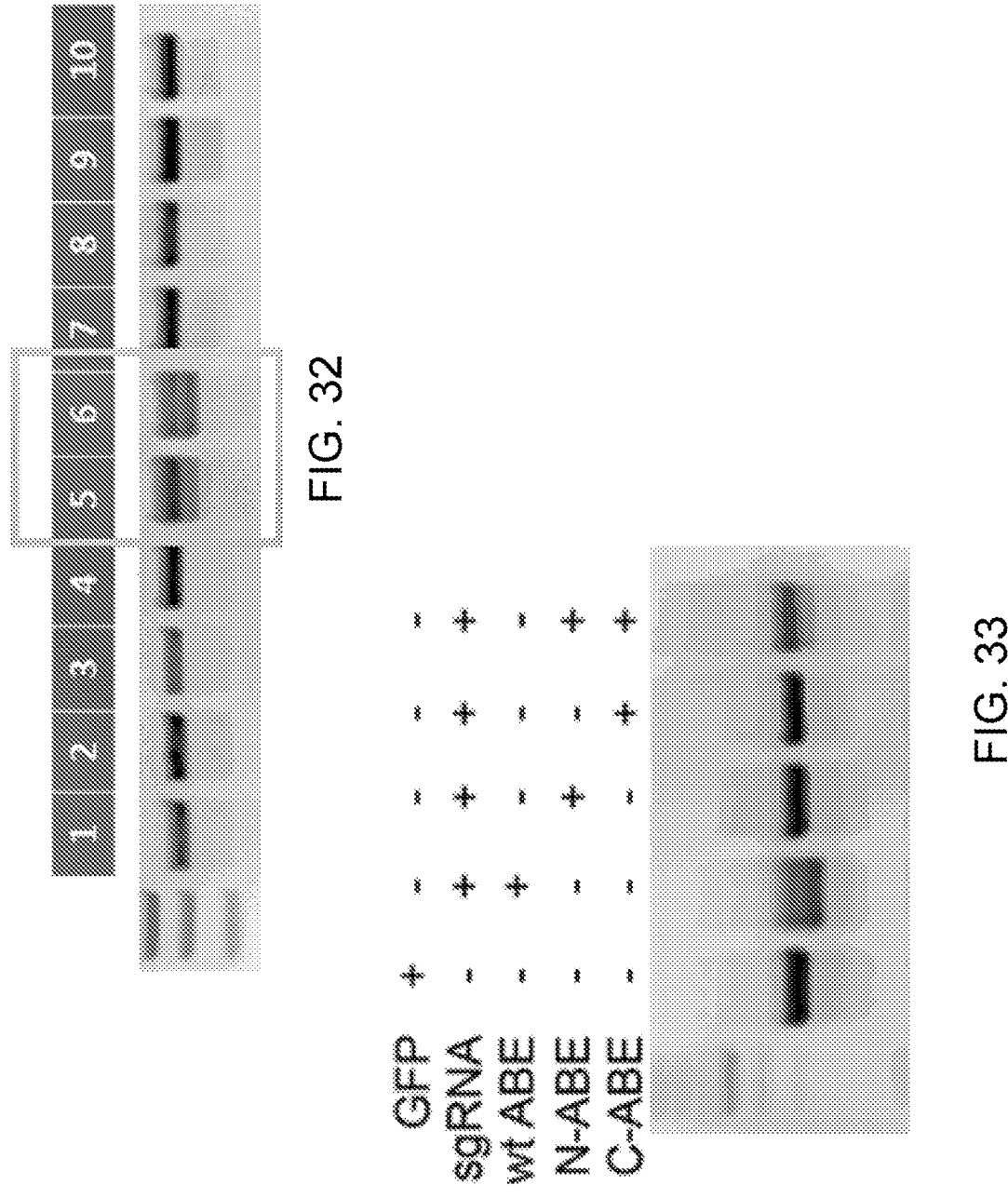

FIG. 32 shows RT-PCR data from the transfections. The numbers correspond to different transfections in Table 8. Data showed that only the Adenine Base Editor (ABE) was successful in skipping Exon 3 of the SNCA gene (lanes 5 and 6).

FIG. 33 shows RT-PCR data for exon 3 skip using different combinations of ABE components.

Figure 34:
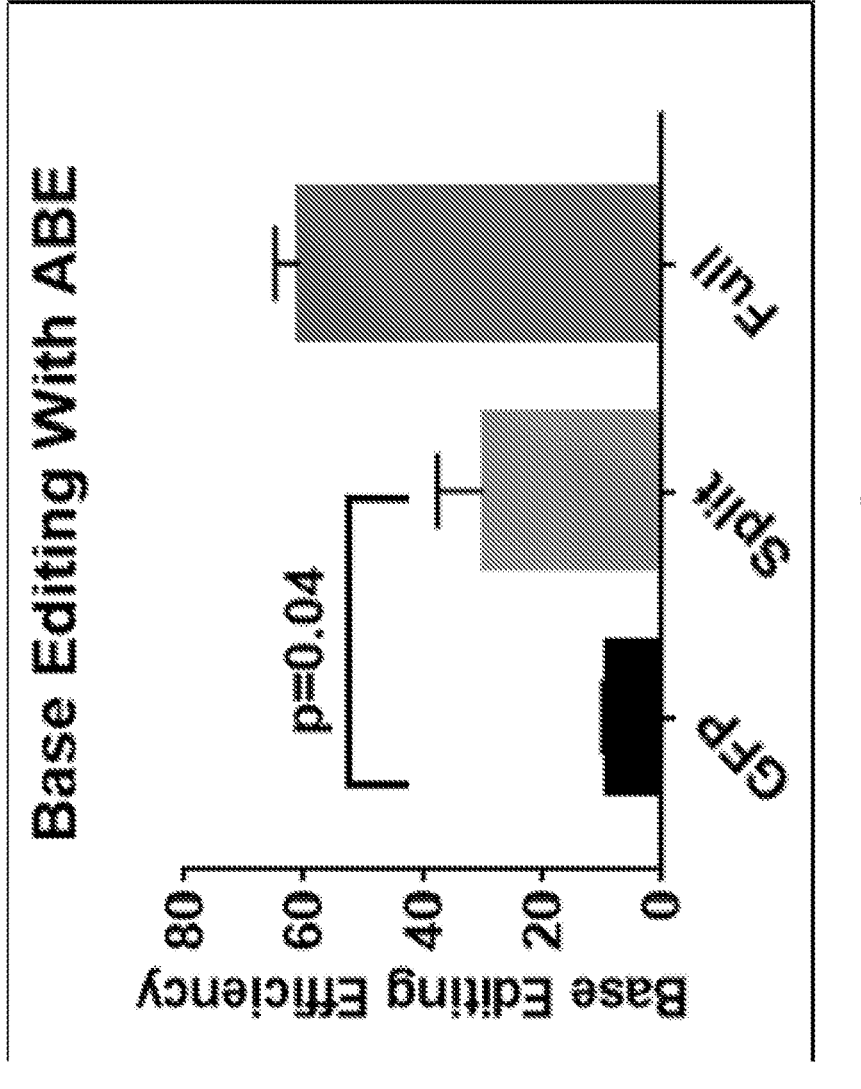

FIG. 34 shows quantification of base editing efficiency with split and full length ABE.

Figure 35:
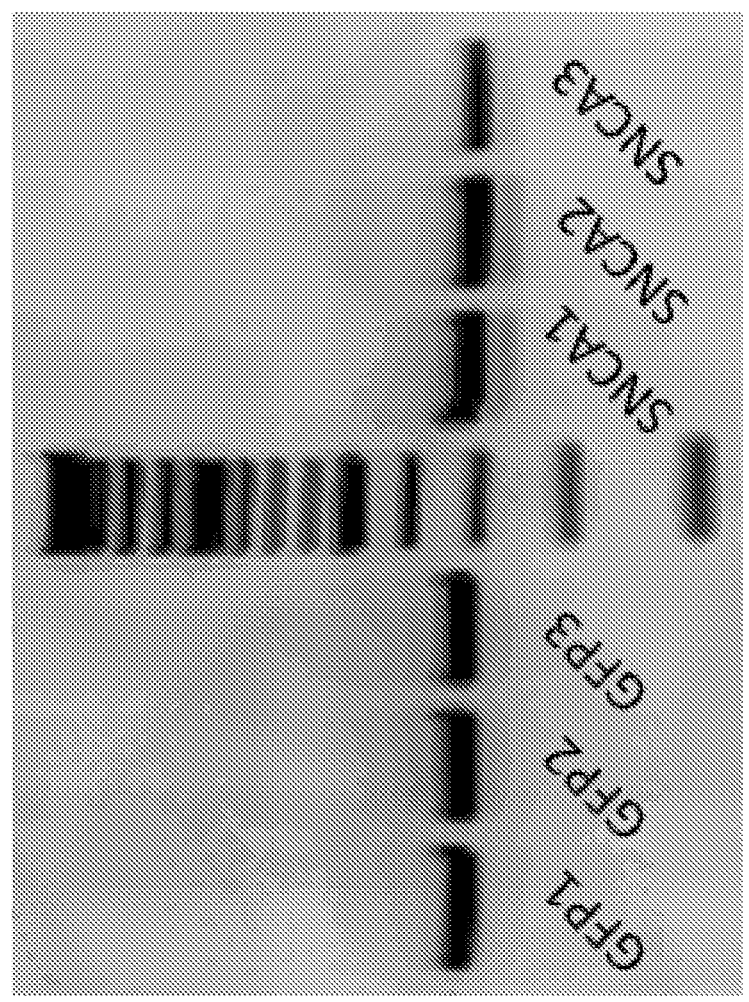

FIG. 35 shows RT-PCR data from AAV transduction.

Figure 36A:
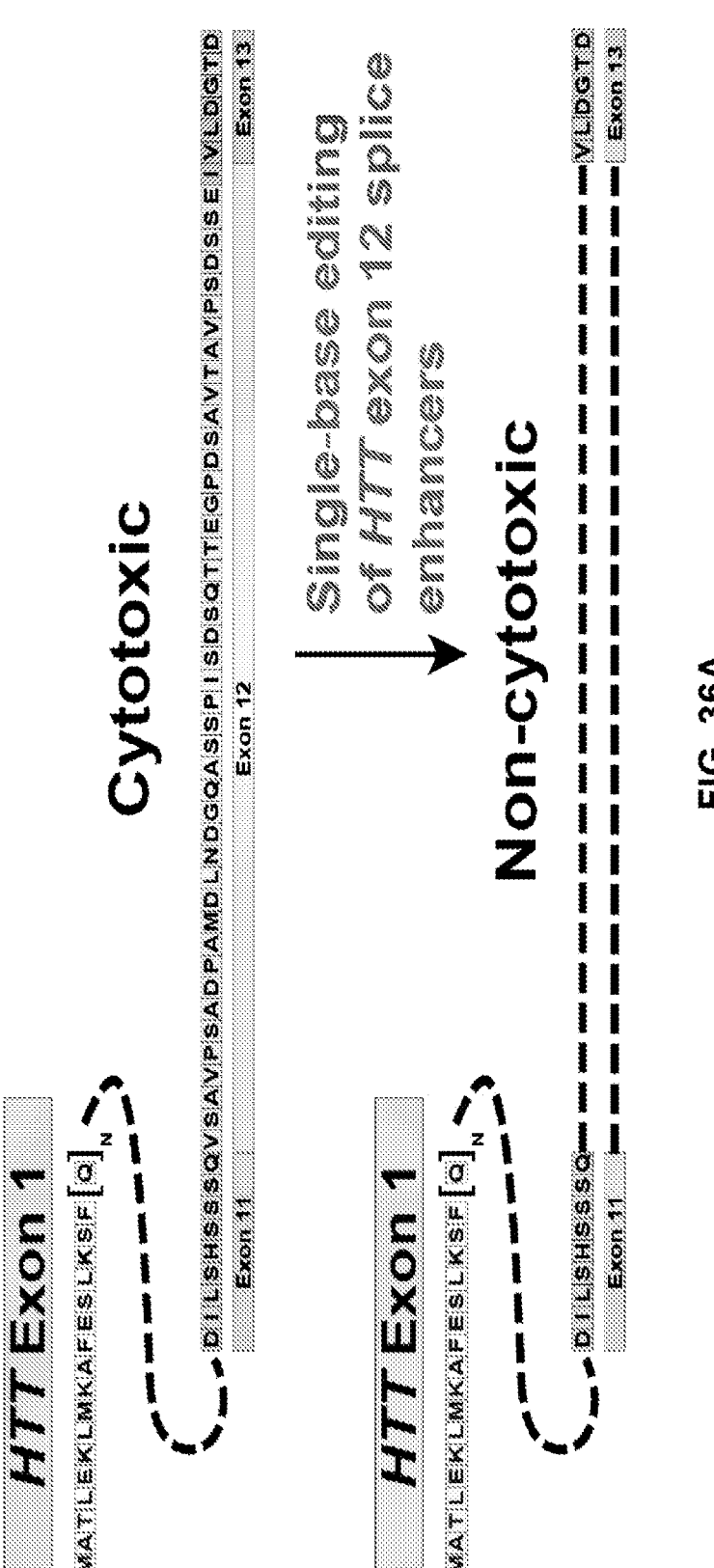
Figure 36B:
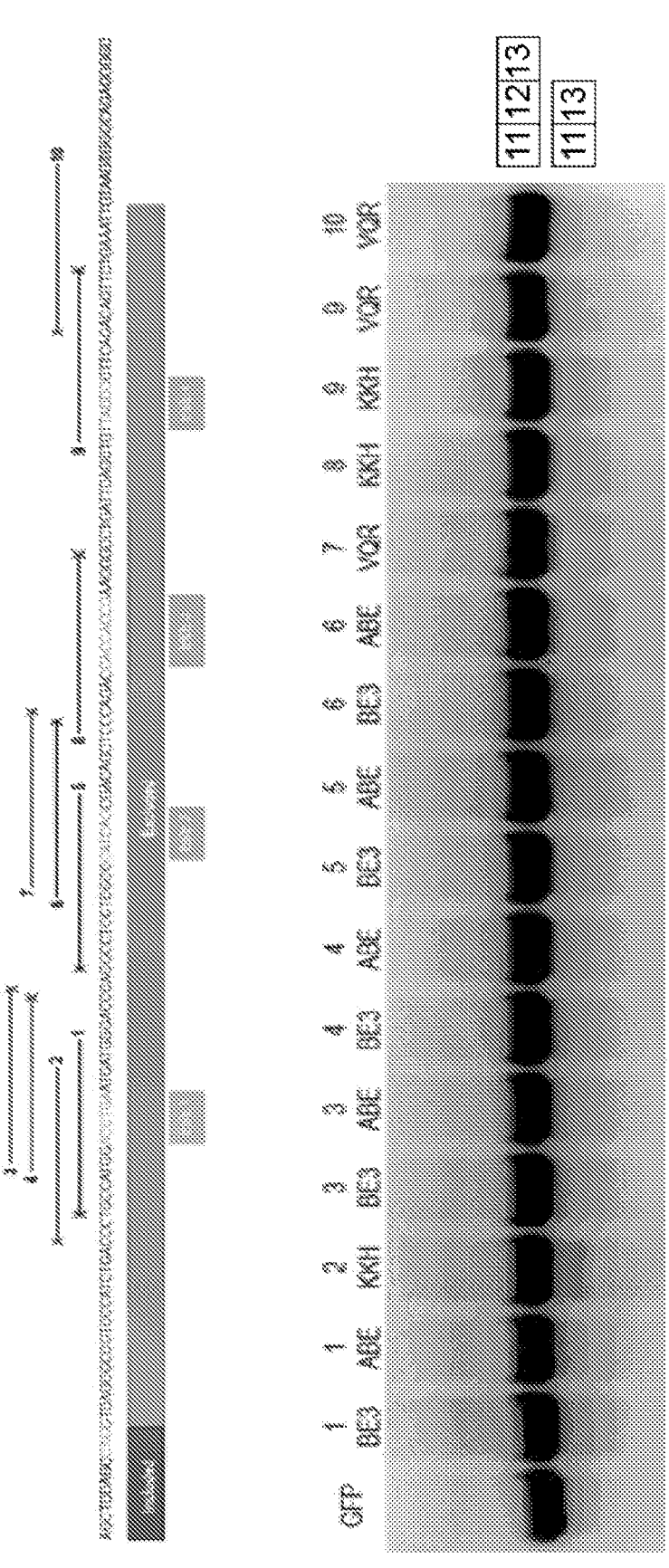

FIGS. 36A-36B illustrate that exon 12 in the HTT gene can be skipped using single-base editors. FIG. 36A shows a schematic representation of the approach for reducing HTT cytotoxicity by exon skipping. HD is caused by genetic amplification of CAG codons within exon 1. Intracellular accumulation of the N-terminal fragments of mutant HTT is cytotoxic after proteolytic cleavage by caspase-6, whose target site is located between exons 12 and 13. Exclusion of exon 12 from mature HTT transcripts created a HTT isoform resistant to proteolysis by caspase-6 that is not cytotoxic. MATLEKLMKAFESLKSF[Q]$_N$ is SEQ ID NO:357, DILSHSSSQVSAVPSADPAMDLNDGQASSPIS-DSQTTEGPDSAVTAVPSDSSEIVLDGT D is SEQ ID NO:358, DILSHSSSQ is SEQ ID NO:359, VLDGTD is SEQ ID NO:360. FIG. 36B shows that HTT exon 12 can be skipped using CRISPR-Cas9 single-base editors. HTT exon 12 has 4 splice enhancers, which were targeted using 10 different sgRNAs in combination with either a SpCas9 C>T editor recognizing NGG PAMs (BE3), SpCas9 C>T editor recognizing NGA PAMs (VQR), SaCas9 C>T editor (KKH), or SpCas9 A>G editor (ABE).

Figure 37:
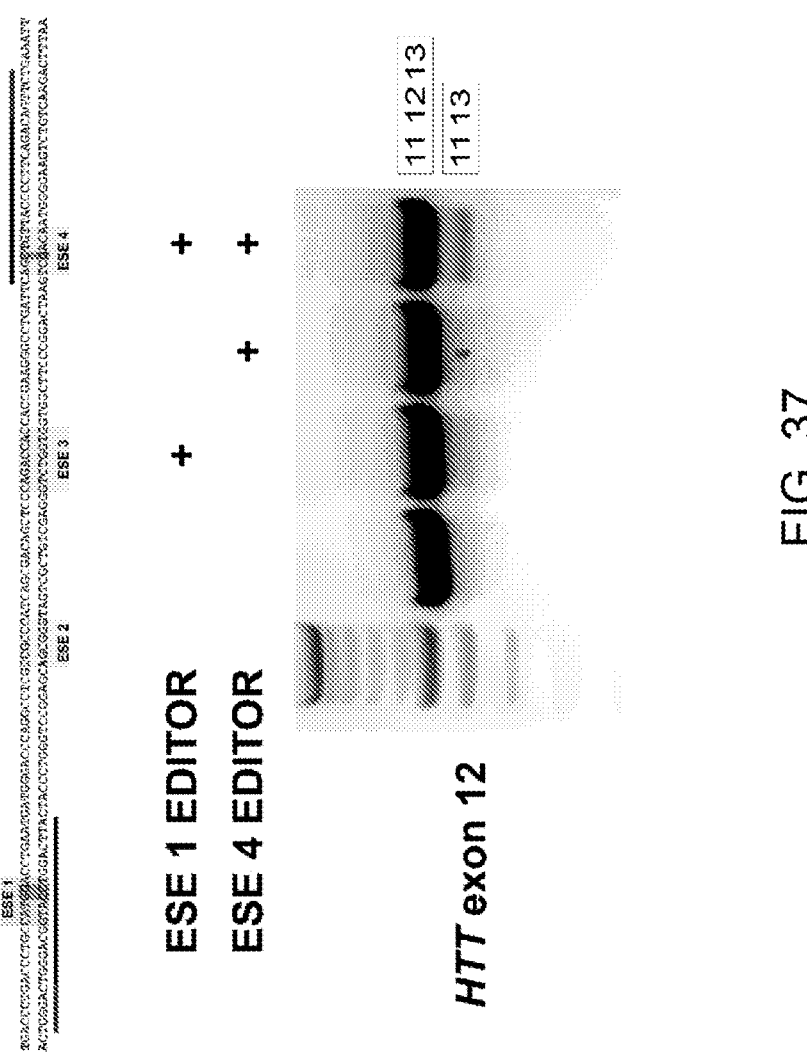

FIG. 37 shows modulation of splicing by disruption of exon splice enhancers (ESEs) using CRISPR-Cas9 split single-base editors. The top panel shows the sequence of the 3' of HTT exon 12. Within this sequence 4 different ESEs were identified, which are highlighted. The top sequence is SEQ ID NO:361, the bottom sequence is SEQ ID NO:362. 2 sgRNAs were designed, which, when used in conjunction with a SaCas9 base editor, target the cytidines highlighted. Analysis of HTT exon 12 splicing by PCR demonstrated that editing the ESE individually was sufficient to induce low levels of exon skipping. Importantly, simultaneous editing of both ESEs function synergistically to generate higher rates of exon skipping.

FIGS. 38A-38C show split base editor architecture for in vivo delivery. FIG. 38A shows the N-terminus of SpCas9 SBE was fused with an N-terminal intein, whereas the C-terminal intein is fused with the C-terminus of SpCas9. Upon translation, both inteins dimerize and reconstitute the full-length SBE. FIG. 38B shows split base editors were targeted to the splice acceptor of JAG1 exon 9, which when mutated, induced skipping of exon 9 from mature mRNA transcripts. When co-transfected, N-BE and C-BE induced exon skipping more efficiently that native SBEs. FIG. 38C shows mice were injected with Angptl3-targeting N-BE and C-BE vectors, Angptl3 protein decreased significantly after 3 weeks.

Figure 39:
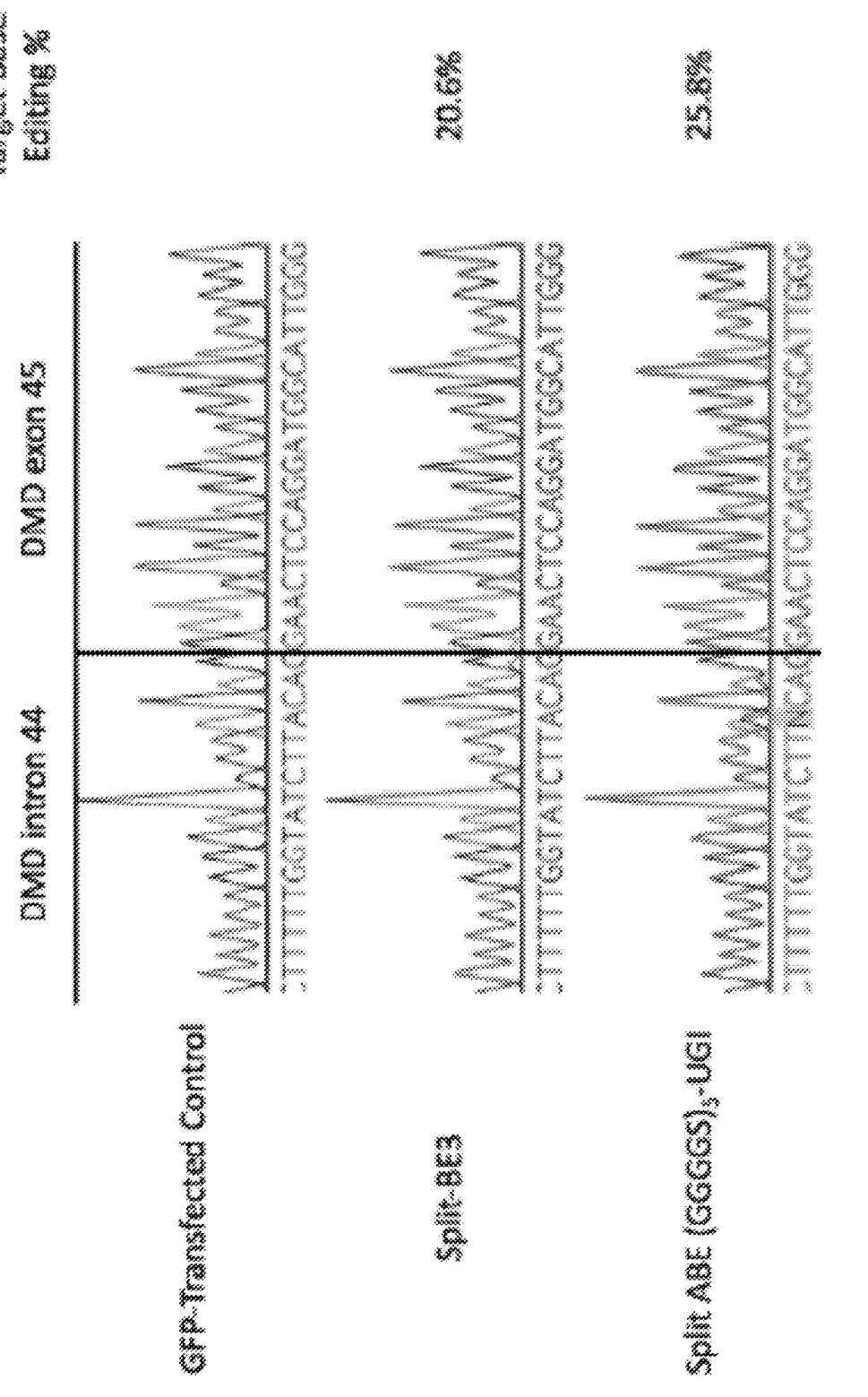

FIG. 39 shows chromatograms and editing percentages achieved with the split versions of each base editor. The top two sequences are SEQ ID NO:363, the bottom sequence is SEQ ID NO:364.

Figure 40:
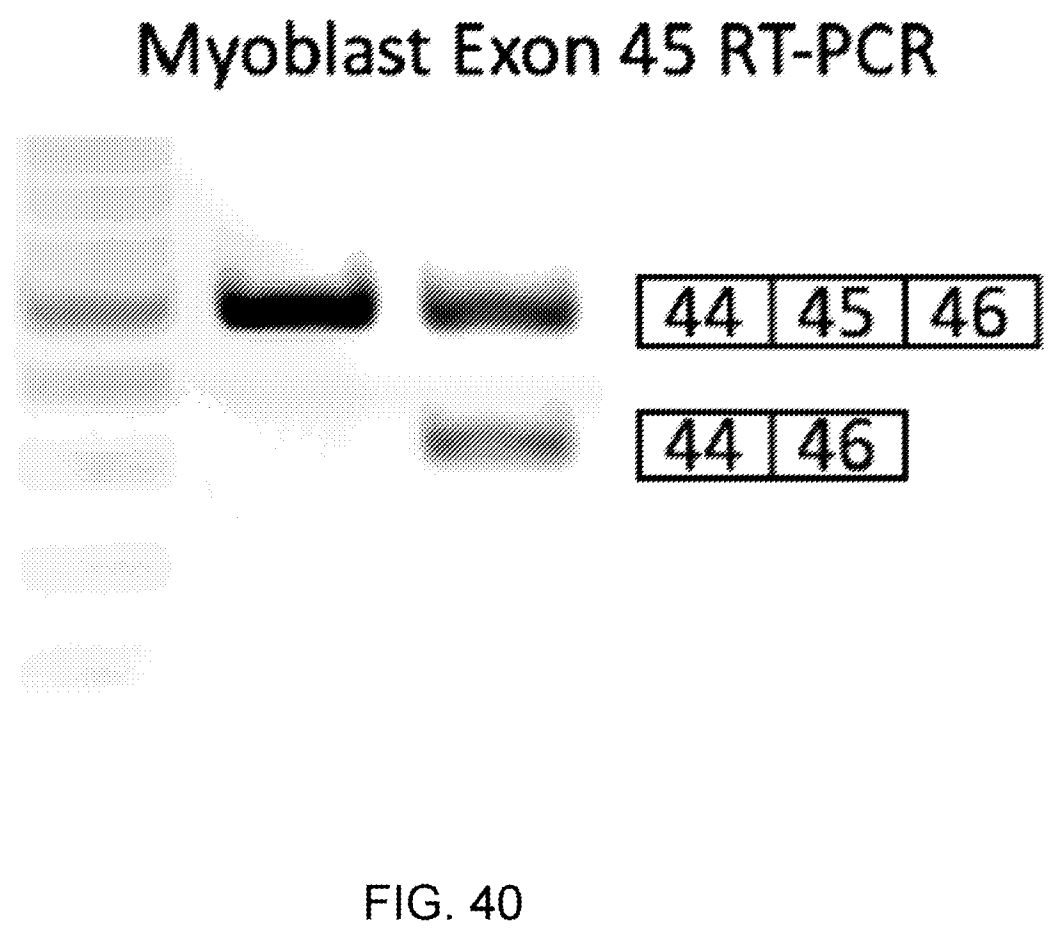

FIG. 40 shows a reverse-transcriptase PCR demonstrating exon 45 skipping in myoblasts (a disease-relevant cell type) after transfection with full-length SpBE3.

Figure 41B:
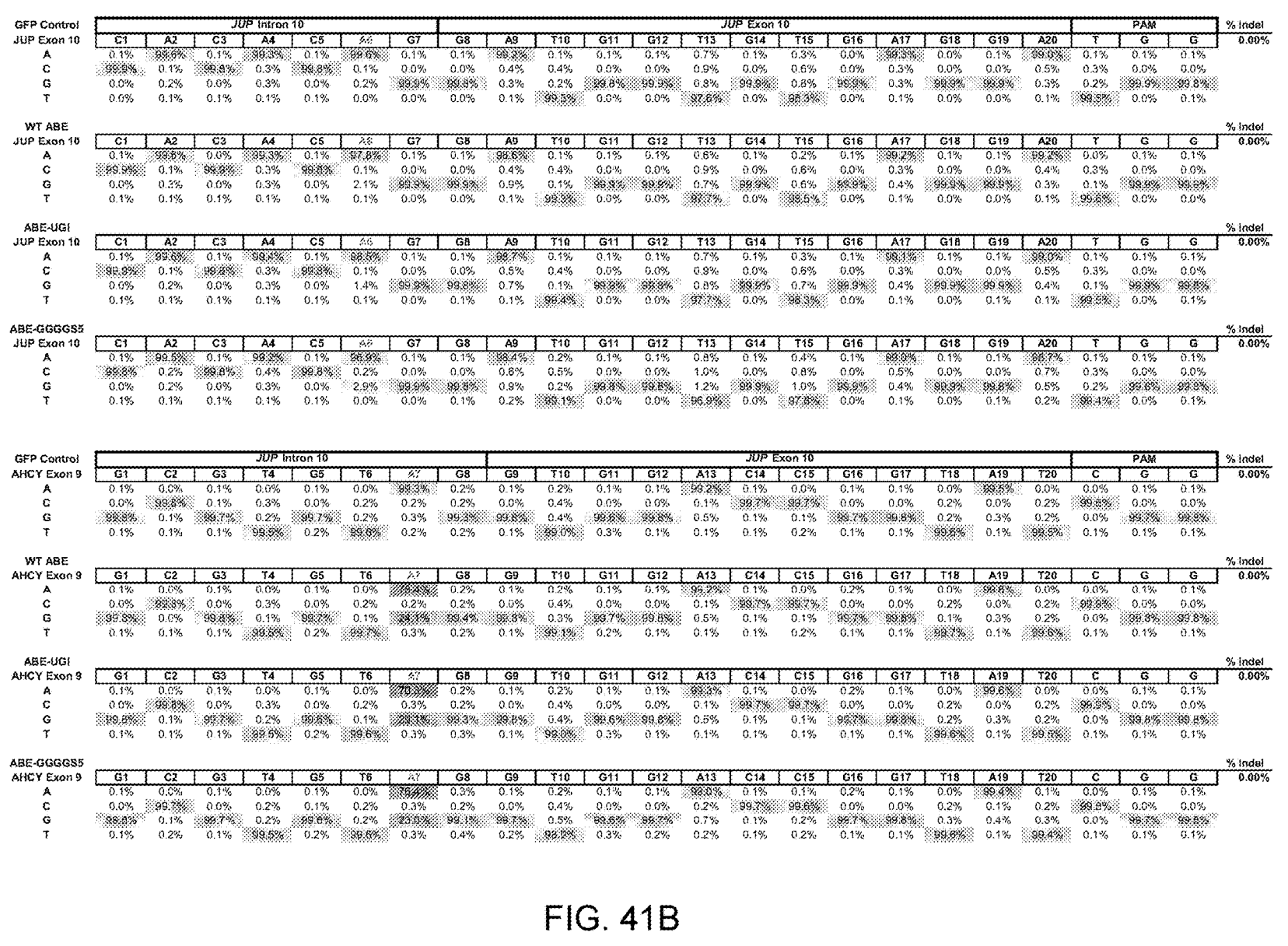

FIGS. 41A-41B show raw base composition data and calculated % indels for HTS results for untreated HEK293T cells as well as cells transfected with WT ABE, ABE-UGI, and ABE-GGGGS5 (SEQ ID NO:7). Reported percentages are the mean values from two replicates.

Figure 42A:
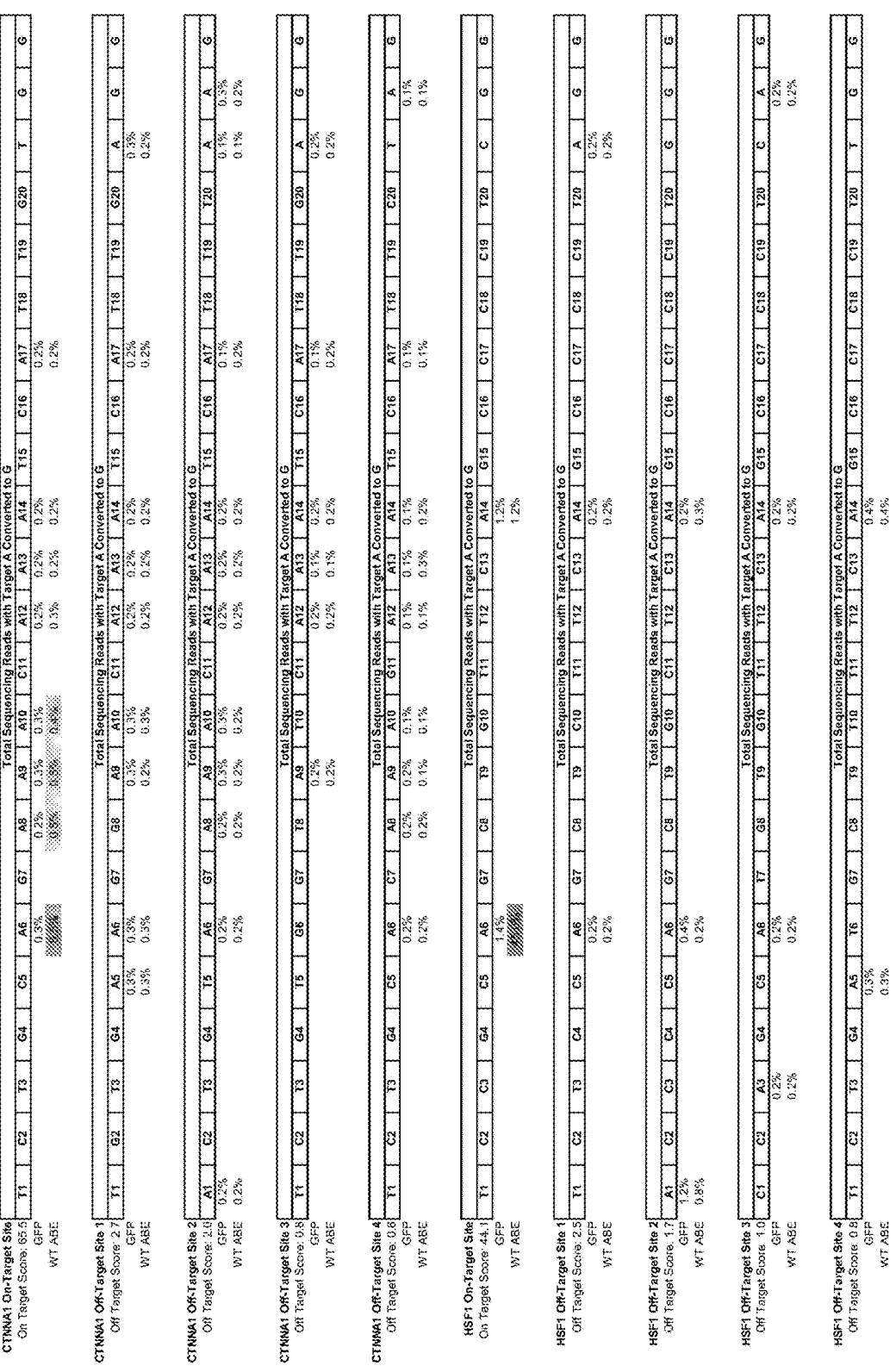
Figure 42B:
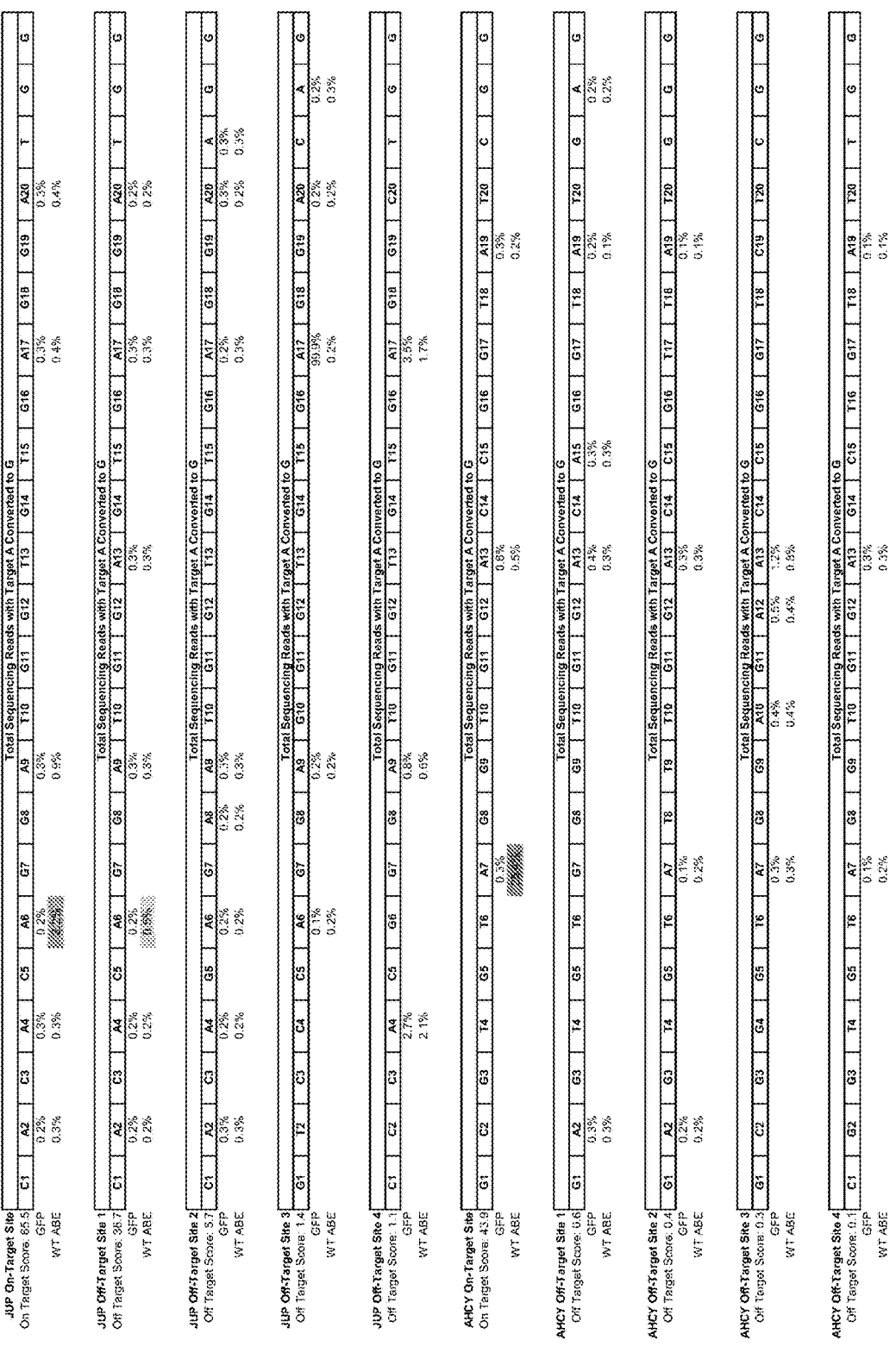

FIGS. 42A-42B show base composition and % indels of predicted off-target sites (Yuan, J. et al. *Mol Cell* 72, 380-394 e387, doi:10.1016/j.molcel.2018.09.002 (2018)) from HTS of genomic DNA from untreated HEK293T cells as well as cells transfected with plasmids encoding WT ABE and the corresponding sgRNA.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

The compositions and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

The disclosure relates to methods and compositions for inducing selective exon skipping using CRISPR-SKIP that uses base editors. To date, techniques for targeted exon skipping are either transient, such as injection of antisense oligonucleotides (Crooke S T: *Biochim Biophys Acta* 1999, 1489:31-44) or require introduction of DSBs into coding and/or non-coding regions of the genome, which could lead to deleterious off-target effects (Mou H, et al: *Genome Biol* 2017, 18:108; Long C, et al: *Sci Adv* 2018, 4:eaap9004). The disclosure is based, at least in part, on the discovery that CRISPR-SKIP, a technology that induces permanent modifications in the genome without DSBs, thus provides a significant advantage over other exon skipping techniques. Since the changes introduced by CRISPR-SKIP are hardwired in the genome after a single treatment, it provides a potential therapeutic tool for a wide variety of human diseases.

A Clustered Regularly Interspersed Short Palindromic Repeats/CRISPR-associated (CRISPR/Cas) system comprises components of a prokaryotic adaptive immune system that is functionally analogous to eukaryotic RNA interference, and that uses RNA base pairing to direct DNA or RNA cleavage. Directing DNA double stranded breaks requires an RNA-guided DNA endonuclease (e.g., Cas9 protein or the equivalent) and CRISPR RNA (crRNA) and tracr RNA (tracrRNA) sequences that aid in directing the RNA-guided DNA endonuclease/RNA complex to target nucleic acid sequence. The modification of a single targeting RNA can be sufficient to alter the nucleotide target of an RNA-guided DNA endonuclease protein. crRNA and tracrRNA can be engineered as a single cr/tracrRNA hybrid to direct the RNA-guided DNA endonuclease cleavage activity. A CRISPR/Cas system, including a CRISPR-SKIP system, can be used in vivo in yeast, fungi, plants, animals, mammals, humans, and in in vitro systems.

A CRISPR system, including a CRISPR-SKIP system, can comprise transcripts and other elements involved in the expression of or directing the activity of CRISPR-associated ("Cas") genes, including sequences encoding an RNA-guided DNA endonuclease gene (i.e. Cas), a tracr (trans-activating CRISPR) sequence (e.g. tracrRNA or an active partial tracrRNA), a tracr-mate sequence (encompassing a "direct repeat" and a tracrRNA-processed partial direct repeat), a guide sequence, or other sequences and transcripts from a CRISPR locus. One or more elements of a CRISPR system can be derived from a type I, type II, type III, type IV, and type V CRISPR system. A CRISPR system comprises elements that promote the formation of a CRISPR complex at the site of a target sequence (also called a protospacer).

The elements of CRISPR systems (e.g., direct repeats, homologous recombination editing templates, guide sequences, tracrRNA sequences, target sequences, priming sites, regulatory elements, and RNA-guided DNA endonucleases) are well known to those of skill in the art. That is, given a target sequence one of skill in the art can design functional CRISPR elements specific for a particular target sequence. The methods described herein are not limited to the use of specific CRISPR elements, but rather are intended to provide unique arrangements, compilations, and uses of the CRISPR elements.

In one embodiment, the disclosure provides a fusion protein comprising (i) at least two tRNA-specific adenosine deaminases (TadA) domains (ii) a linker; and (iii) a RNA-guided DNA endonuclease having nickase activity protein. In one embodiment, the disclosure provides a method for inducing selective exon skipping comprising: contacting one or more DNA target sequences with (i) a single guide RNA (sgRNA) molecule having complementarity to the DNA target sequence; and (ii) the fusion protein comprising (i) at least two tRNA-specific adenosine deaminases (TadA) domains (e.g., 2, 3, 4, 5, or more domains) (ii) a linker; and (iii) a RNA-guided DNA endonuclease having nickase activity protein.

In particular embodiments, the fusion protein can be used to skip multiple exons. For example, multiple constructs can be used to skip 2, 3, 4, 5, 6 or more exons.

The term "deaminase" refers to an enzyme that catalyzes a deamination reaction. In some embodiments, the deaminase is a base editor converting adenine to guanine (e.g., Adenine Base Editor also referred to as ABE). In particular embodiments, the deaminase is a tRNA-specific adenosine deaminase (TadA). In some embodiments, the deaminase is a base editor converting cytidine to thymidine. A TadA can be an *E. coli* TadA, for example, UniProtKB-P68398 A TadA can be a *Bacillus subtilis* TadA, for example UniProtKB 21335. A TadA can be a *Staphylococcus aureus* TadA, for example UniProtKB Q99W51. Other adenosine deaminases and cytosine deaminases can also be used.

In some embodiments, a uracil glycosylase inhibitor (UGI) is used to minimize the natural repair process and increases the generation of the desired T-A base pair. Suitable UGIs include for example, a *Bacillus subtilis* bacteriophage PBS2 inhibitor (Wang et al, *J. Biol. Chem.* 1989 Jan. 15; 264(2):1163-71), an *Escherichia coli* inhibitor (Lundquist et al, *J. Biol. Chem.* 272:21408-21419(1997); Ravishankar et al, Nucleic Acids Res. 26:4880-4887(1998); and Putnam et al, *J. Mol. Biol.* 287:331-346(1999)), a *Staphylococcus aureus* inhibitor (Serrano-Heras G, et al, *Proc Natl Acad Sci USA.* 2008; 105:19044-19049). Other suitable UGI's can also be used. In one embodiment, the UGI sequence is as follows: TNLSDIIEKETGKQLVIQE-SILMLPEEVEEVIGNKPESDILVHTAYDESTDENVM LLTSDAPEYKPWALVIQDSNGENKIKML (SEQ ID NO:1; Uniprot: P14739). The UGI can be positioned at the N-terminus, at the C-terminus, or internally within the fusion protein.

Linkers are short polypeptide sequences that can be used to operably link protein domains. Linkers can comprise flexible amino acid residues (e.g., glycine or serine) to permit adjacent protein domains to move freely related to one another. In some embodiments, a linker joins the nickase, including the Cas9-D10A, and the deaminase. In some embodiments, the linker comprises (AP)$_5$ (SEQ ID NO:2), GGGGS (SEQ ID NO:3), (GGGGS)$_2$ (SEQ ID NO:4), (GGGGS)$_3$ (SEQ ID NO:5), (GGGGS)$_4$ (SEQ ID NO:6), (GGGGS)$_5$ (SEQ ID NO:7), (GGGGS)$_6$ (SEQ ID NO:8), (GGGGS)$_7$ (SEQ ID NO:9), GGGGSSGGSSGGSSG-SETPGTSESATPESSGGSSGGS (SEQ ID NO:10), or (EAAA)$_5$ (SEQ ID NO:11). In particular embodiments, the linker comprises (GGGGS)$_5$ (SEQ ID NO:7), however any suitable linker can be used. In an embodiment, a linker can be present between two TadA domains. In an embodiment a linker can be present between the TadA domain and RNA-guided DNA endonuclease having nickase activity domain. In an embodiment, the spans the C terminus and the N terminus. In an embodiment, a linker can be about 4, 5, 6, 7, 8, 9, 10, 15, 20, 25, 30, or more nucleotides in length.

Wild-type Cas9 possesses two protein domains, RuvC and HNH, each responsible for cutting a strand of DNA. In particular embodiments, a RNA-guided DNA endonuclease having nickase activity is provided. In particular embodiment the RNA-guided DNA endonuclease having nickase activity is any Cas9, including spCas9, SaCas9 or FnCas9, or Cas12a. In particular embodiment the RNA-guided DNA endonuclease having nickase activity is a Cas9 enzyme wherein the RuvC domain has been modified with a DOA (Aspartic Acid to Alanine) mutation to make the Cas9 protein function as a nickase (cleaves a single strand) rather than as a nuclease. Other examples of mutations that render Cas9 a nickase include, without limitation, H840A, N854A, and N863A. In other embodiments, the SaCas9 includes the mutation D10A or N580A and functionally similar mutations in other Cas orthologs.

As used herein, "single guide RNA," "guide RNA (gRNA)," "guide sequence" and "sgRNA" can be used interchangeably herein. A guide RNA is a specific RNA sequence that recognizes a target DNA region of interest and directs an RNA-guided molecule there for editing. A gRNA has at least two regions. First, a CRISPR RNA (crRNA) or spacer sequence, which is a nucleotide sequence complementary to the target nucleic acid, and second a tracr RNA, which serves as a binding scaffold for the RNA-guided molecule. The target sequence that is complementary to the guide sequence is known as the protospacer. The crRNA and tracr RNA can exist as one molecule or as two separate molecules. gRNA and sgRNA as used herein refer to a single molecule comprising at least a crRNA region and a tracr RNA region or two separate molecules wherein the first comprises the crRNA region and the second comprises a tracr RNA region. The crRNA region of the gRNA is a customizable component that enables specificity in every CRISPR reaction.

A guide RNA used in the systems and methods described herein are short, single-stranded polynucleotide molecules about 20 nucleotides to about 300 nucleotides in length. The spacer sequence (targeting sequence) that hybridizes to a complementary region of the target DNA of interest can be about 14, 15, 16, 17, 18, 19, 20, 25, 30, 35 or more nucleotides in length.

sgRNAs can be synthetically generated or by making the sgRNA in vivo or in vitro, starting from a DNA template.

A sgRNA can target a regulatory element (e.g., a promoter, enhancer, or other regulatory element) in the target genome. A sgRNA can also target a protein coding sequence in the target genome.

In particular embodiments, the sgRNA molecule is complementarity to a splice acceptor of a DNA target sequence. A splice acceptor site is present at the end of an intron and terminates the intron. Mutations which abolish or weaken recognition of natural splice acceptor or donor sites produce transcripts lacking corresponding exons or activate adjacent cryptic splice sites of the same phase. A splice acceptor site can be about 10, 12, 15, 20 or more nucleotides. In general a splice acceptor site has (5' to 3') a pyrimidine rich segment that is about 6, 8, or 10 nucleotides in length followed by NCAG (SEQ ID NO:12), NTAG (SEQ ID NO: 13), or NAAG (SEQ ID NO:14). See FIG. 1A. One or more sgRNA molecules (e.g., about 1, 2, 3, 4, 5 or more) have complementarity to one or more splice acceptor sites (e.g., about 1, 2, 3, 4, 5, or more). A sgRNA molecule can be about 15, 16, 17, 18, 19, 20, 21, 22, 23, 24, 25 or more nucleotides in length, wherein the target base occurs at about position 2, 3, 4, 5, 6, 7, 8, 9, or 10 of the sgRNA molecule. See, for example Table 1.

In particular embodiments, the sgRNA molecule is complementarity to a splice enhancer of a DNA target sequence. A splice enhancer is a DNA sequence motif consisting of 6 bases within an exon and adjacent to an intron that directs, or enhances, accurate splicing.

In the context of formation of a CRISPR complex, a target sequence or target nucleic acid molecule is a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence can comprise any polynucleotide, such as DNA or RNA polynucleotides. In some embodiments, a target sequence is located in the nucleus or cytoplasm of a cell. In some embodiments, the target sequence can be within an organelle of a eukaryotic cell, for example, mitochondrion or chloroplast.

In particular embodiments, the target sequence is located at the splice acceptor for exon 3 of the alpha-synuclein protein. In particular embodiments, the target sequence is located at the splice acceptor for exon 45 of the dystrophin gene. In particular embodiments, the target sequence is located at the splice enhancer of exon 12 of the Huntington gene.

The target sequence can be associated with a PAM (protospacer adjacent motif); that is, a short sequence recognized by the CRISPR complex. The precise sequence and length requirements for the PAM differ depending on the RNA-guided DNA endonuclease having nickase activity used, but PAMs are typically 2-5 base pair sequences adjacent to the protospacer (that is, the target sequence). In particular embodiments, a component of the RNA-guided DNA endonuclease having nickase activity domain can be split into two domains using inteins, thus enabling the packaging into vectors, such as viral vectors like AAV vectors with multiple applications for in vivo gene therapy.

An intein is an amino acid sequence that can excise itself from a protein and can rejoin the remaining protein segments (the exteins) via a peptide bond via protein splicing. Inteins are analogous to the introns found in mRNA. Many naturally occurring and engineered inteins and hybrid proteins comprising such inteins are known. As a result, methods for the generation of hybrid proteins from naturally occurring and engineered inteins are known to the skilled artisan. See e.g., For an Gross, Belfort, Derbyshire, Stoddard, & Wood (Eds.) Homing Endonucleases and Inteins Springer Verlag Heidelberg, 2005; ISBN 9783540251064. An intein can catalyze protein splicing in a variety of extein contexts. Therefore, an intein can be introduced into virtually any target protein sequence to create a desired hybrid protein. An intein can be, for example, mTth, Pho_RadA, Tko_RadA, Sce_VMA, mVMA, and Pab_Lon. Intein sequences can be found in InBase, an intein database. See, Perler et al. 1992 Proc Natl Acad Sci USA 89: 5577); Eryilmaz et al., J Biol Chem. 2014 May 23; 289(21): 14506-14511. An extein is the amino acid sequence that is flanked by an intein and is ligated to another extein during the process of protein splicing to form a mature, spliced protein. Typically, an intein is flanked by two extein sequences that are ligated together when the intein catalyzes its own excision. Exteins, accordingly, are the protein analog to exons found in mRNA. Split intein systems may include two polypeptides, wherein one may be of the structure extein(N)-intein(N) and the other may be of the structure intein(C)-extein(C). After dimerization and excision of the two intein fragments and splicing of the two exteins, the resulting structures are extein(N)-extein(C) and intein(N)-intein(C).

In one embodiment, provided herein is a recombinant system comprising a first construct comprising (i) a polynucleotide encoding tRNA-specific adenosine deaminase (TadA) (ii) a polynucleotide encoding a linker (iii) a first part of a polynucleotide encoding a RNA-guided DNA endonuclease having nickase activity domain and (v) a polynucleotide encoding an N-terminal intein and a second construct comprising (iv) a polynucleotide encoding a C-terminal intein and (ii) a second part of a polynucleotide encoding the RNA-guided DNA endonuclease having nickase activity domain.

In some embodiments, the first construct comprises the TadA domains, the linker, 712 amino acids

```
(SEQ ID NO: 15):
(DKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFF

HRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLF

EENPINASGVDAKAILSARLSKSRRLENLIAQLPGEKKNGLFGNLIALS

LGLTPNFKSNFDLAEDAKLQLSKDTYDDDLDNLLAQIGDQYADLFLAAK

NLSDAILLSDILRVNTEITKAPLSASMIKRYDEHHQDLTLLKALVRQQL

PEKYKEIFFDQSKNGYAGYIDGGASQEEFYKFIKPILEKMDGTEELLVK

LNREDLLRKQRTFDNGSIPHQIHLGELHAILRRQEDFYPFLKDNREKIE

KILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLK

TYAHLFDDKVMKQLKRRRYTGWGRLSRKLINGIRDKQSGKTILDFLKSD

GFANRNFMQLIHDDSLTFKEDIQKAQV)
``` of the polynucleotide encoding the RNA-guided DNA endonuclease having nickase activity and the N-terminal intein: (CLAGDTLITLADGRRVPIRELVSQQNFSVWALNPQ-TYRLERARVSRAFCTGIKPVYR LTTRLGRSIRA-TANHRFLTPQGWKRVDELQPGDYLALPRRIPTAS) (SEQ ID NO:16). In some embodiments, the second construct comprises 713-1371 amino acids of the polynucleotide encoding the RNA-guided DNA endonuclease having nickase activity and the C-terminal intein.

In one embodiment, provided herein is a recombinant system comprising a first construct comprising (i) a polynucleotide encoding a cytidine deaminase domain (ii) a polynucleotide encoding a linker (iii) a first part of a polynucleotide encoding nickase SpCas9 and (iv) a polynucleotide encoding an N-terminal intein; a second construct comprising (i) a polynucleotide encoding a C-terminal intein (ii) a second part of a polynucleotide encoding nickase SpCas9 and (iii) a polynucleotide encoding a uracil glycosylase inhibitor.

The terms "polynucleotide", "nucleotide", "nucleotide sequence", "nucleic acid", and "oligonucleotide" are used interchangeably. They refer to a polymeric form of nucleotides of any length, either deoxyribonucleotides or ribonucleotides, or analogs thereof. Polynucleotides can have any three dimensional structure, and can perform any function, known or unknown. Examples of polynucleotides include DNA molecules, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide can comprise one or more modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component.

A gene is any polynucleotide molecule that encodes a polypeptide, protein, or fragments thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene comprise regulatory elements and coding sequences that are derived from different sources, or regulatory elements and coding sequences that are derived from the same source, but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide.

Polynucleotides can comprise additional heterologous nucleotides that do not naturally occur contiguously with the polynucleotides. As used herein the term "heterologous" refers to a combination of elements that are not naturally occurring or that are obtained from different sources.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid sequences present in, for example, a microorganism such as a yeast or bacterium. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise coding sequences for naturally occurring polypeptides or can encode altered sequences that do not occur in nature.

Unless otherwise indicated, the term polynucleotide or gene includes reference to the specified sequence as well as the complementary sequence thereof.

The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, up-regulation, RNA splicing, translation, and post-translational modification of a protein.

Homology refers to the similarity between two nucleic acid sequences. Homology among DNA, RNA, or proteins is typically inferred from their nucleotide or amino acid sequence similarity. Significant similarity is strong evidence that two sequences are related by evolutionary changes from a common ancestral sequence. Alignments of multiple sequences are used to indicate which regions of each sequence are homologous. The term "percent homology" is used herein to mean "sequence similarity." The percentage of identical nucleic acids or residues (percent identity) or the percentage of nucleic acids residues conserved with similar physicochemical properties (percent similarity), e.g. leucine and isoleucine, is used to quantify the homology.

Complement or complementary sequence means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'. Downstream refers to a relative position in DNA or RNA and is the region towards the 3' end of a strand. Upstream means on the 5' side of any site in DNA or RNA.

As described herein, "sequence identity" is related to sequence homology. Homology comparisons can be conducted by eye or using sequence comparison programs. These commercially available computer programs can calculate percent (%) homology between two or more sequences and can also calculate the sequence identity shared by two or more amino acid or nucleic acid sequences.

Sequence homologies may be generated by any of a number of computer programs known in the art, for example BLAST or FASTA.

Percentage (%) sequence identity can be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Ungapped alignments are performed only over a relatively short number of residues. Although this is a very simple and consistent method, it fails to take into consideration that, for example, in an otherwise identical pair of sequences, one insertion or deletion can cause the following amino acid residues to be put out of alignment, thus potentially resulting in a large reduction in percent homology when a global alignment is performed. Therefore, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

In some embodiments, at least one of the first construct and the second construct further comprises a sgRNA expression cassette providing simultaneous delivery of the sgRNA to a cell. In some embodiments, the expression cassette is positioned between the ITR sequences of the constructs. A sgRNA expression cassette can be under the control of a U6, 7Sk, or other RNA-polymerase III promoters.

The term "construct", as used herein refers to an artificially assembled or isolated nucleic acid molecule which can include one or more nucleic acid sequences, wherein the nucleic acid sequences can include coding sequences, regulatory sequences, non-coding sequences, or any combination thereof. The term construct includes, for example, vectors.

Several aspects of the disclosure relate to vector systems comprising one or more vectors. A vector or "expression vector" is a replicon, such as a plasmid, virus, phage, or cosmid, to which another nucleic acid segment can be attached so as to bring about the replication of the attached segment. A vector is capable of transferring polynucleotides (e.g. gene sequences) to target cells.

Expression refers to the process by which a polynucleotide is transcribed from a nucleic acid template (such as into a sgRNA, tRNA or mRNA) and/or the process by which a transcribed mRNA is subsequently translated into peptides, polypeptides, or proteins. Transcripts and encoded polypeptides can be collectively referred to as "gene product."

Many suitable vectors and features thereof are known in the art. Vectors can contain, without limitation, a centromeric (CEN) sequence, an autonomous replication sequence (ARS), a promoter, an origin of replication, and a marker gene (e.g., auxotrophic, antibiotic, or other selectable markers). Examples of expression vectors include plasmids, yeast artificial chromosomes, 2μπι plasmids, yeast integrative plasmids, yeast replicative plasmids, shuttle vectors, episomal plasmids, and viral vectors.

In some embodiments, the first construct and the second construct is flanked by inverted terminal repeats (ITRs). In some embodiments, the ITRs are isolated or derived from an AAV vector of serotype AAV1, AAV2, AAV3, AAV4, AAV5, AAV6, AAV7, AAV 8, AAV9, AAV 10, AAV 11 AAVrh74, AAVrh10 or any combination thereof. In some embodiments, the ITRs comprise or consist of full-length and/or wildtype sequences for an AAV serotype. In some embodiments, the ITRs comprise or consist of truncated sequences for an AAV serotype. In some embodiments, the ITRs comprise or consist of elongated sequences for an AAV serotype. In some embodiments, the ITRs comprise or consist of sequences comprising a sequence variation compared to a wildtype sequence for the same AAV serotype. Other ITRs from different species can be used in the constructs disclosed herein. In some embodiments, the first and second constructs are packaged into a first and second adeno-associated virus (AAV).

The constructs and vectors can comprise promoters. The promoters can be the same or different promoters. A promoter is any nucleic acid sequence that regulates the initiation of transcription for a particular polypeptide-encoding nucleic acid under its control. A promoter minimally includes the genetic elements necessary for the initiation of transcription (e.g., RNA polymerase Ill-mediated transcription), and can further include one or more genetic regulatory elements that serve to specify the prerequisite conditions for transcriptional initiation. A promoter can be inducible or non-inducible A promoter can be a cis-acting DNA sequence, about 10, 20, 30, 40, 50, 60, 70, 80, 90, 100, 110, 120, or more base pairs long and located upstream of the initiation site of a gene, to which RNA polymerase can bind and initiate correct transcription. There can be associated additional transcription regulatory sequences that provide on/off regulation of transcription and/or which enhance (increase) expression of the downstream coding sequence. A coding sequence is the part of a gene or cDNA that codes for the amino acid sequence of a protein, or for a functional RNA such as a tRNA or rRNA.

A promoter can be encoded by an endogenous genome of a cell, or it can be introduced as part of a recombinantly engineered polynucleotide. A promoter sequence can be taken from one species and used to drive expression of a gene in a cell of a different species. A promoter sequence can also be artificially designed for a particular mode of expression in a particular species, through random mutation or rational design. In recombinant engineering applications, specific promoters are used to express a recombinant gene under a desired set of physiological or temporal conditions or to modulate the amount of expression of a recombinant nucleic acid.

Other regulatory elements include enhancers, internal ribosomal entry sites (IRES), and other expression control elements (e.g. transcription termination signals (i.e., terminators), such as polyadenylation signals and poly-U sequences). Vectors described herein can additionally comprise one or more regulatory elements. Regulatory elements include those that direct constitutive expression of a nucleotide sequence in many types of host cell and those that direct expression of the nucleotide sequence only in certain host cells (e.g., tissue-specific regulatory sequences). Regulatory elements can also direct expression in a temporal-dependent manner, such as in a cell-cycle dependent or developmental stage-dependent manner, which may or may not also be tissue or cell-type specific.

Regulatory elements include enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981).

The disclosure further provides a method comprising CRISPR-SKIP that utilizes cytidine deaminase base editors to program exon skipping by mutating target DNA bases within splice acceptor sites. Given its simplicity and precision, CRISPR-SKIP will be broadly applicable in gene therapy and synthetic biology.

In some embodiments, provided herein is a method for inducing selective exon skipping comprising contacting a DNA target sequence with (i) a single guide RNA (sgRNA) molecule having complementarity to the DNA target sequence and (ii) a cytidine deaminase base editor. In particular embodiments, the cytidine deaminase base editor comprises a cytidine deaminase, an uracil glycosylase inhibitor and a RNA-guided DNA endonuclease having nickase activity domain.

As used herein, "cytidine deaminase" refers to any enzyme that is capable of catalyzing the irreversible hydrolytic deamination of cytidine and deoxycytidine to uridine and deoxyuridine, respectively (cytidine deaminase activity). For example, a cytidine deaminase is a member of enzymes in the cytidine deaminase superfamily, and in particular, enzymes of the AID/APOB EC family. Members of the AID/APOBEC enzyme family include activation-induced deaminase (AID) and APOBEC1, APOBEC2, APOBEC4, and APOBEC3 subgroups of enzymes (Conticello et al. *Mol. Biol. Evol.* 22:367-77, 2005; Conticello. *Genome Biol.* 9:229, 2008). The cytidine deaminase superfamily additionally includes cytidine deaminases and CMP deaminases (Muranatsu et al, *J. Biol, Chem* 274: 18470-6, 1999). A cytidine deaminase can be a mammalian cytidine deaminase, such as rat or human, however, any suitable cytidine deaminase can be used. In particular embodiments, the cytidine deaminase base editor is SpCas9-BE3.

Advantageously the methods and compositions disclosed herein result in less than 1%, 2%, 3%, 4%, 5%, 6%, 7%, 8%, 9%, 10%, 11%, 12%, 13%, 14%, or 15% of off-target binding. In other words, the methods and compositions disclosed have a high degree of binding to the to an "on-target" site which refers to a site to which a practitioner desires binding and/or cleavage to occur, while "off-target" refers to a site to which a practitioner does not desire binding and/or cleavage to occur.

In particular embodiments, the methods and compositions disclosed herein advantageously result in 20%, 25%, 30%, 35%, 40%, 45%, 50%, 55%, 60%, 5%, 70%, 75%, 80%, 85%, 90%, or 95% of exon skipping.

Further disclosed herein is a method of treating an alpha synuclein protein defect in a subject comprising contacting a cell in the subject with the systems disclosed herein. Further disclosed herein is a method of treating a dystrophin protein defect in a subject comprising contacting a cell in the subject with the systems disclosed herein. Further disclosed herein is a method of treating Huntington disease in a subject comprising contacting a cell in the subject with (i) a single guide RNA (sgRNA) molecule having complementarity to a target sequence in the Huntington gene and (ii) a cytidine deaminase base editor. In particular embodiments, the sgRNA molecule is complementary to a target sequence in exon 12 of the Huntington gene. Further disclosed herein is a method of treating Duchenne Muscular Dystrophy in a subject comprising contacting a cell in the subject with (i) a single guide RNA (sgRNA) molecule having complementarity to a target sequence in the dystrophin gene and (ii) a cytidine deaminase base editor. In particular embodiments, the sgRNA molecule is complementary to a target sequence in exon 45 of the dystrophin gene.

The term "subject" is intended to include human and non-human animals, particularly mammals. In certain embodiments, the subject is a human patient.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, e.g., arresting its development; or relieving the disease, e.g., causing regression of the disease and/or its symptoms or conditions such as improvement or remediation of damage, for example in a subject who has been diagnosed as having the disease.

The dose of for treatment will vary based on several factors including, but not limited to: route of administration, the nucleic acid expression required to achieve a therapeutic effect, the specific disease treated, any host immune response to the vector, and the stability of the protein expressed. One skilled in the art can determine a rAAV/vector genome dose range to treat a patient having a particular disease or disorder based on the aforementioned factors, as well as other factors.

Methods of administration or delivery include any mode compatible with a subject. Methods and uses of the invention include delivery and administration systemically, regionally or locally, or by any route, for example, by injection or infusion. Such delivery and administration include parenterally, e.g. intraocularly, intravascularly, intravenously, intramuscularly, intraperitoneally, intradermally, subcutaneously, or transmucosal. Exemplary administration and delivery routes include intravenous (i.v.), intraperitoneal (i.p.), intra-arterial, subcutaneous, intra-pleural, intubation, intrapulmonary, intracavity, iontophoretic, intraorgan, intralymphatic. In particular embodiments, a vector, such as an AAV vector is administered or delivered parenterally, such as intravenously, intraarterially, intraocularly, intramuscularly, subcutaneously, or via catheter or intubation.

In certain embodiments, the mode of delivery comprises a DNA based expression system. In certain embodiments, the mode of delivery comprises a RNA or protein/RNA complex system. In certain embodiments, the mode of delivery further comprises selecting a delivery vehicle and/or expression systems from the group consisting of liposomes, lipid particles, nanoparticles, biolistics, or viral-based expression/delivery systems. In certain embodiments, expression is spatiotemporal expression is optimized by choice of conditional and/or inducible expression systems, including controllable CRISPR effector activity optionally a destabilized CRISPR effector and/or a split CRISPR effector, and/or cell- or tissue-specific expression system.

In some embodiments, the systems disclosed herein can be administered directly or they can be used to treat cells in vitro, and the modified cells can optionally be administered (ex vivo).

The compositions disclosed herein can be incorporated into pharmaceutical compositions, e.g., a pharmaceutically acceptable carrier or excipient.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle to a subject.

Without limiting the disclosure, a number of embodiments of the disclosure are described herein for purpose of illustration.

EXAMPLES

The Examples that follow are illustrative of specific embodiments of the disclosure, and various uses thereof. They are set forth for explanatory purposes only and should not be construed as limiting the scope of the disclosure in any way.

Methods

Cell Culture and Transfection

The cell lines HCT116, 293T, MCF7, HEPG2 and Neuro-2A were obtained from the American Tissue Collection Center (ATCC). HCT116, 293T, Hepa 1-6 and Neuro-2A cells were maintained in DMEM supplemented with 10% fetal bovine serum and 1% penicillin/streptomycin at 37° C. with 5% $CO_2$. HEPG2 cells were maintained in DMEM supplemented with 10% fetal bovine serum, 1% penicillin/streptomycin, and 1% L-glutamine at 37° C. with 5% $CO_2$. MCF7 cells were grown in EMEM supplemented with 10% fetal bovine serum, 1% penicillin/streptomycin, 0.1 mM non-essential amino acids, 1 mM sodium pyruvate and 10 nM β-estradiol. All cell lines were transfected in 24-well plates with Lipofectamine 2000 (Invitrogen) following manufacturer's instructions. The amount of DNA used for lipofection was 1 μg per well. Transfection efficiency was routinely higher than 80% for 293T cells as determined by fluorescent microscopy following delivery of a control GFP expression plasmid. Transfection efficiency of other cell lines was lower (10-50%) and, therefore, puromycin selection was used for 48 hours to enrich successfully transfected cells. Puromycin was used at a concentration of 1 μg/mL (HCT116, MCF7), 1 μg/mL (HeLa), 2 μg/mL (HepG2), or 3 μg/mL (Neuro2A).

Plasmids and Cloning

The plasmids used for SpCas9 sgRNA expression and expression of SpCas9, dCas9 and Cas9-D10A were gifts from Charles Gersbach. The plasmids encoding SpCas9-BE3 (pCMV-BE3), SpCas9-VQR-BE3 (pBK-VQR-BE3), and SaCas9-KKH-BE3 (pJL-SaKKH-BE3) were gifts from David Liu (Addgene plasmid #73021, 85171, and 85170). The plasmid used for SaCas9-KKH-BE3 sgRNA expression (BPK2660) was a gift from Keith Joung (Addgene plasmid #70709).

The ABE7.10 plasmid was generated through Gibson assembly of a gBlock Gene Fragment (Integrated DNA Technologies) containing the TadA domains and ABE7.10 linker, as described by Gaudelli et al Nature 551, 464-471, (2017) into the Cas9-D10A backbone. The ABE plasmids containing the various linkers were created through Gibson assembly of gBlock Gene Fragments into the ABE7.1 plasmid. The ABE-UGI plasmid was generated through Gibson assembly of the TadA deaminase domains into an spCas9-BE3 plasmid (pCMV-BE3) that was a gift from David Liu (Addgene plasmid #73021). Split ABE constructs were generated through Gibson assembly of gBlock Gene Fragments. Amino acid sequences are provided in Supplemental Sequences. All base editor constructs were under the control of the CMV promoter, except for N-ABE-AAV which was under the control of an EFS promoter (Tabebordbar, M. et al, Science 351, 407-411 (2016)). To facilitate enrichment of successfully transfected cells, a cassette for expression of puromycin N-acetyl-transferase and GFP tethered with T2A peptide from a PGK promoter was cloned into each of the three BE3 plasmids. All oligonucleotides used in this work were obtained from IDT Technologies. The oligonucleotides for sgRNA generation were hybridized, phosphorylated and cloned into the appropriate sgRNA vector using BbsI sites for pSPgRNA, and BsmBI sites for BPK2660 (Khoo, B., et al, BMC Mol Biol 8, 3, doi: 10.1186/1471-2199-8-3 (2007). Guide sequences are provided in Table 1.

TABLE 1

| Results of CRISPR-SKIP targeting at 18 human sites with 20 sgRNAs. Target base is shown in bold and italics. | | | | |
|---|---|---|---|---|
| Target Gene | Ensembl ID. Exon Number and Target Exon Number (after colon) | BE3 Version | Target Sequence and PAM | Exon Skipped?* |
| BRCA2 | ENST00000380152.7: 10 | SpBE3 | AATCCTGTTAAAGTATAAAA SEQ ID NO: 34 CAG | Y |
| BRCA2 | ENST00030380152.7: 17 | SpBE3 | GAGCCCTGAACAAATAAAAG SEQ ID NO: 35 TAG | N |
| BRCA2 | ENST00000380152.7: 17 | SaBE3-KKH | GAGCCCTGAACAAATAAAAG SEQ ID NO: 36 TAGAAT | N |
| BRCA2 | ENST00000380152.7: 26 | SpBE3-VOR | AATATTCTAAGAAAATAAGT SEQ ID NO: 37 GGA | Y |
| CCNB1 | ENST00000256442.9: 5 | SaBE3-KKH | CTCTTCCTGCAAAAGAAAAT SEQ ID NO: 38 GCTGAT | N |
| CCNB1 | ENST000002564429: 6 | SaBE3-KKH | AATTATTCTGCAATGGGAAT SEQ ID NO: 39 TTCAAT | N |
| EGFR | ENST00000275493.6: 23 | SpBE3-VOR | ACCCCTGAGAGGATGAAGCA SEQ ID NO: 40 AGA | N |
| IL1RAP | ENST0003044 7382.5: 10 | SpBE3-VOR | GGCACTGGAATGAACAACAA SEQ ID NO: 41 AGA | Y |

TABLE 1-continued

Results of CRISPR-SKIP targeting at 18 human sites with 20 sgRNAs.
Target base is shown in bold and italics.

| Target Gene | Ensembl ID. Exon Number and Target Exon Number (after colon) | BE3 Version | Target Sequence and PAM | Exon Skipped?* |
|---|---|---|---|---|
| IL1RAP | ENST00000447382.5: 10 | SpBE3 | TGGCA*C*TGGAATGAACAACA MG SEQ ID NO: 42 | N |
| JAG1 | ENST00000254958.9: 9 | SpBE3 | AATGT*C*TGGTCAACAAGAAA AGG SEQ ID NO: 43 | Y |
| JAG1 | ENST00000254958.9: 12 | SpBE3 | AAATC*C*TAGAAGAGGAGAAG GGG SEQ ID NO: 44 | N |
| LMNA | ENST00000448611.6: 11 | SpBE3 | GAGCC*C*TGGGAAGGGAGACA AGG SEQ ID NO: 45 | N |
| PI4KA | ENST0000025588210: 9 | SpBE3-VOR | TCTTCAC*C*TACCAAGGAAAC AGA SEQ ID NO: 46 | N |
| PIK3CA | ENST00000263967.3: 5 | SpBE3 | TATA*C*TGTAAGAGATTAAGG GGG SEQ ID NO: 47 | Y |
| PIK3CA | ENST00000263967.3: 11 | SaBE3-KKH | TAGTGT*C*TGTGTGGGAGAAA CAAAAT SEQ ID NO: 48 | Y |
| PIK3CA | ENST00000263967.3: 12 | SaBE3-KKH | ATACAT*C*TGTGTATGAGAAA GACAAT SEQ ID NO: 49 | Y |
| RELA | ENST0000040€246.7: 6 | SpBE3-VOR | GGAA*C*TGCCAAGAAAACAGG CGA SEQ ID NO: 50 | N |
| RELA | ENST00000406246.7: 7 | SpBE3 | AC*C*TGAGGCAGTGAAAACAA GGG SEQ ID NO: 51 | Y |
| RELA | ENST00000406246.7: 10 | SaBF_3-KKH | TGGGTC*C*TGTAGGGCAAGGG CTAGGT SEQ ID NO: 52 | Y |
| SCARB1 | ENST00000339570.9: 5 | SpBE3 | GTTGAG*C*TACAGACACAGCA GGG SEQ ID NO: 53 | Y |

*As determined by gel electrophoreses

AAV Vector Production

HEK293T cells were seeded in 15 cm dishes and transfected at 80-90% confluence. GFP-AAV plasmid, N-ABE-AAV or C-ABE-AAV were transfected along with pHelper and pAAV-DJ from the AAV-DJ Packaging System from Cell Biolabs in a 1:1:1 ratio using calcium phosphate and a total of 60 μg per plate. Media was replaced 24 hours post-transfection. Cell pellets were harvested at 72 hours post-transfection through manual cell scraping and centrifuged at 1,500×g for 12 minutes. After aspirating the supernatant, the cell pellet was resuspended in 1 mL AAV lysis buffer (50 mM Tris-HCl pH=8.5, 150 mM NaCl and 2 mM MgCl$_2$). Resuspended pellets were subjected to three freeze-thaw cycles between an ethanol/dry ice bath and a 37° C. water bath. Lysed cell pellets were then spun at 10,000×g for 10 minutes and the supernatant was collected as crude lysate. Lysates were then treated with 50 U benzonase per mL and incubated at 37° C. for 30 minutes to digest unpackaged plasmid. Crude lysates were added directly to cells or flash frozen with liquid nitrogen and stored at −80° C. for future use.

AAV Infection

HEK293T cells were infected in suspension in the wells of a 24 well plate by mixing 100 μL of crude lysate with 20,000 cells in 150 μL of cell culture medium. In the case of the samples containing both N-ABE AAV and C-ABE AAV, 50 μL of each lysate was added. Protamine sulfate was added to the lysate-cell mix at a final concentration of 5 μg/mL to enhance infection efficiency. Cells were incubated for 24 hours at which point the media was aspirated and replaced with 500 μL of fresh medium. Infected cells were incubated for a total of 6 days before harvesting genomic DNA and RNA for analysis.

RT-PCR

RNA was harvested from cell pellets using the RNEASY® (RNA purification) Plus Mini Kit (Qiagen) according to manufacturer's instructions. cDNA synthesis was performed using the QSCRIPT® cDNA Synthesis Kit (Quanta Biosciences) from 400-1000 ng of RNA with the cycling conditions recommended by the supplier. PCR was performed using KAPA2G Robust PCR kits from Kapa Biosystems. The 25 μL reactions used 50 ng of cDNA, Buffer A (5 μL), Enhancer (5 μL), dNTPs (0.5 μL), 10 μM forward primer (1.25 μL), 10 μM reverse primer (1.25 μL), KAPA2G Robust DNA Polymerase (0.5 U) and water (up to 25 μL). Cycling parameters as recommended by the manufacturer were used. The PCR products were visualized in 2% agarose gels and images were captured using a CHEMI-DOC-IT® imager (UVP). The DNA sequences of the primers for each target are provided in Table 2. PCR may favor shorter amplicons and introduce bias in the quantification of ratios of two transcripts of different lengths.

TABLE 2

| | | | | |
|---|---|---|---|---|
| | | | Nucleotide sequences of primers used for all PCRs. | |
| Designation | Target Gene | Target Exon | Primer Sequence | RT PCR or gDNA |
| BRCA2int9 F | BRCA2 | 10 | AACAGGAGAAGGGGTGACTGAC SEQ ID NO: 54 | gDNA |
| BRCA2ex10 R | BRCA2 | 10 | TTCCAATGTGGTCTTTGCAGCT SEQ ID NO: 55 | gDNA |
| BRCA2ex7 F | BRCA2 | 10 | GCTACACCACCCACCCTTAGTT SEQ ID NO: 56 | RT |
| BRCA2ex11 R | BRCA2 | 10 | TTCCTGCAGGCATGACAGAGAA SEQ ID NO: 57 | RT |
| BRCA2int16 F | BRCA2 | 17 | Agatgtgggggtctcactatgttg SEQ ID NO: 58 | gDNA |
| BRCA2ex17 R | BRCA2 | 17 | AGCTGCCAGTTTCCATATGATCCA SEQ ID NO: 59 | gDNA |
| BRCA2ex15 F | BRCA2 | 17 | CACAGCCAGGCAGTCTGTATCT SEQ ID NO: 60 | RT |
| BRCA2ex18 R | BRCA2 | 17 | TGGGGCTTCAAGAGGTGTACAG SEQ ID NO: 61 | RT |
| BRCA2int25 F | BRCA2 | 26 | Aggacttgagccccaatcttcc SEQ ID NO: 62 | gDNA |
| BRCA2ex26 R | BRCA2 | 26 | GTGTACGGCCCTGAAGTACAGT SEQ ID NO: 63 | gDNA |
| BRCA2ex25 F | BRCA2 | 26 | TCTGCTAGTCCAAAAGAGGGCC SEQ ID NO: 64 | RT |
| BRCA2ex27 R | BRCA2 | 26 | CTGTGCAGCCGGAGAAACAAAT SEQ ID NO: 65 | RT |
| CCNB1int4 F | CCNB1 | 5 | Aagcaatctgccaacttcagcc SEQ ID NO: 66 | gDNA |
| CCNB1ex5 R | CCNB1 | 5 | CAGTGACTTCCCGACCCAGTAG SEQ ID NO: 67 | gDNA |
| CCNB1int5 F | CCNB1 | 6 | CCCTTCCAGGATTCTAGCCGAG SEQ ID NO: 68 | gDNA |
| CCNB1ex6 R | CCNB1 | 6 | AAACATGGCAGTGACACCAACC SEQ ID NO: 69 | gDNA |
| CCNB1ex3 F | CCNB1 | 5 and 6 | GagccagaacctgagccTGTTA SEQ ID NO: 70 | RT |
| CCNB1ex7 R | CCNB1 | 5 and 6 | AGGAGGAAAGTGCACCATGTCA SEQ ID NO: 71 | RT |
| EGFRint22 F | EGFR | 23 | Gaggtagactgaggcttccagc SEQ ID NO: 72 | gDNA |
| EGFRint23 R | EGFR | 23 | GATGCAAAGGCCTCAGCTGTTT SEQ ID NO: 73 | gDNA |
| EGFRex20 F | EGFR | 23 | GCTCAACTGGTGTGTGCAGATC SEQ ID NO: 74 | RT |
| EGFRex24 R | EGFR | 23 | TCACGGAACTTTGGGCGACTAT SEQ ID NO: 75 | RT |
| IL1RAPint9 F | IL1RAP | 10 | Accgtggacttcttcaggtage SEQ ID NO: 76 | gDNA |
| IL1RAPex10 R | IL1RAP | 10 | GCTCCAAAACCACAAGCCAGTT SEQ ID NO: 77 | gDNA |
| IL1RAPex8 F | IL1RAP | 10 | CTCGCAATGAGGTTTGGTGGAC SEQ ID NO: 78 | RT |
| IL1RAPex11.12 R | IL1RAP | 10 | GTATTTCCCCCAGGCAGACTGT SEQ ID NO: 79 | RT |
| JAG1int8 F | JAG1 | 9 | CTTGTAGCAGGTGTCTGGCTCT SEQ ID NO: 80 | gDNA |
| JAG1ex9 R | JAG1 | 9 | GGGGCACACACACTTAAATCCG SEQ ID NO: 81 | gDNA |
| JAG1ex8 F | JAG1 | 9 | GAGGCAGCTGTAAGGAGACCTC SEQ ID NO: 82 | RT |
| JAG1ex12 R | JAG1 | 9 | CTGCATAGCCAGGTGGACAGAT SEQ ID NO: 83 | RT |
| JAG1ex7 F | JAG1 | 9 long range | GAACTTGTAGCAACACAGGCCC SEQ ID NO: 84 | RT |
| JAG1ex15 R | JAG1 | 9 long range | AGGAGTTGACACCATCGATGCA SEQ ID NO: 85 | RT |
| JAG1int11 F | JAG1 | 12 | AGCTAAACCGCAACAGTCATGC SEQ ID NO: 86 | gDNA |
| JAG1int12 R | JAG1 | 12 | CCATCTGAGGTTTTGCCACCAC SEQ ID NO: 87 | gDNA |
| JAG1ex9 F | JAG1 | 12 | CGGATTTAAGTGTGTGTGCCCC SEQ ID NO: 88 | RT |
| JAG1ex13 R | JAG1 | 12 | TTCTGGCAGGGATTAGGCTCAC SEQ ID NO: 89 | RT |
| LMNAint10 F | LMNA | 11 | AAGCTTGCTCCCGTTCTCTCTT SEQ ID NO: 90 | gDNA |

TABLE 2-continued

Nucleotide sequences of primers used for all PCRs.

| Designation | Target Gene | Target Exon | Primer Sequence | RT PCR or gDNA |
|---|---|---|---|---|
| LMNAint11 R | LMNA | 11 | CAGAAGAGCCAGAGGAGATGGG SEQ ID NO: 91 | gDNA |
| LMNAex10 F | LMNA | 11 | GACGACGAGGATGAGGATGGAG SEQ ID NO: 92 | RT |
| LMNAex12 R | LMNA | 11 | CACCCCTTTCCCTTGGCTTCTA SEQ ID NO: 93 | RT |
| PI4KAint8 F | PI4KA | 9 | CTGAGGTCTGCACATCCTGGAA SEQ ID NO: 94 | gDNA |
| PI4KAint9 R | PI4KA | 9 | CACTGCAAAACCCCTTCCACTC SEQ ID NO: 95 | gDNA |
| PI4KAex8 F | PI4KA | 9 | ACTGCCCTAGAGCCTGAGTACT SEQ ID NO: 96 | RT |
| PI4KAex10 R | PI4KA | 9 | CACGCAGCATCTTGAACATGGT SEQ ID NO: 97 | RT |
| PI4KAex31 F | PI4KA | 33 | CCATGTTCAAGCTGACCGCAAT SEQ ID NO: 98 | RT |
| PI4KAex36 R | PI4KA | 33 | GCTGGCGGTCAGGTACTTCTTA SEQ ID NO: 99 | RT |
| PIK3CAint4 F | PIK3CA | 5 | Ggggtttcaccgtttttagccag SEQ ID NO: 100 | gDNA |
| PIK3CAex5 R | PIK3CA | 5 | ACATCAAATTGGGCATCCTCCC SEQ ID NO: 101 | gDNA |
| PIK3CAex3 F | PIK3CA | 5 | TCTTCACCAGAATTGCCAAAGC SEQ ID NO: 102 | RT |
| PIK3CAex6 R | PIK3CA | 5 | TCCACCTGGGATTGGAACAAGG SEQ ID NO: 103 | RT |
| PIK3CAex2 F | PIK3CA | 5 long | ACCAGTAGGCAACCGTGAAGAA SEQ ID NO: 104 | RT |
| PIK3CAex9 R | PIK3CA | 5 long | TCGGGATACAGACCAATTGGCA SEQ ID NO: 105 | RT |
| PIK3CAex9 F | PIK3CA | 11 and | TAGCTATTCCCACGCAGGACTG SEQ ID NO: 106 | RT |
| PIK3CAex14 R | PIK3CA | 11 and | TTCCATTGCCTCGACTTGCCTA SEQ ID NO: 107 | RT |
| RELAint5 F | RELA | 6 | TTTCCTGCATCTCCCTCACTGG SEQ ID NO: 108 | gDNA |
| RELAex6 R | RELA | 6 | ACAGCATTCAGGTCGTAGTCCC SEQ ID NO: 109 | gDNA |
| RELAint6 F | RELA | 7 | CAGATTGGCAcccactggacta SEQ ID NO: 110 | gDNA |
| RELAex7 R | RELA | 7 | AGATCTTGAGCTCGGCAGTGTT SEQ ID NO: 111 | gDNA |
| RELAex8 R | RELA | 6 and 7 | CCTGGTCCCGTGAAATACACCT SEQ ID NO: 112 | RT |
| RELAex4 F | RELA | 6 and 7, | CCCACGAGCTTGTAGGAAAGGA SEQ ID NO: 113 | RT |
| RELAex11 R | RELA | 7 long | TGCTCAGGGATGACGTAAAGGG SEQ ID NO: 114 | RT |
| RELAint8 F | RELA | 10 | CAACAGAGGCCTCCAAAAGCTG SEQ ID NO: 115 | gDNA |
| RELAex10 R | RELA | 10 | AATCCTTACCTGGCTTGGGGAC SEQ ID NO: 116 | gDNA |
| RELAex7 F | RELA | 10 | AACACTGCCGAGCTCAAGATCT SEQ ID NO: 117 | RT |
| RELAex11 R | RELA | 10 | TGCTCAGGGATGACGTAAAGGG SEQ ID NO: 118 | RT |
| SCARB1int4 F | SCARB1 | 5 | GgaggaaagccagaCTCTCCTG SEQ ID NO: 119 | gDNA |
| SCARB1int5 R | SCARB1 | 5 | AGAGTGTTCATCCTCCCAGCAC SEQ ID NO: 120 | gDNA |
| SCARB1ex4 F | SCARB1 | 5 | ACTGTGGGTGAGATCATGTGGG SEQ ID NO: 121 | RT |
| SCARB1ex7 R | SCARB1 | 5 | TTCGTTGGGTGGGTAGATGGAC SEQ ID NO: 122 | RT |
| BRCA2ex10off1F | BRCA2 | exon 10 | GCTGCCTACTCTGCCTACTCAG SEQ ID NO: 123 | gDNA |
| BRCA2ex10off1R | BRCA2 | exon 10 | Gtccataggcctcaccagactg SEQ ID NO: 124 | gDNA |
| BRCA2ex10off2F | BRCA2 | exon 10 | TTCTGAAGGAAGACGCCTGGAG SEQ ID NO: 125 | gDNA |
| BRCA2ex10off2R | BRCA2 | exon 10 | Gctgcaataaacatgggtgtgc SEQ ID NO: 126 | gDNA |
| BRCA2ex10off3F | BRCA2 | exon 10 | AATTCCCTGGCATTTAGGTTGAGC SEQ ID NO: 127 | gDNA |

TABLE 2-continued

Nucleotide sequences of primers used for all PCRs.

| Designation | Target Gene | Target Exon | Primer Sequence | RT PCR or gDNA |
|---|---|---|---|---|
| BRCA2ex10off3R | BRCA2 | exon 10 | GCAGAATGCAGACTTTCCCTTTCA SEQ ID NO: 128 | gDNA |
| BRCA2ex10off4F | BRCA2 | exon 10 | GgtgcctatcCCTGCCTTGTAT SEQ ID NO: 129 | gDNA |
| BRCA2ex10off4R | BRCA2 | exon 10 | TTTTACTTCGCCTTGGCACACC SEQ ID NO: 130 | gDNA |
| BRCA2ex17 Sp | BRCA2 | exon 17 | Cacgccctgtaatcccaacta SEQ ID NO: 131 | gDNA |
| BRCA2ex17 Sp | BRCA2 | exon 17 | GTGGTCTTCTTCCCACCTCCTC SEQ ID NO: 132 | gDNA |
| BRCA2ex17 Sp | BRCA2 | exon 17 | Gaaatcacgccactgcattcca SEQ ID NO: 133 | gDNA |
| BRCA2ex17 Sp | BRCA2 | exon 17 | Gattcacccacttttcccagcg SEQ ID NO: 134 | gDNA |
| BRCA2ex17 Sp | BRCA2 | exon 17 Sp OT3 | Tgcaaattcacagcaaagcagga SEQ ID NO: 135 | gDNA |
| BRCA2ex17 Sp | BRCA2 | exon 17 | ACATTGACCCCAGTTGCTCTCT SEQ ID NO: 136 | gDNA |
| BRCA2ex17 Sp | BRCA2 | exon 17 | TGCTGCTACTCTTTTCTGGACACT SEQ ID NO: 137 | gDNA |
| BRCA2ex17 Sp | BRCA2 | exon 17 | GGAGCAATTCCACTGATGCATCTC SEQ ID NO: 138 | gDNA |
| BRCA2ex17 KKH | BRCA2 | exon 17 | GcactcccactgccTGTATTGA SEQ ID NO: 139 | gDNA |
| BRCA2ex17 KKH | BRCA2 | exon 17 | GAGTAGGGGAAAAGAGGGGAGC SEQ ID NO: 140 | gDNA |
| BRCA2ex17 KKH | BRCA2 | exon 17 | TCAGAGACTCCATGATGCCATGTt SEQ ID NO: 141 | gDNA |
| BRCA2ex17 KKH | BRCA2 | exon 17 | Gctatgttgtcctggctagagtgt SEQ ID NO: 142 | gDNA |
| BRCA2ex17 KKH | BRCA2 | exon 17 | GGGTGGTAGACAAGAAGCCTCA SEQ ID NO: 143 | gDNA |
| BRCA2ex17 KKH off3R | BRCA2 OT | exon 17 KKH OT3 | GGCACAGACAGACCACAAAAGG SEQ ID NO: 144 | gDNA |
| JAG1ex9off4F | JAG1 OT | exon 9 OT4 | TGTATGTGAATGAGCGGGTGGT SEQ ID NO: 145 | gDNA |
| JAG1ex9off4R | JAG1 OT | exon 9 OT4 | AGCATGGCTTGATTCCCTGACT SEQ ID NO: 146 | gDNA |
| JAG1ex12off1F | JAG1 OT | exon 12 OT1 | AGTACTGCAGtctggcccaaat SEQ ID NO: 147 | gDNA |
| JAG1ex12off1R | JAG1 OT | exon 12 OT1 | AAGTCAAGCTGTGCTCAGGGAT SEQ ID NO: 148 | gDNA |
| JAG1ex12off2F | JAG1 OT | exon 12 OT2 | Aggagaaaattcttgggcagca SEQ ID NO: 149 | gDNA |
| JAG1ex12off2R | JAG1 OT | exon 12 OT2 | Cctgactctcctgaagacctgc SEQ ID NO: 150 | gDNA |
| JAG1ex12off3F | JAG1 OT | exon 12 OT3 | TGTGTAGCTTGCAAAAGACAGCA SEQ ID NO: 151 | gDNA |
| JAG1ex12off3R | JAG1 OT | exon 12 OT3 | CCCAATTTCCCAATGGCTGCTT SEQ ID NO: 152 | gDNA |
| JAG1ex12off4F | JAG1 OT | exon 12 OT4 | Ttcgagcaattctcctgcctca SEQ ID NO: 153 | gDNA |
| JAG1ex12off4R | JAG1 OT | exon 12 OT4 | GTTCCTGCTTTCCCGTCACTTG SEQ ID NO: 154 | gDNA |
| LMNAex11off1 | LMNA OT | exon 11 OT1 | Tggatccagcagctcaatgaca SEQ ID NO: 155 | gDNA |
| LMNAex11off1 | LMNA OT | exon 11 OT1 | ATACCGGCTGTGTGCTTAGTGT SEQ ID NO: 156 | gDNA |
| LMNAex11off2 | LMNA OT | exon 11 OT2 | GACCCTGTTGTATTGCCCCTCT SEQ ID NO: 157 | gDNA |
| LMNAex11off2 | LMNA OT | exon 11 OT2 | CGTGACAGTCTCAGGGACCAAT SEQ ID NO: 158 | gDNA |
| LMNAex11off3 | LMNA OT | exon 11 OT3 | TAAGGCACTGTGCTGAGAGCTC SEQ ID NO: 159 | gDNA |
| LMNAex11off3 | LMNA OT | exon 11 OT3 | CAGAACAAAGCAGCTGATGGCA SEQ ID NO: 160 | gDNA |
| LMNAex11off4 | LMNA OT | exon 11 OT4 | GtcccttgcctaaCACCTCAGT SEQ ID NO: 161 | gDNA |
| LMNAex11off4 | LMNA OT | exon 11 OT4 | GCCTTGGAACAGAGGATGGGAT SEQ ID NO: 162 | gDNA |
| PI4KAex9off1F | PI4KA OT | exon 9 OT1 | Gaagttcaagaccagcatggcc SEQ ID NO: 163 | gDNA |
| PI4KAex9off1R | PI4KA OT | exon 9 OT1 | AGGGCGAGGTTTGCTACTGAAT SEQ ID NO: 164 | gDNA |

TABLE 2-continued

Nucleotide sequences of primers used for all PCRs.

| Designation | Target Gene | Target Exon | Primer Sequence | RT PCR or gDNA |
|---|---|---|---|---|
| PI4KAex9off2F | PI4KA OT | exon 9 OT2 | GAAACACCATGGAACGTGCACT SEQ ID NO: 165 | gDNA |
| PI4KAex9off2R | PI4KA OT | exon 9 OT2 | TATACGACCACAGGTTCTGGCC SEQ ID NO: 166 | gDNA |
| PI4KAex9off3F | PI4KA OT | exon 9 OT3 | CAGGCCTTCTTGACTGGAGGAA SEQ ID NO: 167 | gDNA |
| PI4KAex9off3R | PI4KA OT | exon 9 OT3 | GTGAGGGGAATGGAGCAGTAGT SEQ ID NO: 168 | gDNA |
| PI4KAex9off4F | PI4KA OT | exon 9 OT4 | Cagaggttgcggtaagtggaga SEQ ID NO: 169 | gDNA |
| PI4KAex9off4R | PI4KA OT | exon 9 OT4 | ATCCTCTGTGTGCTCCAAGGTC SEQ ID NO: 170 | gDNA |
| PIK3CAex5off1 | PIK3CA OT | exon 5 OT1 | AGGGCTAGTTGTCTGAGGACTT SEQ ID NO: 171 | gDNA |
| PIK3CAex5off1 | PIK3CA OT | exon 5 OT1 | TATGAGTGGTCACTGGGCAGAG SEQ ID NO: 172 | gDNA |
| PIK3CAex5off2 | PIK3CA OT | exon 5 OT2 | Ttgcgccaggtaagatttccag SEQ ID NO: 173 | gDNA |
| PIK3CAex5off2 | PIK3CA OT | exon 5 OT2 | Tgcgggtaggggaaaatgttct SEQ ID NO: 174 | gDNA |
| PIK3CAex5off3 | PIK3CA OT | exon 5 OT3 | CATGCCCTGTCTCCAGCTCTTA SEQ ID NO: 175 | gDNA |
| PIK3CAex5off3 | PIK3CA OT | exon 5 OT3 | Cctcaaaccatcctcccacctt SEQ ID NO: 176 | gDNA |
| PIK3CAex5off4 | PIK3CA OT | exon 5 OT4 | ACGTGTATCCATGTCTGTTAGCCT SEQ ID NO: 177 | gDNA |
| PIK3CAex5off4 | PIK3CA OT | exon 5 OT4 | GGTTGATCTCATGTTGCCTTGCTT SEQ ID NO: 178 | gDNA |
| RELAex6off1F | RELA OT | exon 6 OT1 | Catagcccaggaacacaggtca SEQ ID NO: 179 | gDNA |
| RELAex6off1R | RELA OT | exon 6 OT1 | Tgcagctgaaggtaagagaggt SEQ ID NO: 180 | gDNA |
| RELAex6off2F | RELA OT | exon 6 OT2 | AACTCAGGCTCTCAGCTTCAGG SEQ ID NO: 181 | gDNA |
| RELAex6off2R | RELA OT | exon 6 OT2 | Gtgctatggtttcctggtgcac SEQ ID NO: 182 | gDNA |
| RELAex6off3F | RELA OT | exon 6 OT3 | GGCCTGACCCTTTGCTTTCATC SEQ ID NO: 183 | gDNA |
| RELAex6off3R | RELA OT | exon 6 OT3 | GTCTGCTCTGGTTTTGGCTTCC SEQ ID NO: 184 | gDNA |
| RELAex6off4F | RELA OT | exon 6 OT4 | AAGTATATTGAGCGGCCCCTCC SEQ ID NO: 185 | gDNA |
| RELAex6off4R | RELA OT | exon 6 OT4 | CTGTTGGATGCAAGGACAGCTG SEQ ID NO: 186 | gDNA |
| RELAex7off1F | RELA OT | exon 7 OT1 | TgagtgaaCAAAGTGCGGATTCTG SEQ ID NO: 187 | gDNA |
| RELAex7off1R | RELA OT | exon 7 OT1 | Tgacagctgccactcattatctgt SEQ ID NO: 188 | gDNA |
| RELAex7off2F | RELA OT | exon 7 OT2 | GGCACCACAGTACAAATCAGGTG SEQ ID NO: 189 | gDNA |
| RELAex7off2R | RELA OT | exon 7 OT2 | CTTGCTCATGAAAGGCTCTGAGC SEQ ID NO: 190 | gDNA |
| RELAex7off3F | RELA OT | exon 7 OT3 | TGTAATCTCCACCCCTTCTGCAG SEQ ID NO: 191 | gDNA |
| RELAex7off3R | RELA OT | exon 7 OT3 | TTCACCACCTCATTGCACACATG SEQ ID NO: 192 | gDNA |
| BRCA2ex26off1 | BRCA2 OT | exon 26 OT1 | AAGCCACGTTAGCATTTTCCCTTC SEQ ID NO: 193 | gDNA |
| BRCA2ex26off1 | BRCA2 OT | exon 26 OT1 | Aggcacttaatcttagagatgggct SEQ ID NO: 194 | gDNA |
| BRCA2ex26off2 | BRCA2 OT | exon 26 OT2 | Tcagagatatgtcccctgccct SEQ ID NO: 195 | gDNA |
| BRCA2ex26off2 | BRCA2 OT | exon 26 OT2 | Tgctttgaggatgcctttgctg SEQ ID NO: 196 | gDNA |
| BRCA2ex26off3 | BRCA2 OT | exon 26 OT3 | TTCTGCATCAGAGCTGTAAGAGGT SEQ ID NO: 197 | gDNA |
| BRCA2ex26off3 | BRCA2 OT | exon 26 OT3 | CACCAGTAGCTACAAAAAGCAGGA SEQ ID NO: 198 | gDNA |
| BRCA2ex26off4 | BRCA2 OT | exon 26 OT4 | CAGTGGGTGGTATGGGTCCTTT SEQ ID NO: 199 | gDNA |
| BRCA2ex26off4 | BRCA2 OT | exon 26 OT4 | GGTGAATGGGGTTGCAAGGATG SEQ ID NO: 200 | gDNA |
| CCNB1ex5off1F | CCNB1 OT | exon 5 OT1 | TGGGGACGGGGTTAGAAATCAC SEQ ID NO: 201 | gDNA |

TABLE 2-continued

Nucleotide sequences of primers used for all PCRs.

| Designation | Target Gene | Target Exon | Primer Sequence | RT PCR or gDNA |
|---|---|---|---|---|
| CCNB1ex5off1R | CCNB1 OT | exon 5 OT1 | TAAGCAAACAGGGAGCTGAGCT SEQ ID NO: 202 | gDNA |
| CCNB1ex5off2F | CCNB1 OT | exon 5 OT2 | CAGAACAGACGCTGGTAACACAATT SEQ ID NO: 203 | gDNA |
| CCNB1ex5off2R | CCNB1 OT | exon 5 OT2 | GCAGATAATTTTAATGCTCAGCCGC SEQ ID NO: 204 | gDNA |
| CCNB1ex5off3F | CCNB1 OT | exon 5 OT3 | GAGTCAAAGCCAATCGTCGCAA SEQ ID NO: 205 | gDNA |
| CCNB1ex5off3R | CCNB1 OT | exon 5 OT3 | TGTGGTTACTGTAGGCAAGGCA SEQ ID NO: 206 | gDNA |
| CCNB1ex5off4F | CCNB1 OT | exon 5 OT4 | TGCCATTCCCTAAACAACAGTTG SEQ ID NO: 207 | gDNA |
| CCNB1ex5off4R | CCNB1 OT | exon 5 OT4 | Ggaggtgctgttaggaacccat SEQ ID NO: 208 | gDNA |
| CCNB1ex6off1F | CCNB1 OT | exon 6 OT1 | Acccgcctgtaatcccagttac SEQ ID NO: 209 | gDNA |
| CCNB1ex6off1R | CCNB1 OT | exon 6 OT1 | CATTTGAGTTTTGCATGCGCGT SEQ ID NO: 210 | gDNA |
| CCNB1ex6off2F | CCNB1 OT | exon 6 OT2 | ACTGGCCTAGATGTACGTGTCT SEQ ID NO: 211 | gDNA |
| CCNB1ex6off2R | CCNB1 OT | exon 6 OT2 | AtgctctactgCCTTGCTGTCA SEQ ID NO: 212 | gDNA |
| CCNB1ex6off3F | CCNB1 OT | exon 6 OT3 | ACAAGAAAGCTGTACTGGCCCT SEQ ID NO: 213 | gDNA |
| CCNB1ex6off3R | CCNB1 OT | exon 6 OT3 | TTTGTGCAAGGATGAGAGGGGA SEQ ID NO: 214 | gDNA |
| CCNB1ex6off4F | CCNB1 OT | exon 6 OT4 | Cttcactgctggagggaatgga SEQ ID NO: 215 | gDNA |
| CCNB1ex6off4R | CCNB1 OT | exon 6 OT4 | Tggcctccgggtttattcatgt SEQ ID NO: 216 | gDNA |
| EGFRex23off1F | EGFR OT | exon 23 OT1 | Tttgatcacgccactgcattcc SEQ ID NO: 217 | gDNA |
| EGFRex23off1R | EGFR OT | exon 23 OT1 | Ttagctggatatggtggtgggc SEQ ID NO: 218 | gDNA |
| EGFRex23off2F | EGFR OT | exon 23 OT2 | AGGAGGATGCTGGAGTGAGAGA SEQ ID NO: 219 | gDNA |
| EGFRex23off2R | EGFR OT | exon 23 OT2 | Aaggccctgaatctgcattct SEQ ID NO: 220 | gDNA |
| EGFRex23off3F | EGFR OT | exon 23 OT3 | ACTTTAGTCTGCGCCAGAGGAG SEQ ID NO: 221 | gDNA |
| EGFRex23off3R | EGFR OT | exon 23 OT3 | CGGCGTCAGGTAAAACAGGTTC SEQ ID NO: 222 | gDNA |
| EGFRex23off4F | EGFR OT | exon 23 OT4 | CcttgggcccttctGTAATCCA SEQ ID NO: 223 | gDNA |
| EGFRex23off4R | EGFR OT | exon 23 OT4 | CAACCCAGATGGCTCCACTACA SEQ ID NO: 224 | gDNA |
| IL1RAPex10 Sp | IL1RAP OT | exon 10 Sp and | ccagtggagcctctgaagagag SEQ ID NO: 225 | gDNA |
| IL1RAPex10 Sp | IL1RAP OT | exon 10 Sp and | Tcagtagttcaagaccagcccg SEQ ID NO: 226 | gDNA |
| IL1RAPex10 Sp | IL1RAP OT | exon 10 Sp OT2 | ATCTGGGTTGCCACAGAAGTCT SEQ ID NO: 227 | gDNA |
| IL1RAPex10 Sp | IL1RAP OT | exon 10 Sp OT2 | TGGGCTGGTTAGGTAGAGGAGT SEQ ID NO: 228 | gDNA |
| IL1RAPex10 Sp | IL1 RAP OT | exon 10 Sp and | TCAACTCGAGTCCAATTCCCCC SEQ ID NO: 229 | gDNA |
| IL1RAPex10 Sp | IL1 RAP OT | exon 10 Sp and | AGAAGGGCTTTTCAGGAGAGGG SEQ ID NO: 230 | gDNA |
| IL1RAPex10 | IL1RAP OT | exon 10 VQR | Tttagtagagacggggtttcaccg SEQ ID NO: 231 | gDNA |
| IL1RAPex10 | IL1RAP OT | exon 10 VQR | TGATGGGGGCACTGAAGTCAAT SEQ ID NO: 232 | gDNA |
| JAG1ex9off1F | JAG1 OT | exon 9 OT1 | TGACTAGAAGGGTGGCAATGCA SEQ ID NO: 233 | gDNA |
| JAG1ex9off1R | JAG1 OT | exon 9 OT1 | CGGCCTTTTACGTTTAAGCCGT SEQ ID NO: 234 | gDNA |
| JAG1ex9off2F | JAG1 OT | exon 9 OT2 | CTCTTCCTCCCCAGCTTGTCTC SEQ ID NO: 235 | gDNA |
| JAG1ex9off2R | JAG1 OT | exon 9 OT2 | AGTACAGAAAGCGGGCCTTAGG SEQ ID NO: 236 | gDNA |
| JAG1ex9off3F | JAG1 OT | exon 9 OT3 | Aggagggtggatcatctgaggt SEQ ID NO: 237 | gDNA |
| JAG1ex9off3R | JAG1 OT | exon 9 OT3 | TTAAGCCCTGTGAGCCACCTTT SEQ ID NO: 238 | gDNA |
| RELAex7off4F | RELAOT | exon 7 OT4 | CCATCTGTGACAGAGCCTTGGA SEQ ID NO: 239 | gDNA |

TABLE 2-continued

| | | | | | RT PCR |
|---|---|---|---|---|---|
| Designation | Target Gene | Target Exon | Primer Sequence | | or gDNA |
| RELAex7off4R | RELA OT | exon 7 OT4 | CTGGGAGGGGTGGAGCTTTAAA | SEQ ID NO: 240 | gDNA |
| RELAex10off1F | RELA OT | exon 10 OT1 | CCACTTCTCTACCCACTCAGCC | SEQ ID NO: 241 | gDNA |
| RELAex10off1R | RELA OT | exon 10 OT1 | Atggtggcttggatcttggtga | SEQ ID NO: 242 | gDNA |
| RELAex10off2F | RELA OT | exon 10 OT2 | Tgttctcacagagtggagagcg | SEQ ID NO: 243 | gDNA |
| RELAex10off2R | RELA OT | exon 10 OT2 | CCGAGAAATGCAGACCCAGGTA | SEQ ID NO: 244 | gDNA |
| RELAex10off3F | RELA OT | exon 10 OT3 | Ctgcggtctctctgtcttcaca | SEQ ID NO: 245 | gDNA |
| RELAex10off3R | RELA OT | exon 10 OT3 | CCTGCGTGAATTCATAGACGCC | SEQ ID NO: 246 | gDNA |
| RELAex10off4F | RELA OT | exon 10 OT4 | Agacaggttctcgctctgtcac | SEQ ID NO: 247 | gDNA |
| RELAex10off4R | RELA OT | exon 10 OT4 | AATTGCAAGCCGTCAGTGAAGG | SEQ ID NO: 248 | gDNA |
| SCARB1ex5off1 | SCARB1 | exon 5 OT1 | Atctggtgtgaatggggaaggg | SEQ ID NO: 249 | gDNA |
| SCARB1ex5off1 | SCARB1 | exon 5 OT1 | ATACCCACACCTGACCCACAtg | SEQ ID NO: 250 | gDNA |
| SCARB1ex5off2 | SCARB1 | exon 5 OT2 | GACACCATCCTCAACGCCATTG | SEQ ID NO: 251 | gDNA |
| SCARB1ex5off2 | SCARB1 | exon 5 OT2 | CAGCCACCAAAGTATCGGGAGA | SEQ ID NO: 252 | gDNA |
| SCARB1ex5off3 | SCARB1 | exon 5 OT3 | ACCTGCAGCTACCGAGAAACTT | SEQ ID NO: 253 | gDNA |
| SCARB1ex5off3 | SCARB1 | exon 5 OT3 | Tctcaaacagacagcgggcata | SEQ ID NO: 254 | gDNA |
| SCARB1ex5off4 | SCARB1 | exon 5 OT4 | Aatcatcccccattccccatcc | SEQ ID NO: 255 | gDNA |
| SCARB1ex5off4 | SCARB1 | exon 5 OT4 | Aactcccattccctccttctgc | SEQ ID NO: 256 | gDNA |

Densitometry Analysis

Skipping efficiencies were determined by densitometry analysis of the PCR products obtained from RT-PCR and analyzed by agarose gel electrophoresis using ImageJ software. After subtracting background noise, band intensity was compared using the following formula:

$$\% = \text{exon skipping} = \frac{\text{skipped band intensity}}{\text{wt. Band Intensity} + \text{Skipped Band Intensity}}$$

each pixel grayscale value within the selected area of the band.

Amplification of Genomic DNA

Genomic DNA was isolated using DNEASY® Blood and Tissue Kit (Qiagen) or the Animal Genomic DNA Purification Mini Kit (EarthOx). PCR was performed using KAPA2G Robust PCR kits (KAPA Biosystems) as described above, using 20-100 ng of template DNA.

Editing Window Analysis Using Sanger Sequencing and EditR Software

Genomic DNA from samples treated with an ABE-GGGGS (SEQ ID NO:3) variant and an A-rich sgRNA was amplified using the PCR primers listed in Table 3. Sanger sequencing of the PCR amplicons was performed by the W. M. Keck Center for Comparative and Functional Genomics at the University of Illinois at Urbana-Champaign using the primers listed in Table 4. Base editing efficiencies were estimated by analyzing the sanger sequencing traces using EditR 43.

TABLE 3 shows Nucleotide sequences of primers used for RT-PCR.

| Primer | Sequence (5' to T) | | WT Size (bp) | Skip Size (bp) |
|---|---|---|---|---|
| CTNNA1 Ex7 FW | CACCCTGATGTCGCAGCCTATA | SEQ ID NO: 257 | 484 | 280 |
| CTNNAI Ex7 REV | CTGAAACGTGGTCCATGACAGC | SEQ ID NO: 258 | 484 | 280 |
| HSF1 Ex11 FW | TGCCTGGACAAGAATGAGCTCA | SEQ ID NO: 259 | 374 | 308 |
| HSF1 Ex11REV | CTCTAGGAGACAGTGGGGTCCT | SEQ ID NO: 260 | 374 | 308 |
| JUP Ex10 FW | TCTGTGCGTCTCAACTATGGCA | SEQ ID NO: 261 | 565 | 445 |
| JUP Ex10 REV | GCTTCCGGTAGTCTGGGTTCTT | SEQ ID NO: 262 | 565 | 445 |

TABLE 3-continued

| shows Nucleotide sequences of primers used for RT-PCR. | | | | |
|---|---|---|---|---|
| Primer | Sequence (5' to T) | | WT Size (bp) | Skip Size (bp) |
| AHCY Ex9 FW | GTCAAGTGGCTCAACGAGAACG | SEQ ID NO: 263 | 441 | 246 |
| AHCY Ex9 REV | TCCAAGACCACTGAGCTCATGG | SEQ ID NO: 264 | 441 | 246 |
| mCTNNB1 Ex 11 FW | TGTGGTTAAACTCCTGCACCCA | SEQ ID NO: 265 | 371 | 25 |
| mCTNNB1 Ex 11 REV | CCCCTGCAGCTACTCTTTGGAT | SEQ ID NO: 266 | 371 | 251 |
| A-Rich Target 1 FW | ACACTGTCTCTCTCCCTAGGCA | SEQ ID NO: 267 | N/A | N/A |
| A-Rich Target 1 REV | GCAGGACACTAGGGAGTCAAGG | SEQ ID NO: 268 | N/A | N/A |
| A-Rich Target 2 FW | GCTTTCTTTCCTTTCGCGCTCT | SEQ ID NO: 269 | N/A | N/A |
| A-Rich Target 2 REV | GTGGGAGATCTGGTTTCCGGAA | SEQ ID NO: 270 | N/A | N/A |

TABLE 4

| shows Nucleotide sequences of primers used for Sanger sequencing of A-Rich Target PCR amplicons. | |
|---|---|
| Primer | Sequence (5' to 3') |
| A-Rich Target 1 Seq | TCCCGAGCCTCCTTCCTCTC SEQ ID NO: 271 |
| A-Rich Target 2 Seq | ATCCCTGTCCGGATGCTG SEQ ID NO: 272 |

Deep Sequencing

Deep sequencing was performed on PCR amplicons from genomic DNA or RNA harvested from duplicate transfections of 293T cells. After validating the quality of PCR product by gel electrophoresis, the PCR products were isolated by gel extraction using the ZYMOCLEAN™ Gel DNA Recovery Kit (Zymo Research). Shotgun libraries were prepared with the Hyper Library construction kit from Kapa Biosystems without shearing. The library was quantitated by qPCR and sequenced on one MISEQ™ Nano flowcell for 251 cycles from each end of the fragments using a MISEQ™ 500-cycle sequencing kit version 2. Fastq files were generated and demultiplexed with the bcl2fastq v2.17.1.14 Conversion Software (Illumina). All sequencing was performed by the W.M. Keck Center for Comparative and Functional Genomics at the University of Illinois at Urbana-Champaign.

High Throughput Sequencing

HTS was performed on PCR amplicons from genomic DNA or RNA harvested from duplicate transfections of 293T cells. After validating the quality of PCR product by gel electrophoresis, the PCR products were isolated by gel extraction using the ZYMOCLEAN™ Gel DNA Recovery Kit (Zymo Research). Shotgun libraries were prepared with the Hyper Library construction kit from Kapa Biosystems without shearing. Indexed HTS amplicon libraries for samples described in FIGS. 21 and 22 were prepared using a NEXTERA® XT DNA Library Prep Kit (Illumina).The library was quantitated by qPCR and sequenced on one MISEQ™ 500-cycle sequencing kit version 2. Fastq files were generated and demultiplexed with the bcl2fastq v2.17.1.14 Conversion Software (Illumina). All sequencing was performed by the W. M. Keck Center for Comparative and Functional Genomics at the University of Illinois at Urbana-Champaign.

TABLE 5

| shows nucleotide sequences of PCR primers used to generate amplicons for HTS. The number of cycles and type of template DNA used in the PCR is indicated. | | | | |
|---|---|---|---|---|
| Primer | Sequence (5' to 3') | | Template | PCR Cycles |
| CTNNA1 Ex7 ON FW | GTAGGCCATCTTCTGTGGGACA | SEQ ID NO: 273 | gDNA | 30 |
| CTNNA1 Ex7 ON REV | TGTACTCCGAAAGCAGGTCCTG | SEQ ID NO: 274 | gDNA | 30 |
| CTNNA1 Ex7 OFF1 FW | ATGTGCCCGATCTGCGATCTTA | SEQ ID NO: 275 | gDNA | 30 |
| CTNNA1 Ex7 OFF1 REV | GCCAGTCTAACAGCATGCAGTG | SEQ ID NO: 276 | gDNA | 30 |
| CTNNA1 Ex7 OFF2 FW | GCGAAAGGTGTGAACAGATGCT | SEQ ID NO: 277 | gDNA | 30 |
| CTNNA1 Ex7 OFF2 REV | ACATATCCCGTGTTTGCTGCAC | SEQ ID NO: 278 | gDNA | 30 |
| CTNNA1 Ex7 OFF3 FW | AGGAGACTGCACGTTCTTTGGA | SEQ ID NO: 279 | gDNA | 30 |
| CTNNA1 Ex7 OFF3 REV | TTCCTCACCTCCAGGCTTCATG | SEQ ID NO: 280 | gDNA | 30 |
| CTNNA1 Ex7 OFF4 FW | TTTCAATGCAAAGCTCCCCCAC | SEQ ID NO: 281 | gDNA | 30 |
| CTNNA1 Ex7 OFF4 REV | TAAAGCCTGGCCTCGACATGAA | SEQ ID NO: 282 | gDNA | 30 |

TABLE 5 -continued shows nucleotide sequences of PCR primers used to generate amplicons for
HTS. The number of cycles and type of template DNA used in the PCR is indicated.

| Primer | Sequence (5' to 3') | | Template | PCR Cycles |
|---|---|---|---|---|
| CTNNA1 Ex7 cDNA FW | CACCCTGATGTCGCAGCCTATA | SEQ ID NO: 283 | cDNA | 30 |
| CTNNA1 Ex7 cDNA REV | GCAAGTCCCTGGTCTTCTTGGT | SEQ ID NO: 284 | cDNA | 30 |
| HSF1 Ex11 ON FW | CTGTTCTGACTTCCCTCCCTCC | SEQ ID NO: 285 | gDNA | 32 |
| HSF1 Ex11 ON REV | TGGGACTTGGCTCACCTGAATC | SEQ ID NO: 286 | gDNA | 32 |
| HSF1 Ex11 OFF1 FW | CTGTCAATAGGGCCTAGCACCA | SEQ ID NO: 287 | gDNA | 30 |
| HSF1 Ex11 OFF1 REV | CTGCCAAGTGACCTCCTCTCAA | SEQ ID NO: 288 | gDNA | 30 |
| HSF1 Ex11 OFF2 FW | CATCCACCACCAAGAGCTGAGA | SEQ ID NO: 289 | gDNA | 30 |
| HSF1 Ex11 OFF2 REV | CCCACCCTCTCACTCTGTCTTG | SEQ ID NO: 290 | gDNA | 30 |
| HSF1 Ex11 OFF3 FW | ACCACTCATTCTGGCATCGTGA | SEQ ID NO: 291 | gDNA | 30 |
| HSF1 Ex11 OFF3 REV | CCTGCCACTCTCCACTTCTCTC | SEQ ID NO: 292 | gDNA | 30 |
| HSF1 Ex11 OFF4 FW | TGTGCCGGATCTTAGCCTCAAA | SEQ ID NO: 293 | gDNA | 30 |
| HSF1 Ex11 OFF4 REV | AAAGGAGGAGAGCTGCGTTCAT | SEQ ID NO: 294 | gDNA | 30 |
| HSF1 Ex11 cDNA FW | TGCCTGGACAAGAATGAGCTCA | SEQ ID NO: 295 | cDNA | 30 |
| HSF1 Ex11 cDNA REV | TCGGAGAAGTAGGAGCCCTCTC | SEQ ID NO: 296 | cDNA | 30 |
| JUP Ex10 ON FW | CTGTGGGTGTGTGTGTGAATGG | SEQ ID NO: 297 | gDNA | 30 |
| JUP Ex10 ON REV | GCAGGGGGTTGCTAAGTAGTCA | SEQ ID NO: 298 | gDNA | 30 |
| JUP Ex10 OFF1 FW | TGCCTCCTGCTTGTACTCTTCC | SEQ ID NO: 299 | gDNA | 30 |
| JUP Ex10 OFF1 REV | GCTTACTGGGCCATCTCAGTGA | SEQ ID NO: 300 | gDNA | 30 |
| JUP Ex10 OFF2 FW | GTAGGGTTTGGCCTTTTGCTCC | SEQ ID NO: 301 | gDNA | 30 |
| JUP Ex10 OFF2 REV | CCCCAGGTAAAAGCACCAGGTA | SEQ ID NO: 302 | gDNA | 30 |
| JUP Ex10 OFF3 FW | TGTCTGTCCTGGTCACGGATTC | SEQ ID NO: 303 | gDNA | 30 |
| JUP Ex10 OFF3 REV | CCTGTGGTTCTGGGAGTCTCTG | SEQ ID NO: 304 | gDNA | 30 |
| JUP Ex10 OFF4 FW | AAAGGGACTGTGGCATCTCCTC | SEQ ID NO: 305 | gDNA | 30 |
| JUP Ex10 OFF4 REV | TCACAGGCATCAAGGTGGTAGG | SEQ ID NO: 306 | gDNA | 30 |
| JUP Ex10 cDNA FW | TCTGTGCGTCTCAACTATGGCA | SEQ ID NO: 307 | cDNA | 30 |
| JUP Ex10 cDNA REV | TGTTCTCCACCGACGAGTACAG | SEQ ID NO: 308 | cDNA | 30 |
| AHCY Ex9 gON FW | GAGACGGGCTTTCACTGTGTTG | SEQ ID NO: 309 | gDNA | 30 |
| AHCY Ex9 gON REV | AACGGGGTACTTGTCTGGATGG | SEQ ID NO: 310 | gDNA | 30 |
| AHCY Ex9 OFF1 FW | TGCTTTTGAACATGCCAGCCAT | SEQ ID NO: 311 | gDNA | 30 |
| AHCY Ex9 OFF1 REV | CCAGGAAGGCTTTGCTTCCAAG | SEQ ID NO: 312 | gDNA | 30 |
| AHCY Ex9 OFF2 FW | AACCCCTGAACGAGTGGGAATT | SEQ ID NO: 313 | gDNA | 30 |
| AHCY Ex9 OFF2 REV | TCCCACAAATCCTCCACTGGTG | SEQ ID NO: 314 | gDNA | 30 |
| AHCY Ex9 OFF3 FW | ATCCGGTTCAGTGGACTCTGTG | SEQ ID NO: 315 | gDNA | 30 |
| AHCY Ex9 OFF3 REV | AATGTCTGCGGGTCTCTGTCTC | SEQ ID NO: 316 | gDNA | 30 |

TABLE 5 -continued shows nucleotide sequences of PCR primers used to generate amplicons for
HTS. The number of cycles and type of template DNA used in the PCR is indicated.

| Primer | Sequence (5' to 3') | | Template | PCR Cycles |
|---|---|---|---|---|
| AHCY Ex9 OFF4 FW | GGAACACAGGGTTGATGCCATG | SEQ ID NO: 317 | gDNA | 30 |
| AHCY Ex9 OFF4 REV | TCCTGAAGTGCGAGTACTGTGG | SEQ ID NO: 318 | gDNA | 30 |
| AHCY Ex9 cDNA FW | CATCTTTGTCACCACCACAGGC | SEQ ID NO: 319 | cDNA | 30 |
| AHCY Ex9 cDNA REV | AGGTACTGGGCTTGCTTCTCAG | SEQ ID NO: 320 | cDNA | 30 |

Sequence Analysis for Single Base Editors

Following sequence demultiplexing, genomic DNA reads were aligned with Bowtie2 (Langmead B, Salzberg S L: *Nat Methods* 2012, 9:357-359). To estimate base editing efficiency, base distribution was first calculated from the alignment, and duplicates were averaged. To determine statistically significant modification of intronic flanking G at the splice acceptor, P-values were calculated using a two-tailed Wald test assuming equal binomial proportions of G to non-G bases between control and base-edited samples. For the off-target analysis, a maximum likelihood estimate of 0.383% was obtained for the sequencing error rate of MISEQ™ by averaging the fraction of alternate allele depths calculated by samtools mpileup over all 90 on- and off-target sites in the control sample; significant G>A or C>T modifications at on- and off-target sites were then determined using the binomial test at a p-value cutoff of $10^{-5}$, using the estimated sequencing error as the background probability of nucleotide conversions.

Reads from paired-end RNA-seq were mapped to the human genome version GRCh38 with Tophat2 (Kim D, et al, *Genome Biol* 2013, 14:R36) to determine the proportions of canonical and exon-skipped isoforms. Corresponding forward and reverse reads were then combined as one unit for counting analysis. Specifically, reads displaying an occurrence of the exon-skipped junction were counted towards the exon-skipped isoform, and reads displaying the canonical splice junction at the 5' end of the exon to be skipped were contributed toward the canonical isoform. Reads that did not display either the exon-skipped junction or 5' canonical splice junction of the exon to be skipped were discarded from quantification. A single estimate of the proportion and 95% confidence interval were obtained from the duplicates using the function "metaprop" from the R package "meta" with the inverse variance method to combine proportions and the Clopper-Pearson method to calculate the confidence interval. P-values for the RNA isoform quantification were also calculated using the two-tailed Wald test for equal binomial proportions between control and base-edited samples.

Sequence Analysis for Adenine Base Editors

DNA and RNA sequencing reads were demultiplexed by PCR primer sequences and quality trimmed to Phred quality score 20 at the 3' end using cutadapt. Read pairs with at least one mate trimmed to 50 bp or less were discarded. DNA reads were then aligned to the human genome version GRCh38 using Bowtie2. To determine on-target and off-target base editing rates, alternative allele depths were calculated by Samtools mpileup over 120 bp windows centered around the protospacer sequences for on and off targets. A global estimate of sequencing error was made by averaging the fraction of alternative allele depths across all positions. A position-dependent estimate of sequencing error was determined by fraction of alternative allele depth at each genomic position. Significant A>G or T>C conversion was determined by using the one-sided binomial test at ap-value cutoff of $10^{-5}$, using the higher of the global or position-dependent sequencing error estimates as the background probability of nucleotide conversions. Indel rates were calculated using Mutect2. Reads from paired-end RNA-seq were mapped to the human genome version GRCh38 with TopHat2 for isoform quantification. Forward and reverse reads were combined as a single read for analysis. Reads displaying the exon-skipped junction were counted towards the exon skipped transcript and reads displaying either the 5' or 3' canonical splice junction were counted towards the canonical isoform. Reads that did not display any of the previously mentioned splice junctions were excluded from quantification. The exon skipping rate for each biological duplicate was calculated by dividing the number of exon-skipped transcript reads by the sum of the number of exon-skipped and canonical transcript reads. Estimates of the overall exon-skipping rates were made by averaging duplicates.

Website Design and Genome-Wide Targetability Analysis

The website scans all splice acceptor sites of the inner exons (those that are not the first or last exon of a transcript) of protein coding transcripts (genomic assembly GRCh38, GENCODE release 26) for PAMs in the appropriate range. The base editors supported are SaCas9-KKH-BE3, SpCas9-BE3, SpCas9-VRER-BE3, and SpCas9-VQR-BE3; and, only their primary PAMs (NNNRRT, NGG, NGCG, and NGA, respectively) were considered. The base editing efficiencies were estimated from the figures contained in Kim et al, *Nat Biotechnol.* 2017 April; 35(4):371-376. doi: 10.1038/nbt.3803.) The results of different experiments that reported editing efficiencies for the same position and base editor were averaged together. In order to minimize the number of false positives, a conservative estimate of the base editing efficiency at each position was made by reporting a non-zero efficiency at a particular position only if the null hypothesis that the mean efficiency is negative was rejected with ap-value<0.1 according to the t-test. To remove sgRNAs with potential off-targets, for each candidate sgRNA design, the genome for all sequences were scanned with at most two mismatches and calculated their off-target score (Hsu et al, *Nat Biotechnol* 2013, 31:827-832). Any sgRNA that has a top off-target score greater than 10 was removed.

The predicted position-dependent base editing efficiencies for BE3 are identical to those used in Gapinske, M. et al. *Genome Biol* 19, 107, doi:10.1186/s13059-018-1482-5 (2018)). The corresponding efficiency values for ABE were estimated from ABE7.8 efficiency values from Gaudelli, N. et al. *Nature* 551, 464-471, doi:10.1038/nature24644 (2017)). FIG. 3c and Extended Data FIG. 7b by the following method: first, the maximum base editing efficiency was estimated by taking the highest observed editing efficiency across all ABE variants and sites from FIG. 3c; then, the relative base editing efficiencies of ABE7.8 from Extended Data FIG. 7b positions 4-9 were multiplied by the estimated maximum base editing efficiency to obtain the estimated position-dependent base editing efficiencies for ABE. For each candidate sgRNA, the entire genome was scanned for all sequences with at most two mismatches and an off-target score was calculated (Kwak, H., et al, Science 339, 950-953, doi:10.1126/science.1229386 (2013)). Any sgRNA with an off-target score above 10 was removed.

Figure 1B:
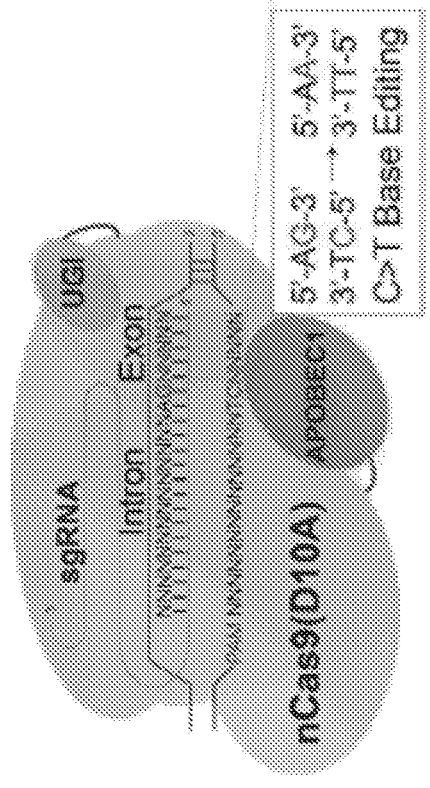
Figure 1A:
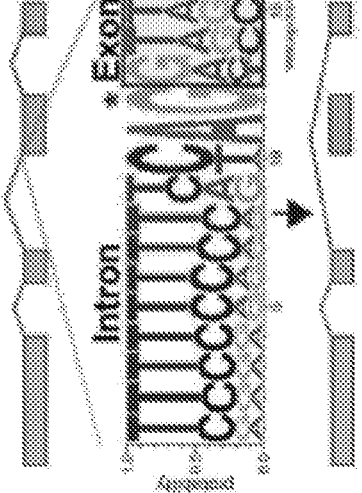

Example 1: Single Base Editing of Splice Acceptor Consensus Sequence Enables Programmable Exon Skipping An essential step during exon splicing is the recognition by the spliceosome machinery of the highly conserved sequences that define exons and introns. More specifically, nearly every intron ends with a guanosine (FIG. 1A). Importantly, this guanosine can be effectively mutated by converting the complementary cytidine to thymidine using CRISPR-Cas9 C>T single-base editors, resulting in mutation of the target guanosine to adenosine and disruption of the highly conserved splice acceptor consensus sequence (FIG. 1B).

Figures 2A, 2B:
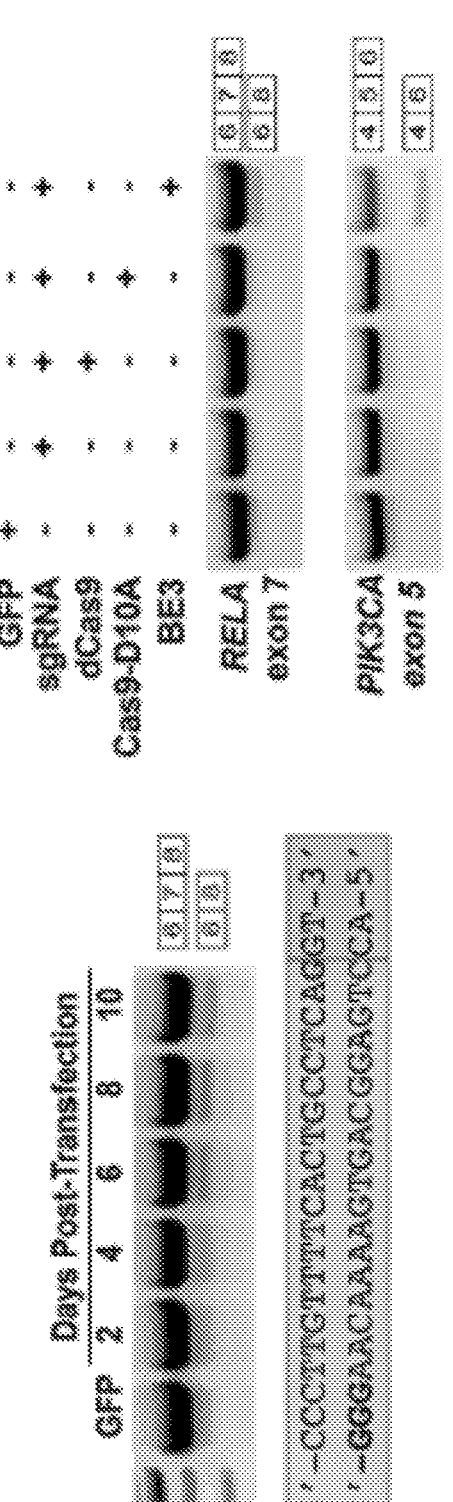

This experiment induced skipping of the 105 base pair (bp)-long exon 7 of RELA, a critical component of the NF-κB pathway implicated in inflammation and multiple types of cancer. An exon whose length is a multiple of 3 was selected to ensure that exon skipping would not create a frameshift, which could lead to nonsense-mediated decay and complicate the detection of novel splicing events. In these experiments, a time-course study was performed in the embryonic kidney cell line 293T using the SpCas9-BE3 base editor (Komor A C, et al., Nature 2016, 533:420-424), which is a combination of the rat APOBEC1 cytidine deaminase, the uracil glycosylase inhibitor of *Bacillus subtilis* bacteriophage PBS1, and the SpCas9-D10A nickase. As a derivative of SpCas9, this base editor recognizes target sites with an NGG protospacer adjacent motif (PAM), such as that existing upstream of RELA exon 7 (FIG. 2A). After transfecting SpCas9-BE3 and a sgRNA targeting the RELA exon 7 splice acceptor, RNA was isolated at different time points over a 10-day period, from which cDNA was prepared and analyzed exon skipping by PCR amplification. By gel electrophoresis, exon skipping was detectable for the first time 4 days after transfection, but the skipping frequency increased significantly on days 6, 8 and 10 (FIG. 2A). Based on these data all subsequent experiments used 6 days after transfection for analysis.

Figure 2E:
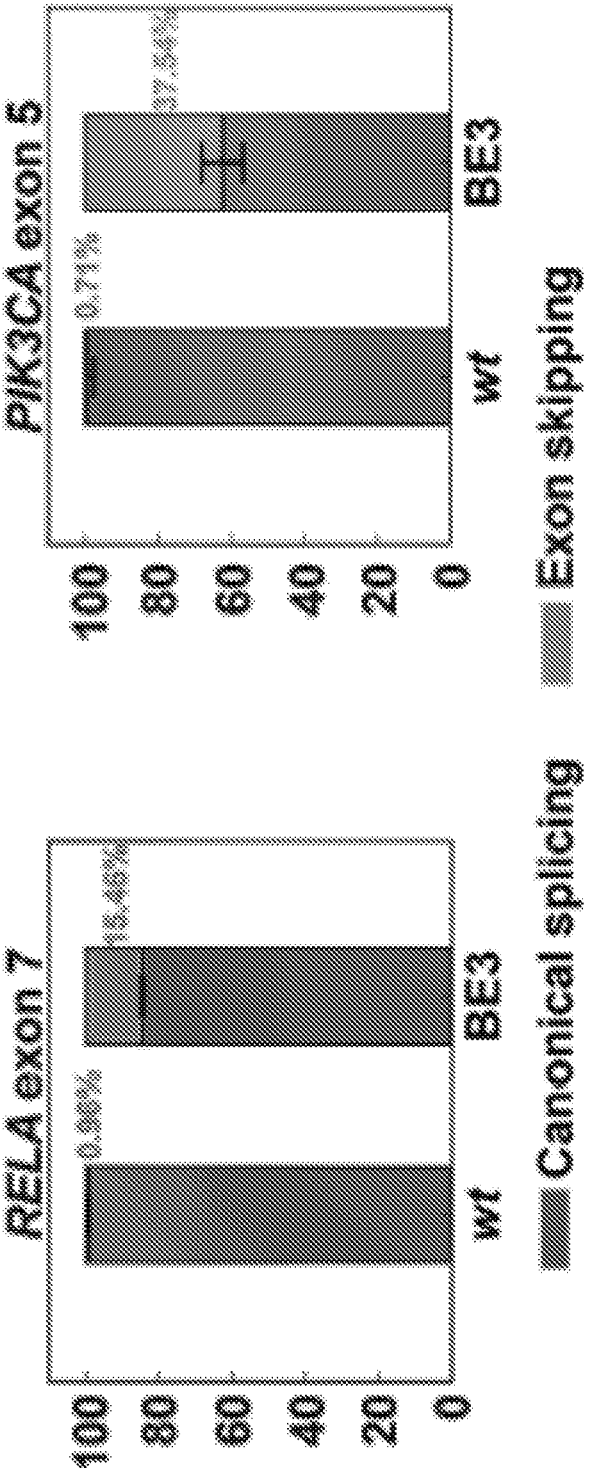
Figure 8:
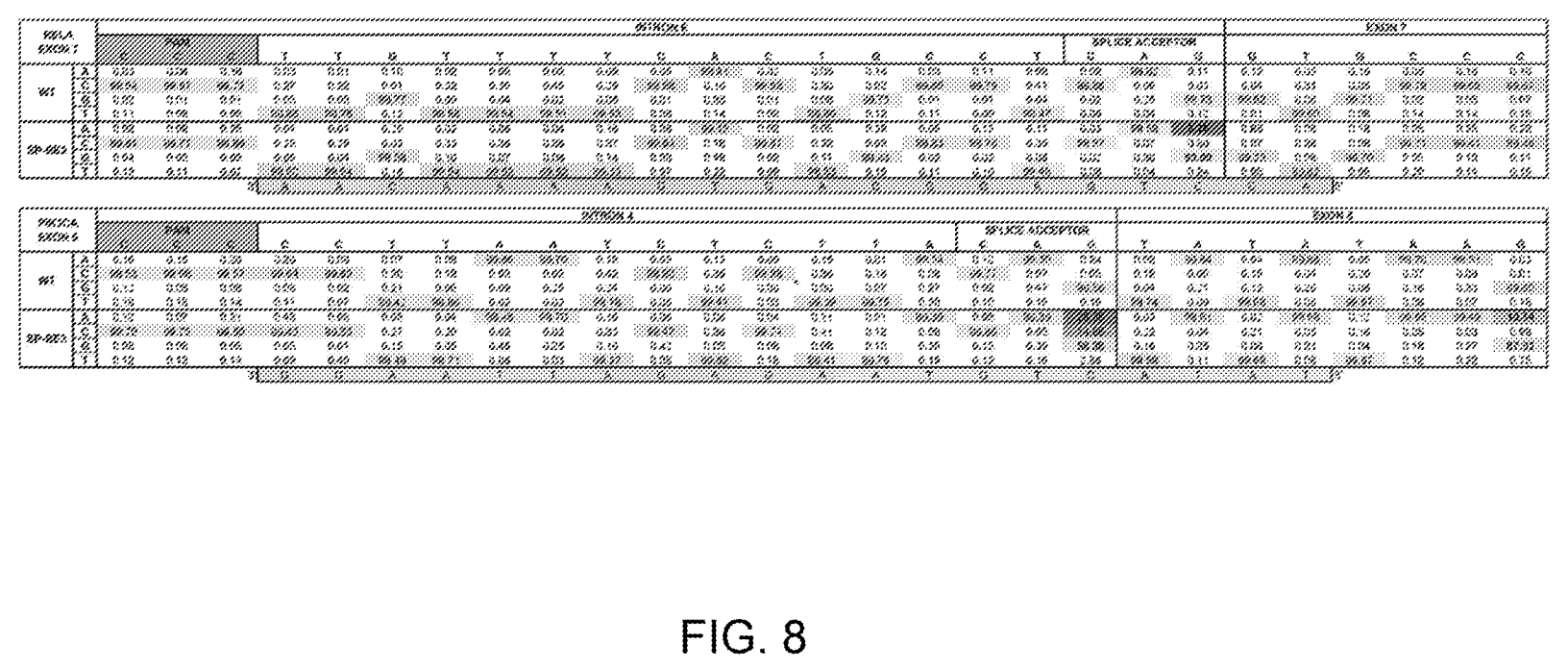

Next, base editing of the splice acceptor was demonstrated to be the mechanism underlying skipping of RELA exon 7 or PIK3CA exon 5, which could not be accomplished by transfection of the sgRNA alone or in combination with catalytically dead SpCas9 or SpCas9-D10A nickase (FIG. 2B). Importantly, Sanger sequencing confirmed the presence of transcripts with exon 6 followed by exon 8 in RELA and transcripts with exon 4 followed by exon 6 in PIK3CA (FIG. 2C). The efficiency of base-editing exon skipping was quantified in genomic DNA and cDNA using deep sequencing, which demonstrated that the G>A modification rates were 6.26% (p<10$^{-323}$) for RELA and 26.38% (p<10$^{-323}$) for PIK3CA (FIG. 2D), leading to exon skipping rates in mRNA of 15.46% (p<10$^{-323}$) for RELA and 37.54% (p=7.38×10$^{-37}$) for PIK3CA (FIG. 2E). Interestingly, G>C (1.66%, p<10-323) and G>T (2.58%, p=2.27×10$^{-197}$) editing events at PIK3CA were detected. Furthermore, PIK3CA also exhibited an unexpected G>A modification (10.34%, p<10$^{-323}$) outside the 20 nucleotide target sequence of the SpCas9-BE3 (FIG. 8).

Figure 9:
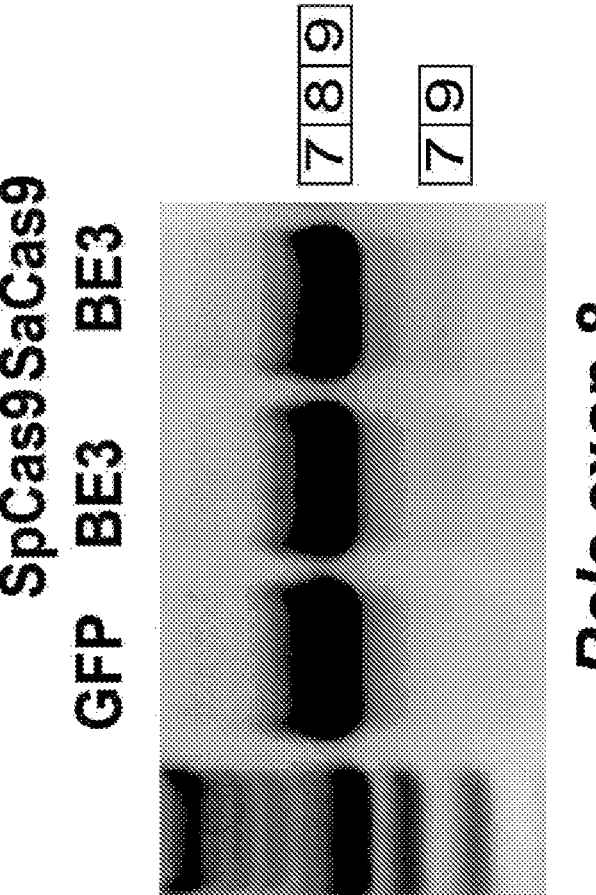
FIG. 9 illustrates that Neuro2A cells were transfected with either SpCas9 or SaCas9-KKH C>T base editors targeting the splice acceptor of Rela exon 8. Analysis of exon skipping by RT-PCR demonstrated that both base editors effectively induced splicing.

To determine whether the programmable exon skipping tools are cell line specific, the same two exons in the human cell lines HCT116, HepG2, and MCF7 were targeted, as well as RELA exon 8 in the mouse cell line Neuro-2A (FIG. 3, FIG. 9). Since the transfection efficiency in these cell lines is typically lower than that in 293T cells, transfected cells were enriched prior to analysis, which revealed successful skipping of the targeted exon in all cell lines tested.

Figure 4:
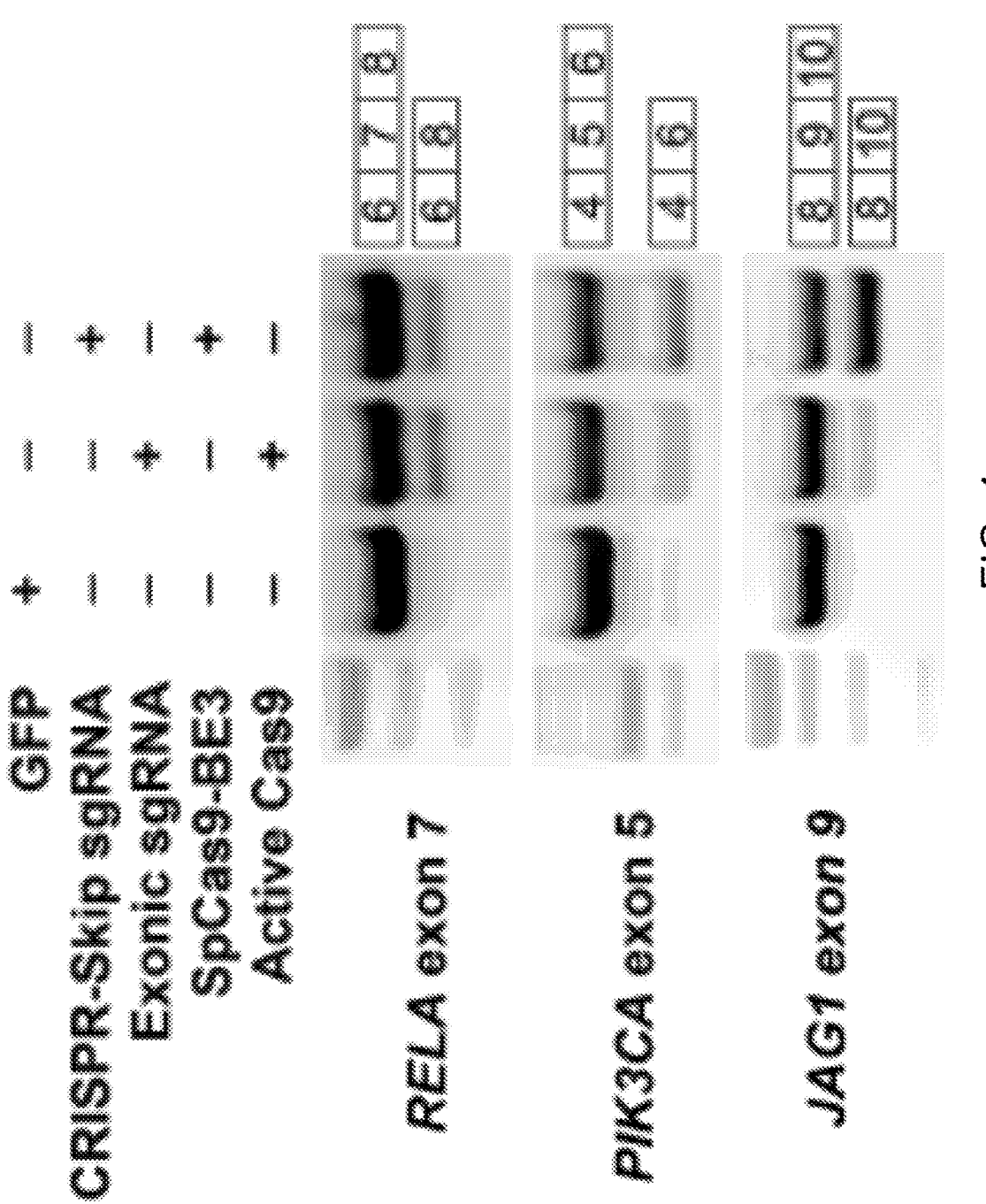

Example 2: Comparison of CRISPR-SKIP with Active SpCas9 for Inducing Exon Skipping This experiment compared CRISPR-SKIP to current state-of-the-art exon skipping using gene editing, which relies on introduction of DSBs to generate random repair outcomes, some of which cause exon skipping (Mou H, et al, *Genome Biol* 2017, 18:108). CRISPR-SKIP was employed and, separately, targeted active SpCas9 to the exons of RELA exon 7, PIK3CA exon 5, and JAG1 exon 9. In each case, an equal or greater degree of exon skipping was achieved with CRISPR-SKIP than with active SpCas9 (FIG. 4). Since introduction of DSBs in the exon required sgRNAs different from those used to target the splice acceptor with CRISPR-SKIP, the comparison of these two techniques might be biased towards that using the more efficient sgRNAs. For this reason, a comparison of exon skipping by active Cas9 and CRISPR-SKIP using identical sgRNAs targeting the splice acceptor across 5 different targets was employed. In these conditions, active Cas9 induced higher rate of exon skipping at 3 targets, while CRISPR-SKIP was more effective at 2 targets. Active Cas9 induced exon skipping at all targets tested, while CRISPR-SKIP was effective at 4 out of 5 targets (FIG. 10).

Example 3: Different Cas9 Scaffolds Increase the Number of CRISPR-SKIP Target Exons One limitation of CRISPR-SKIP using SpCas9-BE3 is its dependence on the presence of a PAM site located 12-17 bp from the target cytidine. SpCas9-BE3 canonically recognizes NGG PAMs, but can also recognize NAG with lower efficiency and both can be used for skipping target exons (Table 1). However, not all exons have one of the SpCas9-BE3 PAMs within the desired range. To expand the number of targetable exons, single-base editors constructed using different Cas9 scaffolds (Kim et al, *Nat Biotechnol.* 2017 April; 35(4):371-376. doi: 10.1038/nbt.3803) were used, which recognize different PAM motifs, can be used in CRISPR-SKIP. Specifically, the SpCas9-VQR-BE3, which recognizes NGA PAMs was used, to skip exon 26 in the BRCA2 gene (FIG. 5A) and the SaCas9-KKH-BE3 editor, which recognizes NNNRRT PAMs, to skip exon 10 in RELA (FIG. 5B). Deep sequencing of SpCas9-VQR-BE3 and SaCas9-KKH-BE3 edited cells revealed targeted G>A modification rates of 0.93% (p=4.74×10$^{-47}$) by SpCas9-VQR-BE3 at BRCA2 exon 26 (FIG. 5C) and 46.61% (p<10$^{-323}$) by SaCas9-KKH-BE3 at RELA exon 10 (FIG. 5D). Interestingly, the first base in RELA exon 10, a guanosine within the optimal target range for SaCas9-KKH-BE3, was modified in 48.95% ($p<10^{-323}$) of the DNA strands (FIG. 5D, FIG. 11). At this target, the exonic base was modified without modifying the intronic base in only 2.9% of the reads, whereas the intronic base was modified without modifying the exonic base in only 0.7% of the reads. Targeted deep sequencing of cDNA was performed on CRISPR-SKIP treated cells to quantify exon skipping events. CRISPR-SKIP resulted in 2.48% ($p=1.33\times10^{-172}$) skipping rate in BRCA2 exon 26 (FIG. 5E) and % ($p<10^{-323}$) skipping rate in RELA exon 10 (FIG. 5F).

Example 4: Off-Target Modification Using CRISPR-SKIP

Cas9 can bind DNA even when the sgRNA is not perfectly matched, which can result in undesired modifications in the genome. To assess the extent of off-target effects, CRISPR-SKIP was targeted to 16 exons using 18 sgRNAs and sequenced the genomic DNA at on-target sites as well as four high scoring (Hsu P D, et al, *Nat Biotechnol* 2013, 31:827-832) off-target sites for each sgRNA. 14 out of 18 (77.78%) sgRNAs successfully modified their respective on-target sites, while only 10 out of 72 (13.89%) predicted off-target sites showed evidence of modification.

These results indicate that CRISPR-SKIP efficiency at inducing exon skipping is higher than gene editing methods that introduce DSBs in coding sequences and similar to methods that introduce DSBs near the splice acceptor (Hu J H, et al., *Nature* 2018, 556:57-63). However, in terms of specificity, it is important to note that the stochasticity of DSB repair, as well as the potential for translocations and other chromosomal aberrations that are not typically detected by current methods for analyzing off-target modifications, renders active Cas9 less predictable and potentially less safe than CRISPR-SKIP.

Figure 6:
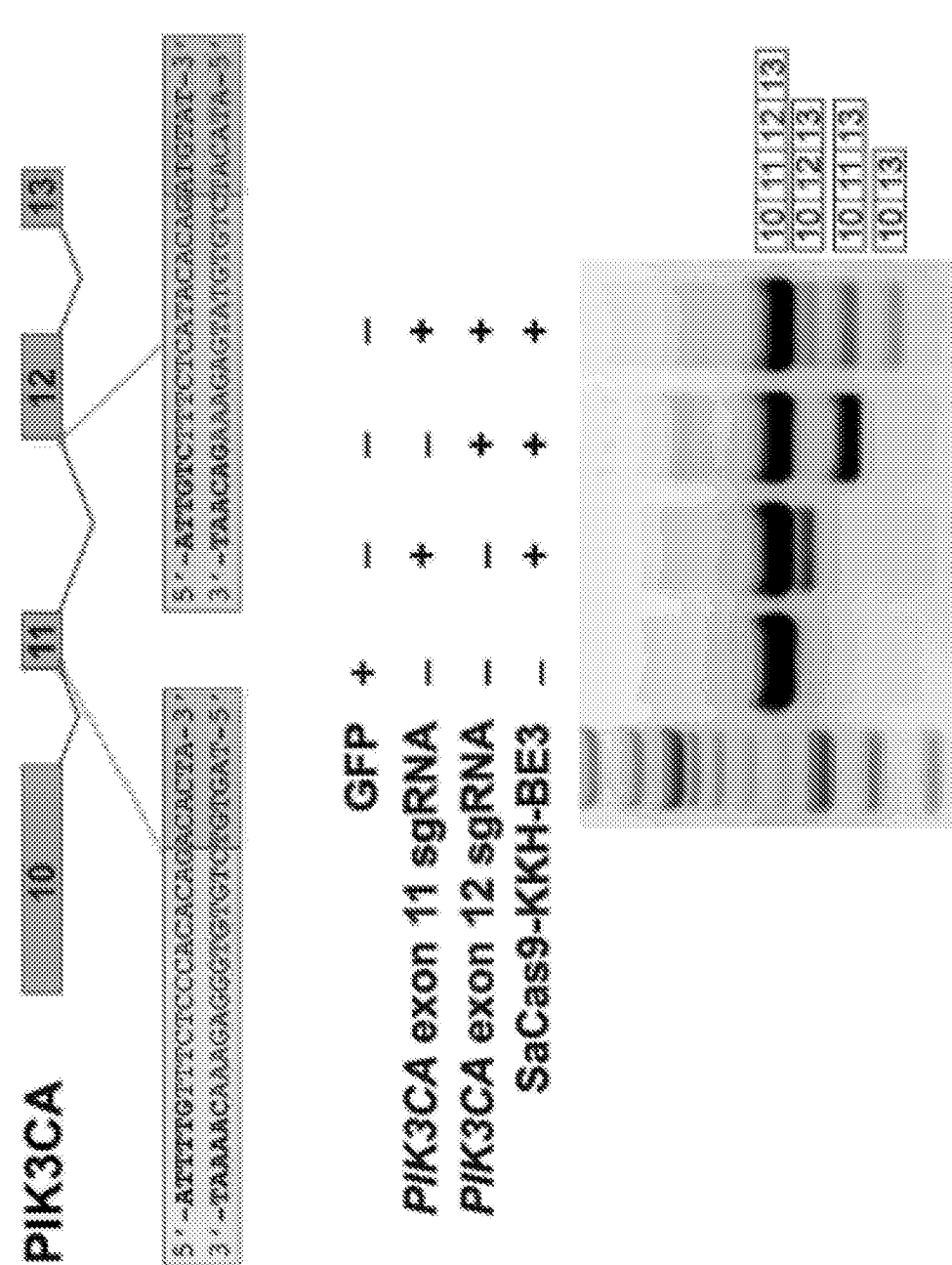

Example 5: CRISPR-SKIP can be Used to Simultaneously Skip Multiple Exons within the Same Transcript Therapeutic exon skipping often requires inducing splicing of multiple exons simultaneously within the same transcript to recover a reading frame (Crooke S T: *Biochim Biophys Acta* 1999, 1489:31-44). Since CRISPR base editing tools are theoretically capable of multiplexing, but this property has not been conclusively demonstrated previously in human cells, it was tested whether CRISPR-SKIP could induce simultaneous skipping of 2 exons by targeting PIK3CA exons 11 and 12. Analysis by RT-PCR revealed that SpCas9-BE3 editing tools can successfully induce skipping of PIK3CA exons 11 or 12 when used individually; and, when combined, they induce skipping of exon 11, exon 12 and both exons 11 and 12 (FIG. 6).

Figure 7A:
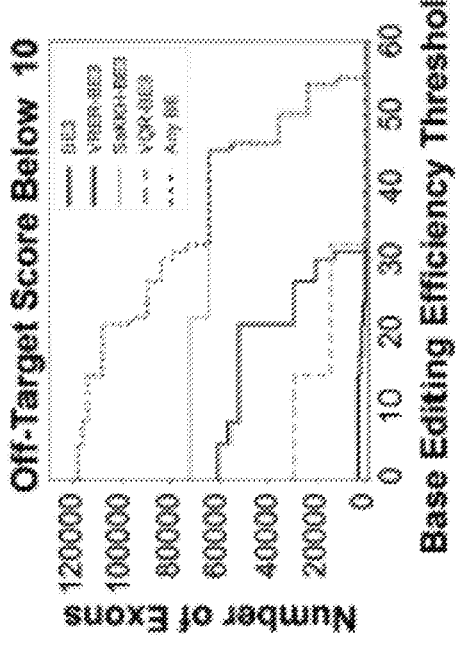
Figure 7B:
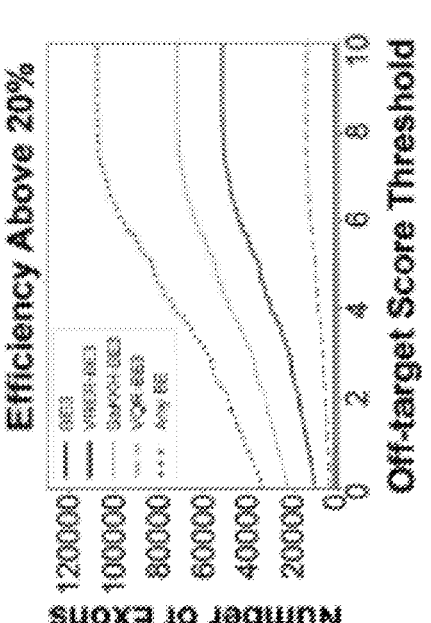

Example 6: Genome-Wide Computational Estimation of Targetability by CRISPR-SKIP To facilitate the identification of exons that can be skipped with the various base editors, a web-based software tool was developed that enables rapid identification of potential CRISPR-SKIP sgRNAs given a desired target gene or exon (song.igb.illinois.edu/crispr-skip/). The software incorporates the known base-editing efficiency profiles of the base editors SpCas9-BE3, SaCas9-KKH-BE3, SpCas9-VQR-BE3, and SpCas9-VRER-BE3 (Kim et al, *Nat Biotechnol.* 2017 April; 35(4):371-376. doi: 10.1038/nbt.3803.) It is estimated that these four base editors together enable targeting of 118,089 out of 187,636 inner exons in protein coding transcripts (genome assembly version GRCh38 and GENCODE release 26) at the off-target score (Hsu P D, et al, *Nat Biotechnol* 2013, 31:827-832) cutoff of 10, where 100 corresponds to perfect matching on targets (FIG. 7, FIG. 12, FIG. 13).

Example 7: Adenine Deaminase Base Editors Enable Programmable Exon Skipping

High throughput sequencing studies have revealed that nearly all splice acceptor sites also have a conserved adenine at the second to last base before each exon begins (FIG. 15). The splice acceptor site of exon 7 within the CTNNA1 gene was targeted. Plasmids encoding ABE7.10, which consists of two engineered *E. coli* TadA adenine deaminase domains fused to a Cas9-D10A nickase11 and an sgRNA targeting the splice acceptor, were transfected into 293T cells. After six days, the RNA was isolated and retrotranscribed to cDNA, which was used in PCRs to detect skipping of exon 7. In samples treated simultaneously with the ABE and the sgRNA, two PCR amplicons were observed, corresponding to the expected size of the full-length mature mRNA and mRNA lacking exon 7. The transcript lacking exon 7 was not observed in samples treated with the sgRNA alone or the sgRNA in combination with dead Cas9 or Cas9-D10A (FIG. 16A). Sanger sequencing of the shorter PCR product confirmed that CTNNA1 exon 6 was followed immediately by exon 8, confirming that exon 7 was skipped (FIG. 16B). High-throughput sequencing (HTS) of genomic DNA samples transfected with ABE and the sgRNA confirmed successful A>G mutation of the CTNNA1 exon 7 splice acceptor site in 6.52% of the strands (FIG. 16C).

To determine the minimum amount of time needed to observe maximal rates of exon skipping a time-course was performed by transfecting 293T cells with plasmids encoding ABE7.10 and the CTNNA1 exon 7 sgRNA, while isolating RNA for analysis at various time points over a 10-day period. Exon skipping was readily detectable at day 2, though the skipping rate continued to steadily increase until reaching a plateau after day 6 (FIG. 17A). For all subsequent experiments, samples were analyzed 6-days post transfection. Additionally, the amounts and ratios of the base editor plasmid and the sgRNA plasmid were varied to determine the optimal transfection conditions. Using 500 ng of sgRNA plasmid in combination with 500 ng of base editor plasmid or 250 ng of base editor plasmid in combination with 750 ng of sgRNA plasmid resulted in the highest rates of exon skipping in HEK293T cells transfected in 24-well plates (FIG. 17B).

Additionally, to demonstrate that the observed exon skipping was not cell line specific, HEPG2 and HCT116, cells with ABE, the CTNNA1 exon 7 sgRNA or an sgRNA targeting AHCY exon 9 respectively. Additionally, to determine if the technique worked in other species, mouse Neuro2A and Hepa1-6 cells were transfected with ABE and a sgRNA targeting CTNNB1exon 11. The target exon was skipped in all cell lines and only in the ABE-treated samples. (FIG. 17C).

Example 8: Modification of Linker Between Adenosine Deaminase Domain and Cas9 Nickase To improve the activity of ABE7.10, the composition of the linker domain between the TadA deaminase domains and the Cas9-D10A was modified. ABE constructs were created with linkers of either five repeats of alanine followed by proline (ABE-AP$_5$), five repeats of four glycine residues and a serine (ABE-GGGGS$_5$) (SEQ ID NO:7), the original ABE7.10 linker fused to GGGGS (SEQ ID NO:3) (ABE-Dual), or 5 repeats of glutamic acid followed by three alanine residues (ABE-EAAAA$_5$) (SEQ ID NO:11). (FIG. 18A). Another construct was generated by adding a uracil glycosylase inhibitor (UGI) domain to the C-terminus of the ABE 7.10 (ABE-UGI) (FIG. 18A). These constructs were transfected into HEK293T cells along with the CTNNA1 exon 7 sgRNA and rates of exon skipping were measured (FIG. 18B). The results demonstrated that ABE with a GGGGS$_5$ (SEQ ID NO:3) linker (7.73%, P=0.002) and the EAAA$_5$ linker (4.73%, P=0.082) induced exon skipping more efficiently than ABE 7.10 (3.73%). Furthermore, ABE-UGI also outperformed the ABE 7.10 with a skipping efficiency of 7.73% (P=0.002).

In order to compare the editing efficiencies of these improved ABE variants across multiple targets, as well as to correlate rates of modification in genomic DNA with rates of exclusion of the targeted exon from mRNA transcripts, HTS was performed on both genomic DNA (FIG. 19) and cDNA (FIG. 20) at multiple target sites in cells transfected with ABE 7.10, ABE-GGGGS$_5$ (SEQ ID NO:7), and ABE-UGI (FIGS. 41A-41B). These results confirmed that use of the ABE-GGGGS$_5$ (SEQ ID NO:7) and ABE-UGI led to significant increases in both A>G base editing rates and exon skipping rates over ABE 7.10 for many of the targets that were tested. In these experiments, the highest observed A>G mutation rates for each target were 9.70% by ABE-GGGGS$_5$ (SEQ ID NO:7) at CTNNA1 exon 7, 52.33% by ABE-GGGGS$_5$ (SEQ ID NO:7) at HSF1 exon 11, 2.90% by ABE-GGGGS$_5$ (SEQ ID NO:7)_at JUP exon 10, and 29.23% by ABE-UGI at AHCY exon 9 (FIG. 19). The highest observed exon skipping rates as determined by RNA-seq for each target were 7.30% by ABE-UGI at CTNNA1 exon 7, 15.310% by ABE-UGI at HSF1 exon 11, 0.45% by ABE-GGGGS$_5$ (SEQ ID NO:7) at JUP exon 10 and 40.45% by ABE-UGI at AHCY exon 9 (FIG. 20; Table 6).

TABLE 6 shows the predicted on-target activity for each sgRNA and observed %indels from HTS of genomic DNA following transfection with plasmids encoding wt Cas9 and the corresponding sgRNA.

| Target | Sequence (5' to 3') | PAM | On-Target Score | % Indels |
|---|---|---|---|---|
| CTNNA1 Exon 7 | CTGCAGAAACAAATCATTG SEQ ID NO: 321 | TGG | 65.5 | 8.49 |
| HSF1 Exon 11 | TCCGCAGCTGTTCAGCCCCT SEQ ID NO: 322 | TGG | 44.1 | 16.48 |
| JUP Exon 10 | ACACAGGATGGTGTGAGGA SEQ ID NO: 323 | CGG | 52.5 | 33.85 |
| AHCY Exon 9 | GCGTGTAGGTGGACCGGTAT SEQ ID NO: 324 | CGG | 43.9 | 11.47 |

To further increase the editing efficiency of the ABE, an additional ABE construct containing both the GGGGS$_5$ (SEQ ID NO:7) linker and the UGI domain (ABE-GGGGS$_5$-UGI) (SEQ ID NO:7) was created (FIG. 21A). Plasmids encoding each ABE were transfected separately into HEK293T cells along with the CTNNA1 exon 7 sgRNA. Rates of exon skipping were measured by RT-PCR (FIG. 21B) and compared using HTS (FIG. 21C). In this set of experiments, ABE-GGGGS$_5$-UGI (SEQ ID NO:7) induced a higher rate of exon skipping than all other constructs tested with 7.73% compared to 3.13% for ABE 7.10 (P=0.013), 4.96% for ABE-GGGGS$_5$ (SEQ ID NO:7) (P=0.061), and 5.53% for ABE-UGI (P=0.139).

Figure 21D:
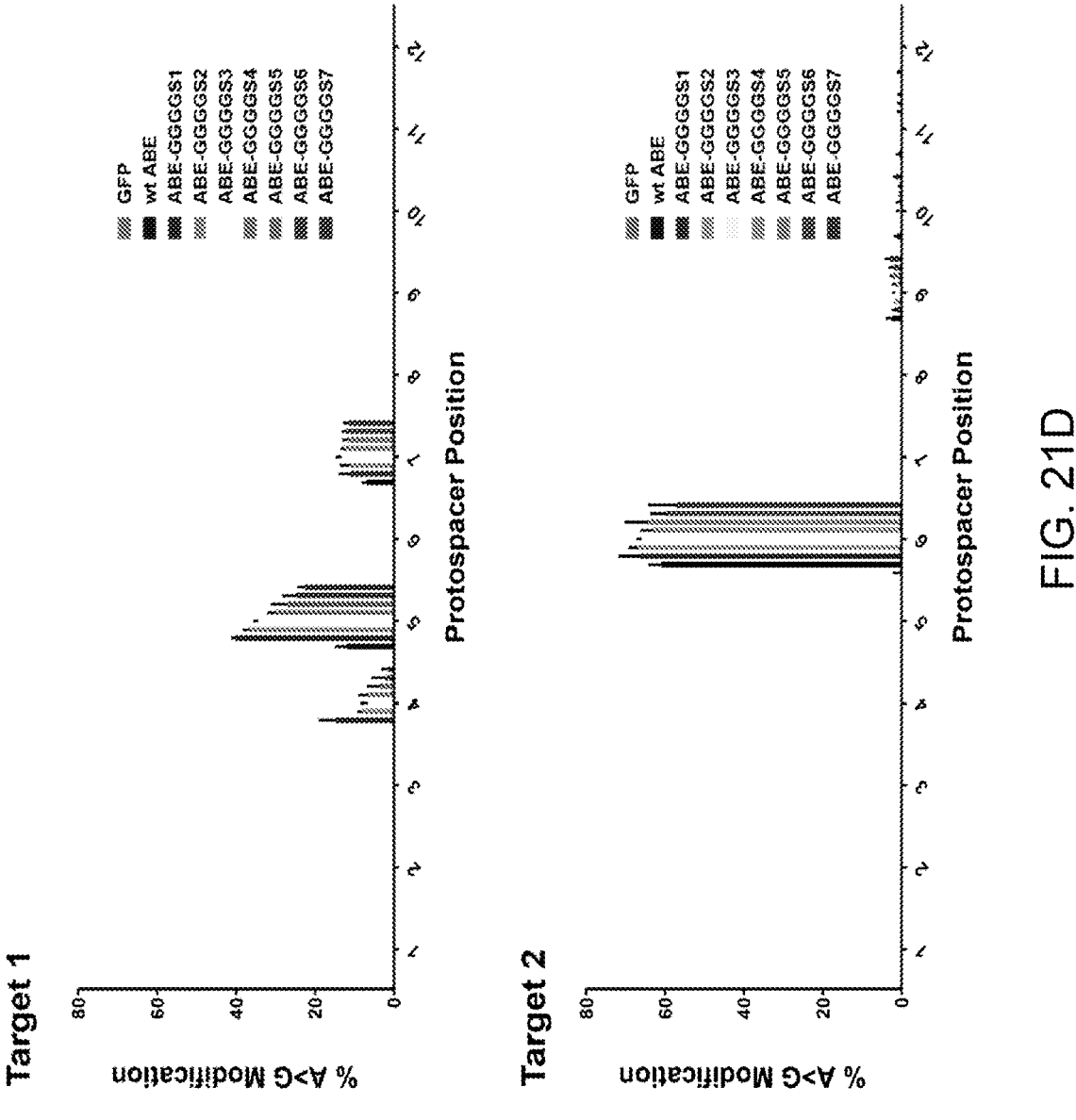

To determine if the length of the linker between the deaminase domain and Cas9-D10A had any effect on the base editing window within the protospacer, ABE constructs with 1 to 7 repeats of the amino acid sequence GGGGS (SEQ ID NO:3) were generated. These constructs were then transfected into HEK293T cells along with one of two A-rich sgRNAs targeting the GAPDH locus ((Table 7)). After three days, genomic DNA was harvested and the editing rates of each of the As within the protospacer were evaluated for each construct (FIG. 21D). Interestingly, the editing window expanded towards the 5' direction of the protospacer for each of the GGGGS (SEQ ID NO:3) constructs compared to ABE 7.10 and resulted in editing of the adenine in position 4, which was not observed with ABE 7.10. Furthermore, the editing efficiencies for positions 4 and 5 increased as the linker length decreased, with ABE GGGGS$_1$ (SEQ ID NO:3) yielding the highest rates of base editing for these positions.

TABLE 7 shows the oligonucleotide sequences used to generate sgRNAs as
well as predicted on-target scores (Mercatante, D. R., et
al, J Biol Chem 277, 49374- 49382, doi:10.1074/jbc.M209236200
(2002). and off-target scores (Yuan, J. et al. Mol Cell 72,
380-394 e387, doi:10.1016/j.molcel.2018.09.002 (2018).

| Designation | Target | Sequence (5' to 3') | PAM | On-Target Score | Off-Target Score |
|---|---|---|---|---|---|
| CTNNA1 Ex7 ABE S | CTNNA1 Exon 7 | CACCGCTGCAGAAACAAATCATTG SEQ ID NO: 325 | TGG | 65.5 | 50.7 |
| CTNNA1 Ex7 ABE AS | CTNNA1 Exon 7 | AAACCAATGATTTGTTTCTGCAGC SEQ ID NO: 326 | TGG | 65.5 | 50.7 |
| HSF1 Ex11 ABE S | HSF1 Exon 11 | CACCGTCCGCAGCTGTTCAGCCCCT SEQ ID NO: 327 | CGG | 44. | 63.7 |
| HSF1 Ex11 ABE AS | HSF1 Exon 11 | AAACAGGGGCTGAACAGCTGCGGAC SEQ ID NO: 328 | CGG | 44.1 | 63.7 |
| JUP Ex10 ABE S | JUP Exon 10 | CACCGACACAGGATGGTGTGAGGA SEQ ID NO: 329 | TGG | 52.5 | 28.1 |
| JUP Ex10 ABE AS | JUP Exon 10 | AAACTCCTCACACCATCCTGTGTC SEQ ID NO: 330 | TGG | 52.5 | 28.1 |
| AHCY Ex9 ABE S | AHCY Exon 9 | CACCGGCGTGTAGGTGGACCGGTAT SEQ ID NO: 331 | CGG | 43.9 | 49.0 |
| AHCY Ex9 ABE AS | AHCY Exon 9 | AAACATACCGGTCCACCTACACGCC SEQ ID NO: 332 | CGG | 43.9 | 49.0 |
| mCTNNB1 Ex11 S | Mouse CTNNB1 Exon 11 | CACCGCTCCTAGGAGGGCGTGCGCA SEQ ID NO: 333 | TGG | 40.4 | 83.7 |
| mCTNNB1 Ex11 AS | Mouse CTNNB1 Exon 11 | AAACTGCGCACGCCCTCCTAGGAGC SEQ ID NO: 334 | TGG | 40.4 | 83.7 |
| A-Rich Target 1 S | GAPDH Exon 1 | CACCGTGAAAGAAAGAAAGGGGAGG SEQ ID NO: 335 | GGG | 54.9 | 20.9 |
| A-Rich Target 1 AS | GAPDH Exon 1 | AAACCCTCCCCTTTCTTTCTTTCAC SEQ ID NO: 336 | GGG | 54.9 | 20.9 |
| A-Rich Target 2 S | GAPDH Intron 3 | CACCGAATCTAGGAAAAGCATCACC SEQ ID NO: 337 | CGG | 64.4 | 37.0 |
| A-Rich Target 2 AS | GAPDH Intron 3 | AAACGGTGATGCTTTTCCTAGATTC SEQ ID NO: 338 | CGG | 64.4 | 37.0 |

Example 9: Split ABE System for Packaging in Virus

While these improvements to the ABE allow for increased editing efficiency, the large size of these gene editing tools have presented a significant roadblock to in vivo base editing studies. For many diseases that can be treated with exon skipping, therapeutic effect is dependent on successful delivery of the system to the affected cells. Adeno-associated viral (AAV) vectors offer a promising and safe delivery vehicle for gene therapy due to their high titer and their ability to infect a broad range of cells, including non-dividing cells, without eliciting more than a mild immune response. Additionally, because they do not integrate into the host genome, and instead persist in the nucleus as concatemers, the risk of disrupting native gene function is low. A major drawback of using AAVs is that the size of the transgene is limited to 4.7 kb for efficient expression, which prevents the packaging of an ABE.

Here, whether ABEs split in two separate expression cassettes using inteins are active in cultured cells was tested. First, the ABE 7.10 open reading frame was split at the aspartic acid residue at amino acid position 1,109 into two plasmids. The N-terminal plasmid contained the TadA domains, the ABE 7.10 linker, and the first 712 amino acids of Cas9-D10A, followed immediately by an N-terminal intein sequence (N-ABE). The second construct contained a C-terminal intein sequence followed by the remaining 666 amino acids of ABE 7.10 (C-ABE) (FIG. 22F). After transfecting HEK293T cells with the HSF1 exon 11 sgRNA with the N-ABE plasmid and C-ABE plasmid, exon skipping was observed only in the samples containing both N- and C-terminus split base editor plasmids or the full-length ABE plasmid, which was transfected as control. Exon skipping levels was not observed above background in cells transfected with just the N-terminus or the C terminus split ABE (FIG. 22G). Surprisingly, RNA-seq revealed that the rate of exon skipping induced by split ABE (31.98%) was higher that the skipping rate measured in samples transfected with ABE 7.10 (26.23%) (P=0.0019), despite a potentially unfavorable reaction kinetic (FIG. 22H). The ability to disrupt splice acceptor sites using adenine base editors further expands the available tools for inducing therapeutic exon skipping. It proves especially useful for exon targets that are not accessible by BE3 due to PAM restrictions and further increases the total amount of exons that can be skipped using single base editors.

It was then tested whether these constructs can be packaged into separate AAV particles and codelivered to achieve base editing and subsequent exon skipping. The open reading frame of ABE-GGGGS$_5$-UGI (SEQ ID NO:7) was split at the same residue in Cas9-D10A as before and cloned the separate constructs between AAV inverted terminal repeats (ITRs) (FIG. 22A). An sgRNA expression cassette under the control of a U6 promoter was also cloned between the ITRs of each construct to enable simultaneous delivery of the sgRNA. After cloning a sgRNA targeting AHCY exon 9 into these plasmids, they were packaged into AAV and used to transduce HEK293T cells. Cells were transduced with the N-ABE AAV, the C-ABE AAV, or both. After 6 days the cells were harvested and confirmed A>G mutations in genomic DNA and exon skipping only in the samples that were treated with both the N-ABE AAV and the C-ABE AAV (FIGS. 22B-22C). Analysis of genomic DNA from three independent experiments revealed A>G modification rates of 13.33% (FIG. 22D), while densitometry analysis of RT-PCR products of the same samples revealed exon skipping rates of 14.85% (FIG. 22E).

Example 10: Genome-Wide Computational Estimation of Targetability of ABE Editors by CRISPR-SKIP To determine the contribution of ABE editors to the CRISPR-SKIP toolbox, the number of inner exons that could be targeted by ABE using genome-wide computational analysis of PAMs compatible with exon skipping through mutation of the adenosine in the splice acceptor was measured. In this analysis, when only highly specific sgRNAs with off-target scores 32 at or below 10 were considered, the number of exons targetable by ABE is higher than the number of exons targeted by BE3 for all base editing efficiency thresholds over 30 (FIG. 23A). Furthermore, the numbers of exons that can targeted by ABE with an off-target threshold lower than 7.5 is larger than the number that can be targeted with BE3 for on-target base editing efficiency above 30% (FIG. 23B). There are 19,953 inner exons in the human genome that can be targeted by both ABE and BE3. ABE provides higher predicted efficiency for targeting 10,803 of these exons (54.1%) (FIG. 23C) and higher specificity in 12,649 inner exons (63.4%) (FIG. 23D). These results support that ABE not only expand the number of exons that can be targeted by CRISPR-SKIP but also enable increasing the efficiency and specificity of CRISPR-SKIP.

Example 11: Off-Target Modification Using CRISPR-SKIP

To investigate the incidence of off-target mutations genomic DNA was analyzed at four predicted off target locations (Hsu, P. D. et al, *Nat Biotechnol* 31, 827-832, doi:10.1038/nbt.2647 (2013) for each sgRNA tested by HTS to detect possible mutations (FIGS. 42A-42B). Off-target A>G mutations were observed at one site within a non-coding region, which was introduced by the JUP exon 10 sgRNA. Notably, this sgRNA had the highest predicted off-target score of all sgRNA tested in this work and the mutation rate was low (~0.5%).

Example 12: Skipping Exons in Synuclein Gene

Parkinson's Disease (PD) is characterized by progressive degeneration of the dopaminergic neurons in the substantia nigra of the brain. There are two kinds of PD-sporadic and familial. Both of these kinds have shown a common trait of toxic alpha-synuclein (a-SNCA) protein aggregation in the affected dopaminergic neurons. This protein is encoded by the synuclein (SNCA) gene. Studies have shown that some forms of familial PD is caused by the mutations in this gene. There are six exons in SNCA gene where exon 1 is non-coding and the last five are coding. Five missense mutations have been identified so far and four out of five of these mutations are located in exon 3. Naturally, different isoforms of SNCA gene exist. A study has shown that isoforms lacking exon 3 and exon 5 showed reduced a-SNCA aggregation when compared to the wild type form, which could be a treatment for sporadic PD.

To determine the best base editors to skip exon 3, 293T cells were transfected with different base editors to identify the best condition as shown in Table 8. The results showed that ABE was successful to skip exon 3 (FIG. 32).

TABLE 8

| Transfection list | | |
|---|---|---|
| | Transfections | PAM |
| 1 | GFP | |
| 2 | SM9 + CMV-BE3 | NAG |
| 3 | SM9 + AID-BE3 | NAG |
| 4 | SM9 + CDA1-BE3 | NAG |
| 5 | SM11 + ABE | NGG |
| 6 | SM12 + ABE | NGG |
| 7 | SM13 + ABE | NAG |
| 8 | GFP | |
| 9 | SM10 + VQR BE3 | NGA |
| 10 | SM10 + xCas9 | NGA |

After confirming that exon 3 skipping was achieved using full length ABE, experiments were conducted to confirm that split ABE was also functional. As seen in FIG. 33, transfecting the cells with one component did not result to exon skip but when both the N and C terminus components were delivered with the sgRNA, exon 3 was skipped confirming that the split ABE system worked.

Statistical analysis was done to quantify the base editing efficiency of the full length and split ABE using EditR. While Split ABE had lower base editing efficiency than full length, it was still significantly higher than the GFP control (FIG. 34).

The split base editors were packaged into two different AAV vectors and delivered to the cells by transduction. AAV for GFP, N-terminus and C-terminus were prepared and 293T cells were transduced. As seen in FIG. 35, RT-PCR showed exon skipping in all replicates.

Example 13: Skipping Exons in Huntingtin (HTT) Gene

Huntington's disease (HD) is a currently incurable, autosomal dominant disorder characterized by a progressive decline in cognitive, motor and psychiatric function. HD affects ~1 in 10,000 individuals and is caused by the expansion of a polyglutamine-encoding CAG repeat within exon 1 of the huntingtin (HTT) gene, which leads to the formation of mutant protein aggregates that destroy medium spiny neurons and cortical neurons that project to the striatum.

Accumulation of full-length mHTT protein is not the sole driver of HD pathogenicity; instead, neurotoxicity is believed to also result from the formation of intracellular inclusions consisting of the N-terminal domain of the mHTT protein generated via proteolytic digestion of the full-length protein. In fact, animal models of the disorder expressing a modified version of mHTT that is resistant to cleavage by caspase-6 maintain normal neuronal function and do not develop striatal neurodegeneration. AONs can be designed to stimulate exon 12 skipping in the HTT pre-mRNA and reduce the formation of the N-terminal HTT protein fragment implicated in HD.

In this example, SBE technology was used to modify splicing to disrupt the caspase-6 cleavage site (located in exons 12 and 13) within the HTT gene to reduce the formation of toxic N-terminal protein fragments (FIGS. 36 & 37).

Example 14: Skipping Exons in Dystrophin (DMD) Gene

Duchenne Muscular Dystrophy is a lethal genetic disease caused by any of several different mutations in the dystrophin (DMD) gene. Approximately 9% of these mutations result in frameshifts that can be addressed by the skipping of DMD exon 45 (Nakamura, Journal of Human Genetics 2017). The splice acceptor of exon 45 was successfully edited with ABE GGGGS$_5$+UGI (SEQ ID NO:7), Split ABE GGGGS$_5$+UGI (SEQ ID NO:7), SpBE3, and Split SpBE3. Specifically, the rate of exon skipping induced by Split SpBE3 was 20.6% and 25.8% for Split ABE GGGGS$_5$+UGI (SEQ ID NO:7) (FIG. 38). Full-length SpBE3 also demonstrated exon 45 skipping in myoblasts (a disease-relevant cell type) as illustrated in FIG. 39.

Supplementary Sequences 1: Amino Acid Sequences of the Disclosure.

Adenine Deaminase Domain

Linker Region

Cas9-D10A

UGI Domain

N-Terminal Intein

C-Terminal Intein

NLS

3×HA Tag

```
wt ABE
                                                    (SEQ ID NO: 17)
MSEVEFSHEYWMRHALTLAKRAWDEREVPVGAVLVHNNRVIGEGWNRPIGRHDP

TAHAEIMALRQGGLVMQNYRLIDATLYVTLEPCVMCAGAMIHSRIGRVVFGARDAK

TGAAGSLMDVLHHPGMNHRVEITEGILADECAALLSDFFRMRRQEIKAQKKAQSST

DSGGSSGGSSGSETPGTSESATPESSGGSSGGSSEVEFSHEYWMRHALTLAKRA

RDEREVPVGAVLVLNNRVIGEGWNRAIGLHDPTAHAEIMALRQGGLVMQNYRLIDA

TLYVTFEPCVMCAGAMIHSRIGRVVFGVRNAKTGAAGSLMDVLHYPGMNHRVEITE

GILADECAALLCYFFRMPRQVFNAQKKAQSSTDSGGSSSGGSSGSETPGTSESATP

ESSGGSSGGSDKKYSIGLAIGTNSVGWAVITDEYKVPSKKFKVLGNTDRHSIKKNLI

GALLFDSGETAEATRLKRTARRRYTRRKNRICYLQEIFSNEMAKVDDSFFHRLEESF

LVEEDKKHERHPIFGNIVDEVAYHEKYPTIYHLRKKLVDSTDKADLRLIYLALAHMIKF

RGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPL

ARGNSRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTVKQLKED

YFKKIECFDSVEISGVEDRFNASLGTYHDLLKIIKDKDFLDNEENEDILEDIVLTLTLFE

DREMIEERLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIKKGILQTV

KVVDELVKVMGRHKPENIVIEMARENQTTQKGQKNSRERMKRIEEGIKELGSQILKE

HPVENTQLQNEKLYLYYLQNGRDMYVDQELDINRLSDYDVDHIVPQSFLKDDSIDN

KVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMIAK

SEQEIGKATAKYFFYSNIMNFFKTEITLANGEIRKRPLIETNGETGEIVWDKGRDFAT
```

-continued

VRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIK

LPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHL

FTLTNLGAPAAFKYFDTTIDRKRYTSTKEVLDATLIHQSITGLYETRIDLSQLGGDSR

ADPKKKRKV*

ABE-AP<sub>5</sub>

(SEQ ID NO: 18)

MSEVEFSHEYWMRHALTLAKRAWDEREVPVGAVLVHNNRVIGEGWNRPIGRHDP

TAHAEIMALRQGGLVMQNYRLIDATLYVTLEPCVMCAGAMIHSRIGRVVFGARDAK

TGAAGSLMDVLHHPGMNHRVEITEGILADECAALLSDFFRMRRQEIKAQKKAQSST

DSGGSSGGSSGSETPGTSESATPESSGGSSGGSSEVEFSHEYWMRHALTLAKRA

REDREVPVGAVLVLNNRVIGEGWNRAIGLHDPTAHAEIMALRQGGLVMQNYRLIDA

TLYVTFEPCVMCAGAMIHSRIGRVVFGVRNAKTGAAGSLMDVLHYPGMNHREITE

GILADECAALLCYFFRMPRQVFNAQKKAQSSTDASAPAPAPAPAPGTDKKYSIGLAI

GTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDE

VAYHEKYPTIYHLRKKLVDSTDKADLRLIYLALAHMIKFRGHFLIEGDLNPDNSDVDK

LFIQLVQTYNQLFEENPINASGVDAKAILSARLSKSRRLENLIAQLPGEKKNGLFGNLI

ALSLGLTPNFKSNFDLAEDAKLQLSKDTYDDDLDNLLAQIGDQYADLFLAAKNLSDA

ILLSDILRVNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGSIPHQIHL

GELHAILRRQEDFYPFLKDNREKIEKILTFRIPYYVGPLARGNSRFAWMTRKSEETIT

PWNFEEVVDKGASAQSFIERMTNFDKNLPNEKVLPKHSLLYEYFTVYNELTKVKYV

TEGMRKPAFLSGEQKKAIVDLLFKTNRKVTVKQLKEDYFKKIECFDSVEISGVEDRF

NASLGTYHDLLKIIKDKDFLDNEENEDILEDIVLTLTLFEDREMIEERLKTYAHLFDDK

VMKQLKRRRYTGWGRLSRKLINGIRDKQSGKTILDFLKSDGFANRNFMQLIHDDSL

TFKEDIQKAQVSGQGDSLHEHIANLAGSPAIKKGILQTVKVVDELVKVMGRHKPENI

VIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKL

KSVKELLGITIMERSSFEKNPIDFLEAKGYKEVKKDLIIKLPKYSLFELENGRKRMLAS

AGELQKGNELALPSKYVNFLYLASHYEKLKGSPEDNEQKQLFVEQHKHYLDEIIEQI

-continued

SEFSKRVILADANLDKVLSAYNKHRDKPIREQAENIIHLFTLTNLGAPAAFKYFDTTID

RKRYTSTKEVLDATLIHQSITGLYETRIDLSQLGGDSRADPKKKRKV*

ABE-GGGGS₅

(SEQ ID NO: 19)

MSEVEFSHEYWMRHALTLAKRAWDEREVPVGAVLVHNNRVIGEGWNRPIGRHDP

TAHAEIMALRQGGLVMQNYRLIDATLYVTLEPCVMCAGAMIHSRIGRVVFGARDAK

TGAAGSLMDVLHHPGMNHRVEITEGILADECAALLSDFFRMRRQEIKAQKKAQSST

DSGGSSGGSSGSETPGTSESATPESSGGSSGGSSEVEFSHEYWMRHALTLTLAKRA

RDEREVPVGAVLVLNNRVIGEGWNRAIGLHDPTAHAEIMALRQGGLVMQNYRLIDA

TLYVTFEPCVMCAGAMIHSRIGRVVFGVRNAKTGAAGSLMDVLHYPGMNHRVEITE

GILADECAALLCYFFRMPRQVENAQKKAQSSTDASGGGGSGGGGSGGGGSGGG

GSGGGGSGTDKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYLALAHMIKF

RGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPL

ARGNSRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTVKQLKED

YFKKIECFDSVEISGVEDRFNASLGTYHDLLKIIKDKDFLDNEENEDILEDIVLTLTLFE

DREMIEERLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIKKGILQTV

KVVDELVKVMGRHKPENIVIEMARENQTTQKGQKNSRERMKRIEEGIKELGSQILKE

HPVENTQLQNEKLYLYYLQNGRDMYVDQELDINRLSDYDVDHIVPQSFLKDDSIDN

KVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMIAK

SEQEIGKATAKYFFYSNIMNFFKTEITLANGEIRKRPLIETNGETGEIVWDKGRDFAT

VRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIK

LPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHL

FTLTNLGAPAAFKYFDTTIDRKRYTSTKEVLDATLIHQSITGLYETRIDLSQLGGDSR

ADPKKKRKV*

ABE-Dual (SEQ ID NO: 20)

MSEVEFSHEYWMRHALTLAKRAWDEREVPVGAVLVHNNRVIGEGWNRPIGRHDP

TAHAEIMALRQGGLVMQNYRLIDATLYVTLEPCVMCAGAMIHSRIGRVVFGARDAK

TGAAGSLMDVLHHPGMNHRVEITEGILADECAALLSDFFRMRRQEIKAQKKAQSST

DSGGSSGGSSGSETPGTSESATPESSGGSSGGSSEVEFSHEYWMRHALTLAKRA

-continued

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVFNAQKKAQSSTD*ASSGGSSGGSSGSETPGTSESA

TPESSGGSSGGSGGGGSGGGGSGGGGSGGGGSGGGGSGT*DKKYSIGLAIGTNS*

*VGWAVITDEYKVPSKKFKVLGNTDRHSIKKNLIGALLFDSGETAEATRLKRTARRRY*

*TRRKNRICYLQEIFSNEMAKVDDSFFHRLEESFLVEEDKKHERHPIFGNIVDEVAYH*

*EKYPTIYHLRKKLVDSTDKADLRLIYLALAHMIKFRGHFLIEGDLNPDNSDVDKLFIQL*

*VQTYNQLFEENPINASGVDAKAILSARLSKSRRLENLIAQLPGEKKNGLFGNLIALSL*

*GLTPNFKSNFDLAEDAKLQLSKDTYDDDLDNLLAQIGDQYADLFLAAKNLSDAILLS*

*DILRVNTEITKAPLSASMIKRYDEHHQDLTLLKALVRQQLPEKYKEIFFDQSKNGYAG*

*YIDGGASQEEFYKFIKPILEKMDGTEELLVKLNREDLLRKQRTFDNGSIPHQIHLGEL*

*HAILRRQEDFYPFLKDNREKIEKILTFRIPYYVGPLARGNSRFAWMTRKSEETITPW*

*NFEEVVDKGASAQSFIERMTNFDKNLPNEKVLPKHSLLYEYFTVYNELTKVKYVTE*

*GMRKPAFLSGEQKKAIVDLLFKTNRKVTVKQLKEDYFKKIECFDSVEISGVEDRFNA*

*SLGTYHDLLKIIKDKDFLDNEENEDILEDIVLTLTLFEDREMIEERLKTYAHLFDDKVM*

*KQLKRRRYTGWGRLSRKLINGIRDKQSGKTILDFLKSDGFANRNFMQLIHDDSLTFK*

*EDIQKAQVSGQGDSLHEHIANLAGSPAIKKGILQTVKVVDELVKVMGRHKPENIVIE*

*MARENQTTQKGQKNSRERMKRIEEGIKELGSQILKEHPVENTQLQNEKLYLYYLQN*

*GRDMYVDQELDINRLSDYDVDHIVPQSFLKDDSIDNKVLTRSDKNRGKSDNVPSEE*

*WVKKMKNYWRQLLNAKLITQRKFDNLTKAERGGLSELDKAGFIKRQLVETRQITKHV*

*AQILDSRMNTKYDENDKLIREVKVITLKSKLVSDFRKDFQFYKVREINNYHHAHDAY*

*LNAVVGTALIKKYPKLESEFVYGDYKVYDVRKMIAKSEQEIGKATAKYFFYSNIMNFF*

*KTEITLANGEIRKRPLIETNGETGEIVWDKGRDFATVRKVLSMPQVNIVKKTEVQTG*

*GFSKESILPKRNSDKLIARKKDWDPKKYGGFDSPTVAYSVLVVAKVEKGKSKKLKS*

*VKELLGITIMERSSFEKNPIDFLEAKGYKEVKKDLIIKLPKYSLFELENGRKRMLASAG*

*ELQKGNELALPSKYVNFLYLASHYEKLKGSPEDNEQKQLFVEQHKHYLDEIIEQISE*

*FSKRVILADANLDKVLSAYNKHRDKPIREQAENIIHLFTLTNLGAPAAFKYFDTTIDRK*

*RYTSTKEVLDATLIHQSITGLYETRIDLSQLGGDSRAD*PKKKRKV*

ABE-EAAA₅

(SEQ ID NO: 21)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVEGARDAK*

*TGAAGSLMDVLHHPGMNHRVETTEGILADECAALLSDFFRMRRQEIKAQKKAQSST*

*DSGGSSGGSSGSETPGTAESATPESSGGSSGGS*SEVEFSHEYWMRHALTLAKRA

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVFNAQKKAQSSTD*ASEAAAEAAAEAAAEAAAEAAAG

T*DKKYSIGLAIGTNSVGWAVITDEYKVPSKKFKVLGNTDRHSIKKNLIGALLFDSGET*

*AEATRLKRTARRRYTRRKNRICYLQEIFSNEMAKVDDSFFHRLEESFLVEEDKKHE*

*RHPIFGNIVDEVAYHEKYPTIYHLRKKLVDSTDKADLRLIYLALAHMIKFRGHFLIEGD*

*LNPDNSDVDKLFIQLVQTYNQLFEENPINASGVDAKAILSARLSKSRRLENLIAQLPG*

*EKKNGLFGNLIALSLGLTPNFKSNFDLAEDAKLQLSKDTYDDDLDNLLAQIGDQYAD*

-continued

LFLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFA

WMTRKSEETITPWNFEEVVDKGASAQSFIERMTNFDKNLPNEKVLPKHSLLYEYFT

VYNELTKVKYVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLTLFEDREMIEERL

KTYAHLFDDKVMKQLRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKVR

EINNYHHAHDAYLNAVVGTALIKKYPKLESEFVYGDYKVYDVRKMIAKSEQEIGKAT

AKYFFYSNIMNFFKTEITLANGEIRKRPLIETNGETGEIVWDKGRDFATVRKVLSMPQ

VNIVKKTEVQTGGFSKESILPKRNSDKLIARKKDWDPKKYGGFDSPTVAYSVLVVAK

VEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQH

KHYLDEIIEQISEFSKRVILADANLDKVLSAYNKHRDKPIREQAENIIHLFTLTNLGAPA

AFKYFDTTIDRKRYTSTKEVLDATLIHQSITGLYETRIDLSQLGGDSRAD<u>PKKKRKV</u>*

ABE-UGI (SEQ ID NO: 22)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVEITEGILADECAALLSDFFRMRRQEIKAQKKAQSST*

<u>*DSGGSSGGSSGS*</u>*ETPGTSESATPESSGGSSGGSSEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVENAQKKAQSSTD<u>SGGSSGGSSGSETPGTSESATP*</u>

<u>*ESSGGSSGGS*</u>*DKKYSIGLAIGTNSVGWAVITDEYKVPSKKFKVLGNTDRHSIKKNLI*

*GALLFDSGETAEATRLKRTARRRYTRRKNRICYLQEIFSNEMAKVDDSFFHRLEESF*

*LVEEDKKHERHPIFGNIVDEVAYHEKYPTIYHLRKKLVDSTDKADLRLIYLALAHMIKF*

*RGHFLIEGDLNPDNSDVDKLFIQLVQTYNQLFEENPINASGVDAKAILSARLSKSRRL*

*ENLIAQLPGEKKNGLFGNLIALSLGLTPNFKSNFDLAEDAKLQLSKDTYDDDLDNLLA*

*QIGDQYADLFLAAKNLSDAILLSDILRVNTEITKAPLSASMIKRYDEHHQDLTLLKALV*

*RQQLPEKYKEIFFDQSKNGYAGYIDGGASQEEFYKFIKPILEKMDGTEELLVKLNRE*

*DLLRKQRTFDNGSIPHQIHLGELHAILRRQEDFYPFLKDNREKIEKILTFRIPYYVGPL*

*ARGNSRFAWMTRKSEETITPWNFEEVVDKGASAQSFIERMTNFDKNLPNEKVLPK*

*HSLLYEYFTVYNELTKVKYVTEGMRKPAFLSGEQKKAIVDLLFKTNRKVTVKQLKED*

*YFKKIECFDSVEISGVEDRFNASLGTYHDLLKIIKDKDFLDNEENEDILEDIVLTLTLFE*

*DREMIEERLKTYAHLFDDKVMKQLRRRYTGWGRLSRKLINGIRDKQSGKTILDFLK*

*SDGFANRNFMQLIHDDSLTFKEDIQKAQVSGQGDSLHEHIANLAGSPAIKKGILQTV*

-continued

KVVDELVKVMGRHKPENIVIEMARENQTTQKGQKNSRERMKRIEEGIKELGSQILKE

HPVENTQLQNEKLYLYYLQNGRDMYVDQELDINRLSDYDVDHIVPQSFLKDDSIDN

KVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMIAK

SEQEIGKATAKYFFYSNIMNFFKTEITLANGEIRKRPLIETNGETGEIVWDKGRDFAT

VRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIK

LPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHL

FTLTNLGAPAAFKYFDTTIDRKRYTSTKEVLDATLIHQSITGLYETRIDLSQLGGDSR

ADS<u>GGGS</u>TNLSDIIEKETGKQLVIQESILMLPEEVEEVIGNKPESDILVHTAYDESTDE

NVMLLTSDAPEYKPWALVIQDSNGENKIKML<u>SGGS</u><u>PKKKRKV</u>*

ABE-GGGGS1-UGI (SEQ ID NO:23)
*MSEVEFSHEYWMRHALTLAKRAWDEREVPVGAVLVHNNRVIGEGWNRPIGRHDP*

*TAHAEIMALRQGGGLVMQNYRLIDATLYVTLEPCVMCAGAMIHSRIGRVVFGARDAK*

*TGAAGSLMDVLHHPGMNHRVEITEGILADECAALLSDFERMRRQEIKAQKKAQSST*

<u>*DSGGSSGGSSGS*ETPGTSESATPESSGGSSGGSS</u>*SEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVFNAQKKAQSSTD*<u>ASGGGGSGT</u>DKKYSIGLAIGTNS

VGWAVITDEYKVPSKKFKVLGNTDRHSIKKNLIGALLFDSGETAEATRLKRTARRRY

TRRKNRICYLQEIFSNEMAKVDDSFFHRLEESFLVEEDKKHERHPIFGNIVDEVAYH

EKYPTIYHLRKKLVDSTDKADLRLIYLALAHMIKFRGHFLIEGDLNPDNSDVDKLFIQL

VQTYNQLFEENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKNLSDAILLS

DILRVNTEITKAPLSASMIKRYDEHHQDLTLLKALVRQQLPEKYKEIFFDQSKNGYAG

YIDGGASQEEFYKFIKPILEKMDGTEELLVKLNREDLLRKQRTFDNGSIPHQIHLGEL

HAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTE

GMRKPAFLSGEQKKAIVDLLFKTNRKVTVKQLKEDYFKKIECFDSVEISGVEDRFNA

SLGTYHDLLKIIKDKDFLDNEENEDILEDIVLTLTLFEDREMIEERLKTYAHLFDDKVM

KQLKRRRYTGWGRLSRKLINGIRDKQSGKTILDFLKSDGFANRNFMQLIHDDSLTFK

EDIQKAQVSGQGDSLHEHIANLAGSPAIKKGILQTVKVVDELVKVMGRHKPENIVIE

MARENQTTQKGQKNSRERMKRIEEGIKELGSQILKEHPVENTQLQNEKLYLYYLQN

GRDMYVDQELDINRLSDYDVDHIVPQSFLKDDSIDNKVLTRSDKNRGKSDNVPSEE

WVKKMKNYWRQLLNAKLITQRKFDNLTKAERGGLSELDKAGFIKRQLVETRQITKHV

AQILDSRMNTKYDENDKLIREVKVITLKSKLVSDFRKDFQFYKVREINNYHHAHDAY

LNAVVGTALIKKYPKLESEFVYGDYKVYDVRKMIAKSEQEIGKATAKYFFYSNIMNFF

KTEITLANGEIRKRPLIETNGETGEIVWDKGRDFATVRKVLSMPQVNIVKKTEVQTG

GFSKESILPKRNSDKLIARKKDWDPKKYGGFDSPTVAYSVLVVAKVEKGKSKKLKS

-continued

VKELLGITIMERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRK

RYTSTKEVLDATLIHQSITGLYETRIDLSQLGGDSRAD<u>SGGS</u>TNLSDIIEKETGKQLV

IQESILMLPEEVEEVIGNKPESDILVHTAYDESTDENVMLLTSDAPEYKPWALVIQD

VIQDSNGENKIKML<u>SGGS</u><u>PKKKRKV</u>*

ABE-GGGGS2-UGI (SEQ ID NO: 24)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVEITEGILADECAALLSDFFRMRRQIEKAQKKAQSST*

<u>*DSGGSSGGSSGS*ETPGTSESATPES*SGGSSGGS*</u>*SEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVETTE*

*GILADECAALLCYFFRMPRQVFNAQKKAQSST*<u>DASGGGGSGGGGSGT</u>DKKYSIGL

AIGTNSVGWAVITDEYKVPSKKFKVLGNTDRHSIKKNLIGALLFDSGETAEATRLKRT

ARRRYTRRKNRICYLQEIFSNEMAKVDDSFFHRLEESFLVEEDKKHERHPIFGNIVD

EVAYHEKYPTIYHLRKKLVDSTDKADLRLIYLALAHMIKFRGHFLIEGDLNPDNSDVD

KLFIQLVQTYNQLFEENPINASGVDAKAILSARLSKSRRLENLIAQLPGEKKNGLFGN

LIALSLGLTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNGSIPHQIH

LGELHAILRRQEDFYPFLKDNREKIEKILTFRIPYYVGPLARGNSRFAWMTRKSEETI

TPWNFEEVVDKGASAQSFIERMTNFDKNLPNEKVLPKHSLLYEYFTVYNELTKVKY

VTEGMRKPAFLSGEQKKAIVDLLFKTNRKVTVKQLKEDYFKKIECFDSVEISGVEDR

FNASLGTYHDLLKIIKDKDFLDNEENEDILEDIVLTLTLFEDREMIEERLKTYAHLFDD

KVMKQLKRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVMGRHKPEN

IVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVP

SEEVVKKMKNYWRQLLNAKLITQRKFDNLTKAERGGLSELDKAGFIKRQLVETRQIT

KHVAQILDSRMNTKYDENDKLIREVKVITLKSKLVSDFRKDFQFYKVREINNYHHAH

DAYLNAVVGTALIKKYPKLESEFVYGDYKVYDVRKMIAKSEQEIGKATAKYFFYSNI

MNFFKTEITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKVEKGKSK

KLKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEIIE

QISEFSKRVILADANLDKVLSAYNKHRDKPIREQAENIIHLFTLTNLGAPAAFKYFDTT

-continued

IDRKRYTSTKEVLDATLIHQSITGLYETRIDLSQLGGDSRADSGGSTNLSDIIEKETG

KQLVIQESILMLPEEVEEVIGNKPESDILVHTAYDESTDENVMLLTSDAPEYKPWAL

VIQDSNGENKIKMLSGGSPKKKRKV*

ABE-GGGGS₃-UGI (SEQ ID NO: 25)

MSEVEFSHEYWMRHALTLAKRAWDEREVPVGAVLVHNNRVIGEGWNRPIGRHDP

TAHAEIMALRQGGLVMQNYRLIDATLYVTLEPCVMCAGAMIHSRIGRVVFGARDAK

TGAAGSLMDVLHHPGMNHRVEITEGILADECAALLSDFFRMRRQEIKAQKKAQSST

DSGGSSGGSSGSETPGTSESATPESSGGSSGGS*SEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNRVEITE*

*GILADECAALLCYFFRMPRQVFNAQKKAQSSTDA*ASGGGGSGGGGSGGGGSGTDK

KYSIGLAIGTNSVGWAVITDEYKVPSKKFKVLGNTDRHSIKKNLIGALLFDSGETAEA

TRLKRTARRRYTRRKNRICYLQEIFSNEMAKVDDSFFHRLEESFLVEEDKKHERHPI

FGNIVDEVAYHEKYPTIYHLRKKLVDSTDKADLRLIYLALAHMIKFRGHFLIEGDLNPD

NSDVDKLFIQLVQTYNQLFEENPINASGVDAKAILSARLSKSRRLENLIAQLPGEKKN

GLFGNLIALSLGLTPNFKSNFDLAEDAKLQLSKDTYDDDLDNLLAQIGDQYADLFLA

AKNLSDAILLSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRKQRTFDN

GSIPHQIHLGELHAILRRQEDFYPFLKDNREKIEKILTFRIPYYVGPLARGNSRFAWM

TRKSEETITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKIECFDSVEI

SGVEDRFNASLGTYHDLLKIIKDKDFLDNEENEDILEDIVLTLTLFEDREMIEERLKTY

AHLFDDKVMKQLKRRRYTGWGRLSRKLINGIRDKQSGKTILDFLKSDGFANRNFMQ

LIHDDSLTFKEDIQKAQVSGQGDSLHEHIANLAGSPAIKKGILQTVKVVDELVKVMG

RHKPENIVIEMARENQTTQKGQKNSRERMKRIEEGIKELGSQILKEHPVENTQLQNE

KLYLYYLQNGRDMYVDQELDINRLSDYDVDHIVPQSFLKDDSIDNKVLTRSDKNRG

KSDNVPSEEVVKKMKNYWRQLLNAKLITQRKFDNLTKAERGGLSELDKAGFIKRQL

VETRQITKHVAQILDSRMNTKYDENDKLIREVKVITLKSKLVSDFRKDFQFYKVREIN

NYHHAHDAYLNAVVGTALIKKYPKLESEFVYGDYKVYDVRKMIAKSEQEIGKATAKY

FFYSNIMNFFKTEITLANGEIRKRPLIETNGETGEIVWDKGRDFATVRKVLSMPQVNI

VKKTEVQTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPKYSLFELENG

RKRMLASAGELQKGNELALPSKYVNFLYLASHYEKLKGSPEDNEQKQLFVEQHKH

YLDEIIEQISEFSKRVILADANLDKVLSAYNKHRDKPIREQAENIIHLFTLTNLGAPAAF

KYFDTTIDRKRYTSTKEVLDATLIHQSITGLYETRIDLSQLGGDSRADSGGSTNLSDII

EKETGKQLVIQESILMLPEEVEEVIGNKPESDILVHTAYDESTDENVMLLTSDAPEY

KPWALVIQDSNGENKIKMLSGGSPKKKRKV*

ABE-GGGGS₄-UGI (SEQ ID NO: 26)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVETTEGILADECAALLSDFFRMRRQEIKAQKKAQSST*

*DSGGSSGGSSGSETPGTSESATPESSGGSSGGSSEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVENAQKKAQSSTDASGGGGSGGGGSGGGGSGGG*

*GSGT*DKKYSIGLAIGTNSVGWAVITDEYKVPSKKFKVLGNTDRHSIKKNLIGALLFDS

GETAEATRLKRTARRRYTRRKNRICYLQEIFSNEMAKVDDSFFHRLEESFLVEEDK

KHERHPIFGNIVDEVAYHEKYPTIYHLRKKLVDSTDKADLRLIYLALAHMIKFRGHFLI

EGDLNPDNSDVDKLFIQLVQTYNQLFEENPINASGVDAKAILSARLSKSRRLENLIAQ

LPGEKKNGLFGNLIALSLGLTPNFKSNFDLAEDAKLQLSKDTYDDDLDNLLAQIGDQ

YADLFLAAKNLSDAILLSDILRVNTEITKAPLSASMIKRYDEHHQDLTLLKALVRQQLP

EKYKEIFFDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPKHSLLY

EYFTVYNELTKVKYVTEGMRKPAFLSGEQKKAIVDLLFKTNRKVTVKQLKEDYFKKI

ECFDSVEISGVEDRFNASLGTYHDLLKIIKDKDFLDNEENEDILEDIVLTLTLFEDREM

IEERLKTYAHLFDDKVMKQLKRRRYTGWGRLSRKLINGIRDKQSGKTILDFLKSDGF

ANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVE

NTQLQNEKLYLYYLQNGRDMYVDQELDINRLSDYDVDHIVPQSFLKDDSIDNKVLT

RSDKNRGKSDNVPSEEVVKKMKNYWRQLLNAKLITQRKFDNLTKAERGGLSELDK

AGFIKRQLVETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKMIAKSEQE

IGKATAKYFFYSNIMNFFKTEITLANGEIRKRPLIETNGETGEIVWDKGRDFATVRKV

LSMPQVNIVKKTEVQTGGFSKESILPKRNSDKLIARKKDWDPKKYGGFDSPTVAYS

VLWVAKVEKGKSKKLKSVKELLGITIMERSSFEKNPIDFLEAKGYKEVKKDLIIKLPKY

SLFELENGRKRMLASAGELQKGNELALPSKYVNFLYLASHYEKLKGSPEDNEQKQL

FVEQHKHYLDEIIEQISEFSKRVILADANLDKVLSAYNKHRDKPIREQAENIIHLFTLTN

LGAPAAFKYFDTTIDRKRYTSTKEVLDATLIHQSITGLYETRIDLSQLGGDSRAD*SGG*

*S*TNLSDIIEKETGKQLVIQESILMLPEEVEEVIGNKPESDILVHTAYDESTDENVMLL

TSDAPEYKPWALVIQDSNGENKIKML*SGGS*PKKKRKV\*

ABE-GGGGS~5~-UGI (SEQ ID NO: 27)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVEITEGILADECAALLSDFFRMRRQEIKAQKKAQSST*

*DSGGSSGGSSGSETPGTSESATPESSGGSSGGSSEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVENAQKKAQSSTDASGGGGSGGGGSGGGGSGGG*

*GSGGGGSGT*DKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFFHRLEESFL

-continued

VEEDKKHERHPIFGNIVDEVAYHEKYPTIYHLRKKLVDSTDKADLRLIYLALAHMIKF

RGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPL

ARGNSRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTVKQLKED

YFKKIECFDSVEISGVEDRFNASLGTYHDLLKIIKDKDFLDNEENEDILEDIVLTLTLFE

DREMIEERLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIKKGILQTV

KVVDELVKVMGRHKPENIVIEMARENQTTQKGQKNSRERMKRIEEGIKELGSQILKE

HPVENTQLQNEKLYLYYLQNGRDMYVDQELDINRLSDYDVDHIVPQSFLKDDSIDN

KVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFR

KDFQFYKVREINNYHHAHDAYLNAVVGTALIKKYPKLESEFVYGDYKVYDVRKMIAK

SEQEIGKATAKYFFYSNIMNFFKTEITLANGEIRKRPLIETNGETGEIVWDKGRDFAT

VRKVLSMPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYKEVKKDLIIK

LPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHL

FTLTNLGAPAAFKYFDTTIDRKRYTSTKEVLDATLIHQSITGLYETRIDLSQLGGDSR

ADSGGGSTNLSDIIEKETGKQLVIQESILMLPEEVEEVIGNKPESDILVHTAYDESTDE

NVMLLTSDAPEYKPWALVIQDSNGENKIKMLSGGSPKKKRKV\*

ABE-GGGGS₆-UGI
                                                                (SEQ ID NO: 28)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVEITEGILADECAALLSDFFRMRRQEIKAQKKAQSST*

DSGGSSGGSSGSETPGTSESATPESSGGSSGGS*SEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVENAQKKAQSST*DASGGGGSGGGGSGGGGSGGG

GSGGGGSGGGGSGTDKKYSIGLAIGTNSVGWAVITDEYKVPSKKFKVLGNTDRHSI

KKNLIGALLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKADLRLIYLALA

HMIKFRGHFLIEGDLNPDNSDVDKLFIQLVQTYNQLFEENPINASGVDAKAILSARLS

KSRRLENLIAQLPGEKKNGLFGNLIALSLGLTPNFKSNFDLAEDAKLQLSKDTYDDD

LDNLLAQIGDQYADLFLAAKNLSDAILLSDILRVNTEITKAPLSASMIKRYDEHHQDLT

LLKALVRQQLPEKYKEIFFDQSKNGYAGYIDGGASQEEFYKFIKPILEKMDGTEELLV

KLNREDLLRKQRTFDNGSIPHQIHLGELHAILRRQEDFYPFLKDNREKIEKILTFRIPY

-continued

YVGPLARGNSRFAWMTRKSEETITPWNFEEVVDKGASAQSFIERMTNFDKNLPNE

KVLPKHSLLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEENEDILEDIVL

TLTLFEDREMIEERLKTYAHLFDDKVMKQLKRRRYTGWGRLSRKLINGIRDKQSGK

TILDFLKSDGFANRNFMQLIHDDSLTFKEDIQKAQVSGQGDSLHEHIANLAGSPAIKK

GILQTVKVVDELVKVMGRHKPENIVIEMARENQTTQKGQKNSRERMKRIEEGIKEL

GSQILKEHPVENTQLQNEKLYLYYLQNGRDMYVDQELDINRLSDYDVDHIVPQSFL

KDDSIDNKVLTRSDKNRGKSDNVPSEEVVKKMKNYWRQLLNAKLITQRKFDNLTKA

ERGGLSELDKAGFIKRQLVETRQITKHVAQILDSRMNTKYDENDKLIREVKVITLKSK

LVSDFRKDFQFYKVREINNYHHAHDAYLNAVVGTALIKKYPKLESEFVYGDYKVYDV

RKMIAKSEQEIGKATAKYFFYSNIMNFFKTEITLANGEIRKRPLIETNGETGEIVWDK

GRDFATVRKVLSMPQVNIVKKTEVQTGGFSKESILPKRNSDKLIARKKDWDPKKYG

GFDSPTVAYSVLVVAKVEKGKSKKLKSVKELLGITIMERSSFEKNPIDFLEAKGYKEV

KKDLIIKLPKYSLFELENGRKRMLASAGELQKGNELALPSKYVNFLYLASHYEKLKG

SPEDNEQKQLFVEQHKHYLDEIIEQISEFSKRVILADANLDKVLSAYNKHRDKPIREQ

AENIIHLFTLTNLGAPAAFKYFDTTIDRKRYTSTKEVLDATLIHQSITGLYETRIDLSQL

GGDSRAD<u>SGGS</u>TNLSDIIEKETGKQLVIQESILMLPEEVEEVIGNKPESDILVHTAY

DESTDENVMLLTSDAPEYKPWALVIQDSNGENKIKML<u>SGGS</u><u>PKKKRKV</u>*

ABE-GGGGS<sub>7</sub>-UGI (SEQ ID NO:29)
*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVETTEGILADECAALLSDFFRMRRQEIKAQKKAQSST*

<u>*DSGGSSGGSSGS*ETPGTSESTPESS*GGSSGGS*</u>*SEVEFSHEYWMRHALTLAKRA*

*RDEREVPVGALVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVFNAQKKAQSSTDA*<u>SGGGGSGGGGSGGGGSGGG</u>

<u>GSGGGGSGGGGSGGGGS</u>GTDKKYSIGLAIGTNSVGWAVITDEYKVPSKKFKVLGN

TDRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDAK

AILSARLSKSRRLENLIAQLPGEKKNGLFGNLIALSLGLTPNFKSNFDLAEDAKLQLS

KDTYDDDLDNLLAQIGDQYADLFLAAKNLSDAILLSDILRVNTEITKAPLSASMIKRYD

EHHQDLTLLKALVRQQLPEKYKEIFFDQSKNGYAGYIDGGASQEEFYKFIKPILEKM

DGTEELLVKLNREDLLRKQRTFDNGSIPHQIHLGELHAILRRQEDFYPFLKDNREKIE

KILTFRIPYYVGPLARGNSRFAWMTRKSEETITPWNFEEVVDKGASAQSFIERMTNF

DKNLPNEKVLPKHSLLYEYFTVYNELTKVKYVTEGMRKPAFLSGEQKKAIVDLLFKT

NRKVTVKQLKEDYFKKIECFDSVEISGVEDRFNASLGTYHDLLKIIKDKDFLDNEENE

DILEDIVLTLTLFEDREMIEERLKTYAHLFDDKVMKQLKRRRYTGWGRLSRKLINGIR

DKQSGKTILDFLKSDGFANRNFMQLIHDDSLTFKEDIQKAQVSGQGDSLHEHIANLA

GSPAIKKGILQTVKVVDELVKVMGRHKPENIVIEMARENQTTQKGQKNSRERMKRI

EEGIKELGSQILKEHPVENTQLQNEKLYLYYLQNGRDMYVDQELDINRLSDYDVDHI

-continued

VPQSFLKDDSIDNKVLTRSDKNRGKSDNVPSEEVVKKMKNYWRQLLNAKLITQRKF

DNLTKAERGGLSELDKAGFIKRQLVETRQITKHVAQILDSRMNTKYDENDKLIREVK

VITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGET

GEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFL

EAKGYKEVKKDLIIKLPKYSLFELENGRKRMLASAGELQKGNELALPSKYVNFLYLA

SHYEKLKGSPEDNEQKQLFVEQHKHYLDEIIEQISEFSKRVILADANLDKVLSAYNKH

RDKPIREQAENIIHLFTLTNLGAPAAFKYFDTTIDRKRYTSTKEVLDATLIHQSITGLYE

TRIDLSQLGGDSRAD<u>SGGS</u>TNLSDIIEKETGKQLVIQESILMLPEEVEEVIGNKPESD

ILVHTAYDESTDENVMLLTSDAPEYKPWALVIQDSNGENKIKMLSGGS<u>PKKKRKV</u>*

N-ABE (SEQ ID NO: 30)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVEITEGILADECAALLSDFFRMRRQEIKAQKKAQSST*

<u>*DSGGSSGGSSGSETPGTSESATPESSGGSSGGS*</u>*SEVEFSHEYWMRHALTLAKRA*

*RDEREVPVGAVLVLNNRVIGEGWNRAIGLHDPTAHAEIMALRQGGLVMQNYRLIDA*

*TLYVTFEPCVMCAGAMIHSRIGRVVFGVRNAKTGAAGSLMDVLHYPGMNHRVEITE*

*GILADECAALLCYFFRMPRQVENAQKKAQSST*<u>*DSGGSSGGSSGSETPGTSESATP*</u>

<u>*ESSGGSSGGS*</u>DKKYSIGLAIGTNSVGWAVITDEYKVPSKKFKVLGNTDRHSIKKNLI

GALLFDSGETAEATRLKRTARRRYTRRKNRICYLQEIFSNEMAKVDDSFFHRLEESF

LVEEDKKHERHPIFGNIVDEVAYHEKYPTIYHLRKKLVDSTDKADLRLIYLALAHMIKF

RGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPL

ARGNSRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTVKQLKED

YFKKIECFDSVEISGVEDRFNASLGTYHDLLKIIKDKDFLDNEENEDILEDIVLTLTLFE

DREMIEERLKTYAHLFDDKVMKQLKRRRYTGWGRLSRKLINGIRDKQSGKTILDFLK

SDGFANRNFMQLIHDDSLTFKEDIQKAQVCLAGDTLITLADGRRVPIRELVSQQNF

SVWALNPQTYRLERARVSRAFCTGIKPVYRLTTRLGRSIRATANHRFLTPQGWKR

VDELQPGDYLALPRRIPTAS*

C-ABE (SEQ ID NO: 31)

*MAAACPELRQLAQSDVYWDPIVSIEPDGVEEVEDLIVPGPHNEVANDIIAHNS*GQG

DSLHEHIANLAGSPAIKKGILQTVKVVDELVKVMGRHKPENIVIEMARENQTTQKGQ

KNSRERMKRIEEGIKELGSQILKEHPVENTQLQNEKLYLYYLQNGRDMYVDQELDIN

RLSDYDVDHIVPQSFLKDDSIDNKVLTRSDKNRGKSDNVPSEEVVKKMKNYWRQL

LNAKLITQRKFDNLTKAERGGLSELDKAGFIKRQLVETRQITKHVAQILDSRMNTKY

DENDKLIREVKVITLKSKLVSDFRKDFQFYKVREINNYHHAHDAYLNAVVGTALIKKY

-continued

PKLESEFVYGDYKVYDVRKMIAKSEQEIGKATAKYFFYSNIMNFFKTEITLANGEIRK

RPLIETNGETGEIVWDKGRDFATVRKVLSMPQVNIVKKTEVQTGGFSKESILPKRNS

DKLIARKKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGNELALPSK

YVNFLYLASHYEKLKGSPEDNEQKQLFVEQHKHYLDEIIEQISEFSKRVILADANLDK

VLSAYNKHRDKPIREQAENIIHLFTLTNLGAPAAFKYFDTTIDRKRYTSTKEVLDATLI

HQSITGLYETRIDLSQLGGDSRAD<u>PKKKRKV</u>*

N-ABE-AAV (SEQ ID NO: 32)

*MSEVEFSHEYWMRHALTLAKRAWDEREVPVGAVLVHNNRVIGEGWNRPIGRHDP*

*TAHAEIMALRQGGLVMQNYRLIDATLYVTLEPCVMCAGAMIHSRIGRVVFGARDAK*

*TGAAGSLMDVLHHPGMNHRVEITEGILADECAALLSDFFRMRRQEIKAQKKAQSST*

<u>DSGGSSGGSSGS</u>ETPGTSESATPESSGGSSGGS*SEVEFSHEYWMRHALTLAKRA*

*RDEREVPVGAVLVLNNRVIGEGWNRAIGLHDPTAHAEIMALRQGGLVMQNYRLIDA*

*TL YVTFEPCVMCAGAMIHSRIGRVVFGVRNAKTGAAGSLMDVLHYPGMNHRVEITE*

*GILADECAALLCYFFRMPRQVFNAQKKAQSST*<u>DASGGGGSGGGGSGGGGSGGG</u>

<u>GSGGGGSGG</u>TDKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYLALAHMIKF

RGHFLIEGDLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNRE

DLLRKQRTFDNGSIPHQIHLGELHAILRRQEDFYPFLKDNREKIEKILTFRIPYYVGPL

ARGNSRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTVKQLKED

YFKKIECFDSVEISGVEDRFNASLGTYHDLLKIIKDKDFLDNEENEDILEDIVLTLTLFE

DREMIEERLKTYAHLFDDKVMKQLRRRYTGWGRLSRKLINGIRDKQSGKTILDFLK

SDGFANRNFMQLIHDDSLTFKEDIQKAQVCLAGDTLITLADGRRVPIRELVSQQNF

SVWALNPQTYRLERARVSRAFCIGIKPVYRLITRLGRSIRATANHRFLTPQGWKR

VDELQPGDYLALPRRIPTAS*

C-ABE-AAV (SEQ ID NO: 33)

*MAAACPELRQLAQSDVYWDPIVSIEPDGVEEVFDTVPGPHFVANDIIAHNS*GQG

DSLHEHIANLAGSPAIKKGILQTVKVVDELVKVMGRHKPENIVIEMARENQTTQKGQ

KNSRERMKRIEEGIKELGSQILKEHPVENTQLQNEKLYLYYLQNGRDMYVDQELDIN

RLSDYDVDHIVPQSFLKDDSIDNKVLTRSDKNRGKSDNVPSEEVVKKMKNYWRQL

LNAKLITQRKFDNLTKAERGGLSELDKAGFIKRQLVETRQITKHVAQILDSRMNTKY

DENDKLIREVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEITLANGEIRK

RPLIETNGETGEIVWDKGRDFATVRKVLSMPQVNIVKKTEVQTGGFSKESILPKRNS

DKLIARKKDWDPKKYGGFDSPTVAYSVLVVAKVEKGKSKKLKSVKELLGITIMERSS

-continued

FEKNPIDFLEAKGYKEVKKDLIIKLPKYSLFELENGRKRMLASAGELQKGNELALPSK

YVNFLYLASHYEKLKGSPEDNEQKQLFVEQHKHYLDEIIEQISEFSKRVILADANLDK

VLSAYNKHRDKPIREQAENIIHLFTLTNLGAPAAFKYFDTTIDRKRYTSTKEVLDATLI

HQSITGLYETRIDLSQLGGDSGGSTNLSDIIEKETGKQLVIQESILMLPEEVEEVIGN

KPESDILVHTAYDESTDENVMLLTSDAPEYKPWALVIQDSNGENKIKMLS_YPYDVP_

_DYAYPYDVPDYAYPYDVPDYA_SGGS_PKKKRKV*_

---

The invention claimed is:

1. A method for inducing selective exon skipping comprising: contacting one or more DNA target sequences with (i) a single guide RNA (sgRNA) molecule having complementarity to the one or more DNA target sequences; and (ii) a fusion protein comprising (i) at least two tRNA-specific adenosine deaminases (TadA) domains (ii) a linker; and (iii) an RNA-guided DNA endonuclease having nickase activity capable of causing single stranded breaks in the one or more DNA target sequences, such that an exon is selectively skipped.

2. The method of claim 1, wherein the sgRNA molecule is complementary to a splice acceptor or a splice enhancer of the one or more DNA target sequences.

3. The method of claim 1, wherein the one or more DNA target sequences are adjacent to a protospacer adjacent motif (PAM).

4. The method of claim 1, wherein the linker comprises (AP)$_5$ (SEQ ID NO:2), GGGGS (SEQ ID NO:3), (GGGGS)$_2$ (SEQ ID NO:4), (GGGGS)$_3$ (SEQ ID NO:5), (GGGGS)$_4$ (SEQ ID NO:6), (GGGGS)$_5$ (SEQ ID NO:7), (GGGGS)$_6$ (SEQ ID NO:8), (GGGGS)$_7$ (SEQ ID NO:9), GGGGSSGGSSGGSSGSETPGTSESATPESSGGSSGGS (SEQ ID NO:10), or (EAAA)$_5$ (SEQ ID NO:11).

5. The method of claim 1, wherein the fusion protein further comprises a uracil glycosylase inhibitor (UGI) protein.

6. The method of claim 1, wherein the linker comprises (GGGGS)$_5$ (SEQ ID NO:7).

7. The method of claim 1, wherein the fusion protein is encoded by
   (a) a first construct comprising (i) a polynucleotide encoding the at least two tRNA-specific adenosine deaminases (TadA) (ii) a polynucleotide encoding the linker (iii) a first part of a polynucleotide encoding the RNA-guided DNA endonuclease having nickase activity and (iv) a polynucleotide encoding an N-terminal intein; and
   (b) a second construct comprising (i) a polynucleotide encoding a C-terminal intein and (ii) a second part of the polynucleotide encoding the RNA-guided DNA endonuclease having nickase activity.

8. The method of claim 7, wherein the second construct further comprises a polynucleotide encoding an uracil glycosylase inhibitor (UGI) protein.

9. The method of claim 7, wherein the linker comprises (GGGGS)$_5$ (SEQ ID NO:7).

10. The method of claim 7, wherein at least one of the first construct and the second construct further comprise a sgRNA expression cassette.

11. The method of claim 7, wherein at least one of the first construct and the second construct are flanked by inverted terminal repeats (ITRs).

12. The method of claim 7, wherein the first and second constructs are packaged into a first and second adeno-associated virus (AAV).

13. The method of claim 1, wherein the at least two TadA domains are obtained from *Escherichia coli, Bacillus subtilis*, or *Staphylococcus aureus*.

14. The method of claim 1, wherein the one or more DNA target sequences are selected from a splice acceptor of exon 3 of an alpha-synuclein protein, a splice acceptor of exon 45 of a dystrophin gene, or a splice enhancer of exon 12 of a Huntington gene.

* * * * *